United States Patent
Son et al.

(10) Patent No.: US 11,515,483 B2
(45) Date of Patent: Nov. 29, 2022

(54) ORGANIC COMPOUND AND ORGANIC ELECTROLUMINESCENT DEVICE USING THE SAME

(71) Applicant: SOLUS ADVANCED MATERIALS CO., LTD., Iksan-si (KR)

(72) Inventors: Ho Jun Son, Yongin-si (KR); Young Bae Kim, Yongin-si (KR); Hyung Chan Bae, Yongin-si (KR)

(73) Assignee: SOLUS ADVANCED MATERIALS CO., LTD., Iksan-si (KR)

( * ) Notice: Subject to any disclaimer, the term of this patent is extended or adjusted under 35 U.S.C. 154(b) by 385 days.

(21) Appl. No.: 16/628,462

(22) PCT Filed: Jul. 3, 2018

(86) PCT No.: PCT/KR2018/007521
§ 371 (c)(1),
(2) Date: Jan. 3, 2020

(87) PCT Pub. No.: WO2019/009591
PCT Pub. Date: Jan. 10, 2019

(65) Prior Publication Data
US 2021/0135118 A1    May 6, 2021

(30) Foreign Application Priority Data
Jul. 4, 2017  (KR) .................. 10-2017-0084834

(51) Int. Cl.
| | | |
|---|---|---|
| *H01L 51/00* | (2006.01) | |
| *C07D 403/14* | (2006.01) | |
| *C07D 405/14* | (2006.01) | |
| *C07D 409/14* | (2006.01) | |
| *C09K 11/06* | (2006.01) | |
| *H01L 51/50* | (2006.01) | |

(52) U.S. Cl.
CPC ........ *H01L 51/0067* (2013.01); *C07D 403/14* (2013.01); *C07D 405/14* (2013.01); *C07D 409/14* (2013.01); *C09K 11/06* (2013.01); *H01L 51/0052* (2013.01); *H01L 51/0054* (2013.01); *H01L 51/0072* (2013.01); *H01L 51/0073* (2013.01); *H01L 51/0074* (2013.01); *C09K 2211/1018* (2013.01); *H01L 51/5016* (2013.01)

(58) Field of Classification Search
CPC ............. H01L 51/0067; H01L 51/0052; H01L 51/0054; H01L 51/0072; H01L 51/0073; H01L 51/0074
See application file for complete search history.

(56) References Cited

U.S. PATENT DOCUMENTS

| | | |
|---|---|---|
| 9,153,788 B2 | 10/2015 | Adachi et al. |
| 2013/0264561 A1 | 10/2013 | Dobbs et al. |
| 2018/0123049 A1 | 5/2018 | Lee et al. |

FOREIGN PATENT DOCUMENTS

| | | |
|---|---|---|
| CN | 103959502 B | 3/2017 |
| CN | 106883215 A | 6/2017 |
| KR | 10-2014-0015298 A | 2/2014 |
| KR | 10-2014-0106631 A | 9/2014 |
| KR | 10-2015-0105201 A | 9/2015 |
| KR | 10-2016-0116297 A | 10/2016 |
| KR | 10-2017-0113808 A | 10/2017 |
| KR | 10-2027025 B1 | 10/2019 |

OTHER PUBLICATIONS

International Search Report for PCT/KR2018/007521 dated Oct. 12, 2018 (PCT/ISA/210).

*Primary Examiner* — Anthony Ho
(74) *Attorney, Agent, or Firm* — Sughrue Mion, PLLC

(57) ABSTRACT

The present disclosure relates to a novel organic compound which has excellent thermal stability, electron transporting ability, and light emitting ability, and to an organic EL device containing the same. As the organic compound is used in an organic material layer of the organic EL device, the thermal stability, luminous efficiency, driving voltage, and life of the device can be improved.

19 Claims, No Drawings

ORGANIC COMPOUND AND ORGANIC ELECTROLUMINESCENT DEVICE USING THE SAME

CROSS REFERENCE TO RELATED APPLICATIONS

This application is a National Stage of International Application No. PCT/KR2018/007521 filed Jul. 3, 2018, claiming priority based on Korean Patent Application No. 10-2017-0084834 filed Jul. 4, 2017.

TECHNICAL FIELD

The present disclosure relates to a novel organic compound and an organic electroluminescent device using the same, and more particularly, to a compound having excellent thermal stability and electron transporting ability, and an organic electroluminescence device improved in terms of luminous efficiency, driving voltage, life, etc. by including the compound in one or more organic layers.

BACKGROUND ART

In organic electroluminescence devices (hereinafter, "EL devices"), upon application of voltage between two electrodes, holes are injected from an anode to an organic layer and electrons are injected from a cathode into the organic layer. Injected holes and electrons meet each other to form excitons, and light emission occurs when the excitons fall to a ground state. In this case, materials used for the organic layer may be classified into, for example, luminescent materials, hole injection materials, hole transporting materials, electron transporting materials and electron injection materials depending on their function.

Light emitting materials of an organic EL device may be classified into blue, green and red luminescent materials depending on their emission colors. Besides, yellow and orange luminescent materials may be used as a luminescent material for realizing better natural colors. In addition, a host/dopant system may be employed in the luminescent material to increase color purity and luminous efficiency through energy transfer. Dopant materials may be classified into fluorescent dopants using organic materials and phosphorescent dopants using metal complex compounds which include heavy atoms such as Ir and Pt. The developed phosphorescent materials may improve the luminous efficiency theoretically up to four times as compared to fluorescent materials, so attention is given to phosphorescent dopants as well as phosphorescent host materials.

To date, NPB, BCP and $Alq_3$ are widely known as materials used in the hole injection layer, the hole transporting layer, the hole blocking layer and the electron transporting layer, and anthracene derivatives have been reported as fluorescent dopant/host materials for luminescent materials. Particularly, metal complex compounds including Ir, such as Firpic, $Ir(ppy)_3$, and $(acac)(btp)_2Ir$, are known as phosphorescent dopant materials for efficiency improvement among luminescent materials, and they are used as blue, green and red dopant materials. Up to this day, CBP has shown excellent properties as a phosphorescent host material.

However, conventional materials, despite their good luminescence properties, have low glass transition temperatures and poor thermal stability and thus are not satisfactory in terms of life characteristics of organic EL devices. Accordingly, there is a demand for luminescent materials having excellent thermal stability as well as high luminescence performance.

DETAILED DESCRIPTION OF THE INVENTION

Technical Problem

Aspects of the present disclosure are directed to a novel organic compound that may be used to form an organic layer (e.g., an emissive layer) of an organic electroluminescence device due to its high glass transition temperature, excellent electron transporting ability and light emitting ability.

In addition, aspects of the present disclosure are also directed to an organic electroluminescence device that includes the organic compound, thereby exhibiting low driving voltage, high luminous and current efficiency, high thermal stability and long life.

TECHNICAL SOLUTION

The present disclosure provides a compound represented by the following Chemical Formula 1:

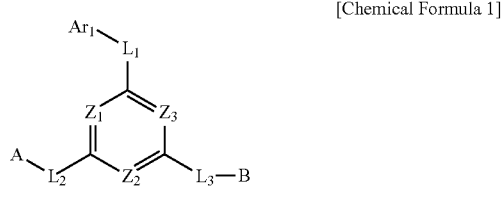

[Chemical Formula 1]

where in Chemical Formula 1, $Z_1$ to $Z_3$ are the same as or different from each other, each independently being N or $C(R_1)$, wherein at least one of $Z_1$ to $Z_3$ is N, wherein when $C(R_1)$ are plural in number, the plurality of $R_1$, are the same or different from each other and each independently selected from the group consisting of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{10}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group and a $C_6$ to $C_{60}$ arylamine group, $L_1$ to $L_3$ are the same as or different from each other, each independently being a single bond, or selected from the group consisting of: a $C_6$ to $C_{18}$ arylene group and a heteroarylene group having 5 to 18 nuclear atoms, $Ar_1$ is selected from the group consisting of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group, and a $C_6$ to $C_{60}$ arylamine group, and A and B are the same as or different from each other and each independently selected from the group consisting of: substituents having asymmetric structures represented by the following Chemical Formulas 2 and 3, and substituents represented by the following Chemical Formulas 4 and 5, wherein at least one of A and B is a substituent having an asymmetric structure represented by the following Chemical Formula 2 or 3,

[Chemical Formula 2]

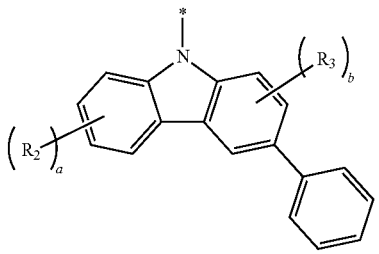

[Chemical Formula 3]

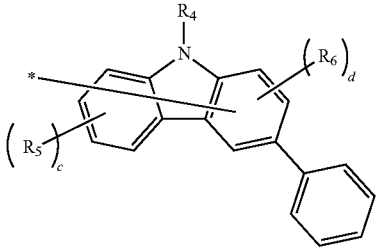

[Chemical Formula 4]

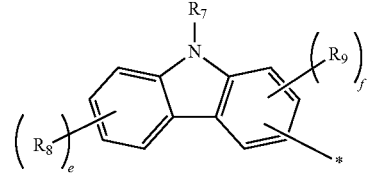

[Chemical Formula 5]

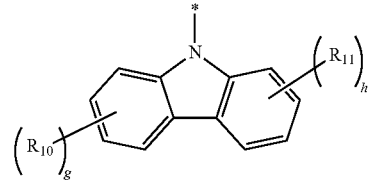

where in Chemical Formulas 2 to 5,

"*" are each a site connected to $L_2$ or $L_3$ of Chemical Formula 1, a, c, e, g and h are each an integer ranging from 0 to 4, while b, d and f are each an integer ranging from 0 to 3, wherein c+d is in a range of 0≤c+d≤6, wherein a plurality of $R_2$ are the same or different from each other, a plurality of $R_3$ are the same or different from each other, a plurality of $R_4$ are the same or different from each other, a plurality of $R_5$ are each the same or different from each other, a plurality of $R_6$ are the same as or different from each other, a plurality of $R_7$ are the same as or different from each other, a plurality of the $R_8$ are the same as or different from each other, a plurality of the $R_9$ are the same as or different from each other, a plurality of the $R_{10}$ are the same as or different from each other, a plurality of $R_{11}$ are each the same or different from each other, $R_2$ to $R_{11}$ are each independently selected from the group consisting of: deuterium, a halogen group, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group, or may combine with an adjacent group to form a fused ring, and the arylene group and the heteroarylene group of $L_1$ to $L_3$; and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the alkylphosphine group, the arylphosphine group, the arylphosphine oxide group and the arylamine group of $Ar_1$ and $R_1$ to $R_{11}$ are each independently substituted or unsubstituted with one or more kinds of substituents selected from the group consisting of: deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_6$ to $C_{60}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group and a $C_6$ to $C_{60}$ arylsilyl group, wherein when the substituents are plural in number, the substituents are the same as or different from each other.

In addition, the present disclosure provides an organic electroluminescence device, including an anode, a cathode and one or more organic layers disposed between the anode and the cathode. At least one of the one or more organic layers includes the compound represented by Chemical Formula 1.

In such a case, the one or more organic layers include an emissive layer, and the emissive layer includes the compound represented by the above Chemical Formula 1.

Effects of the Invention

A compound represented by Chemical Formula 1 may be used as a material for an organic layer of an organic EL device (e.g., a host material of an emissive layer) of an organic EL device by virtue of its excellent electron transporting ability, light emission performance, and thermal stability.

In addition, by including the compound represented by Chemical Formula 1 as a host material of an emissive layer, the organic EL device according to the present disclosure is excellent in light emission performance, has a low driving voltage, has high stability and long life, and thus may improve the performance and life of full color display panels, as compared to organic EL devices using conventional host materials.

MODE FOR CARRYING OUT THE INVENTION

Hereinafter, the present disclosure will be described in detail.

<Novel Organic Compound>

An organic compound according to the present disclosure is a compound, represented by Chemical Formula 1, that has a basic structure in which two carbazole derivatives are introduced into a 6-membered nitrogen (N)-containing heteroaromatic ring moiety, and at least one of the two carbazole derivatives is a carbazole derivative having an asymmetric structure where a phenyl group is introduced at position 3 (or 6) of the carbazole basic skeleton. When an organic EL device includes the compound of Chemical Formula 1, a driving voltage of the device is low, luminous and current efficiency and thermal stability is high, and the device has a long life. In such a case, the position numbers of carbon or nitrogen of the carbazole basic skeleton are as follows.

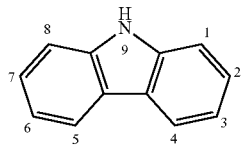

Specifically, in the compound represented by Chemical Formula 1, the 6-membered N-containing heteroaromatic ring moiety corresponds to a portion that has high electron withdrawing characteristics. When two carbazole derivatives are introduced into this moiety, since the carbazole derivative is an electron donating group (EDG) that has high electron donating characteristics, the entire molecule has bipolar properties. Accordingly, when the compound of the present disclosure is used as a material, preferably a host material, for an organic layer of an organic EL device (e.g., OLED), the compound may increase a binding force between holes and electrons in an emissive layer, thereby improving luminous characteristics of the organic EL device.

In addition, as two carbazole derivatives are introduced into the six-membered N-containing heteroaromatic ring moiety, carrier balance becomes excellent, leading to high generation of excitons, which is suitable for the emissive layer. In addition, since the compound of Chemical Formula 1 has a small LUMO energy level difference with a dopant by including two carbazole derivatives, energy transfer to the dopant is high, thus improving the luminous efficiency of the device, and durability and stability of the device may be improved, thus efficiently increasing the life of the device.

In addition, the compound of Chemical Formula 1 is at least one of the two carbazole derivatives and includes a carbazole derivative having an asymmetric structure. In such an embodiment, the carbazole derivative of the asymmetric structure has an asymmetric structure by introducing a phenyl group at position 3 (or 6) of the carbazole basic skeleton. By blocking the position 3 (or 6), which is an active site, with a phenyl group, electrochemical stability of the organic EL device is improved along with thermal stability thereof, thus improving the life of the device, as compared to the case where other aryl groups (e.g., a biphenyl group, a naphthyl group, etc.) are introduced.

As such, the compound represented by Chemical Formula 1, by virtue of its excellent luminous characteristics, may be used as a material for one of a hole injection layer, a hole transporting layer, an emissive layer, an electron transporting layer, and an electron injection layer, which are organic layers of the organic EL device, and preferably, as a material for the emissive layer, and more preferably, as a phosphorescent green host (PGH).

Accordingly, the organic EL device including the compound represented by Chemical Formula 1 may have greatly improved performance and life characteristics, and full-color organic EL panels to which the organic EL device is applied may also substantially maximize its performance.

In the compound represented by Chemical Formula 1 according to the present disclosure, $Z_1$ to $Z_3$ are the same as or different from each other, each independently being N or $C(R_1)$. However, at least one of $Z_1$ to $Z_3$ is N.

As an example, all of $Z_1$ to $Z_3$ may be N. In such a case, as compared to the case where one of $Z_1$ to $Z_3$ is N or where two of $Z_1$ to $Z_3$ are N, the balance of carriers (holes/electrons) in an emissive layer is excellent, and thus the luminous characteristics of the organic EL device may be improved.

In such a case, when $C(R_1)$ are plural in number, the plurality of $R_1$ are the same or different from each other and each independently selected from the group consisting of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group and a $C_6$ to $C_{60}$ arylamine group. Specifically, the plurality of $R_1$ may be selected from the group consisting of: hydrogen, deuterium (D), halogen, a cyano group, a nitro group, a $C_1$ to $C_{40}$ alkyl group (more specifically, a $C_1$ to $C_{12}$ alkyl group), a $C_6$ to $C_{60}$ aryl group (more specifically, a $C_6$ to $C_{20}$ aryl group), and a heteroaryl group having 5 to 60 nuclear atoms (more specifically, a heteroaryl group having 5 to 20 nuclear atoms). In this case, the heterocycloalkyl group and the heteroaryl group each include one or more heteroatoms selected from the group consisting of: N, S, O and Se.

In addition, $L_1$ to $L_3$ are divalent linkers, which are the same as or different from each other, each independently being a single bond, or selected from the group consisting of: a $C_6$ to $C_{18}$ arylene group and a heteroarylene group having 5 to 18 nuclear atoms. Specifically, $L_1$ to $L_3$ may be the same as or different from each other, each independently being a single bond, or selected from the group consisting of a $C_6$ to $C_{18}$ arylene group. In this case, the heteroarylene group includes one or more heteroatoms selected from the group consisting of: N, S, O and Se.

As an example, $L_1$ to $L_3$ may be the same as or different from each other, each independently being a single bond, or a phenylene group.

In such an embodiment, $Ar_1$ is selected from the group consisting of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group, and a $C_6$ to $C_{60}$ arylamine group. Specifically, $Ar_1$ may be selected from the group consisting of: hydrogen, deuterium (D), a $C_6$ to $C_{60}$ aryl group, and a heteroaryl group having 5 to 60 nuclear atoms, and more specifically, may be selected from the group consisting of: a $C_6$ to $C_{30}$ aryl group and a heteroaryl group having 5 to 30 nuclear atoms. Each of the heterocycloalkyl group and the heteroarylene group includes one or more heteroatoms selected from the group consisting of: N, S, O and Se.

As an example, $Ar_1$ may be a substituent selected from the group consisting of: the following substituents S1 to S8.

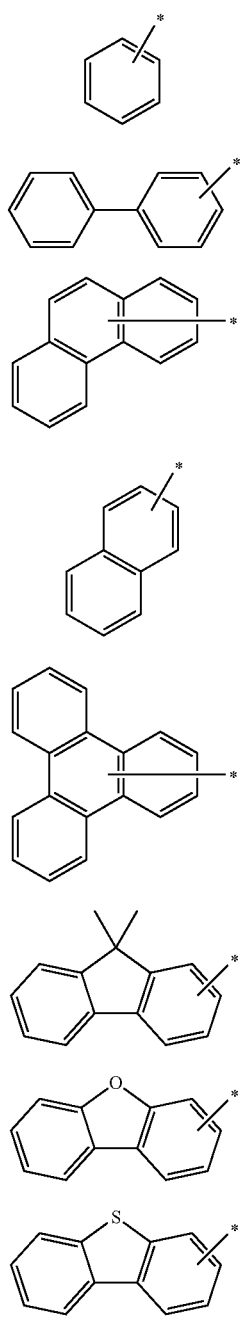

In addition, A and B are the same as or different from each other and each independently selected from the group consisting of: substituents having an asymmetric structure represented by the above Chemical Formulas 2 and 3 and substituents represented by the above Chemical Formulas 4 and 5, but at least one of A and B is a substituent having an asymmetric structure represented by the above Chemical Formula 2 or 3.

As an example, A and B may be the same as or different from each other and each independently selected from the group consisting of: substituents having an asymmetric structure represented by the above Chemical Formulas 2 and 3 and substituents represented by the above Chemical Formulas 4 and 5, but at least one of A and B may be a substituent having an asymmetric structure represented by the above Chemical Formula 2.

As another example, A may be a substituent having an asymmetric structure represented by Chemical Formula 2, and B may be a substituent selected from the group consisting of: a substituent having an asymmetric structure represented by the above Chemical Formula 2 and substituents represented by the above Chemical Formulas 4 and 5.

In Chemical Formulas 2 to 5, each "*" represents portions connected to $L_2$ or $L_3$ of Chemical Formula 1.

For example, in the substituents represented by Chemical Formulas 2 and 5, nitrogen at position 9 (N position) of the carbazole basic skeleton is connected to $L_1$ or $L_2$ of Chemical Formula 1. In the substituent represented by the above Chemical Formula 3, any one carbon (specifically, carbon at position 6 or 7) of carbons at position 1, 2, 4 to 8 of the carbazole basic skeleton is connected to a carbon or a heteroatom of $L_1$ or $L_2$ of Chemical Formula 1. In the substituent represented by Chemical Formula 4, any one carbon (specifically, carbon at position 2 or 3) of carbons at position 1 to 4 of the carbazole basic skeleton is connected to a carbon or a heteroatom of $L_1$ or $L_2$ of Chemical Formula 1.

Specifically, examples of the substituent represented by Chemical Formula 3 include a substituent represented by Chemical Formula 3a, a substituent represented by Chemical Formula 3b, and the like, and examples of the substituent represented by Chemical Formula 4 include a substituent represented by Chemical Formula 4a, a substituent represented by the following Chemical Formula 4b and the like, but embodiments are not limited thereto.

[Chemical Formula 3a]

[Chemical Formula 3b]

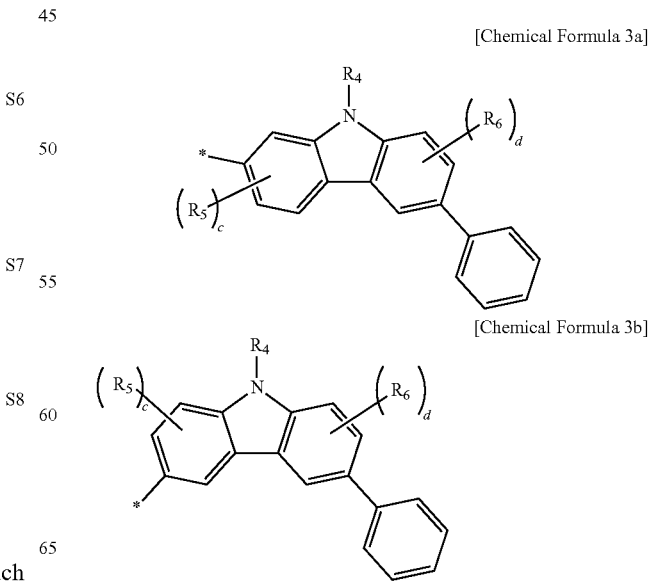

-continued

[Chemical Formula 4a]

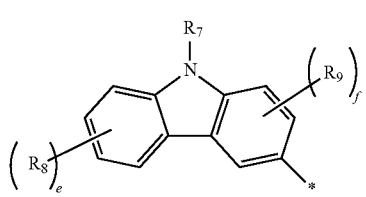

[Chemical Formula 4b]

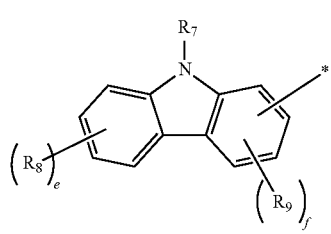

(In Chemical Formulas 3a, 3b, 4a, and 4b, $R_4$ to $R_9$, c, d, e, f and "*" are the same as those defined in in Chemical Formulas 3 and 4, respectively)

In Chemical Formulas 2 to 5, a, c, e, g and h are each an integer ranging from 0 to 4, b, d and f are each an integer ranging from 0 to 3, but c+d is an integer ranging from 0 to 6.

In this case, when each of a, b, c, d, e, f and g is 0, it means that hydrogen is not substituted with each substituent ($R_2$ to $R_{11}$). On the other hand, when each of a, c, e, g and h is an integer ranging from 1 to 4 and when each of b, d and f is 1 or 2, it means that hydrogen is substituted with each substituent ($R_2$ to $R_{11}$).

When each of a, c, e, g and h is an integer ranging from 1 to 4, and/or when each of b, d and f is 1 or 2, the plurality of $R_2$ to the plurality of $R_{11}$ are the same or different from each other, and each independently selected from the group consisting of: deuterium, a halogen group, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group, and a $C_6$ to $C_{60}$ arylamine group, or may combine with an adjacent group to form a fused ring. Specifically, the plurality of $R_2$ to the plurality of $R_{11}$ may be the same or different from each other, and each independently selected from the group consisting of: deuterium and a $C_6$ to $C_{60}$ aryl group. More Specifically, the plurality of $R_2$ to the plurality of $R_{11}$ are the same or different from each other, and each independently selected from the group consisting of: a $C_6$ to $C_{30}$ aryl group. In an example, the plurality of $R_2$ to the plurality of $R_{11}$ may be the same or different from each other, and each independently be a phenyl group or a biphenyl group. In Chemical Formula 2, when a is an integer of 1 or greater, and when one of one or more $R_2$ exists at position 6 of the carbazole basic skeleton, it is preferable that the case where $R_2$ is a phenyl group is excluded. In Chemical Formula 3, when c is an integer of 1 or greater, and one of one or more $R_5$ exists at position 6 of the carbazole base skeleton, it is preferable that the case where $R_5$ is a phenyl group is excluded.

In Chemical Formula 1, the arylene group and the heteroarylene group of $L_1$ to $L_3$; and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the alkylphosphine group, the arylphosphine group, the arylphosphine oxide group and the arylamine group of $Ar_1$ and $R_1$ to Ru may each be independently substituted or unsubstituted with one or more kinds of substituents selected from the group consisting of: deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_6$ to $C_{60}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group and a $C_6$ to $C_{60}$ arylsilyl group, and specifically may each be independently substituted or unsubstituted with one or more kinds of substituents selected from the group consisting of: deuterium, halogen, a cyano group, a nitro group, a $C_1$ to $C_{21}$ alkyl group, a $C_6$ to $C_{30}$ aryl group, and a heteroaryl group having 5 to 30 nuclear atoms. In such a case, when the substituents are plural in number, the substituents are the same as or different from each other.

According to an embodiment of the present disclosure, the compound represented by Chemical Formula 1 may be a compound represented by the following Chemical Formula 6.

[Chemical Formula 6]

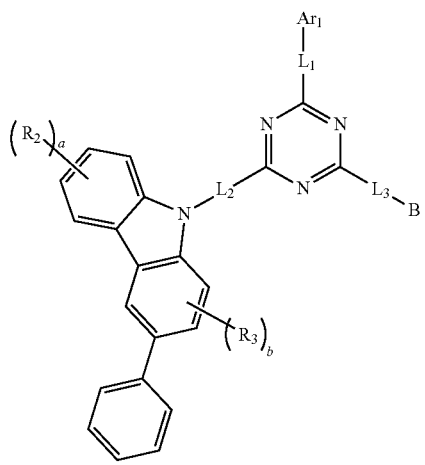

(In Chemical Formula 6, $L_1$ to $L_3$, $Ar_1$, $R_2$, $R_3$, a and b are the same as those defined in Chemical Formula 1, and B is one of the substituents represented by Chemical Formulas 2 to 5).

According to another embodiment of the present disclosure, the compound represented by Chemical Formula 1 may be a compound represented by any one of the following Chemical Formulas 7 to 10.

[Chemical Formula 7]
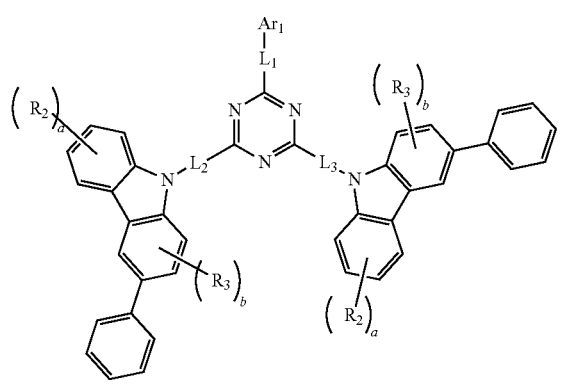
[Chemical Formula 8]
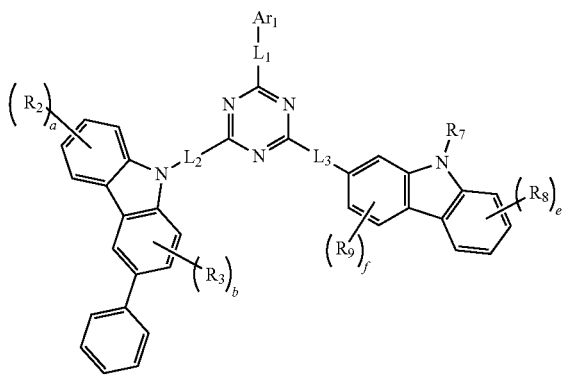
[Chemical Formula 9]
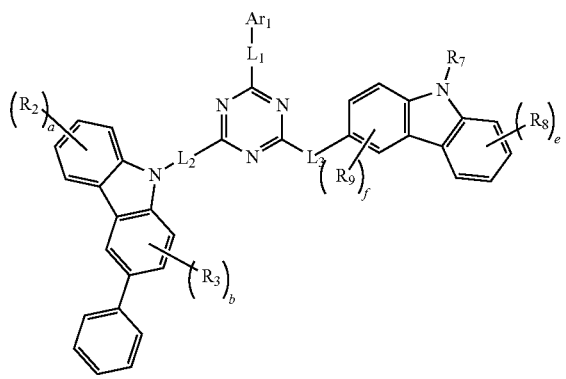
[Chemical Formula 10]
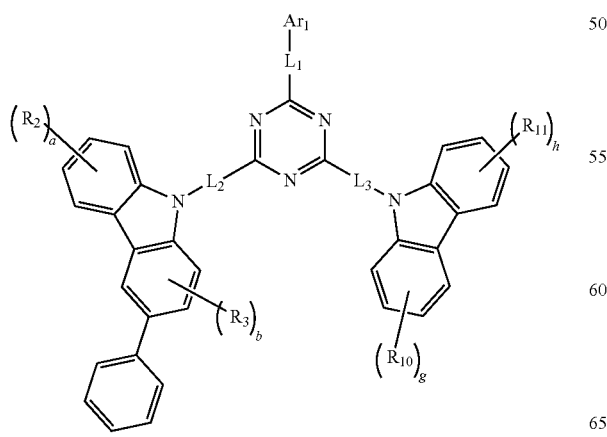
(In Chemical Formulas 7 to 10,
$L_1$ to $L_3$, $Ar_1$, $R_2$, $R_3$, $R_7$ to $R_{11}$, a, b, e, f, g and h are the same as those defined in claim 1, respectively).
Specific examples of the compound of Chemical Formula 1 according to the present disclosure include the followings, but embodiments are not limited thereto:
A-1
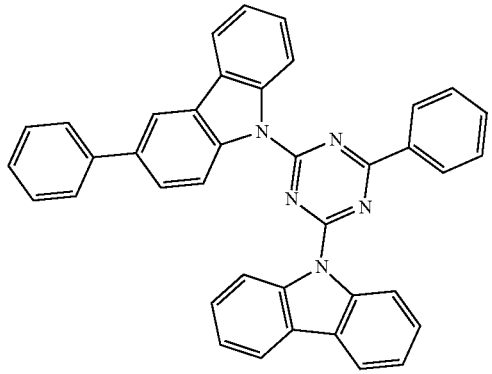
A-2
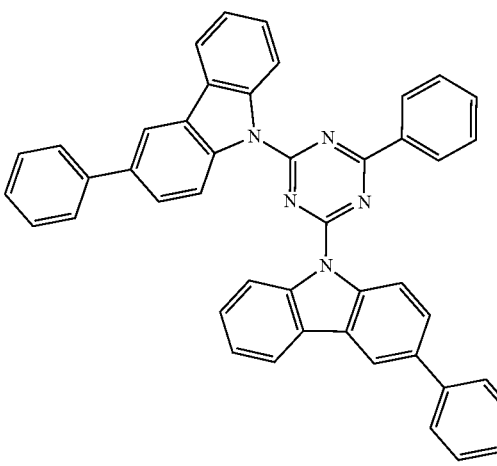
A-3
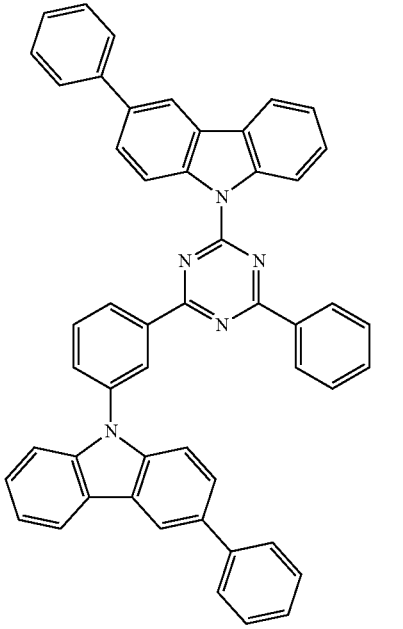

A-4
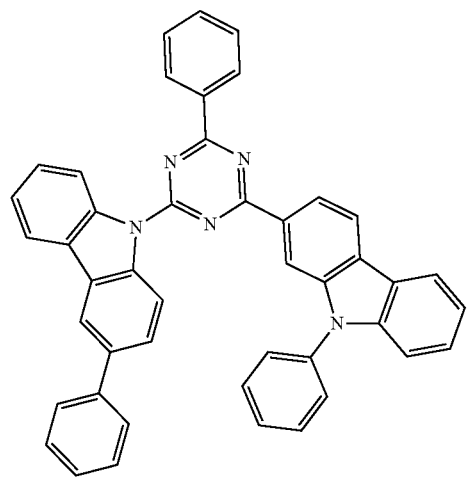
A-5
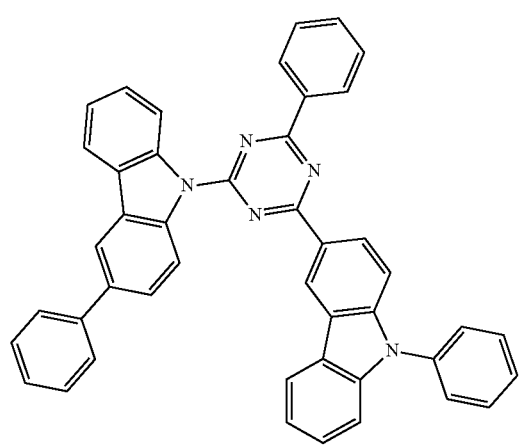
A-6
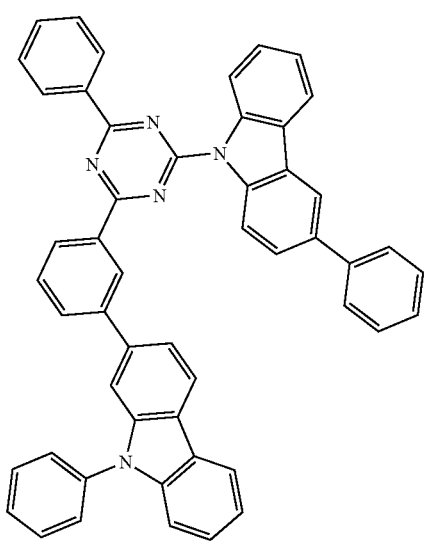
A-7
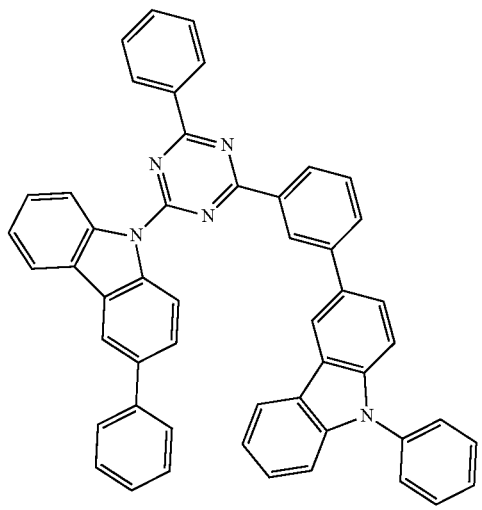
A-8
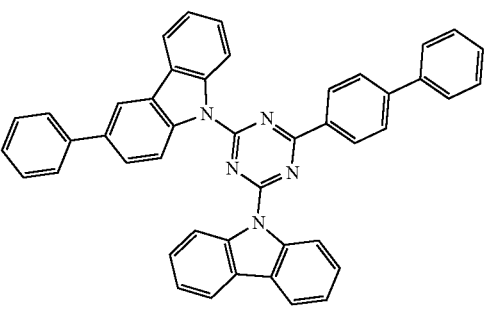
A-9
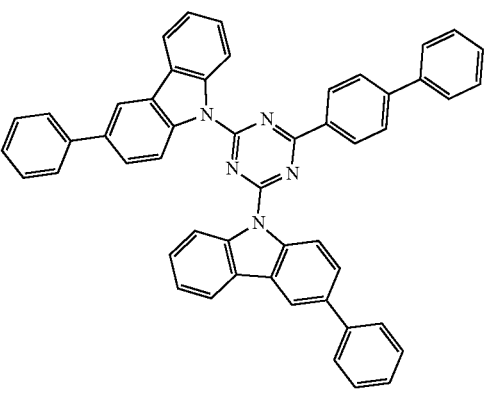

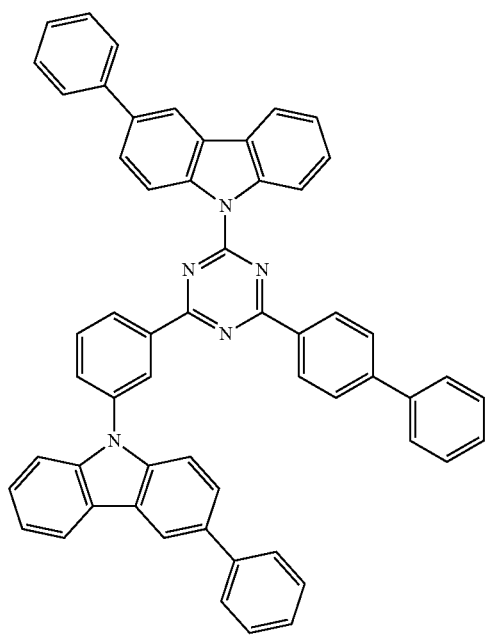
A-10
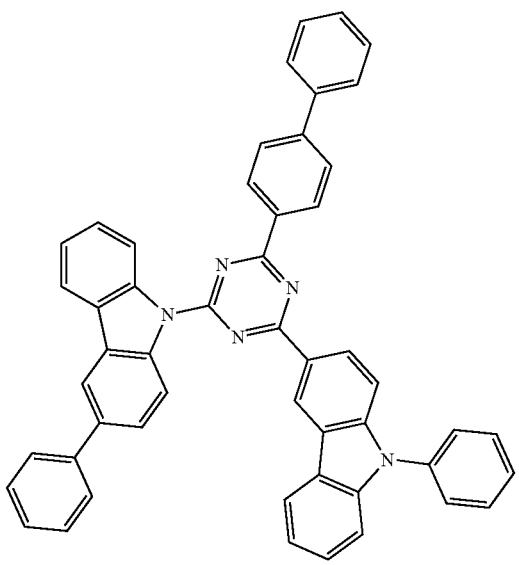
A-12
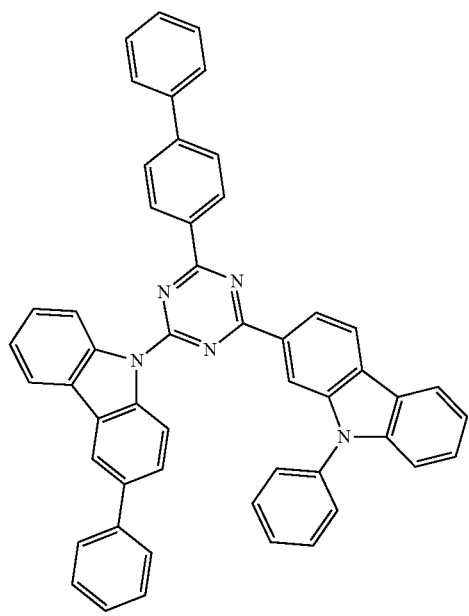
A-11
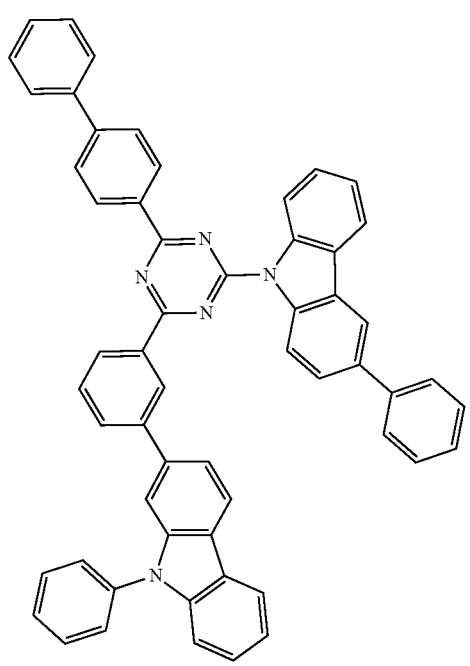
A-13

A-14
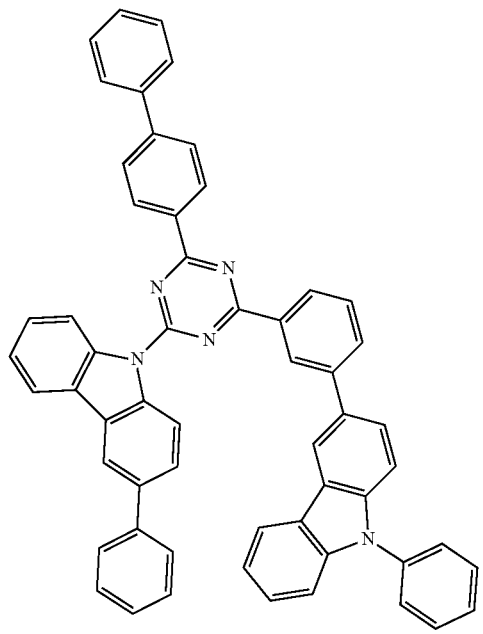
A-17
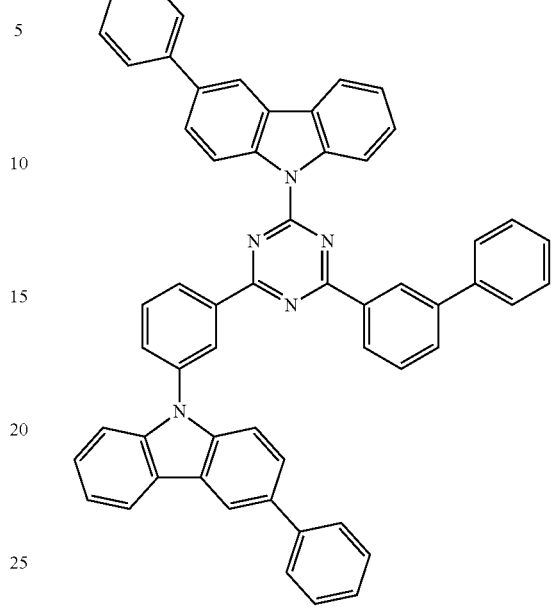
A-15
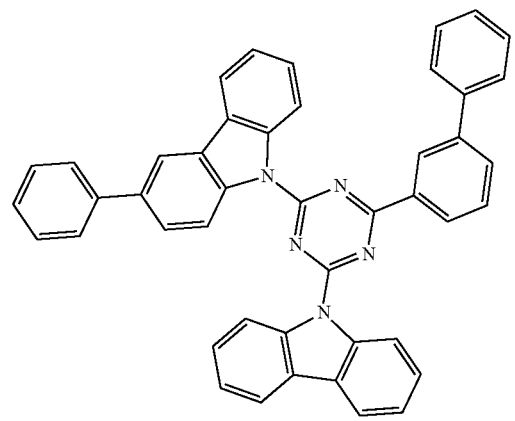
A-16
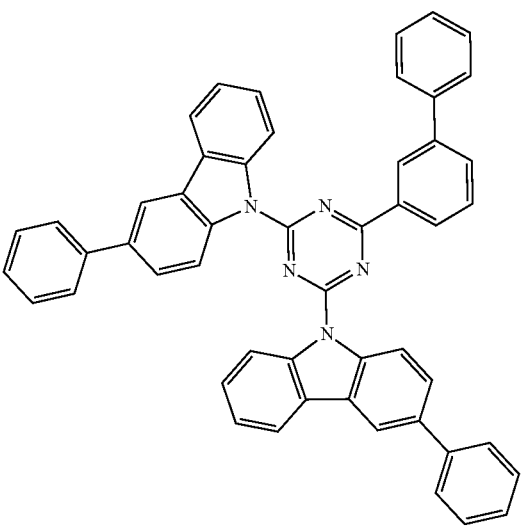
A-18
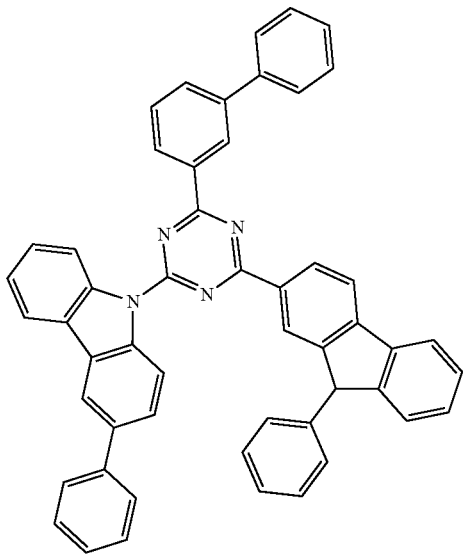

A-19
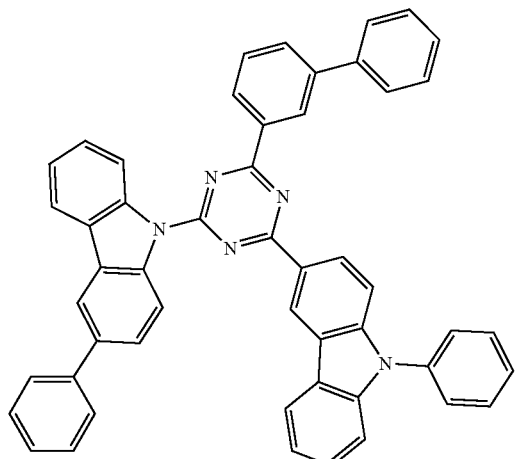
A-20
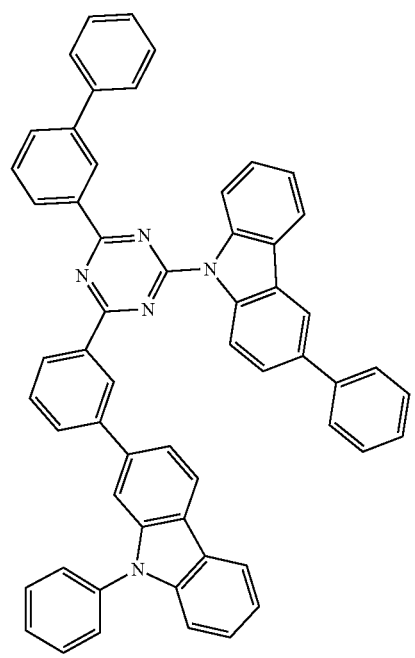
A-21
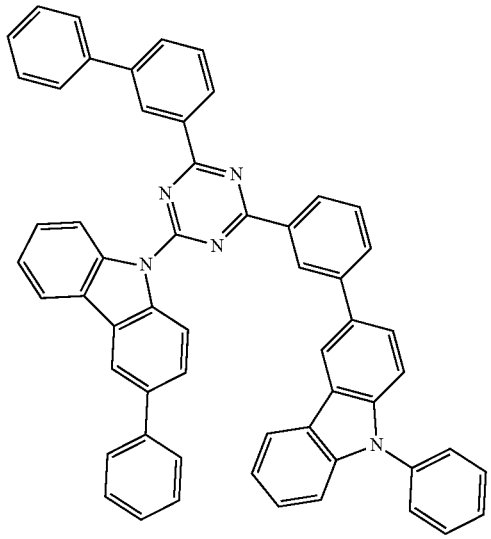
A-22
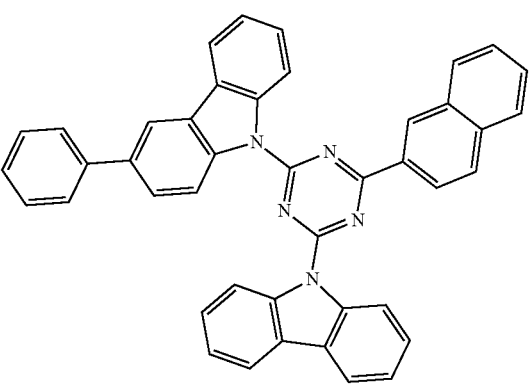
A-23
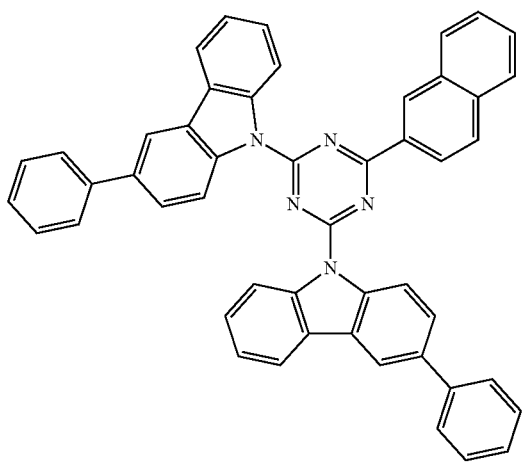

A-24
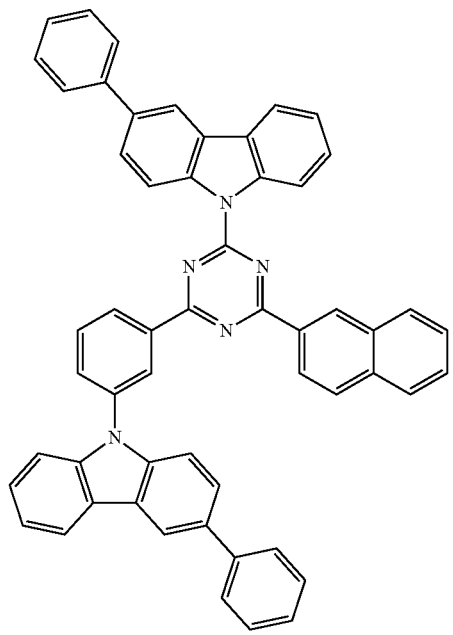
A-26
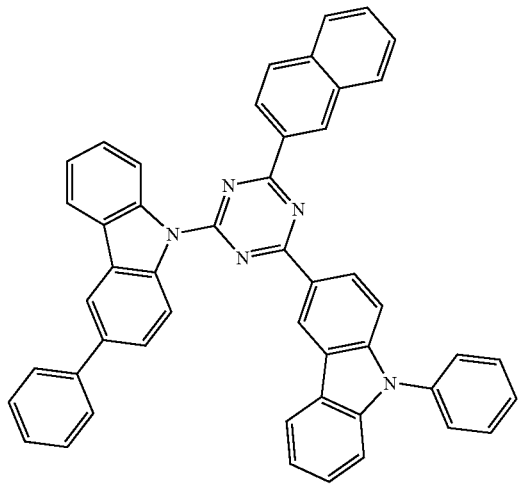
A-25
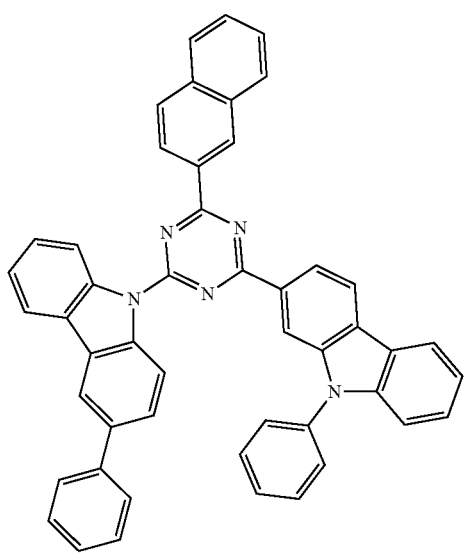
A-27
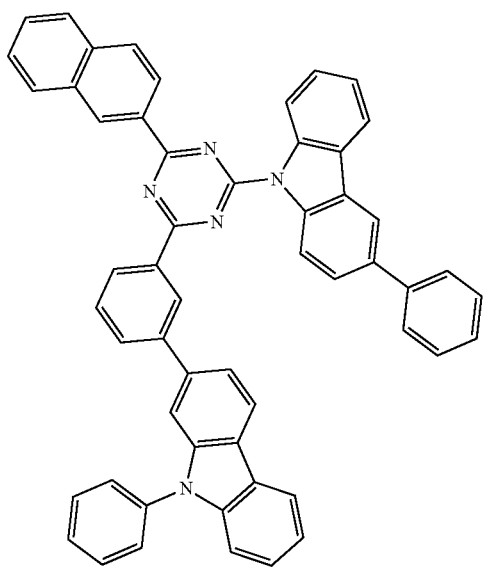

A-28
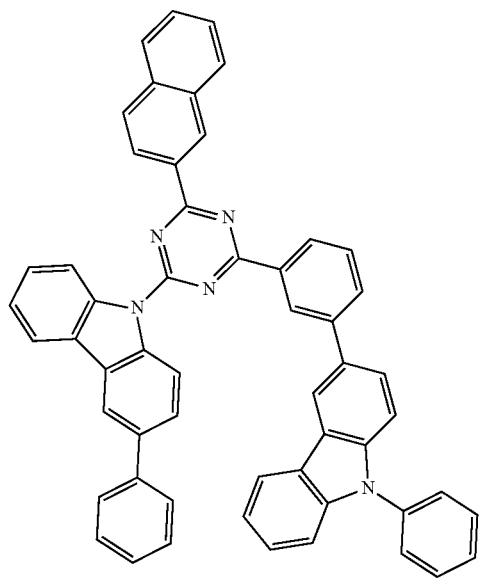
A-31
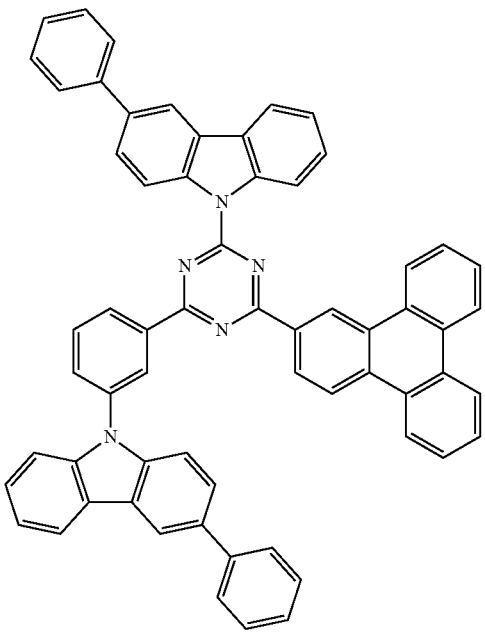
A-29
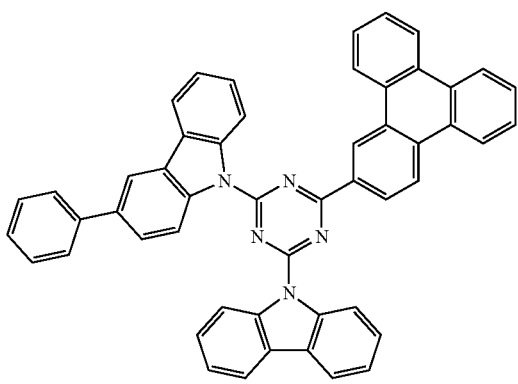
A-30
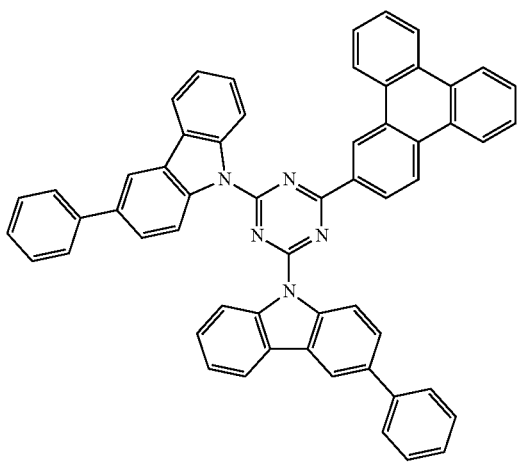
A-32
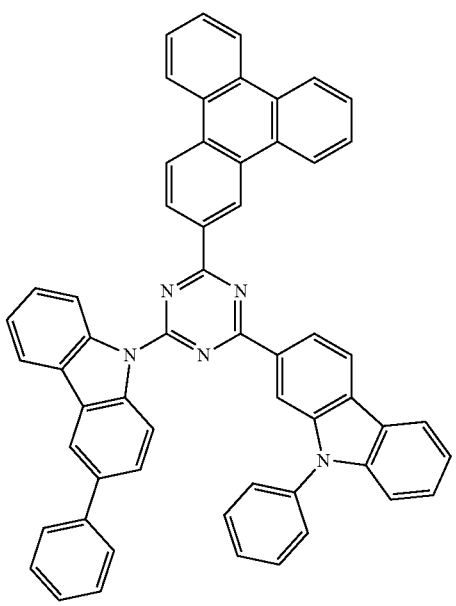

-continued
A-33
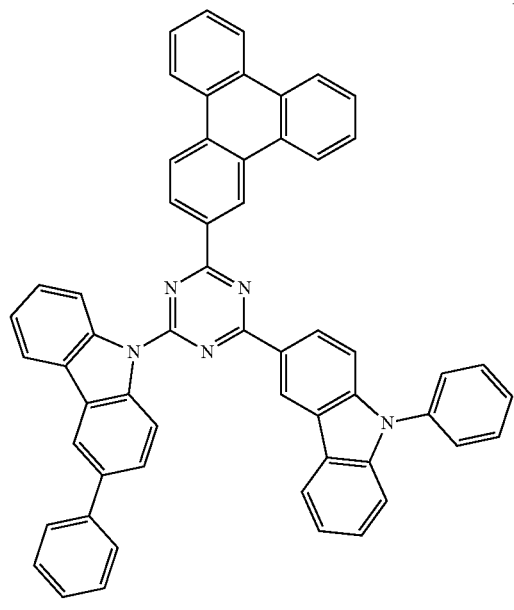
A-34
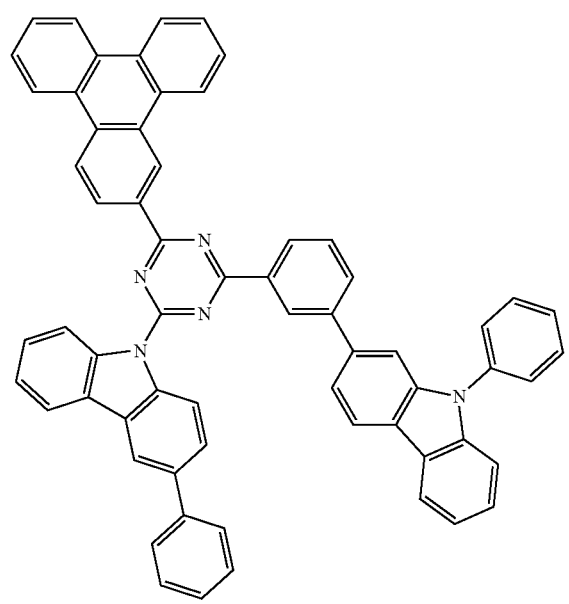
A-35
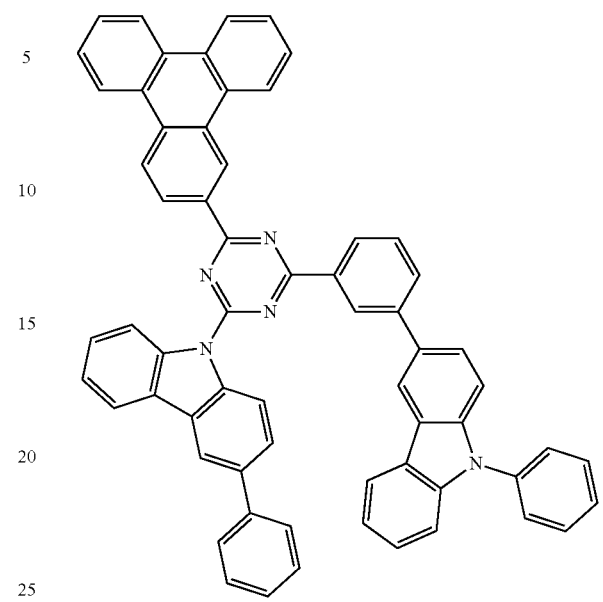
A-36
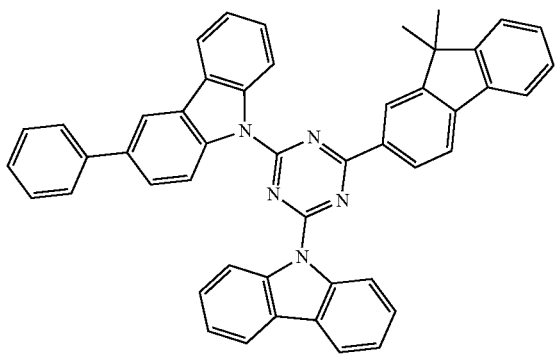
A-37
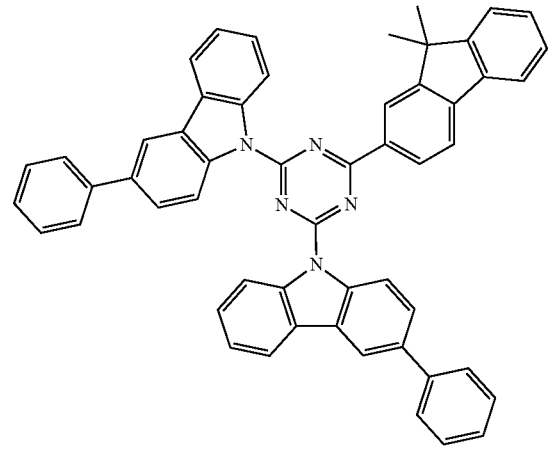

A-38
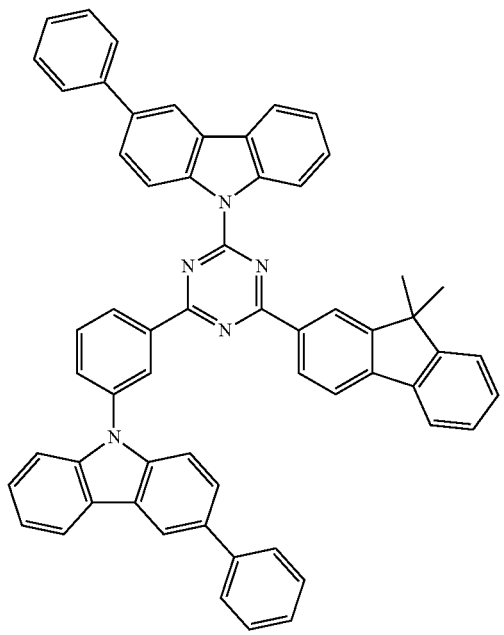
A-40
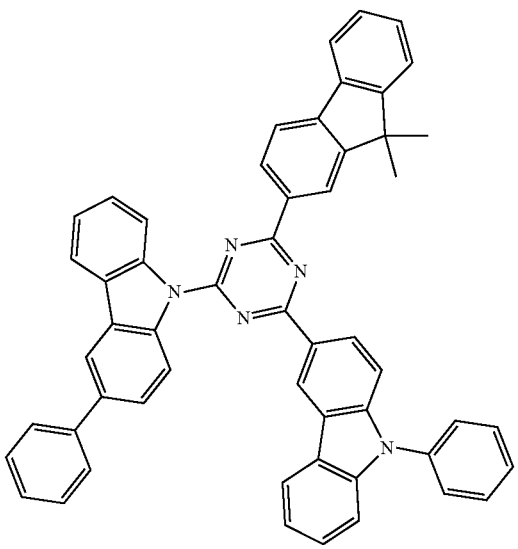
A-39
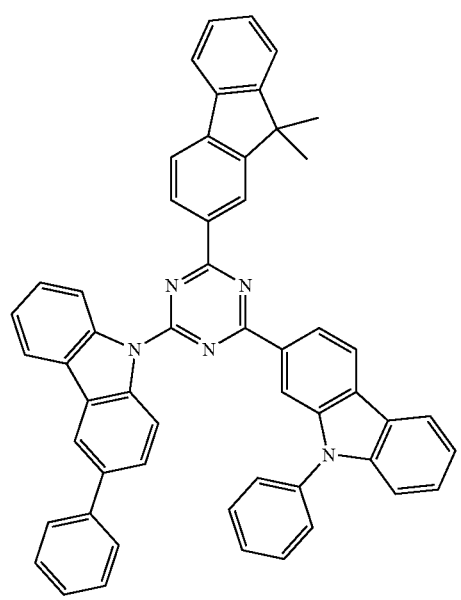
A-41
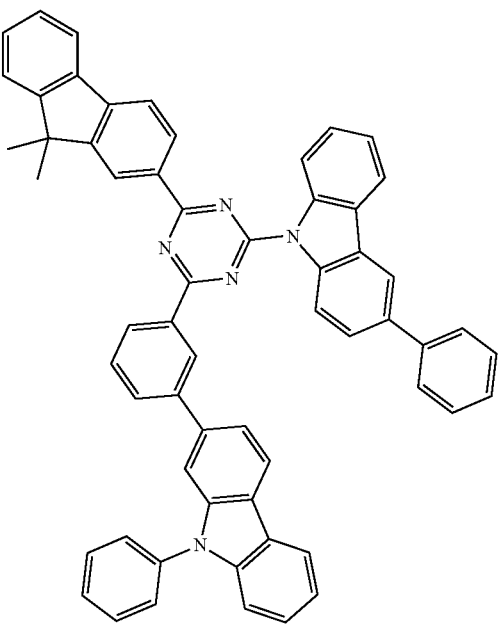

A-42
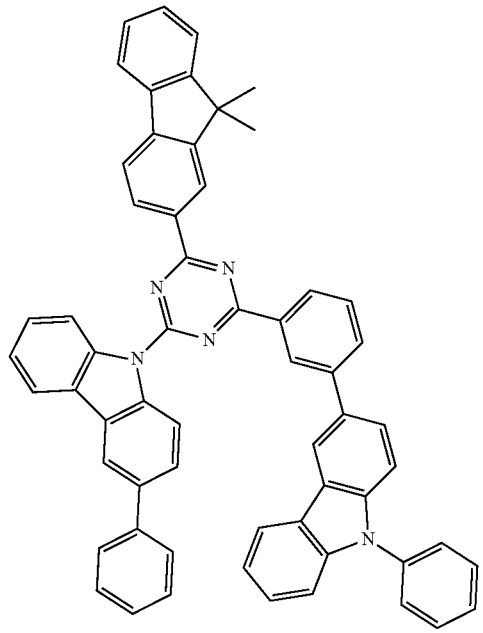
A-43
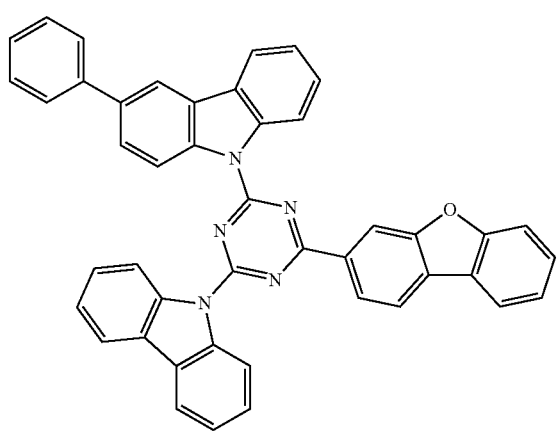
A-44
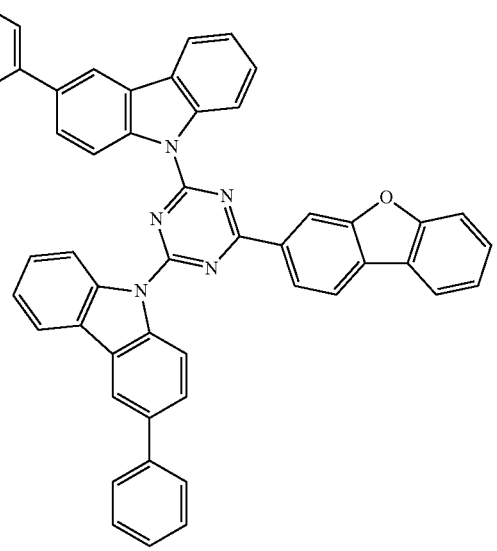
A-45
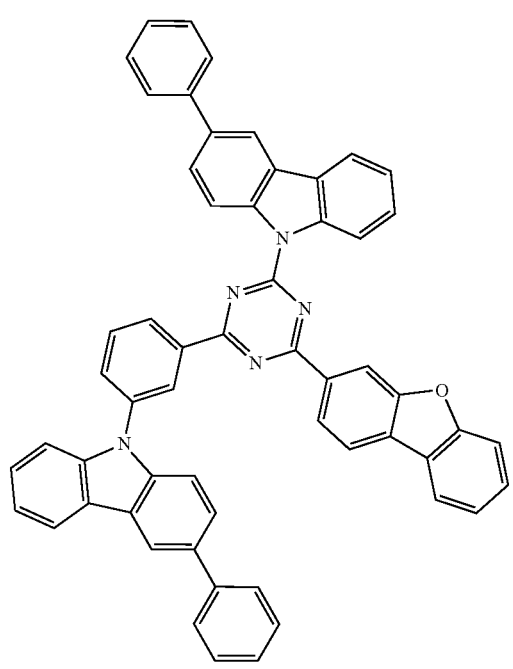

A-46
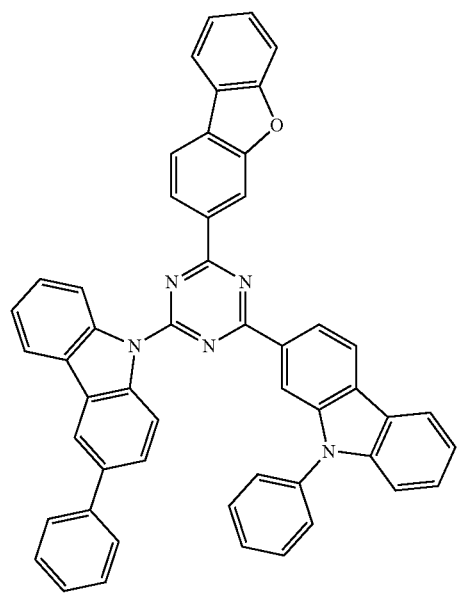
A-47
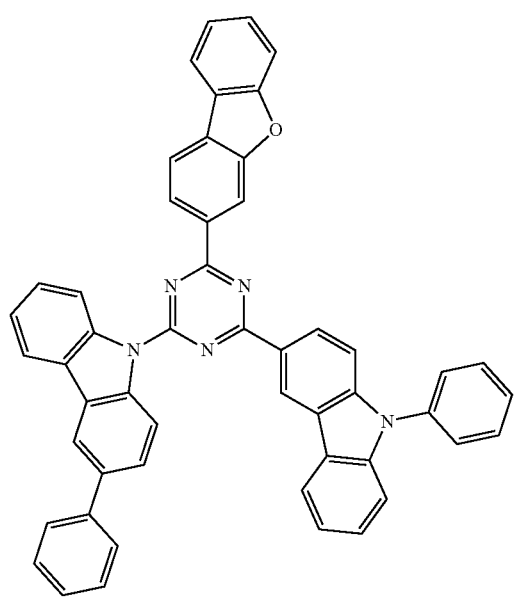
A-48
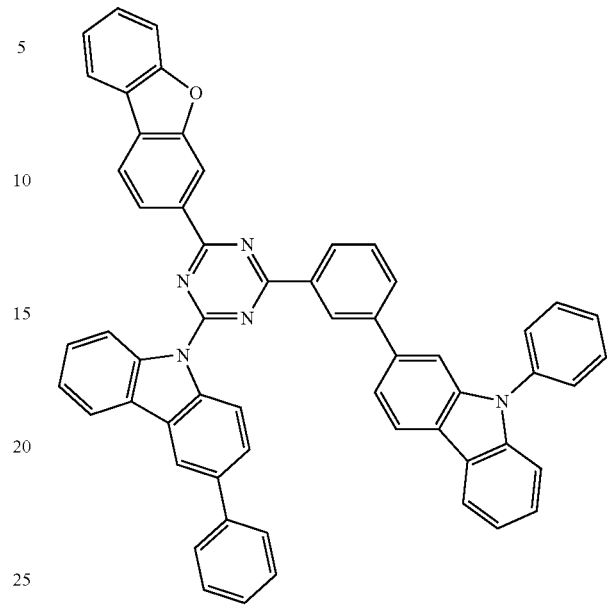
A-49
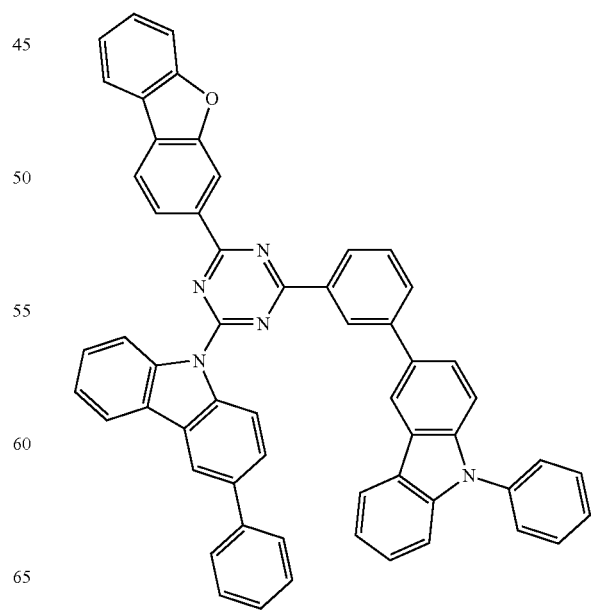

A-50
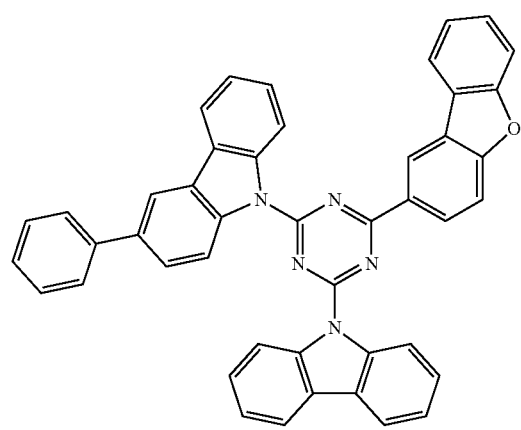
A-51
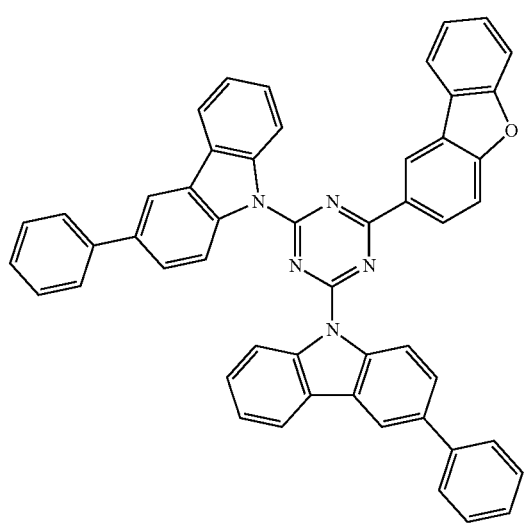
A-52
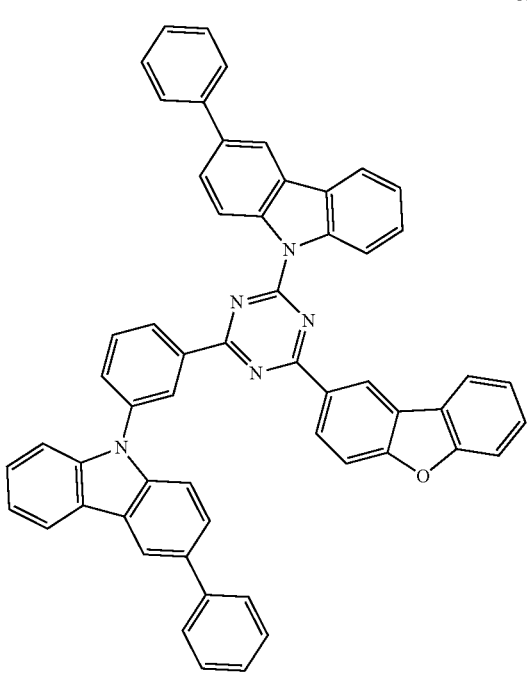
A-53
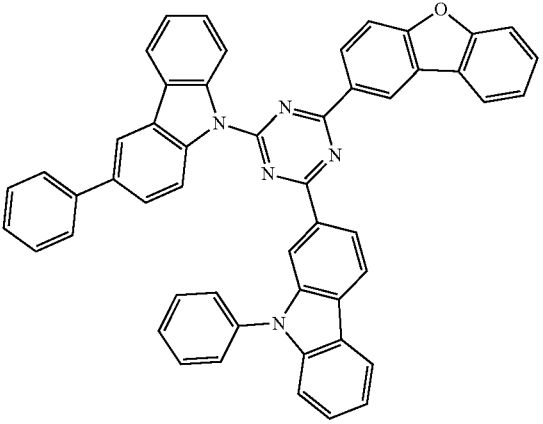
A-54
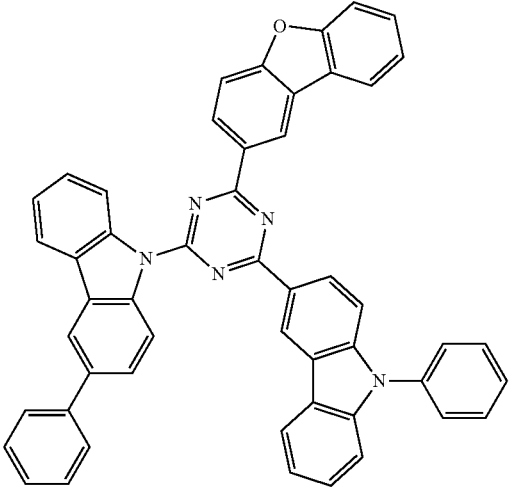
A-55
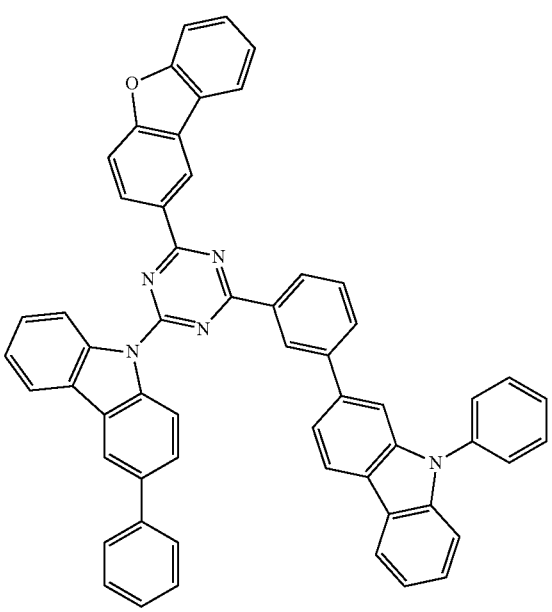

A-56
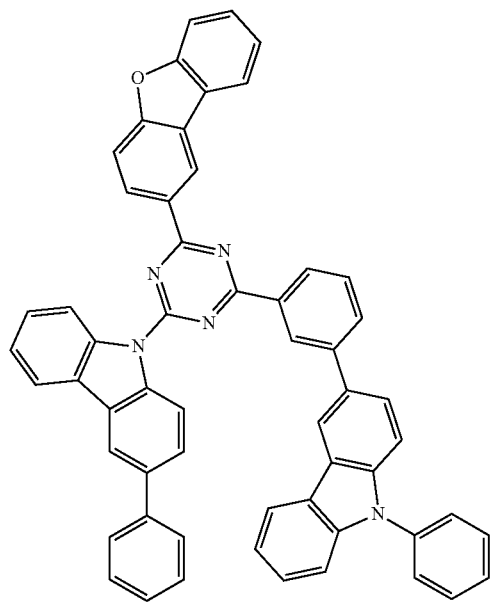
A-57
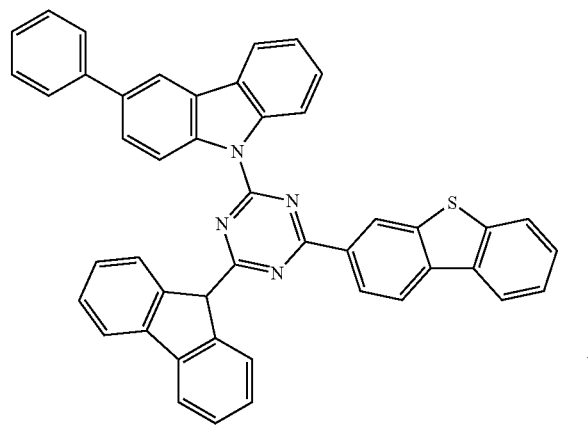
A-58
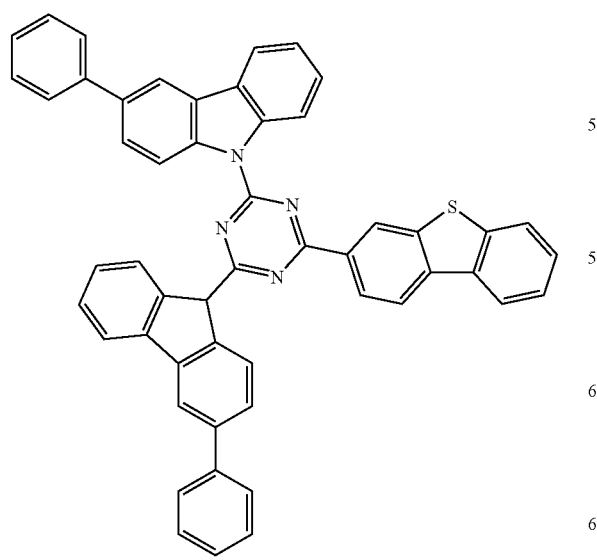
A-59
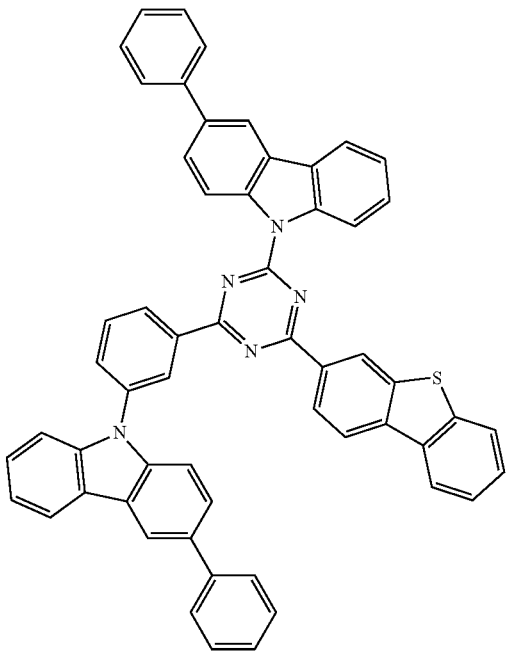
A-60
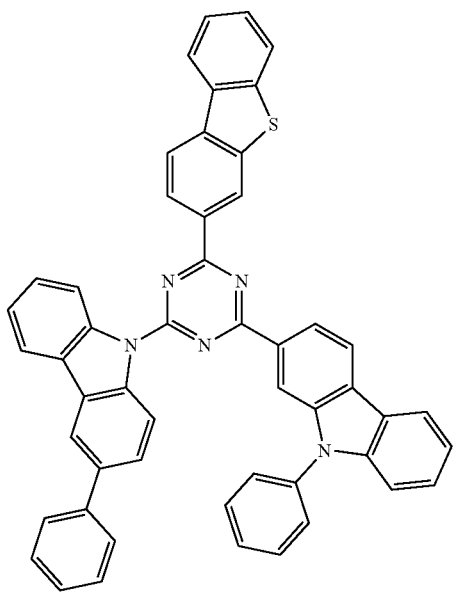

A-61
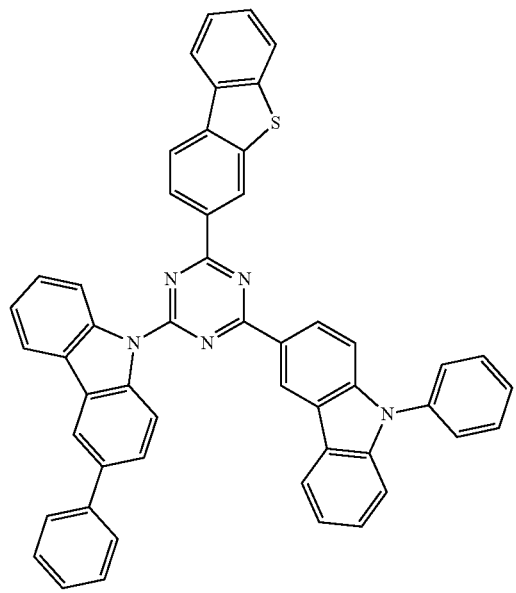
A-62
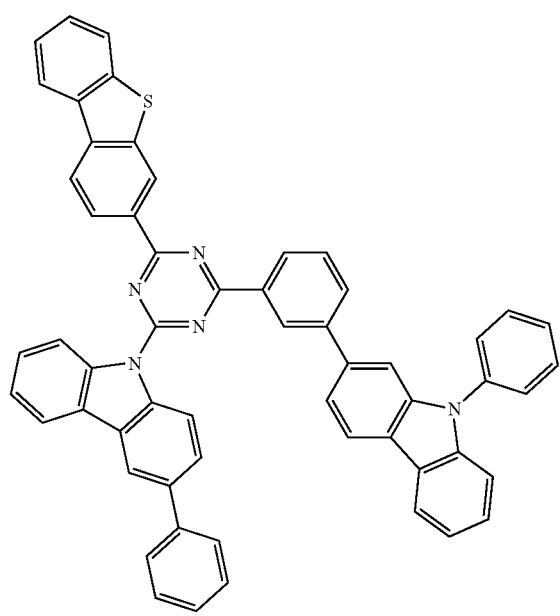
A-63
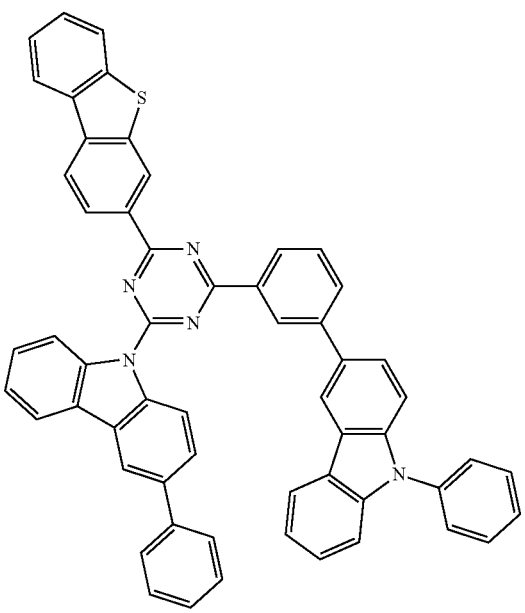
A-64
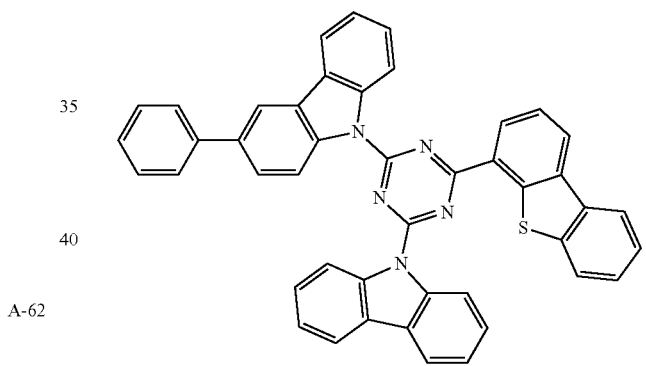
A-65
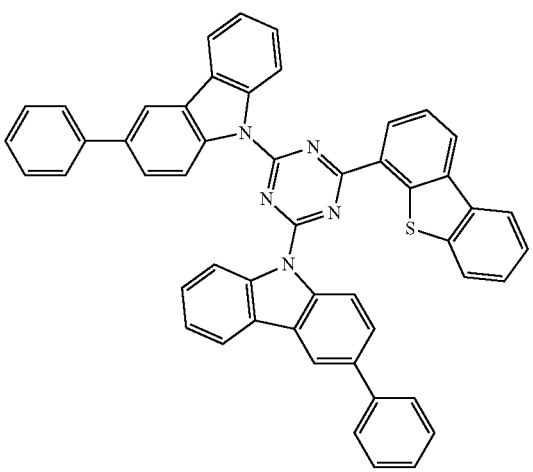

A-66
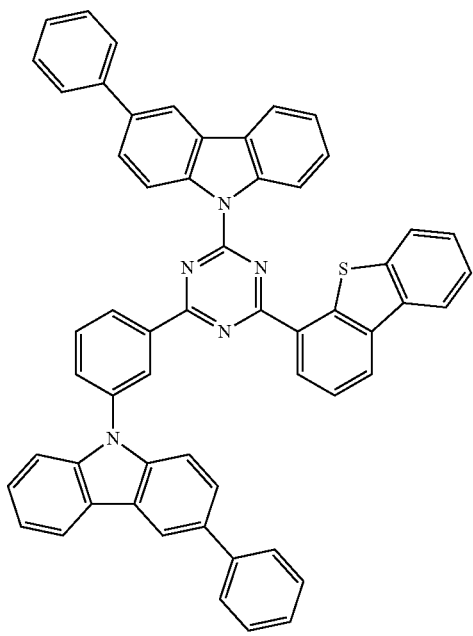
A-67
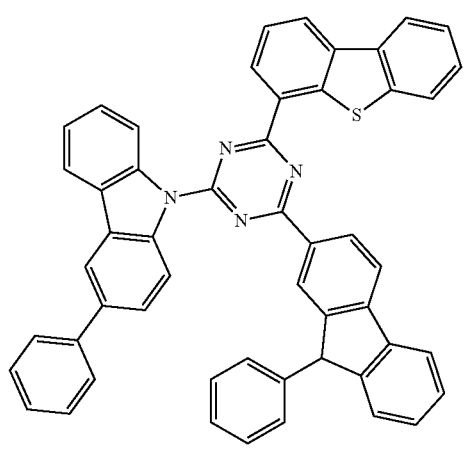
A-68
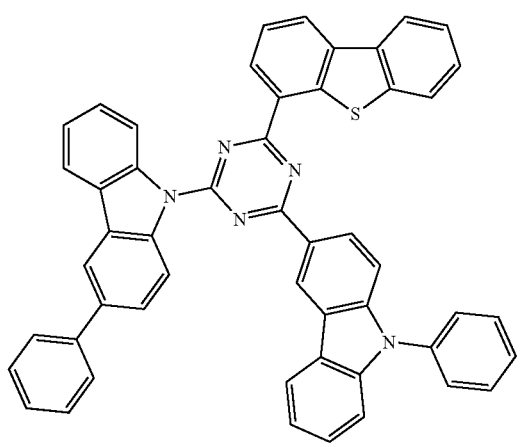
A-69
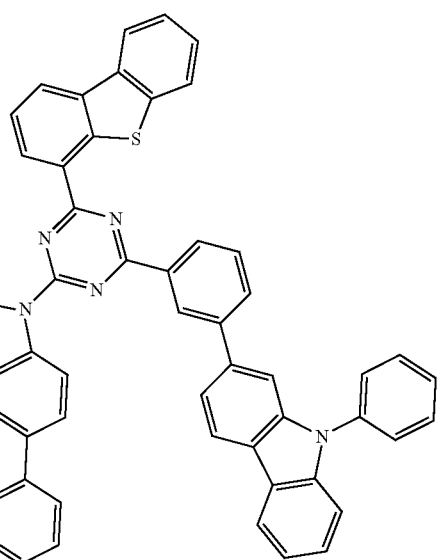
A-70
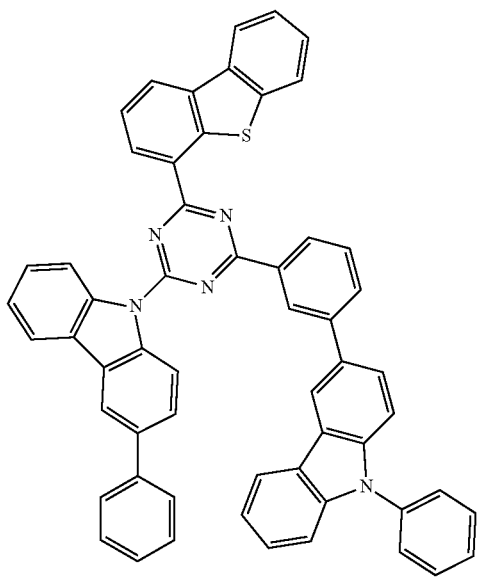
A-71
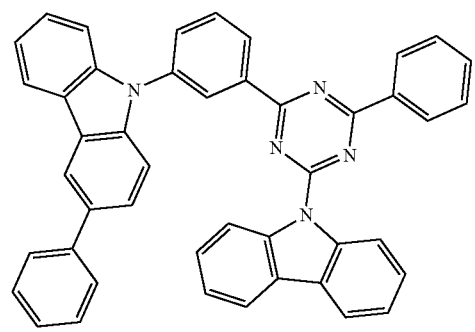

A-72
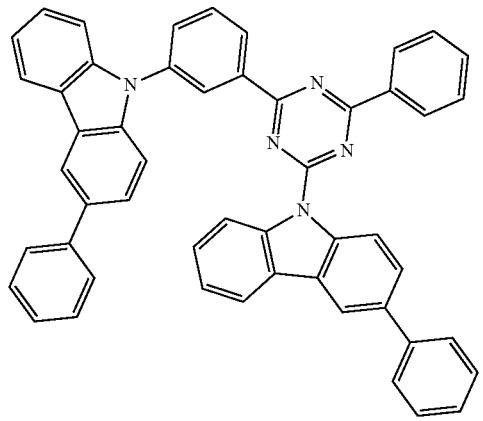
A-73
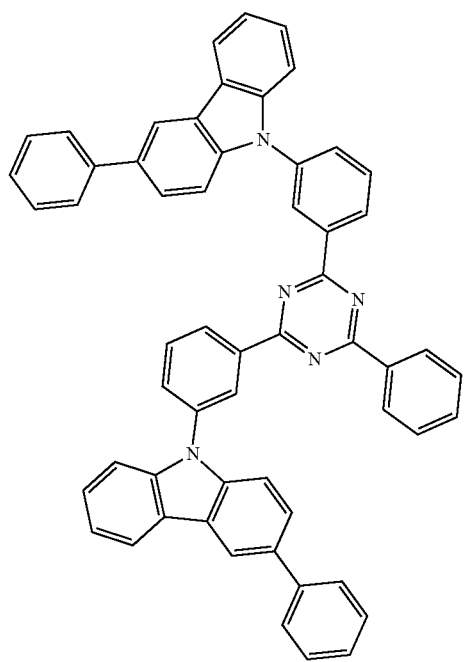
A-74
A-75
A-76
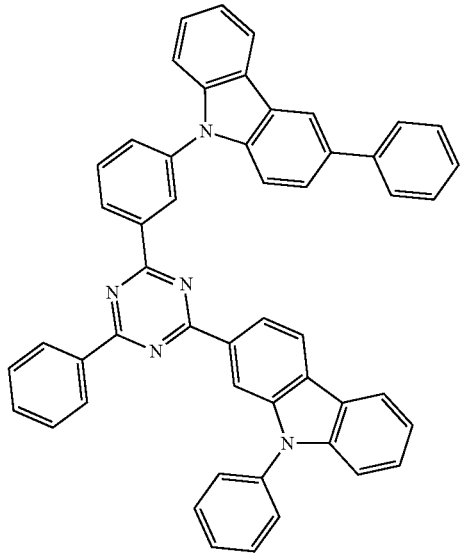

A-77
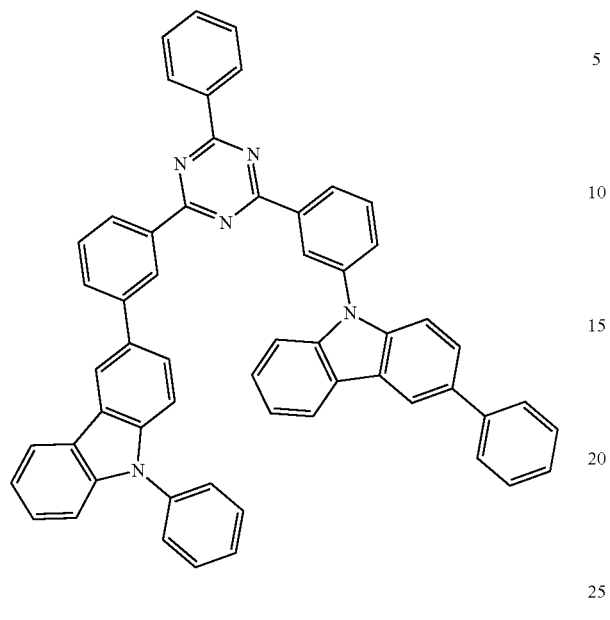
A-78
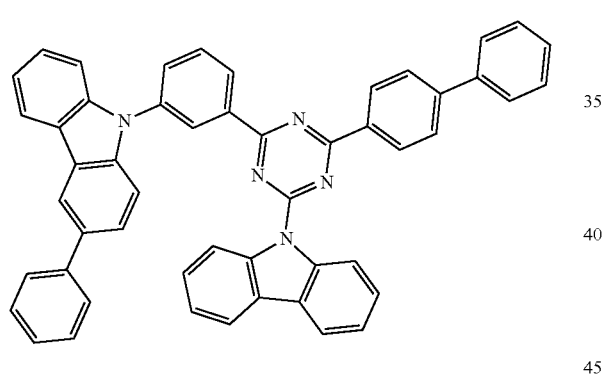
A-79
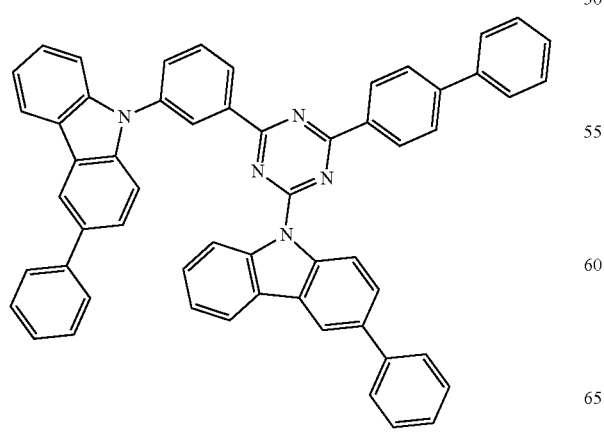
A-80
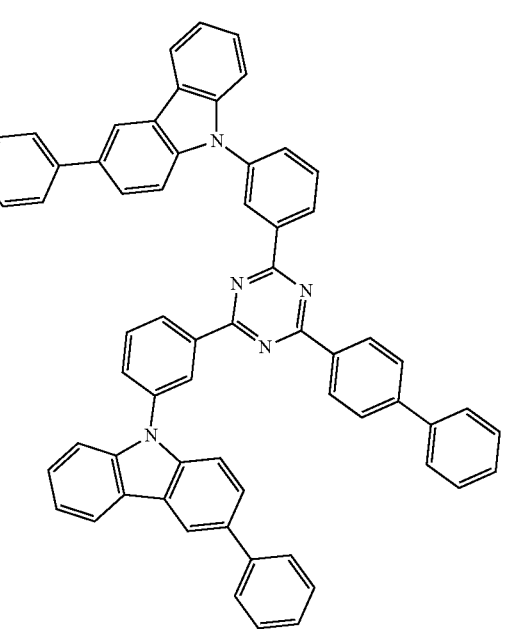
A-81
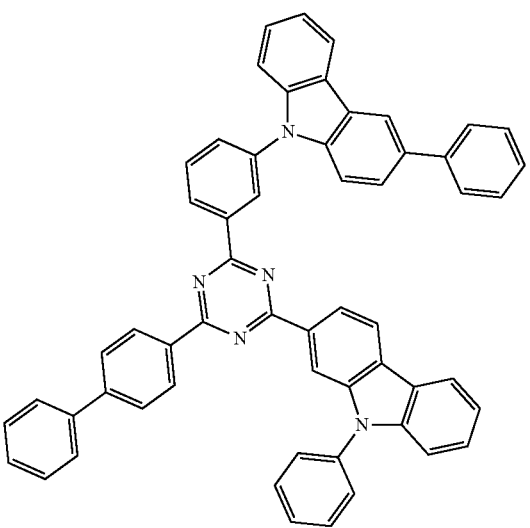

A-82
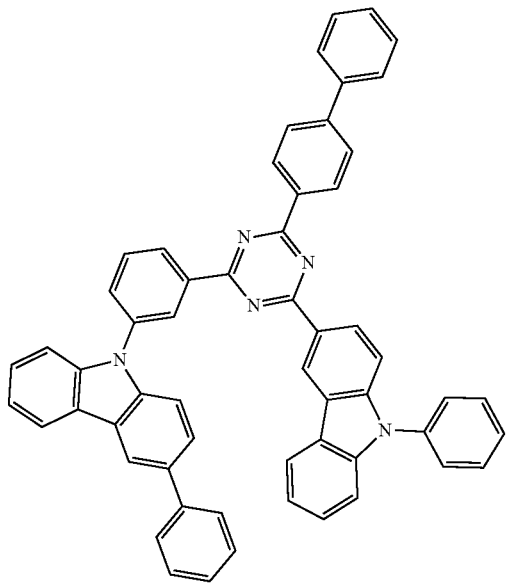
A-83
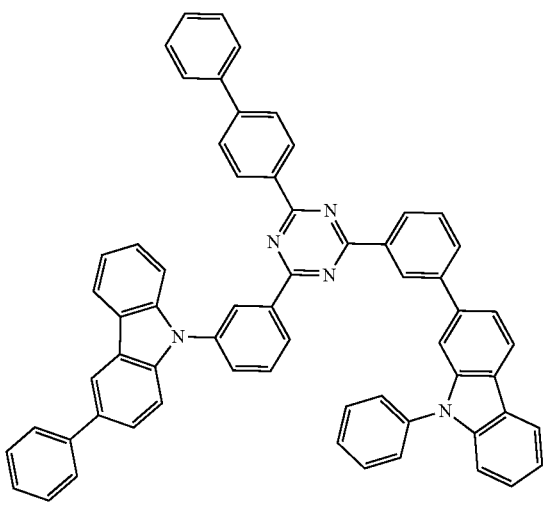
A-84
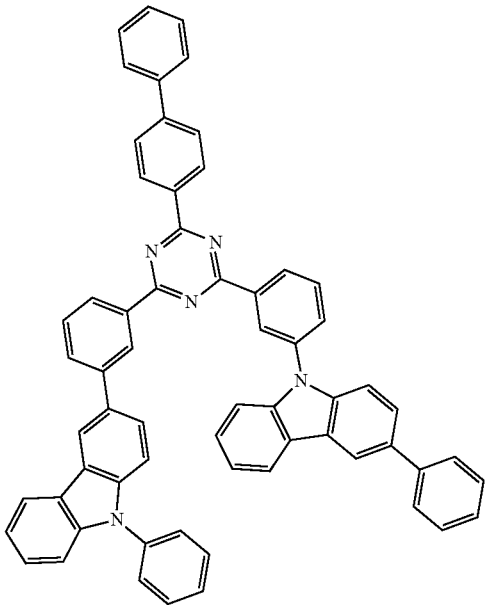
A-85
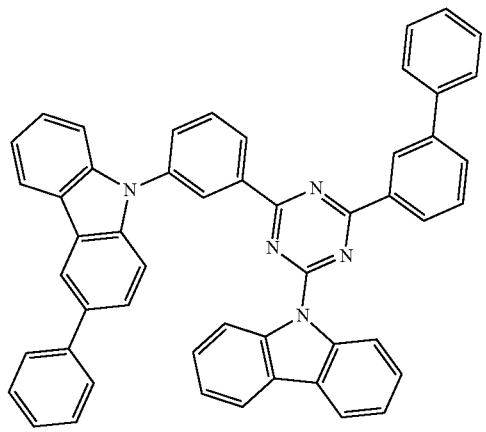
A-86
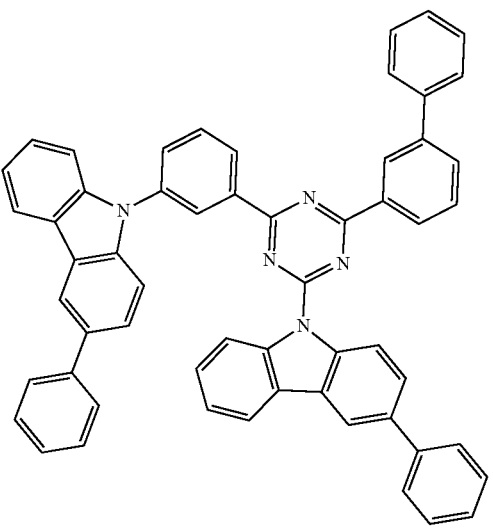

A-87
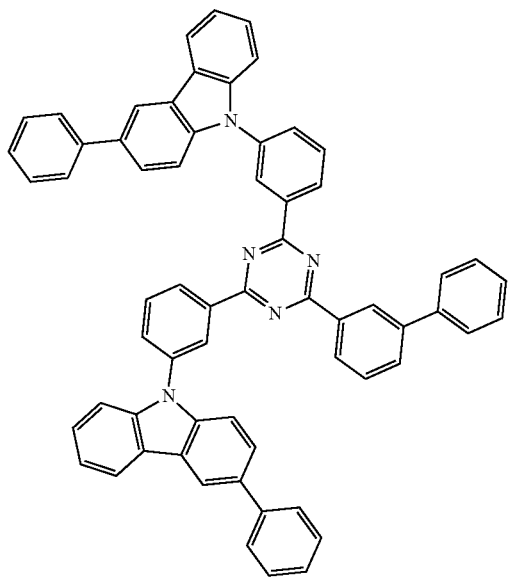
A-88
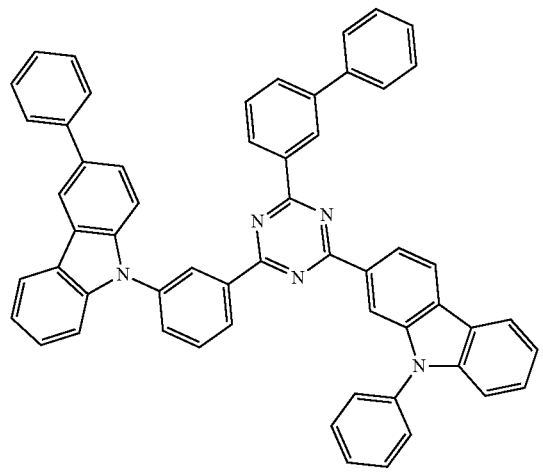
A-89
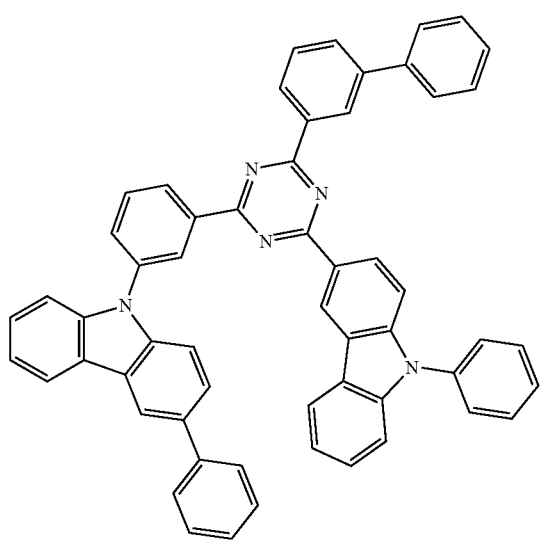
A-90
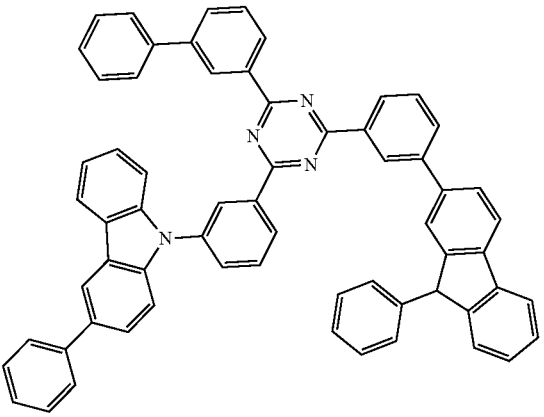
A-91
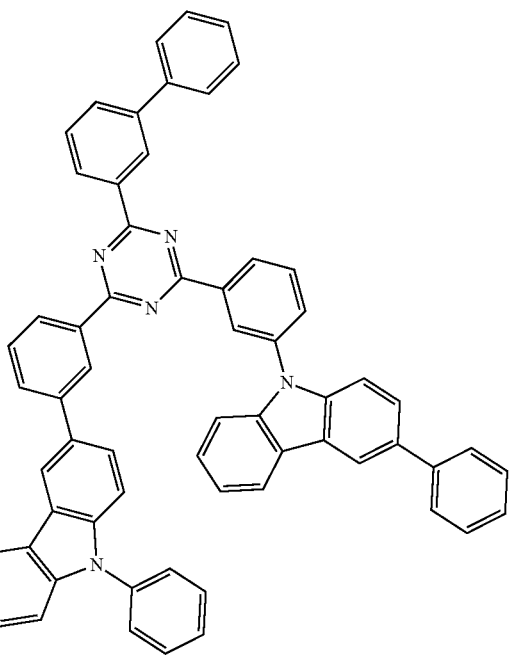
A-92
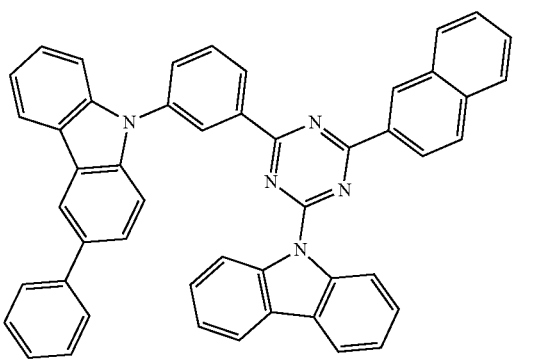

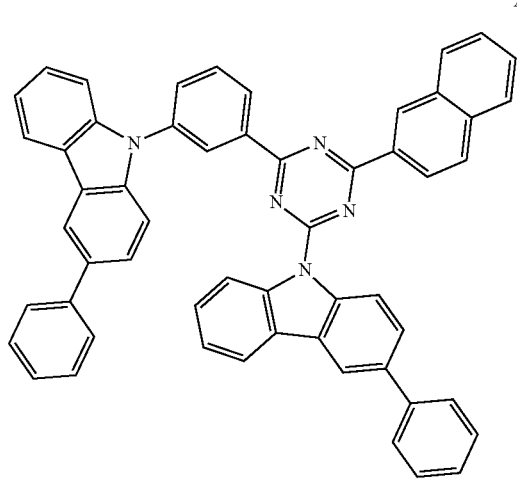
A-93
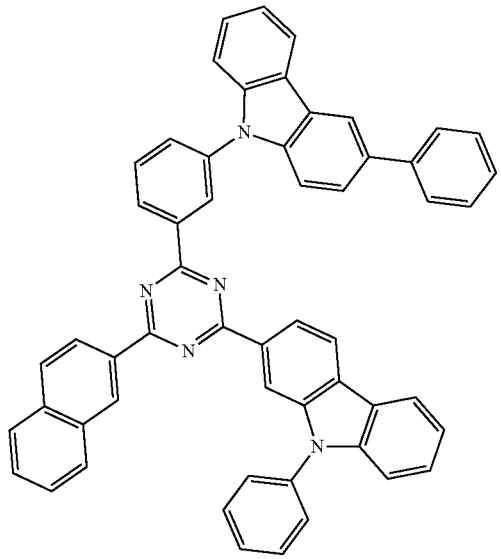
A-95
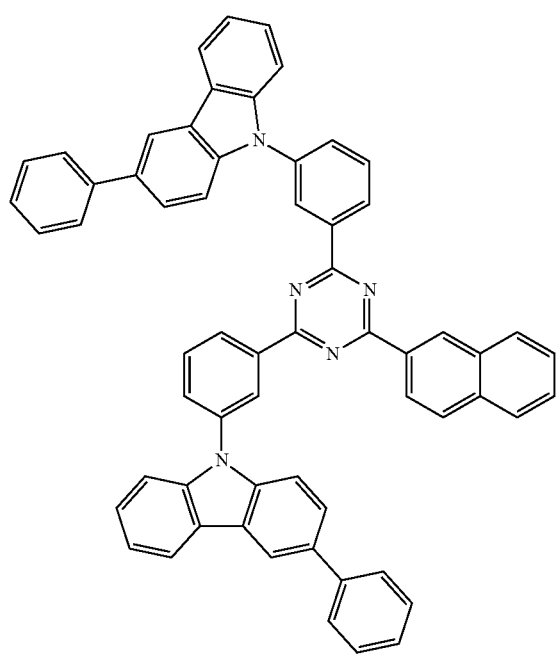
A-94
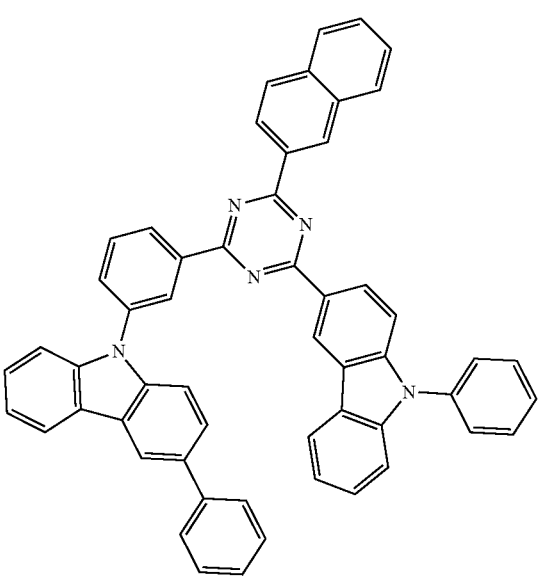
A-96

A-97
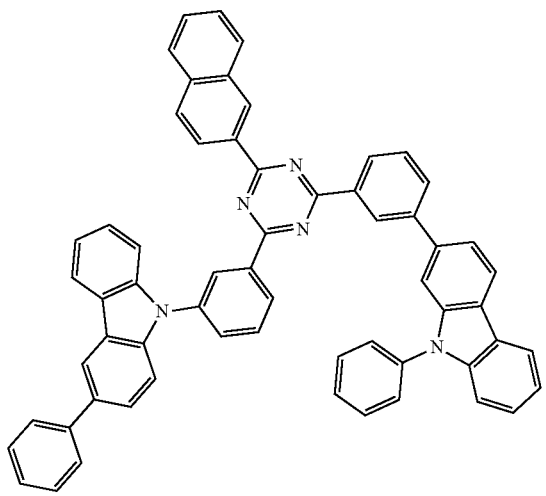
A-98
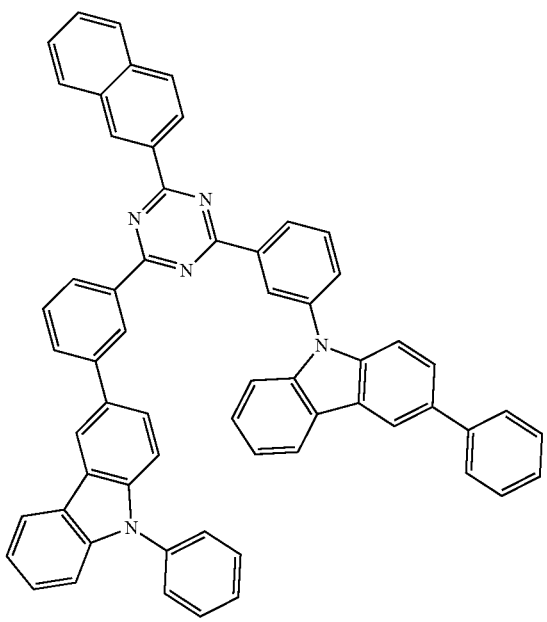
A-99
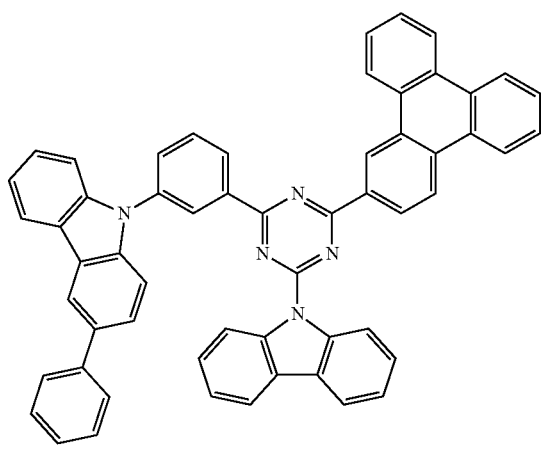
A-100
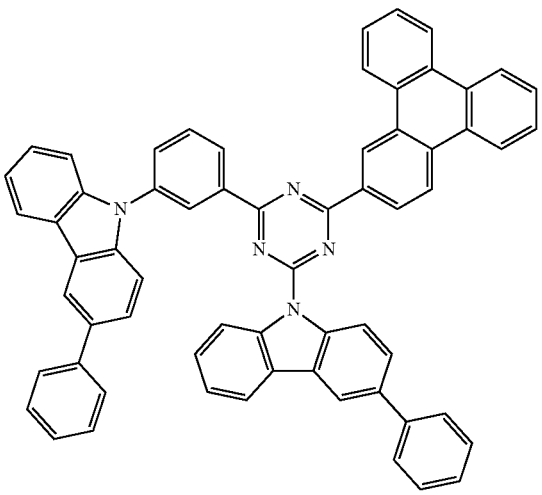
A-101
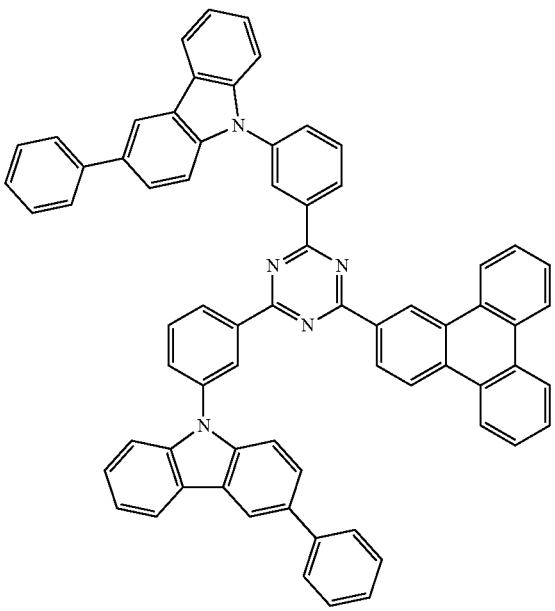

A-102
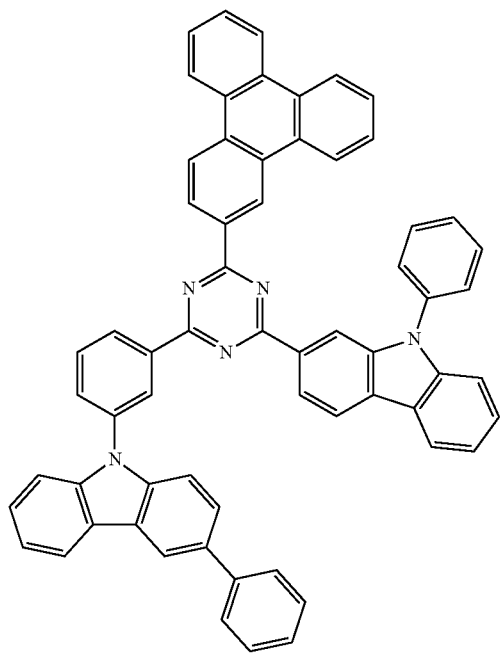
A-103
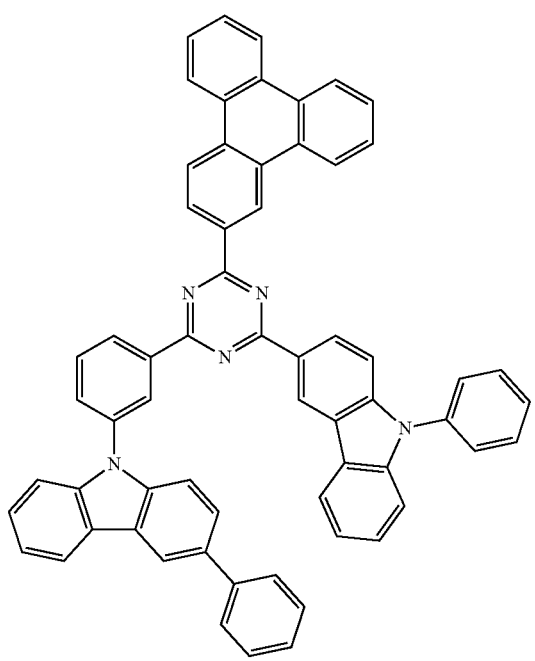
A-104
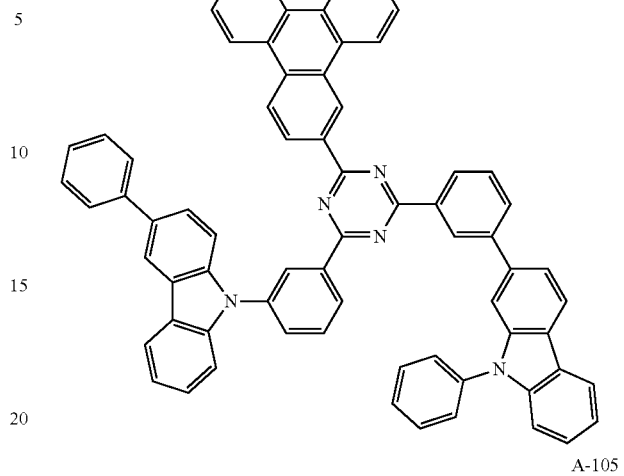
A-105
A-106
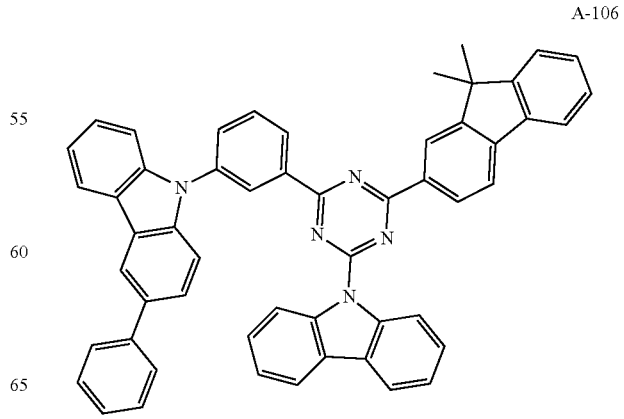

A-107
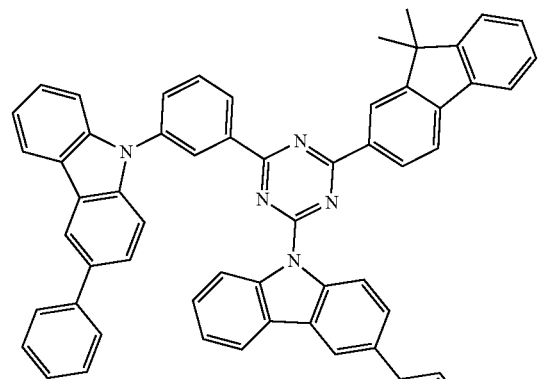
A-108
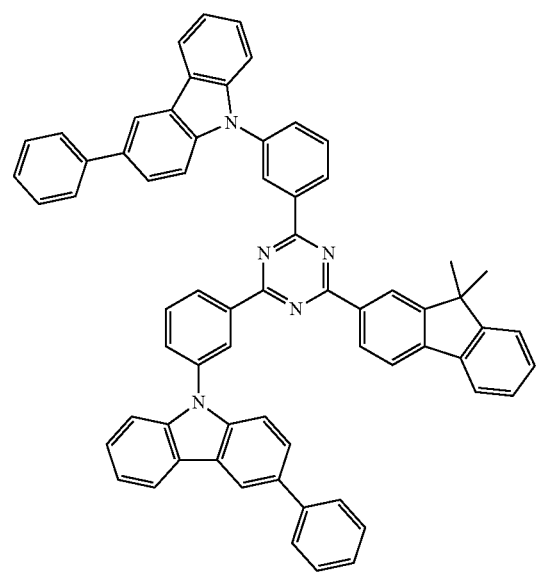
A-109
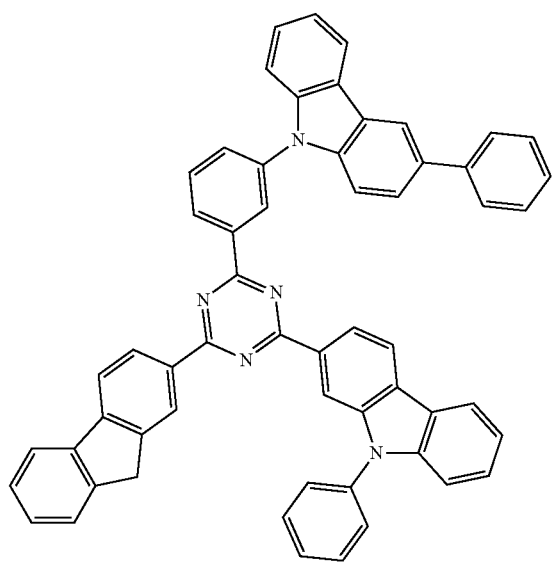
A-110
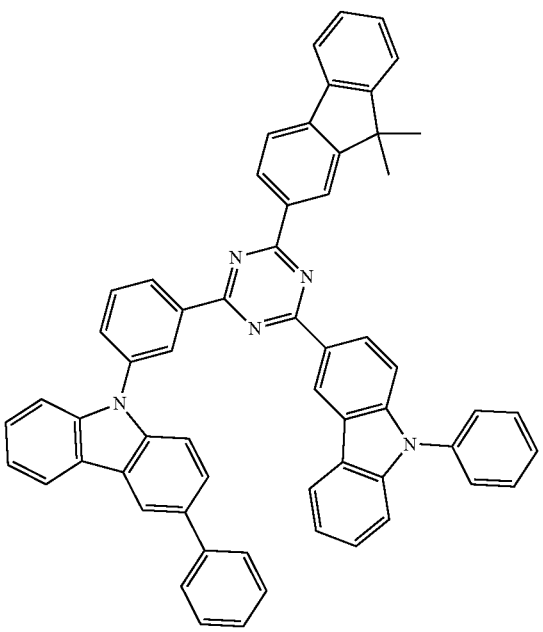
A-111
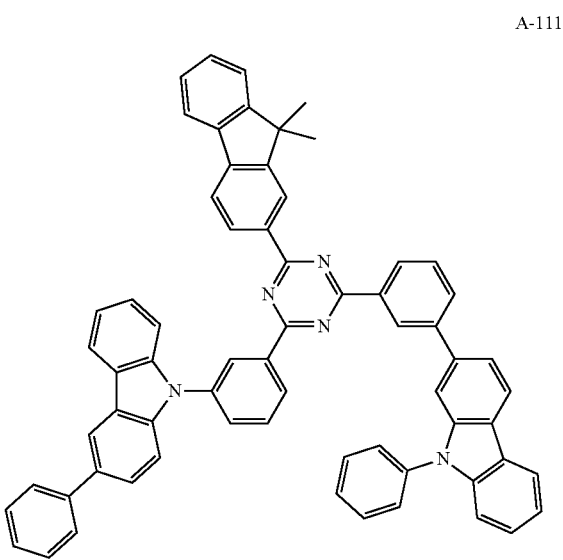

A-112
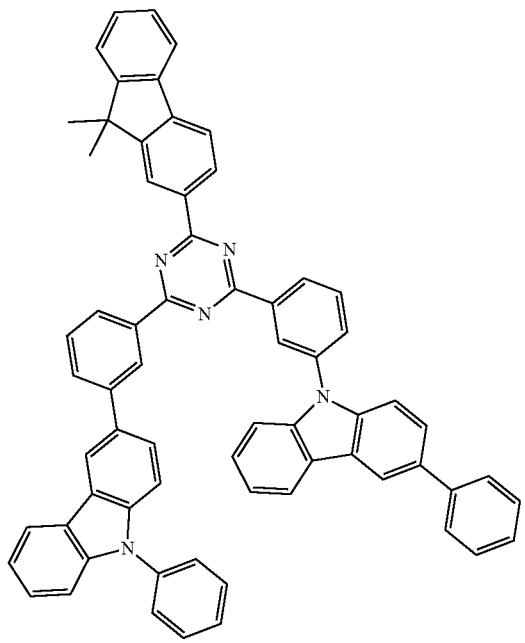
A-113
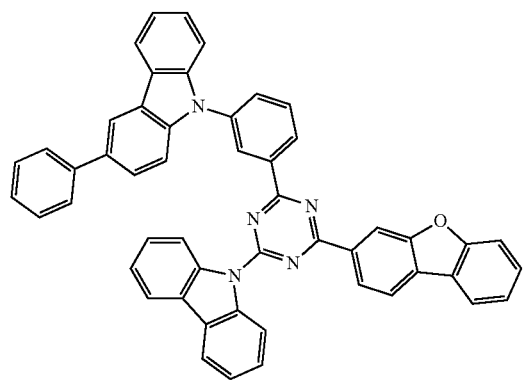
A-114
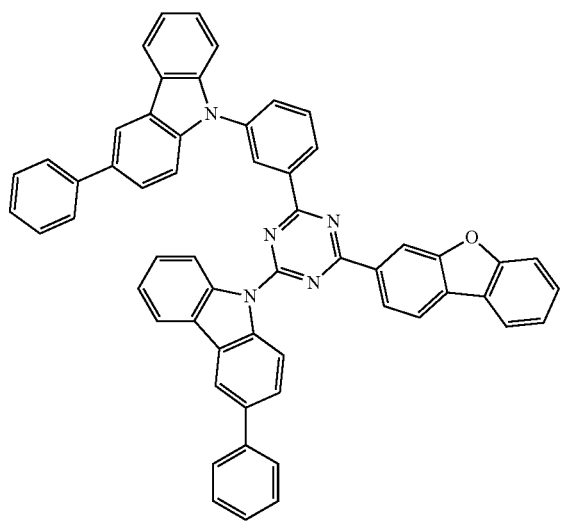
A-115
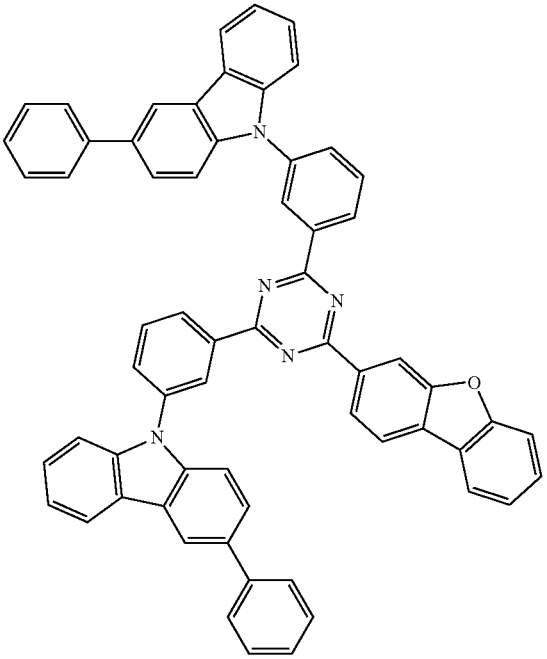
A-116
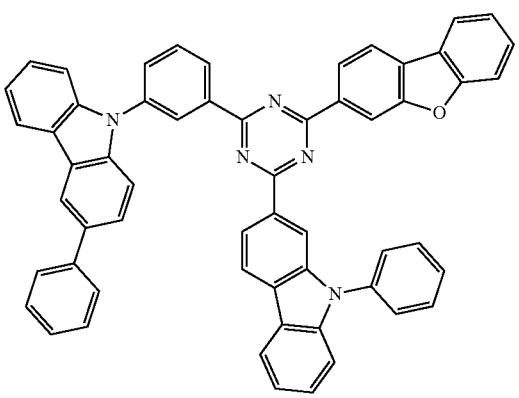

A-117
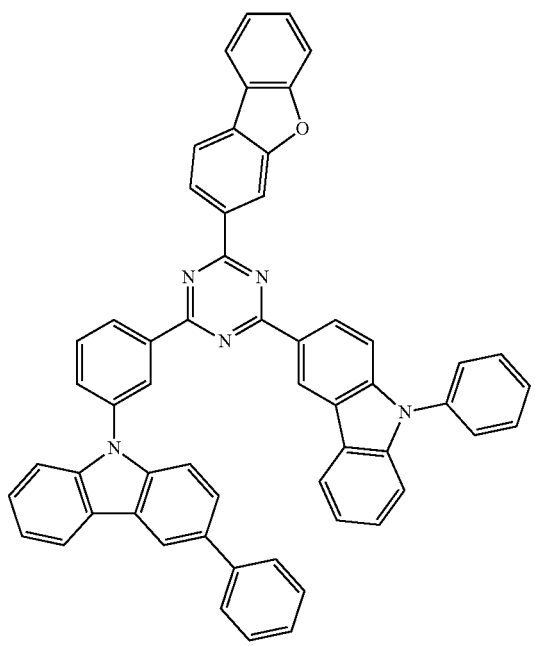
A-118
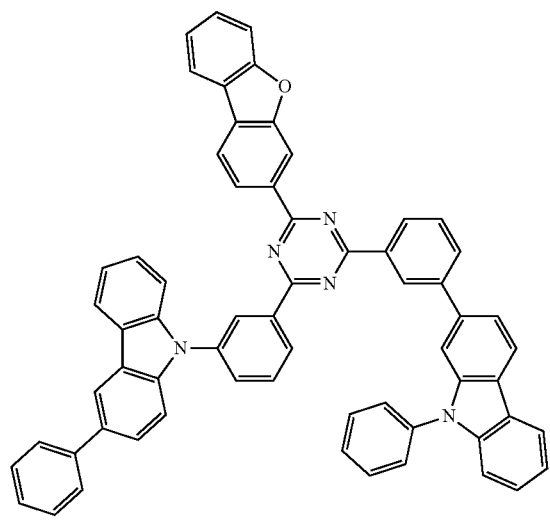
A-119
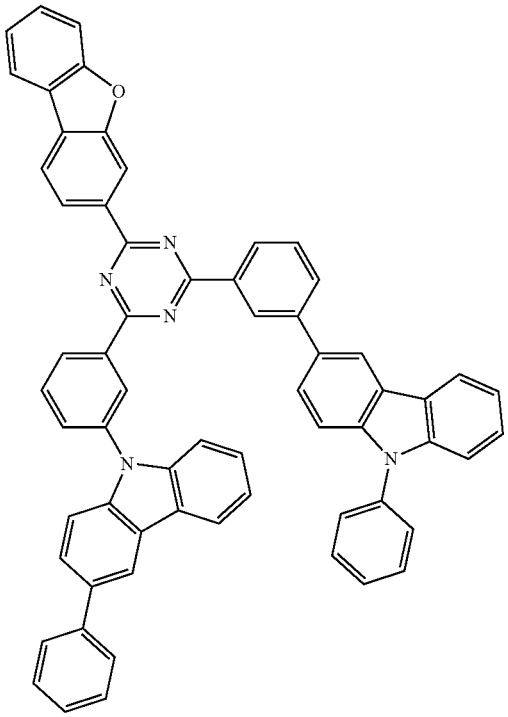
A-120
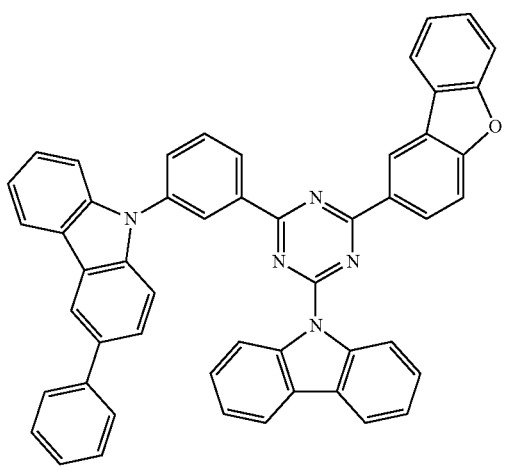

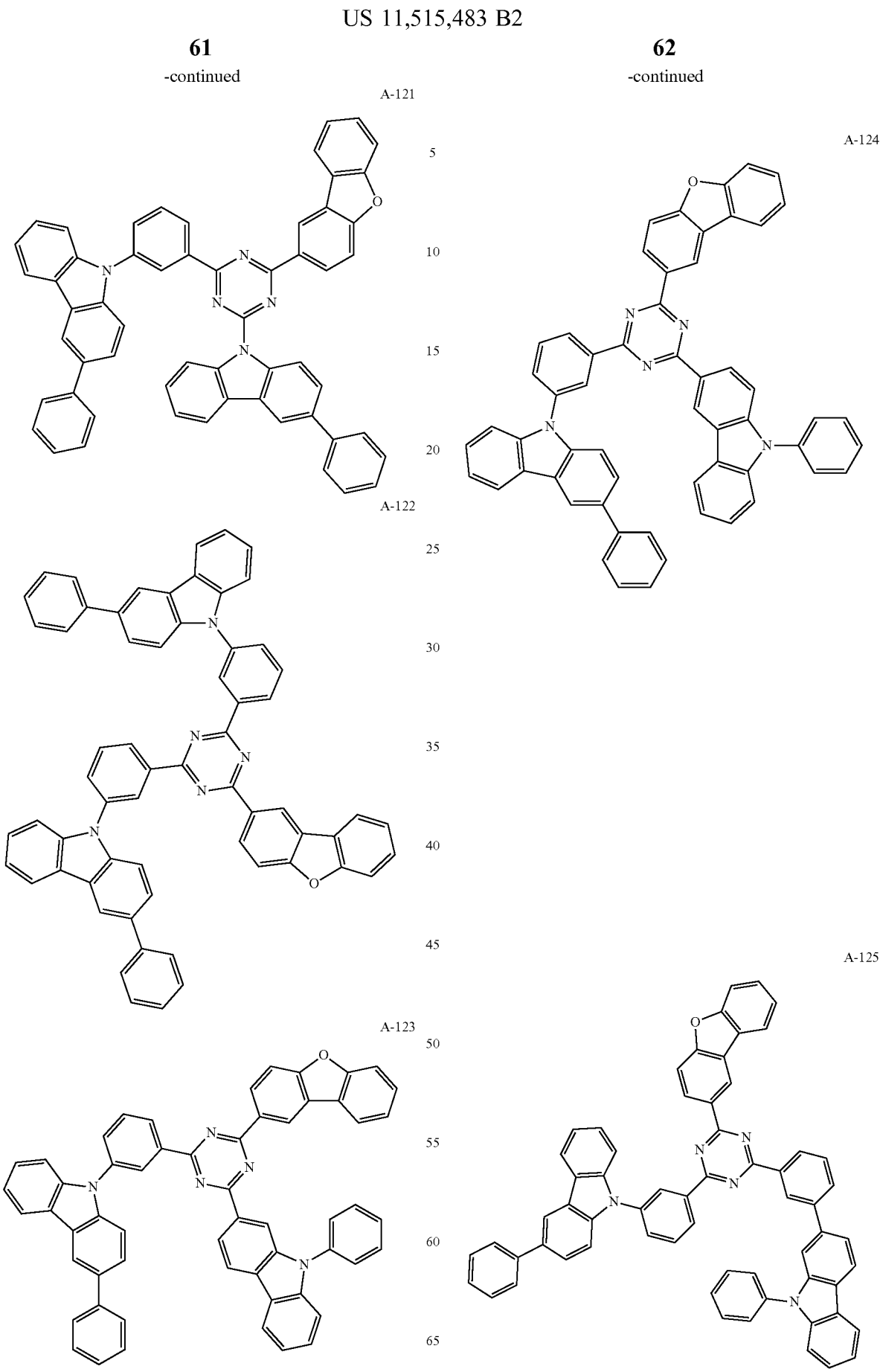

A-126
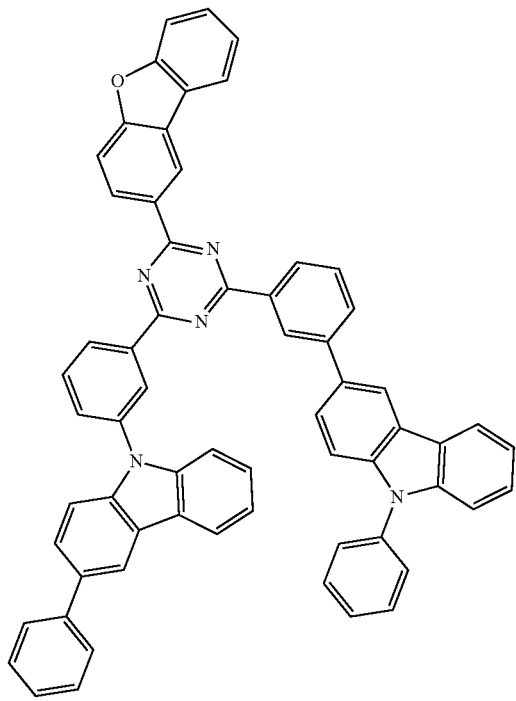
A-127
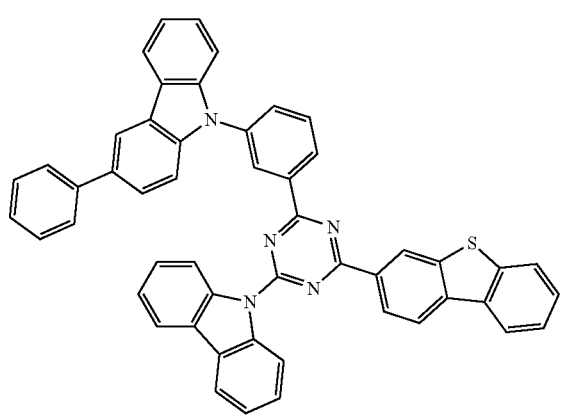
A-128
A-129
A-130
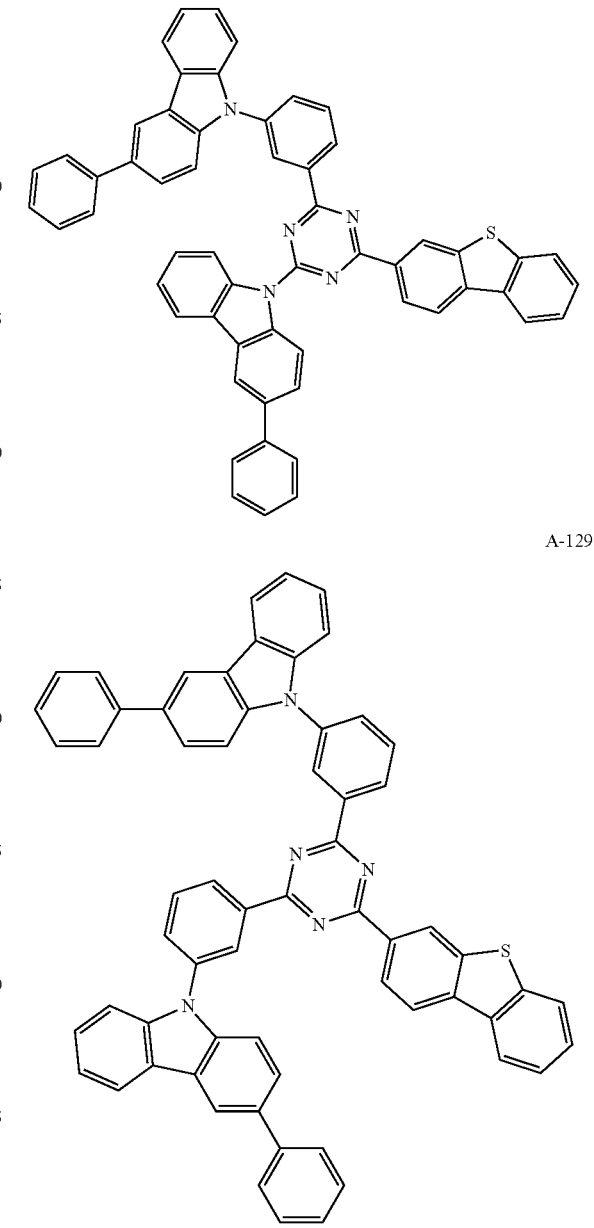

A-131
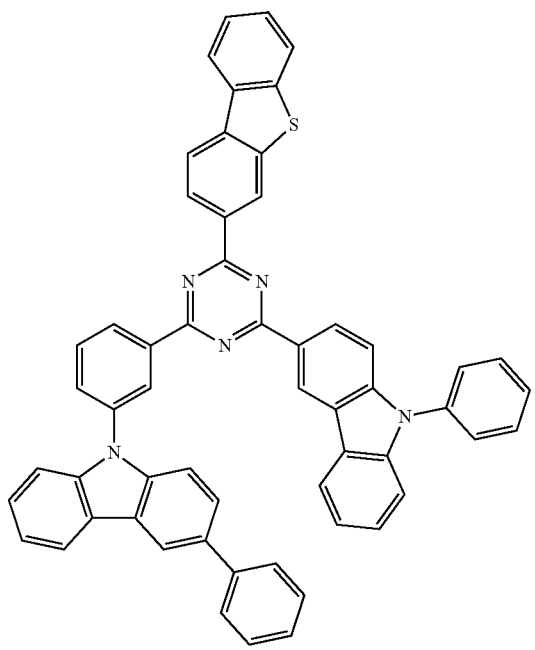
A-132
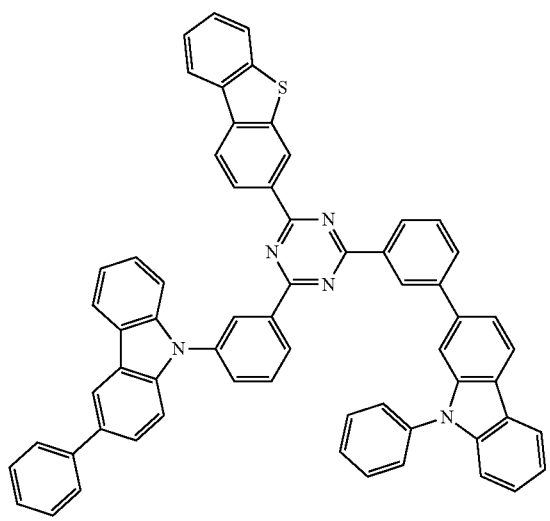
A-133
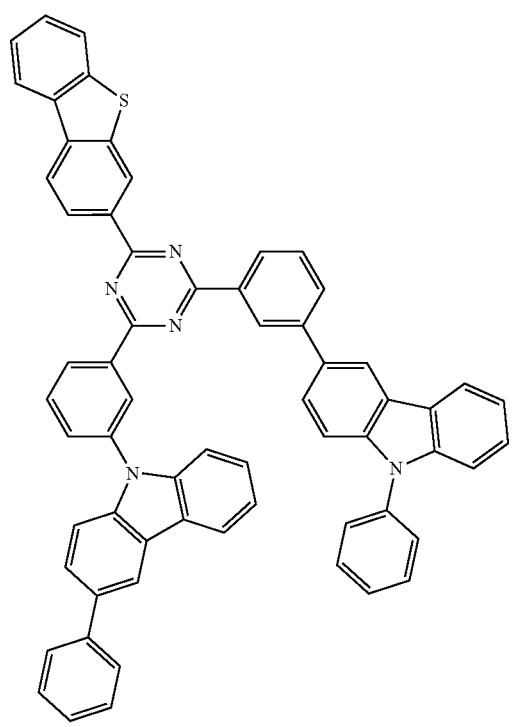
A-134
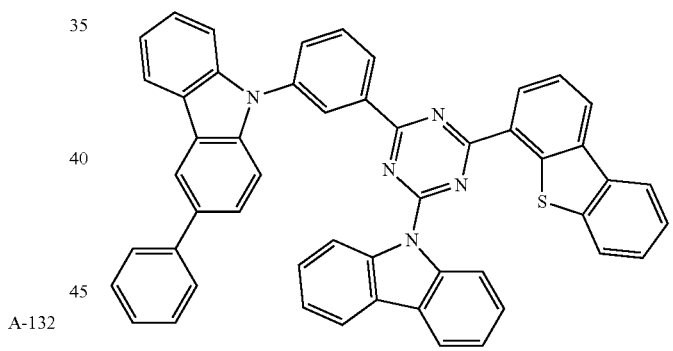
A-135
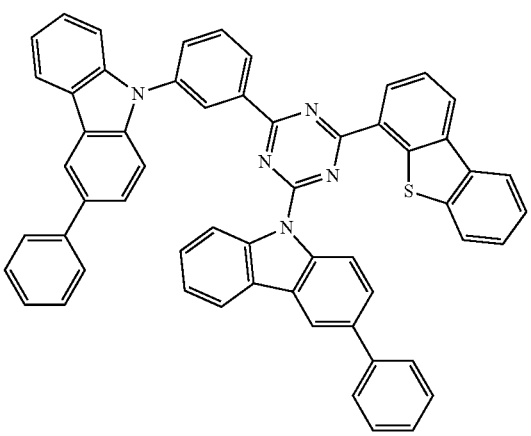

A-136
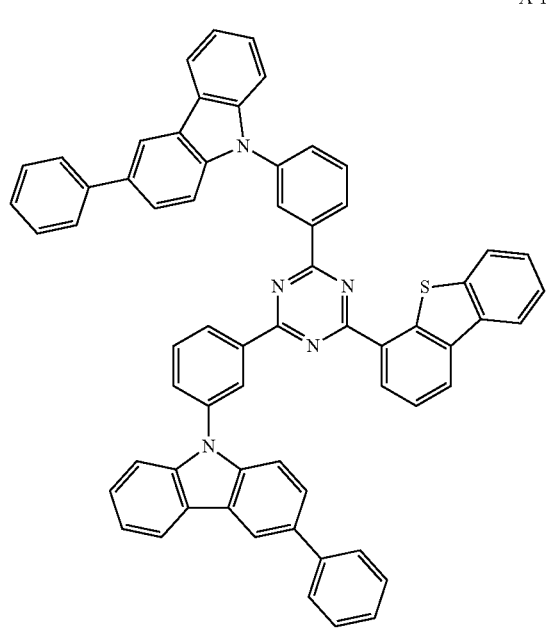
A-137
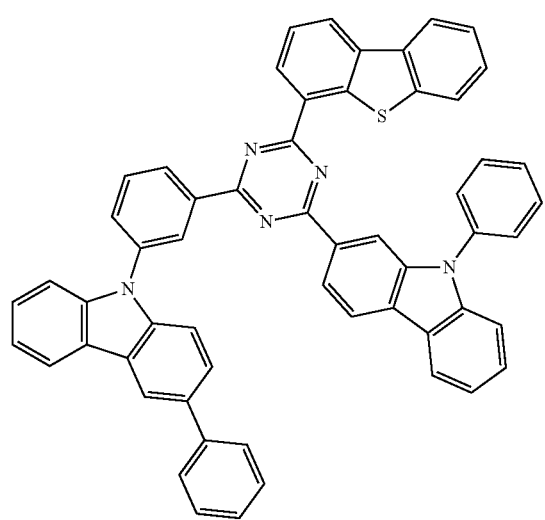
A-138
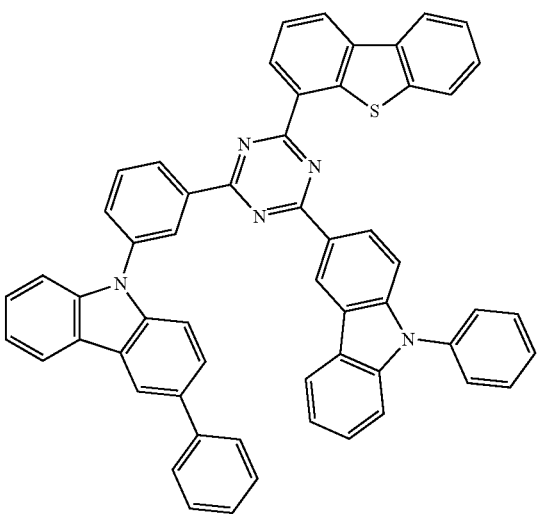
A-139
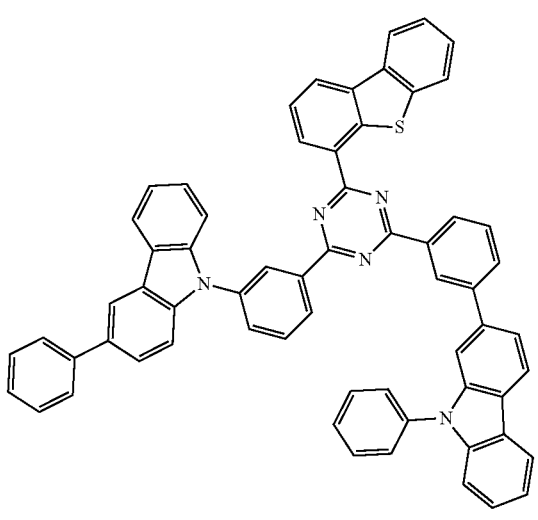

-continued

A-140

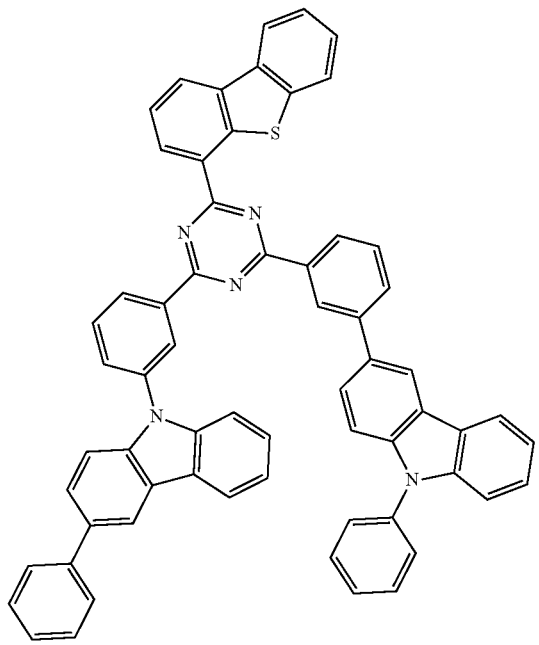

As used herein, "alkyl" refers to a monovalent substituent derived from a saturated, linear or branched hydrocarbon having 1 to 40 carbon atoms. Examples of such alkyl may include, but are not limited to, methyl, ethyl, propyl, isobutyl, sec-butyl, pentyl, iso-amyl, hexyl or the like.

As used herein, "alkenyl" refers to a monovalent substituent derived from an unsaturated, linear or branched hydrocarbon having 2 to 40 carbon atoms, having at least one carbon-carbon double bond. Examples of such alkenyl may include, but are not limited to, vinyl, allyl, isopropenyl, 2-butenyl or the like.

As used herein, "alkynyl" refers to a monovalent substituent derived from an unsaturated, linear or branched hydrocarbon having 2 to 40 carbon atoms, having at least one carbon-carbon triple bond. Examples of such alkynyl may include, but are not limited to, ethynyl, 2-propynyl or the like.

As used herein, "cycloalkyl" refers to a monovalent substituent derived from a monocyclic or polycyclic non-aromatic hydrocarbon having 3 to 40 carbon atoms. Examples of such cycloalkyl may include, but are not limited to, cyclopropyl, cyclopentyl, cyclohexyl, norbornyl, adamantine or the like.

As used herein, "heterocycloalkyl" refers to a monovalent substituent derived from a non-aromatic hydrocarbon having 3 to 40 nuclear atoms, where one or more carbons in the ring, preferably one to three carbons, are substituted with a heteroatom such as N, O, S or Se. Examples of such heterocycloalkyl may include, but are not limited to, morpholine, piperazine or the like.

As used herein, "aryl" refers to a monovalent substituent derived from a $C_6$ to $C_{60}$ aromatic hydrocarbon which is in a structure with a single ring or two or more rings combined with each other. In addition, a form in which two or more rings are pendant (e.g., simply attached) to or condensed with each other may also be included. Examples of such aryl may include, but are not limited to, phenyl, naphthyl, phenanthryl, anthryl or the like.

As used herein, "heteroaryl" refers to a monovalent substituent derived from a monoheterocyclic or polyheterocyclic aromatic hydrocarbon having 5 to 60 nuclear atoms. In such a case, one or more carbons in the ring, preferably one to three carbons, are substituted with a heteroatom such as N, O, S or Se. In addition, a form in which two or more rings are pendant to or condensed with each other may be included, and a form condensed with an aryl group may be included. Examples of such heteroaryl may include, but are not limited to, a 6-membered monocyclic ring such as pyridyl, pyrazinyl, pyrimidinyl, pyridazinyl and triazinyl; a polycyclic ring such as phenoxathienyl, indolizinyl, indolyl, purinyl, quinolyl, benzothiazole and carbazolyl; 2-furanyl; N-imidazolyl; 2-isoxazolyl; 2-pyridinyl; 2-pyrimidinyl or the like.

As used herein, "alkyloxy" refers to a monovalent substituent represented by R'O—, where R' is alkyl having 1 to 40 carbon atoms. Such alkyloxy may include a linear, branched or cyclic structure. Examples of such alkyloxy may include, but are not limited to, methoxy, ethoxy, n-propoxy, 1-propoxy, t-butoxy, n-butoxy, pentoxy or the like.

As used herein, "aryloxy" refers to a monovalent substituent represented by RO—, where R is aryl having 6 to 60 carbon atoms. Examples of such aryloxy may include, but are not limited to, phenyloxy, naphthyloxy, diphenyloxy or the like.

As used herein, "alkylsilyl" refers to silyl substituted with alkyl having 1 to 40 carbon atoms and includes di- and tri-alkylsilyl as well as mono-alkylsilyl. In addition, "arylsilyl" refers to silyl substituted with aryl having 5 to 60 carbon atoms and includes poly-arylsilyl such as di- and tri-arylsilyl as well as mono-arylsilyl.

As used herein, "alkylboron group" refers to a boron group substituted with alkyl having 1 to 40 carbon atoms, and "arylboron group" refers to a boron group substituted with aryl having 6 to 60 carbon atoms.

As used herein, "alkylphosphinyl group" refers to a phosphine group substituted with alkyl having 1 to 40 carbon atoms and includes a di-alkylphosphinyl group as well as a mono-alkylphosphinyl group. As used herein, "arylphosphinyl group" refers to a phosphine group substituted with monoaryl or diaryl having 6 to 60 carbon atoms, and includes a di-arylphosphinyl group as well as a mono-arylphosphinyl group.

As used herein, "arylamine" refers to amine substituted with aryl having 6 to 60 carbon atoms and includes di-arylamine as well as mono-arylamine.

As used herein, the term "fused ring" refers to a fused aliphatic ring, a fused aromatic ring, a fused heteroaliphatic ring, a fused heteroaromatic ring, or a combination thereof <Organic Electroluminescence Device>

Another aspect of embodiments of the present disclosure is related to an organic electroluminescence device (hereinafter, "organic EL device") including the compound represented by Chemical Formula 1.

More specifically, the organic EL device according to the present disclosure includes an anode, a cathode, and one or more organic layers interposed between the anode and the cathode. At least one of the one or more organic layers include the compound represented by Chemical Formula 1. In such a case, the compound may be used solely or as a combination of two or more kinds thereof.

For example, the one or more organic layers include an emissive layer and optionally include one or more of a hole injection layer, a hole transporting layer, an electron transporting layer and an electron injection layer. The emissive layer includes the compound represented by Chemical Formula 1. In this case, the compound represented by Chemical Formula 1 is included in the organic EL device as a material for the emissive layer, preferably as blue, green and red hosts, more preferably as a phosphorescent green host (PGH). In this case, by including the compound represented by Chemical Formula 1, the organic EL device of the present disclosure is excellent in electron transporting ability in the emissive layer, leading to a high binding force between holes and electrons in the emissive layer, and thus is also excellent in luminous efficiency, power efficiency, life, luminance, driving voltage and thermal stability.

Optionally, the emissive layer may further include a dopant together with the compound represented by Chemical Formula 1. In a case where the emissive layer uses a mixture of the compound represented by Chemical Formula 1 and the dopant, a mixing ratio of the compound represented by Chemical Formula 1 and the dopant is not particularly limited. For example, an amount of the compound represented by Chemical Formula 1 may be in a range from about 70 wt % to about 99.9 wt %, and an amount of the dopant may be in a range from about 0.1 wt % to about 30 wt %.

The dopant is not particularly limited as long as it is known in the art, and non-limiting examples thereof may include metal complex compounds including anthracene derivatives, pyrene derivatives, arylamine derivatives, iridium (Ir) or platinum (Pt).

In this case, when the emissive layer includes the compound represented by Chemical Formula 1 and the dopant, in order to achieve low driving voltage and long life characteristics of the organic EL device, it is preferable that an LUMO energy level of the dopant is substantially equal to an LUMO energy level of the compound represented by Chemical Formula 1 or slightly higher than the LUMO energy level of the compound represented by Chemical Formula 1.

The emissive layer described above may be a single layer or may include two or more layers. When the emissive layer includes a plurality of layers, the organic EL device may emit light of various colors. In addition, when the emissive layer includes a plurality of layers, the driving voltage of the device is increased, while a current value in the organic EL device is constant, thereby providing an organic EL device having improved luminous efficiency by the number of emissive layers.

The structure of the organic EL device of the present disclosure is not particularly limited. For example, the organic EL device may have a structure in which the anode, the one or more organic layers and the cathode are sequentially stacked on the substrate, and an insulating layer or an adhesive layer may be further inserted at interfaces between the electrode and the organic layer.

As an example, the organic EL device may have a structure in which an anode, a hole injection layer, a hole transporting layer, an emissive layer, an electron transporting layer, and a cathode are sequentially stacked on a substrate. Optionally, an electron injection layer may be located between the electron transporting layer and the cathode. The organic EL device of the present disclosure may be manufactured by forming organic layers and electrodes in conventional methods with conventional materials known in the art, except that at least one of the aforementioned organic layers (e.g., the emissive layer or the electron transporting layer) include the compound represented by Chemical Formula 1.

The organic layer may be formed by a vacuum deposition method or a solution coating method. Examples of the solution coating method may include, but are not limited to, spin coating, dip coating, doctor blading, inkjet printing, thermal transfer or the like.

The substrate used for manufacturing the organic electroluminescence device of the present disclosure is not particularly limited, but silicon wafers, quartz, glass plates, metal plates, plastic films, sheets or the like may be used.

In addition, a material of the anode may include, but is not limited to, a metal such as vanadium, chromium, copper, zinc and gold or an alloy thereof; a metal oxide such as zinc oxide, indium oxide, indium tin oxide (ITO) and indium zinc oxide (IZO); a combination of oxide with metal such as $ZnO:Al$ or $SnO_2:Sb$; a conductive polymer such as polythiophene, poly(3-methylthiophene), poly[3,4-(ethylene-1, 2-dioxy)thiophene] (PEDT), polypyrrole and polyaniline; carbon black or the like.

In addition, a material of the cathode may include, but is not limited to, a metal such as magnesium, calcium, sodium, potassium, titanium, indium, yttrium, lithium, gadolinium, aluminum, silver, tin and lead or an alloy thereof; a multi-layered material such as $LiF/Al$ and $LiO_2/Al$ or the like.

In addition, materials of the hole injection layer, the hole transporting layer, the electron injection layer, and the electron transporting layer are not particularly limited and conventional materials known in the art may be used.

Hereinafter, the present disclosure will be described in detail with reference to the following embodiments. However, the following embodiments are merely to illustrate the invention, and the present disclosure is not limited by the following embodiments.

FABRICATION EXAMPLE 1 FABRICATION OF COMPOUND A-1

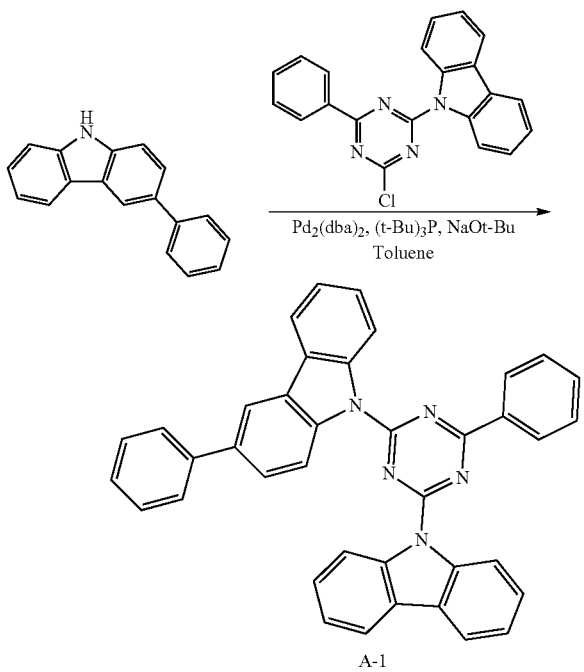

A-1

3-phenyl-9H-carbazole (3 g, 12.3 mmol), 9-(4-chloro-6-phenyl-1,3,5-triazin-2-yl)-9H-carbazole (4.8 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-1 (5.5 g, yield 80%), was obtained through column chromatography.

[LCMS]: 564

FABRICATION EXAMPLE 2 FABRICATION OF COMPOUND A-2

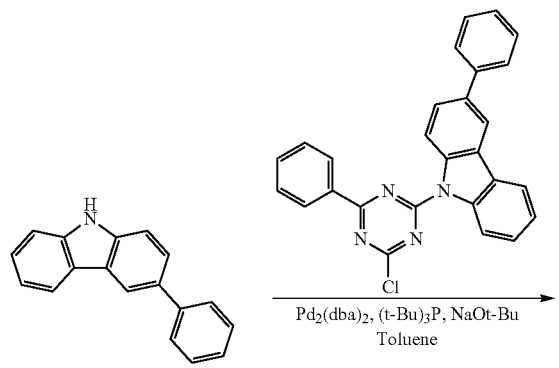

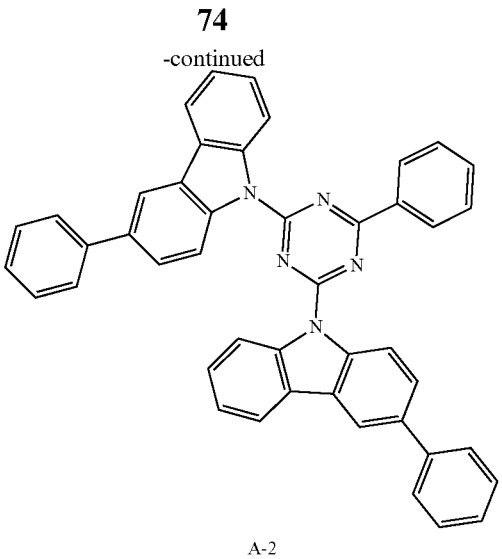

A-2

3-phenyl-9H-carbazole (3 g, 12.3 mmol), 9-(4-chloro-6-phenyl-1,3,5-triazin-2-yl)-3-phenyl-9H-carbazole (5.9 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-2 (6.1 g, yield 78%), was obtained through column chromatography.

[LCMS]: 640

FABRICATION EXAMPLE 3 FABRICATION OF COMPOUND A-3

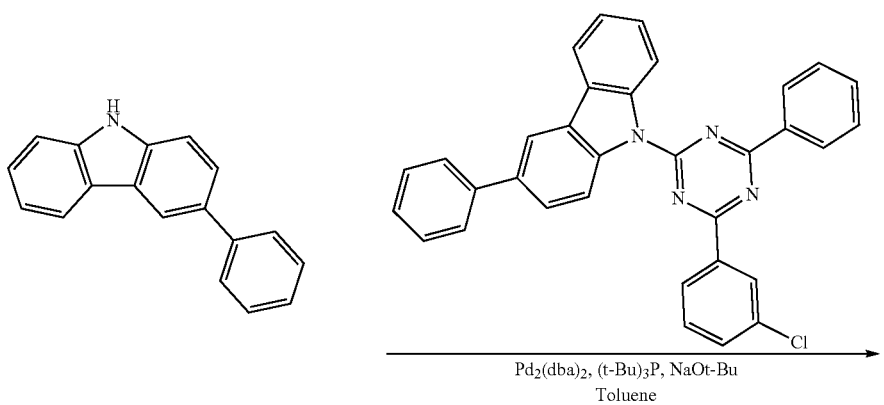

-continued

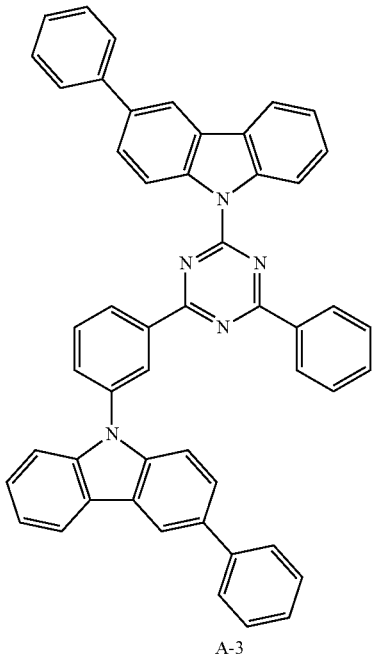

A-3

3-phenyl-9H-carbazole (3 g, 12.3 mmol), 9-(4-(3-chlorophenyl)-6-phenyl-1,3,5-triazin-2-yl)-3-phenyl-9H-carbazole (6.9 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-3 (6.9 g, yield 79%), was obtained through column chromatography.

[LCMS]: 716

FABRICATION EXAMPLE 4 FABRICATION OF COMPOUND A-4

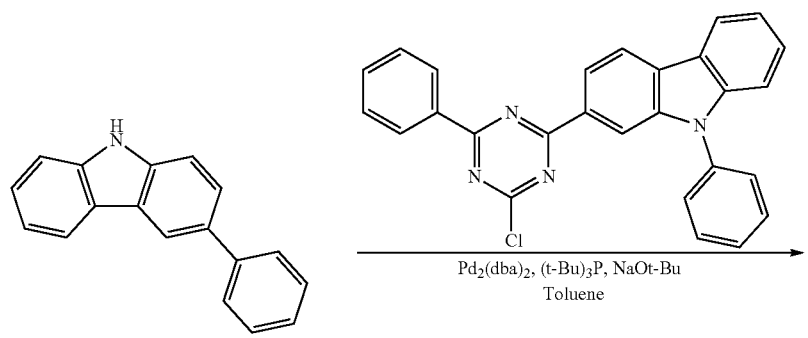

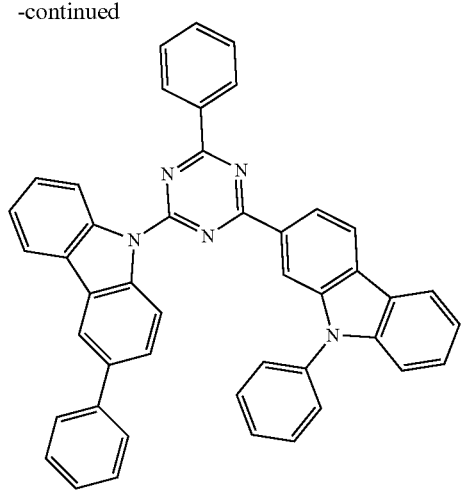

A-4

3-phenyl-9H-carbazole (3 g, 12.3 mmol), 2-(4-chloro-6-phenyl-1,3, 5-triazin-2-yl)-9-phenyl-9H-carbazole (5.9 g, 13.5 mmol), $Pd_2(dba)_3$ (0.6 g, 0.6 mmol), $(t-Bu)_3P$ (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, $MgSO_4$ was added thereto and the organic layer was filtered. After removing the solvent from the filtered organic layer, the target compound, Compound A-4 (6.2 g, yield 79%), was obtained through column chromatography.

[LCMS]: 640

FABRICATION EXAMPLE 5 FABRICATION OF COMPOUND A-5

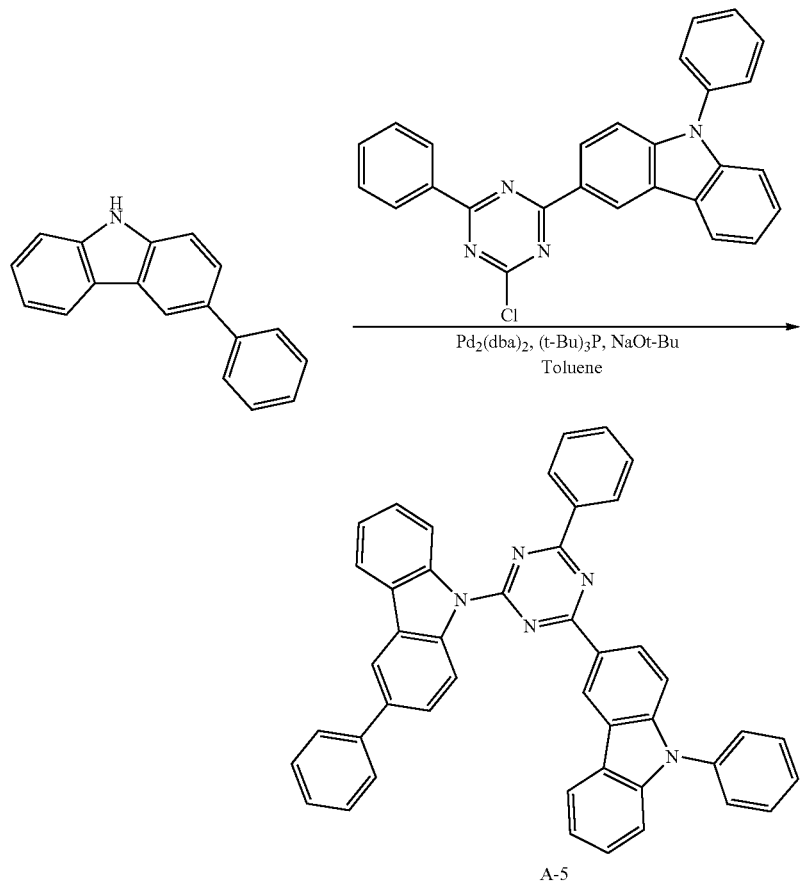

A-5

3-phenyl-9H-carbazole (3 g, 12.3 mmol), 3-(4-chloro-6-phenyl-1,3,5-triazin-2-yl)-9-phenyl-9H-carbazole (5.9 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-5 (6.1 g, yield 77%), was obtained through column chromatography.

[LCMS]: 640

FABRICATION EXAMPLE 6 FABRICATION OF COMPOUND A-8

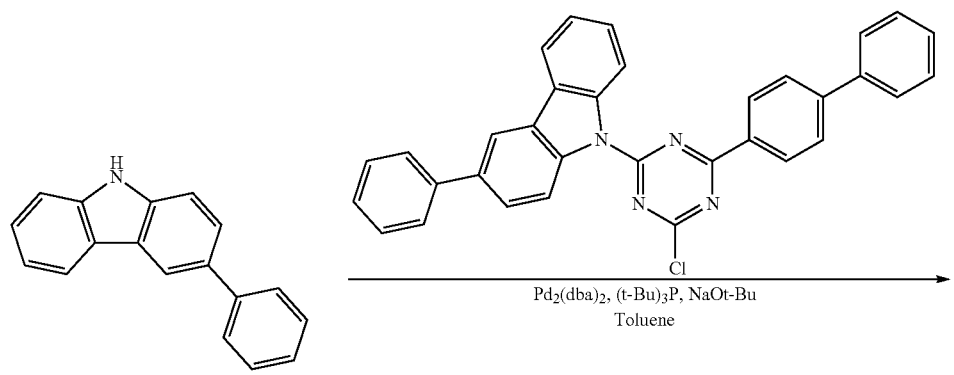

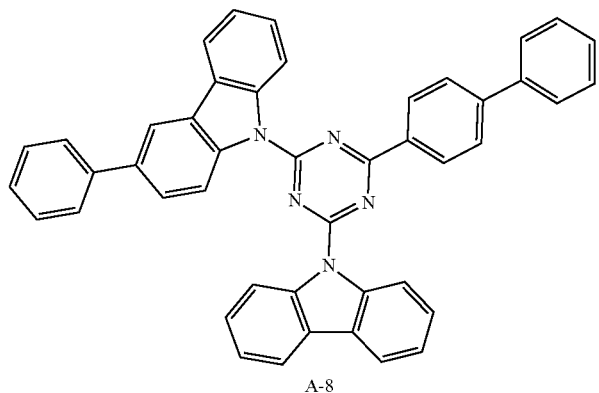

A-8

3-phenyl-9H-carbazole (3 g, 12.3 mmol), 9-(4-([1,1'-biphenyl]-4-yl)-6-chloro-1,3,5-triazin-2-yl)-3-phenyl-9H-carbazole (6.9 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-8 (6.3 g, yield 80%), was obtained through column chromatography.

[LCMS]: 640

FABRICATION EXAMPLE 7 FABRICATION OF COMPOUND A-15

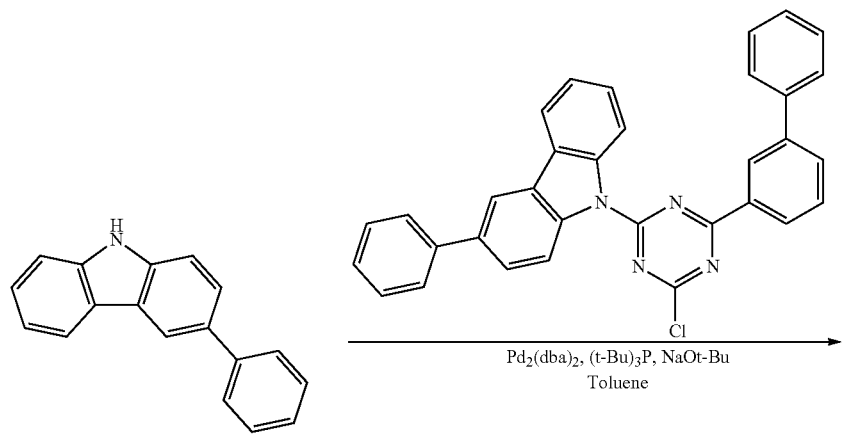

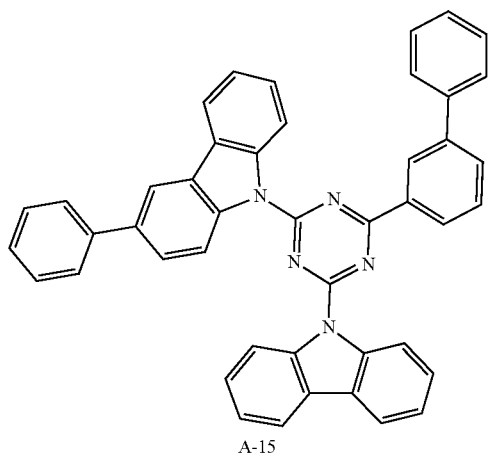

A-15

3-phenyl-9H-carbazole (3 g, 12.3 mmol), 9-(4-([1,1'-biphenyl]-3-yl)-6-chloro-1,3,5-triazin-2-yl)-3-phenyl-9H-carbazole (6.9 g, 13.5 mmol), $Pd_2(dba)_3$ (0.6 g, 0.6 mmol), $(t-Bu)_3P$ (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, $MgSO_4$ was added thereto and the organic layer was filtered. After removing the solvent from the filtered organic layer, the target compound, Compound A-15 (6.0 g, yield 76%), was obtained through column chromatography.

[LCMS]: 640

FABRICATION EXAMPLE 8 FABRICATION OF COMPOUND A-24

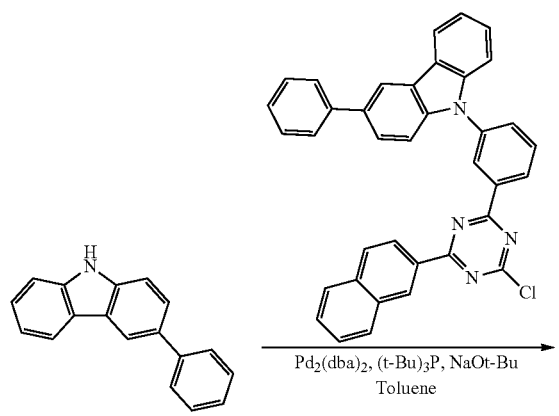

-continued

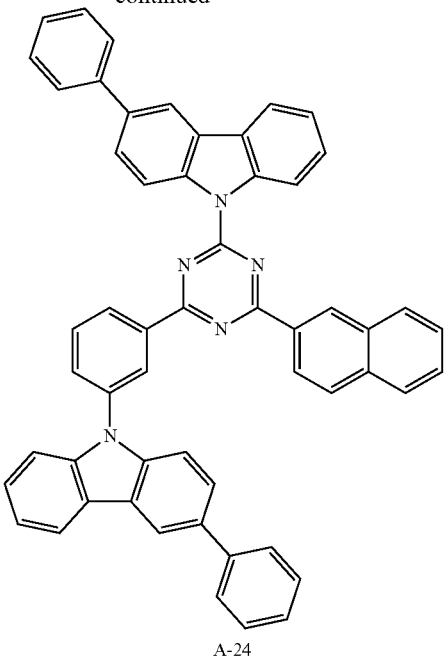

A-24

3-phenyl-9H-carbazole (3 g, 12.3 mmol), 9-(3-(4-chloro-6-(naphthalen-2-yl)-1,3,5-triazin-2-yl)phenyl)-3-phenyl-9H-carbazole (7.6 g, 13.5 mmol), $Pd_2(dba)_3$ (0.6 g, 0.6 mmol), $(t-Bu)_3P$ (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, $MgSO_4$ was added thereto and the organic layer was filtered. After removing the solvent from the filtered organic layer, the target compound, Compound A-24 (7.0 g, yield 74%), was obtained through column chromatography.

[LCMS]: 766

FABRICATION EXAMPLE 9 FABRIATION OF COMPOUND A-29

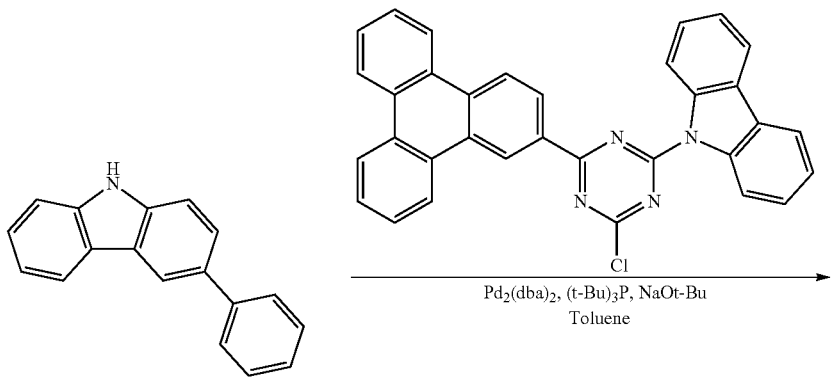

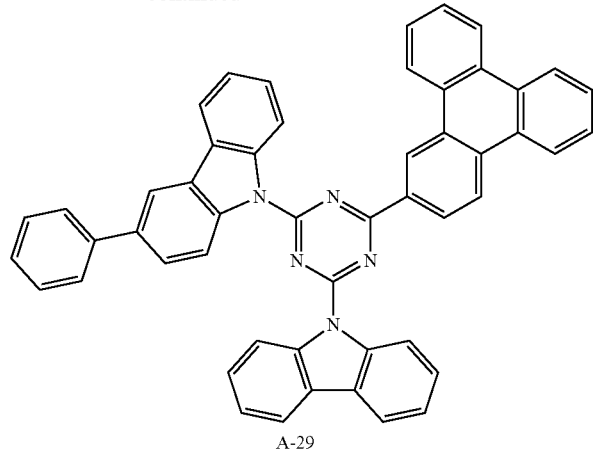

A-29

3-phenyl-9H-carbazole (3 g, 12.3 mmol), 9-(4-chloro-6-(triphenylen-2-yl)-1,3,5-triazin-2-yl)-9H-carbazole (6.9 g, 13.5 mmol), $Pd_2(dba)_3$ (0.6 g, 0.6 mmol), $(t\text{-}Bu)_3P$ (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, $MgSO_4$ was added thereto and the organic layer was filtered. After removing the solvent from the filtered organic layer, the target compound, Compound A-29 (6.6 g, yield 75%), was obtained through column chromatography.

[LCMS]: 714

FABRICATION EXAMPLE 10 FABRICATION OF COMPOUND A-36

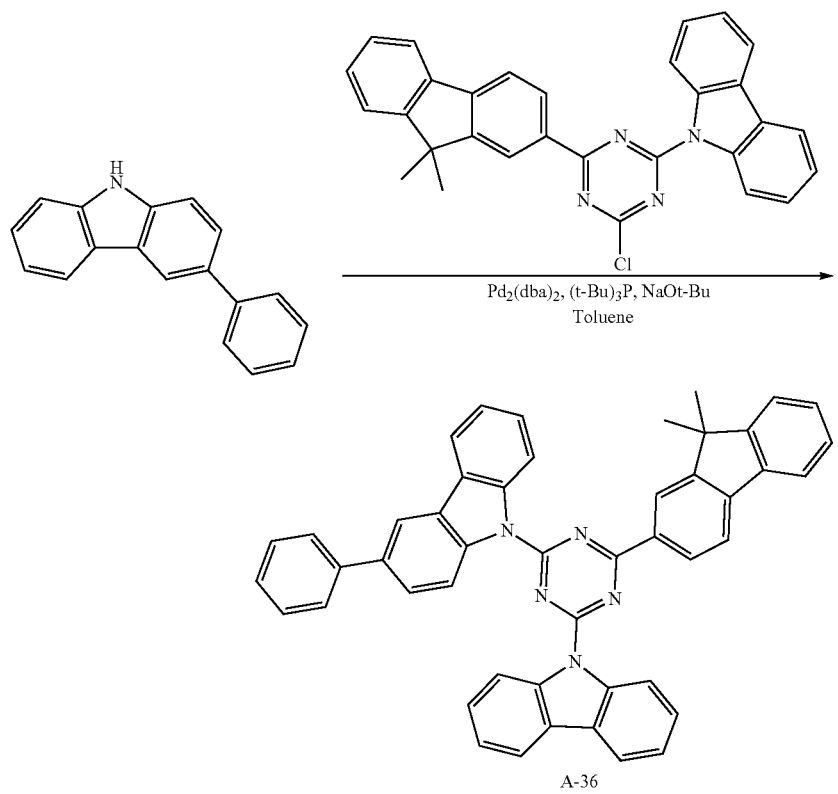

A-36

3-phenyl-9H-carbazole (3 g, 12.3 mmol), 9-(4-chloro-6-(9,9-dimethyl-9H-fluoren-2-yl)-1,3,5-triazin-2-yl)-9H-carbazole (5.9 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-36 (6.3 g, yield 75%), was obtained through column chromatography.

[LCMS]: 680

FABRICATION EXAMPLE 11 FABRICATION OF COMPOUND A-39

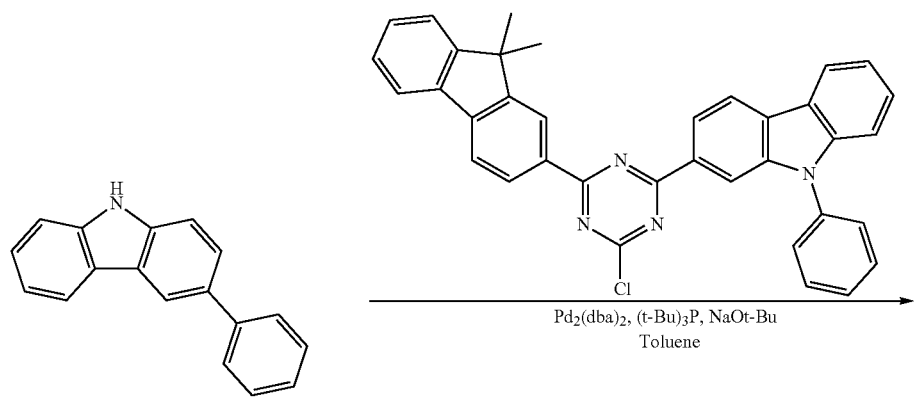

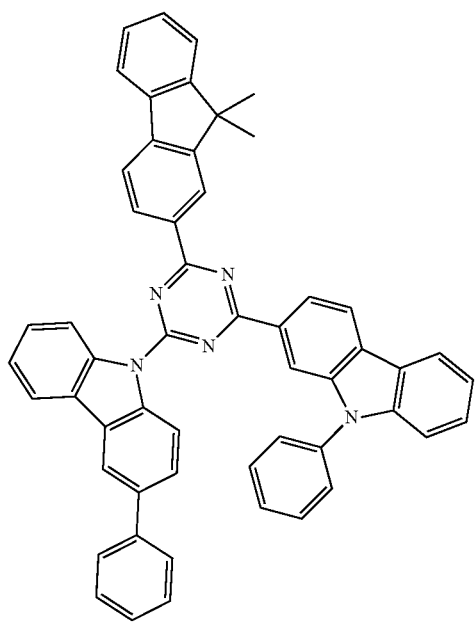

A-39

3-phenyl-9H-carbazole (3 g, 12.3 mmol), 2-(4-chloro-6-(9,9-dimethyl-9H-fluoren-2-yl)-1,3,5-triazin-2-yl)-9-phenyl-9H-carbazole (7.5 g, 13.5 mmol), $Pd_2(dba)_3$ (0.6 g, 0.6 mmol), $(t-Bu)_3P$ (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, $MgSO_4$ was added thereto and the organic layer was filtered. After removing the solvent from the filtered organic layer, the target compound, Compound A-39 (7.4 g, yield 79%), was obtained through column chromatography.

[LCMS]: 756

FABRICATION EXAMPLE 12 FABRICATION OF COMPOUND A-43

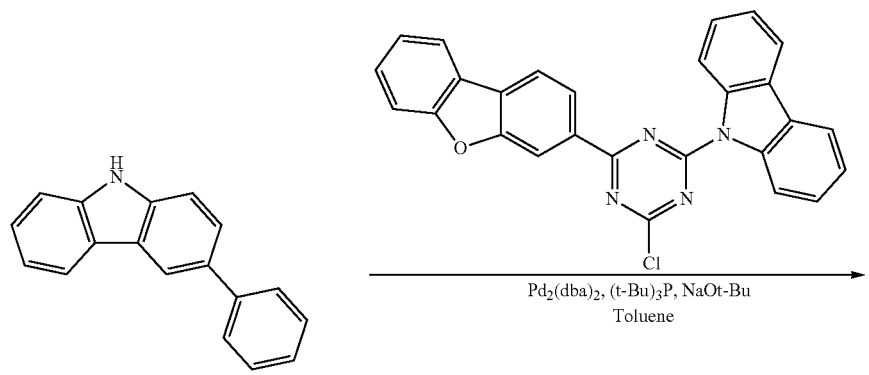

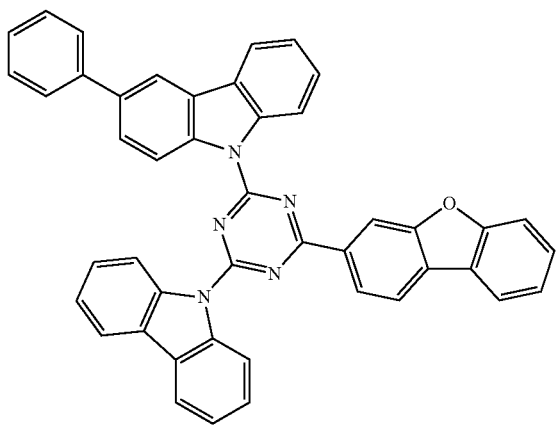

A-43

3-phenyl-9H-carbazole (3 g, 12.3 mmol), 9-(4-chloro-6-(dibenzo[b,d]furan-3-yl)-1,3,5-triazin-2-yl)-9H-carbazole (6.1 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-43 (6.4 g, yield 79%), was obtained through column chromatography.

[LCMS]: 654

FABRICATION EXAMPLE 13 FABRICATION OF COMPOUND A-51

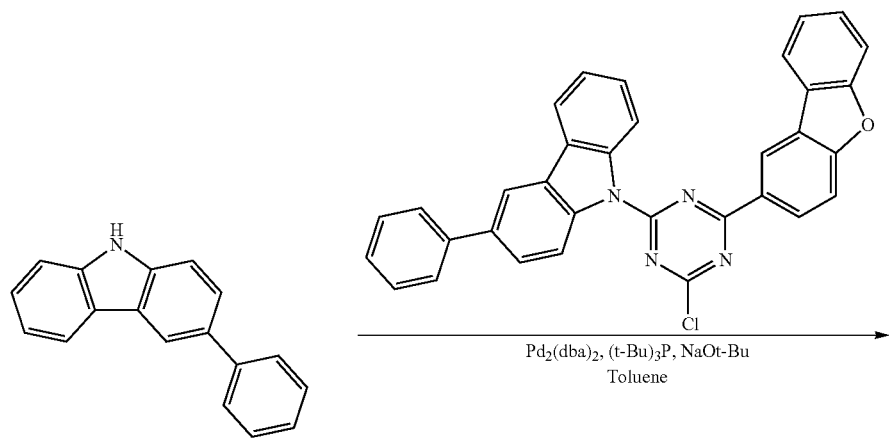

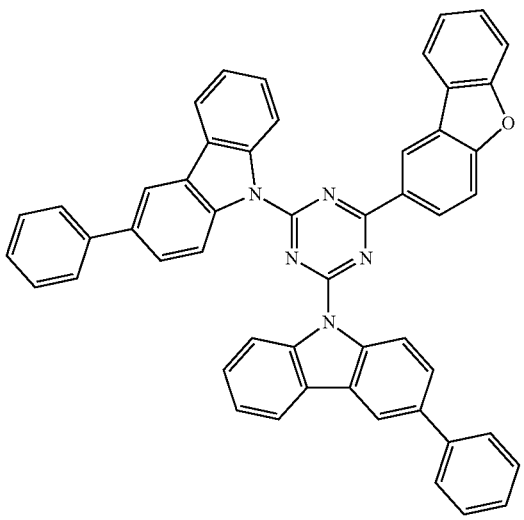

A-51

3-phenyl-9H-carbazole (3 g, 12.3 mmol), 9-(4-chloro-6-(dibenzo[b,d]furan-2-yl)-1,3,5-triazin-2-yl)-3-phenyl-9H-carbazole (7.1 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-51 (6.7 g, yield 75%), was obtained through column chromatography.

[LCMS]: 730

FABRICATION EXAMPLE 14 FABRICATION OF COMPOUND A-57

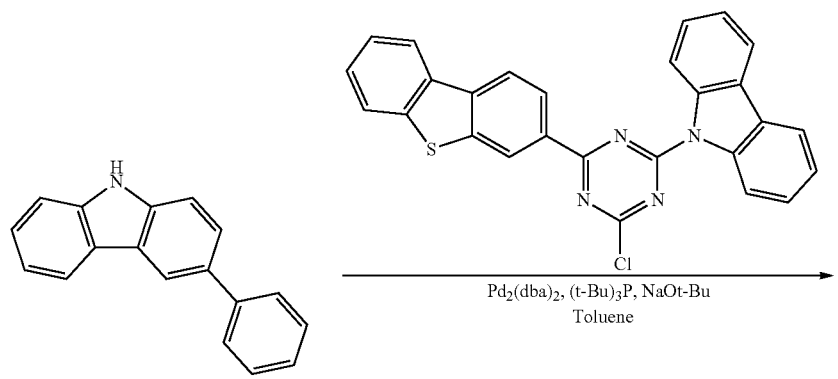

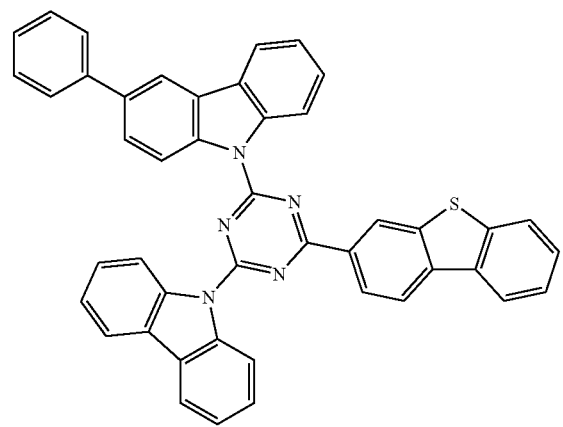

A-57

3-phenyl-9H-carbazole (3 g, 12.3 mmol), 9-(4-chloro-6-(dibenzo[b,d]thiophen-3-yl)-1,3,5-triazin-2-yl)-9H-carbazole (6.3 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-57 (6.0 g, yield 73%), was obtained through column chromatography.

[LCMS]: 670

FABRICATION EXAMPLE 15 FABRICATION OF COMPOUND A-61

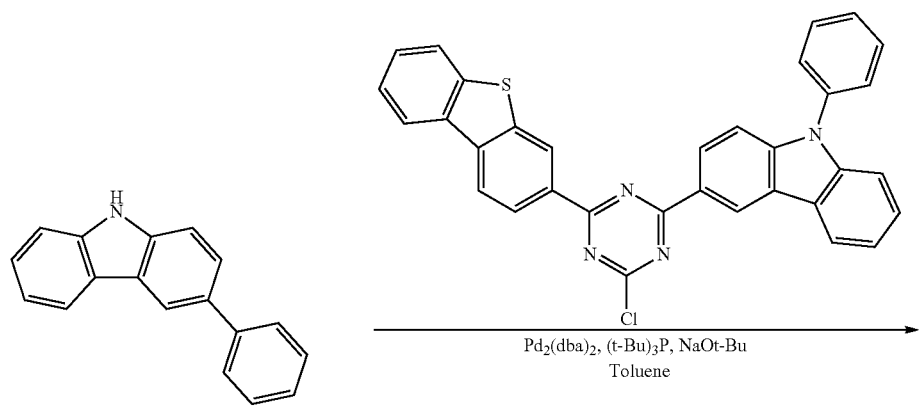

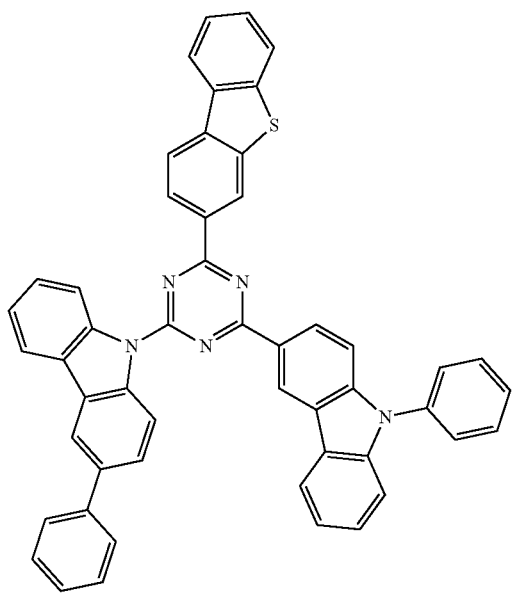

A-61

3-phenyl-9H-carbazole (3 g, 12.3 mmol), 3-(4-chloro-6-(dibenzo[b,d]thiophen-3-yl)-1,3,5-triazin-2-yl)-9-phenyl-9H-carbazole (7.3 g, 13.5 mmol), $Pd_2(dba)_3$ (0.6 g, 0.6 mmol), $(t-Bu)_3P$ (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, $MgSO_4$ was added thereto and the organic layer was filtered. After removing the solvent from the filtered organic layer, the target compound, Compound A-61 (7.0 g, yield 76%), was obtained through column chromatography.

[LCMS]: 746

FABRICATION EXAMPLE 16 FABRICATION OF COMPOUND A-64

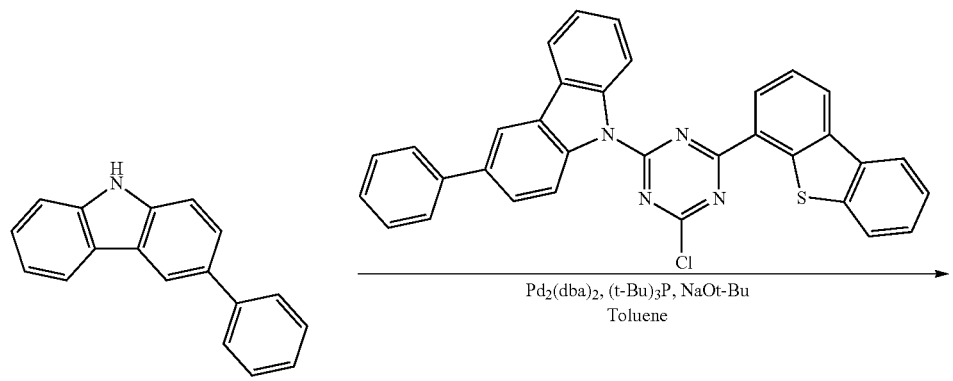

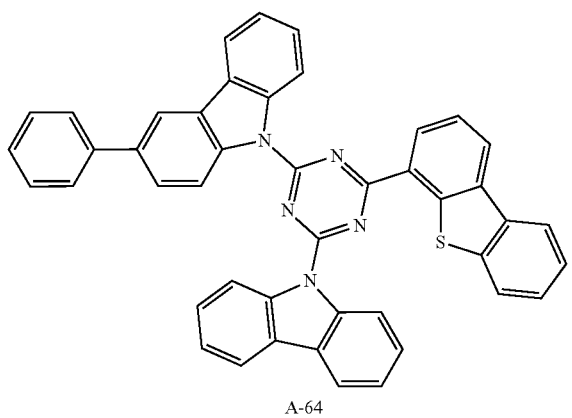

A-64

3-phenyl-9H-carbazole (3 g, 12.3 mmol), 9-(4-chloro-6-(dibenzo[b,d]thiophen-4-yl)-1,3,5-triazin-2-yl)-3-phenyl-9H-carbazole (7.3 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-64 (7.0 g, yield 76%), was obtained through column chromatography.

[LCMS]: 746

FABRICATION EXAMPLE 17 FABRICATION OF COMPOUND A-71

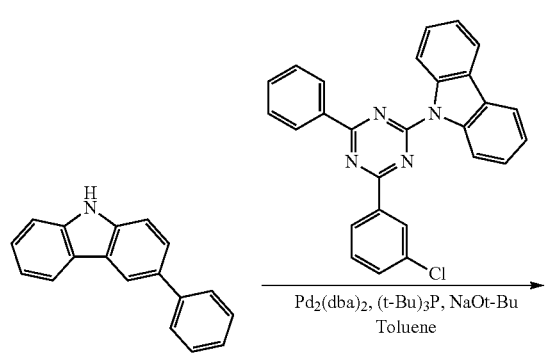

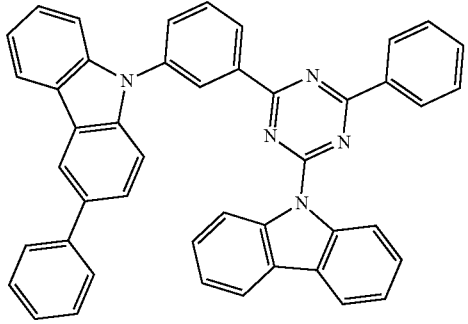

A-71

3-phenyl-9H-carbazole (3 g, 12.3 mmol), 9-(4-(3-chlorophenyl)-6-phenyl-1,3,5-triazin-2-yl)-9H-carbazole (5.9 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-71 (6.3 g, yield 80%), was obtained through column chromatography.

[LCMS]: 640

FABRICATION EXAMPLE 18 FABRICATION OF COMPOUND A-72

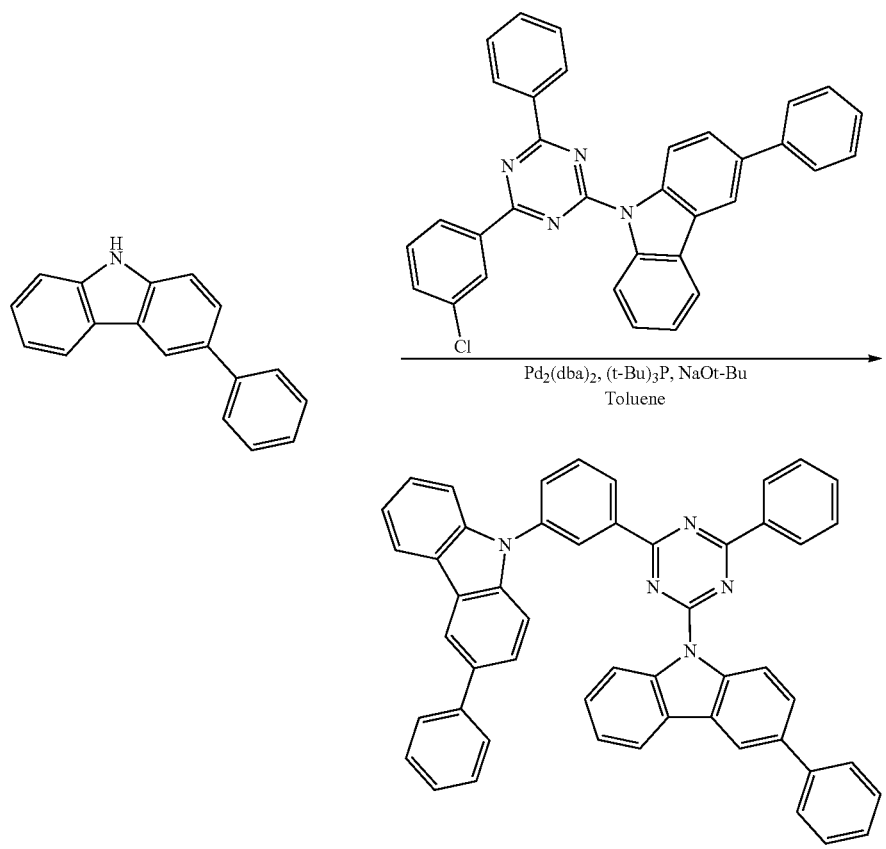

A-72

3-phenyl-9H-carbazole (3 g, 12.3 mmol), 9-(4-(3-chlorophenyl)-6-phenyl-1,3,5-triazin-2-yl)-3-phenyl-9H-carbazole (6.9 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-72 (7.0 g, yield 79%), was obtained through column chromatography.

[LCMS]: 716

FABRICATION EXAMPLE 19 FABRICATION OF COMPOUND A-73

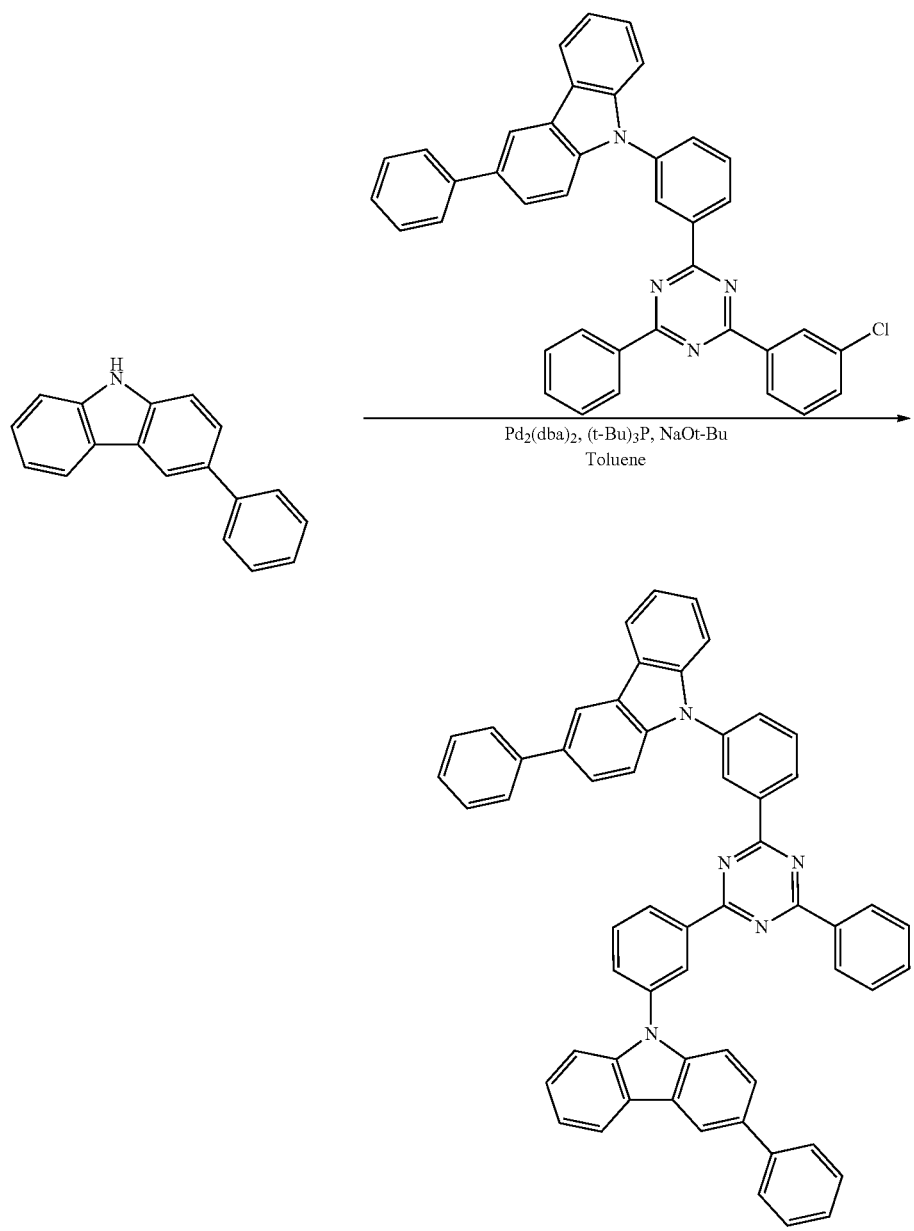

A-73

3-phenyl-9H-carbazole (3 g, 12.3 mmol), 9-(3-(4-(3-chlorophenyl)-6-phenyl-1,3,5-triazin-2-yl)phenyl)-3-phenyl-9H-carbazole (7.9 g, 13.5 mmol), $Pd_2(dba)_3$ (0.6 g, 0.6 mmol), $(t\text{-}Bu)_3P$ (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, $MgSO_4$ was added thereto and the organic layer was filtered. After removing the solvent from the filtered organic layer, the target compound, Compound A-73 (7.7 g, yield 79%), was obtained through column chromatography.

[LCMS]: 792

FABRICATION EXAMPLE 20 FABRICATION OF COMPOUND A-74

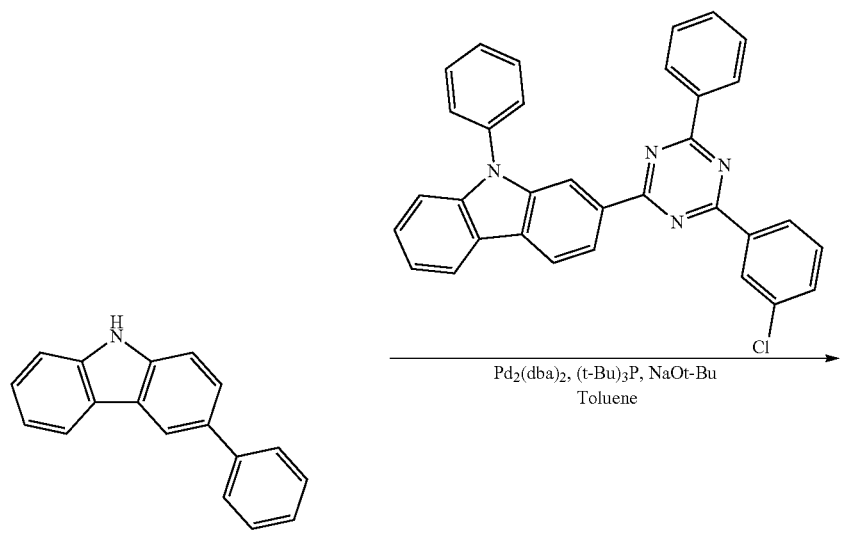

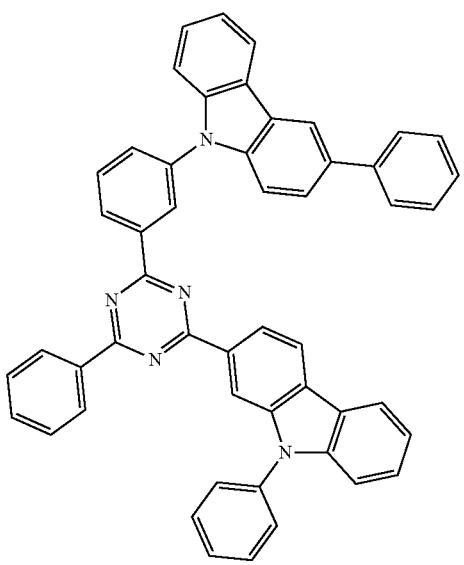

A-74

3-phenyl-9H-carbazole (3 g, 12.3 mmol), 2-(4-(3-chlorophenyl)-6-phenyl-1,3,5-triazin-2-yl)-9-phenyl-9H-carbazole (6.9 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-74 (7.0 g, yield 79%), was obtained through column chromatography.

[LCMS]: 716

FABRICATION EXAMPLE 21 FABRICATION OF COMPOUND A-75

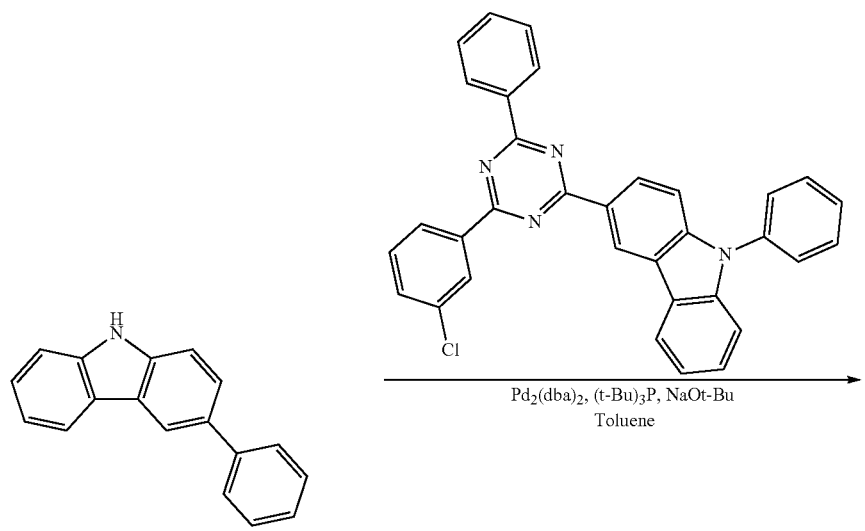

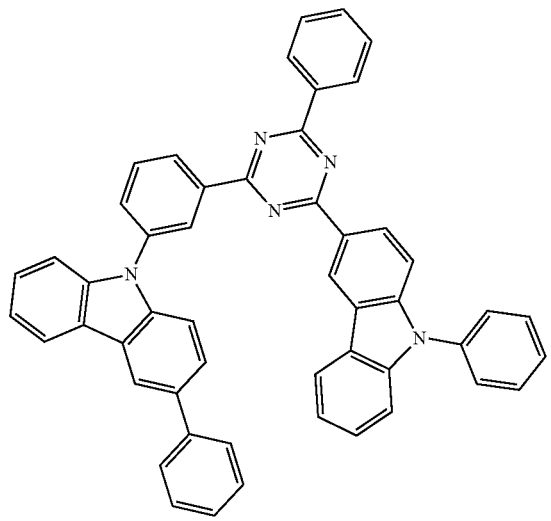

A-75

3-phenyl-9H-carbazole (3 g, 12.3 mmol), 3-(4-(3-chlorophenyl)-6-phenyl-1,3,5-triazin-2-yl)-9-phenyl-9H-carbazole (6.9 g, 13.5 mmol), $Pd_2(dba)_3$ (0.6 g, 0.6 mmol), $(t-Bu)_3P$ (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, $MgSO_4$ was added thereto and the organic layer was filtered. After removing the solvent from the filtered organic layer, the target compound, Compound A-75 (6.8 g, yield 77%), was obtained through column chromatography.

[LCMS]: 716

FABRICATION EXAMPLE 22 FABRICATION OF COMPOUND A-78

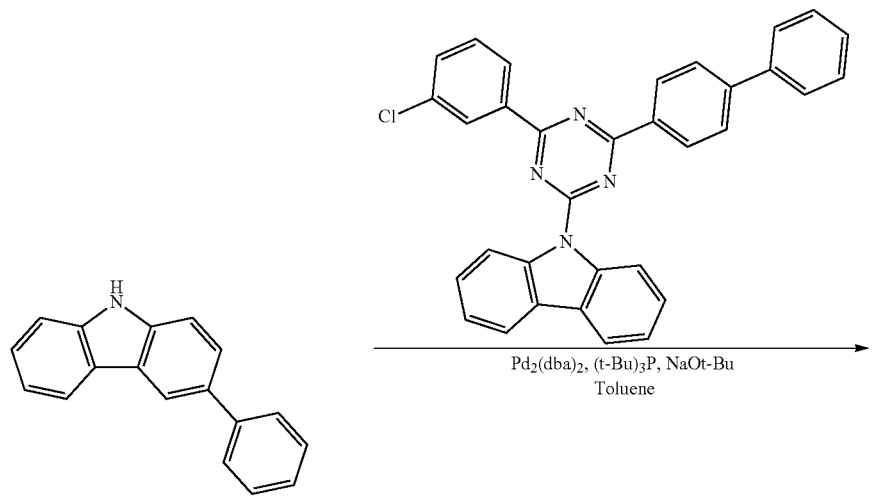

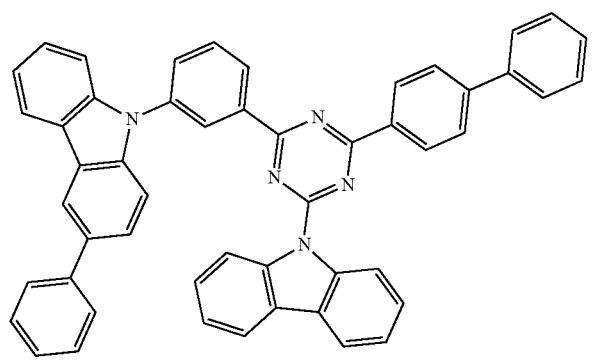

A-78

3-phenyl-9H-carbazole (3 g, 12.3 mmol), 9-(4-([1,1'-biphenyl]-4-yl)-6-(3-chlorophenyl)-1,3,5-triazin-2-yl)-9H-carbazole (6.9 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-78 (6.8 g, yield 77%), was obtained through column chromatography.

[LCMS]: 716

FABRICATION EXAMPLE 23 FABRICATION OF COMPOUND A-85

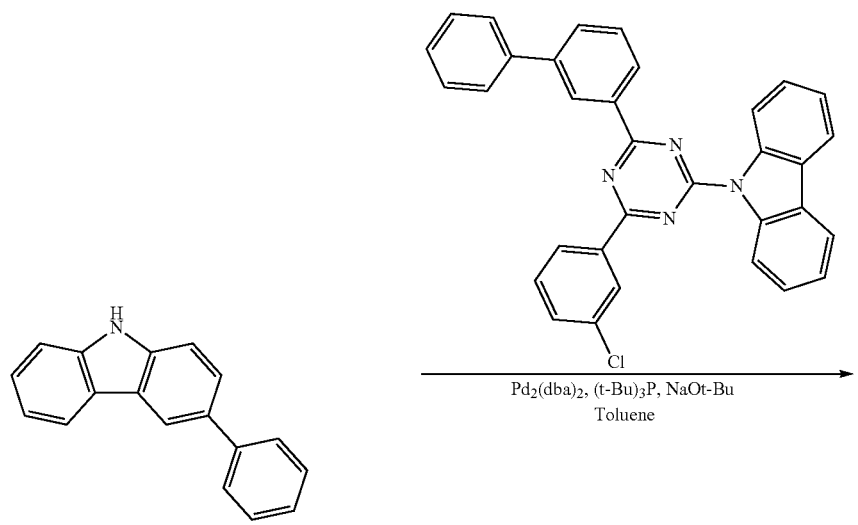

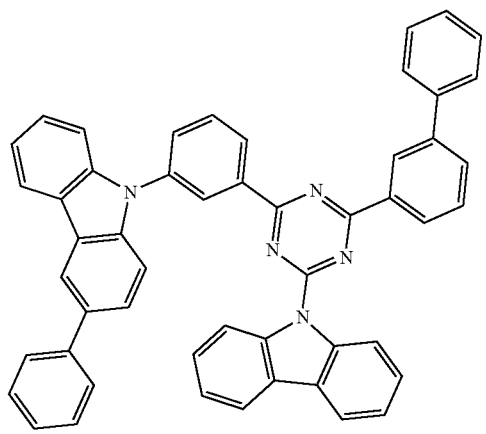

A-85

3-phenyl-9H-carbazole (3 g, 12.3 mmol), 9-(4-([1,1'-biphenyl]-3-yl)-6-(3-chlorophenyl)-1,3,5-triazin-2-yl)-9H-carbazole (6.9 g, 13.5 mmol), Pd₂(dba)₃ (0.6 g, 0.6 mmol), (t-Bu)₃P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO₄ was added thereto and the organic layer was filtered. After removing the solvent from the filtered organic layer, the target compound, Compound A-85 (6.7 g, yield 76%), was obtained through column chromatography.

[LCMS]: 716

FABRICATION EXAMPLE 24 FABRICATION OF COMPOUND A-94

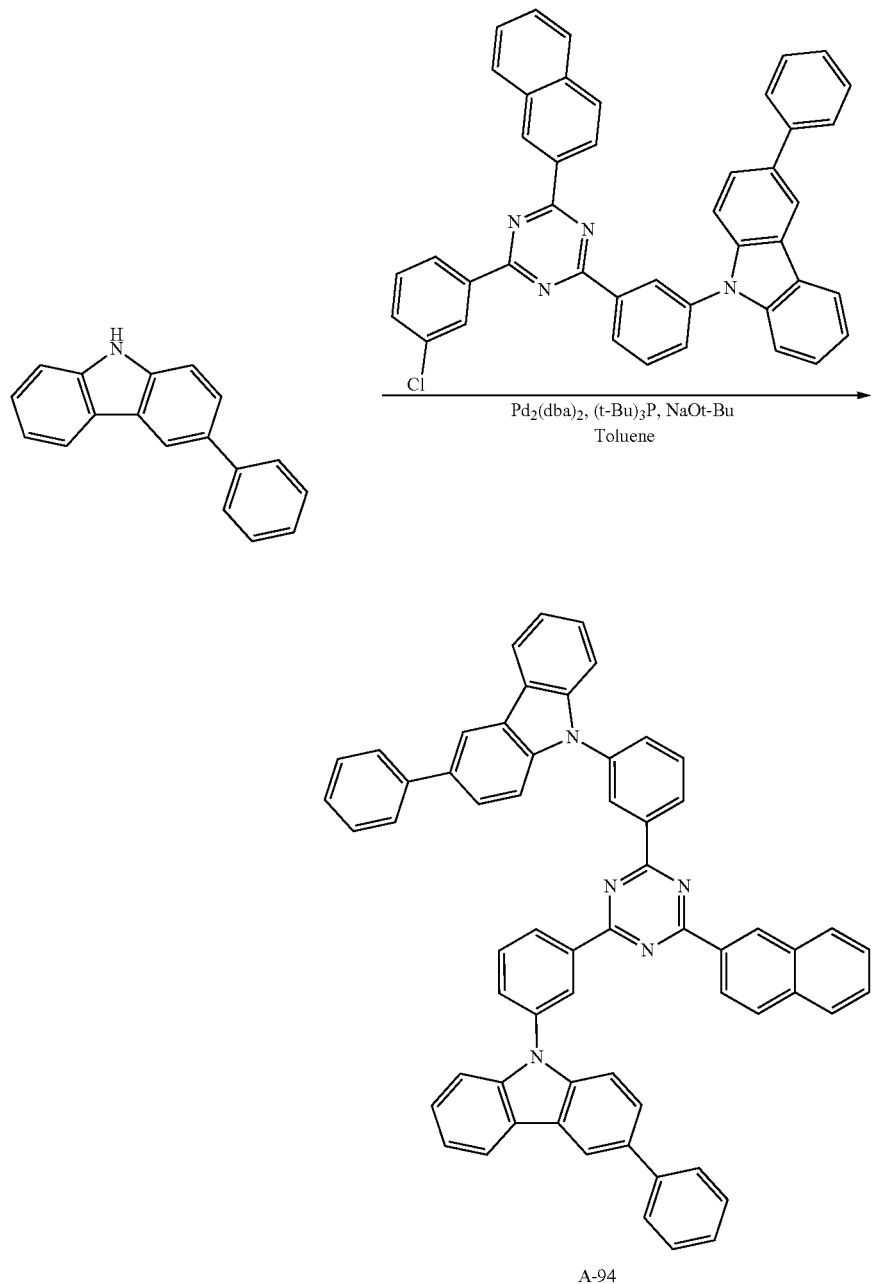

A-94

3-phenyl-9H-carbazole (3 g, 12.3 mmol), 9-(3-(4-(3-chlorophenyl)-6-(naphthalen-2-yl)-1,3,5-triazin-2-yl)phenyl)-3-phenyl-9H-carbazole (8.6 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-94 (7.7 g, yield 74%), was obtained through column chromatography.

[LCMS]: 843

FABRICATION EXAMPLE 25 FABRICATION OF COMPOUND A-99

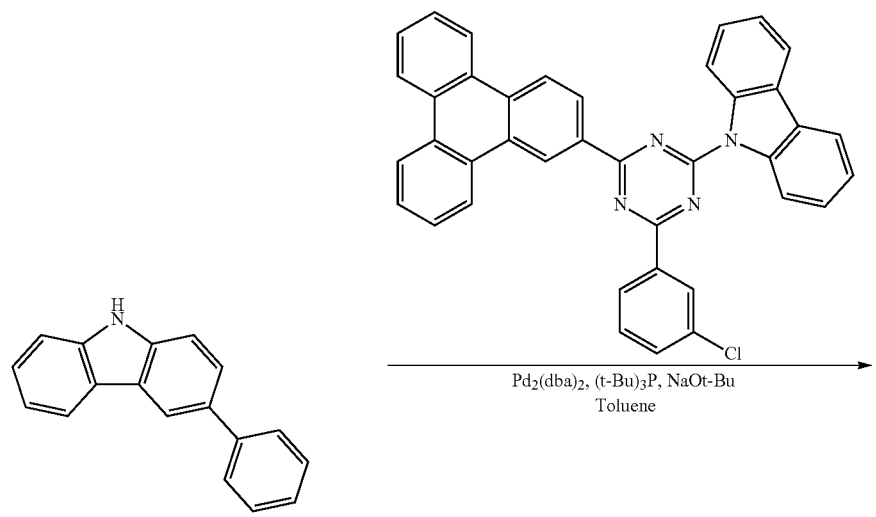

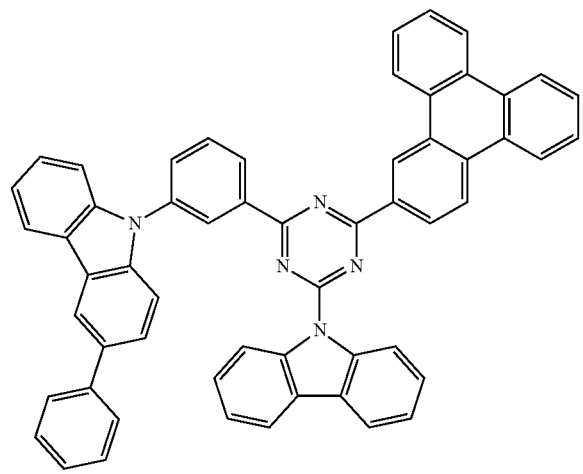

A-99

3-phenyl-9H-carbazole (3 g, 12.3 mmol), 9-(4-(3-chlorophenyl)-6-(triphenylen-2-yl)-1,3,5-triazin-2-yl)-9H-carbazole (7.9 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-99 (7.3 g, yield 75%), was obtained through column chromatography.

[LCMS]: 790

FABRICATION EXAMPLE 26 FABRICATION OF COMPOUND A-106

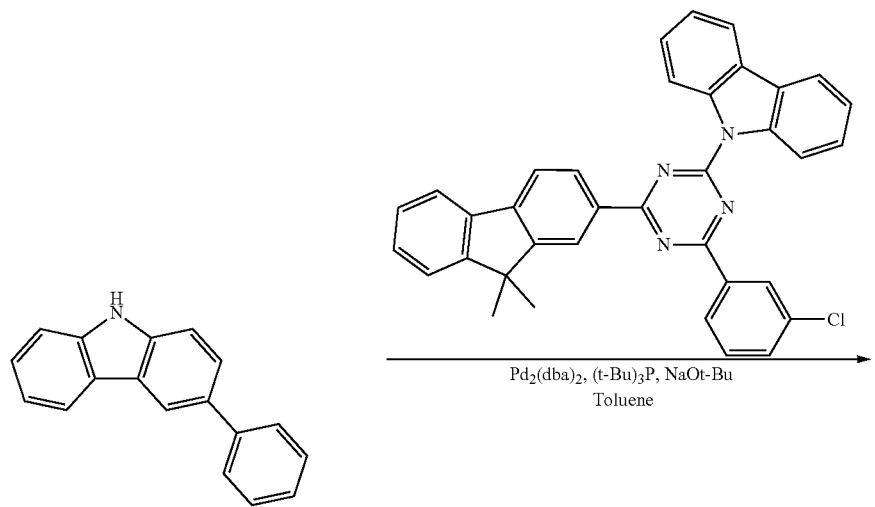

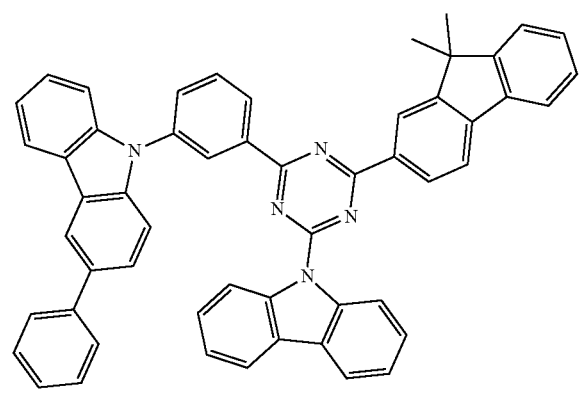

A-106

3-phenyl-9H-carbazole (3 g, 12.3 mmol), 9-(4-(3-chlorophenyl)-6-(9,9-dimethyl-9H-fluoren-2-yl)-1,3,5-triazin-2-yl)-9H-carbazole (7.4 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-106 (7.0 g, yield 75%), was obtained through column chromatography.

[LCMS]: 756

FABRICATION EXAMPLE 27 FABRICATION OF COMPOUND A-109

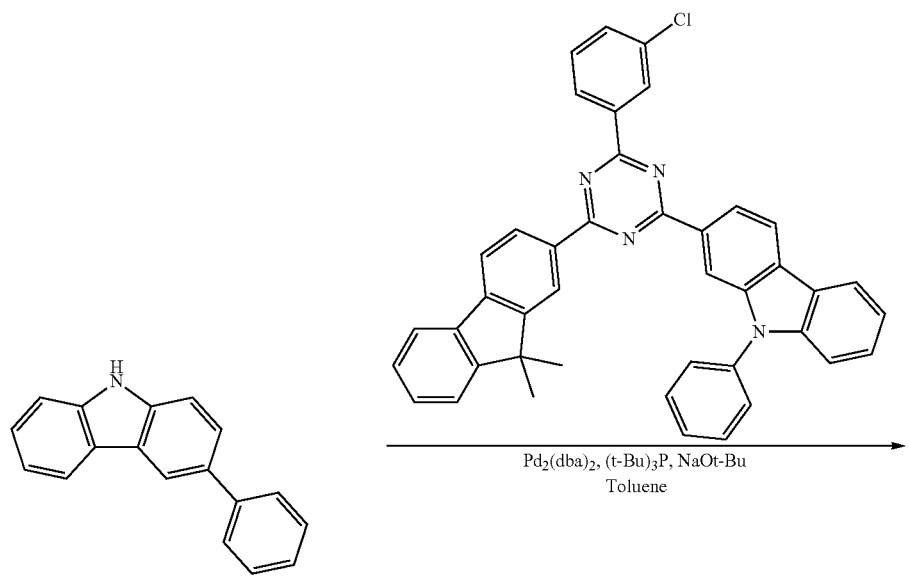

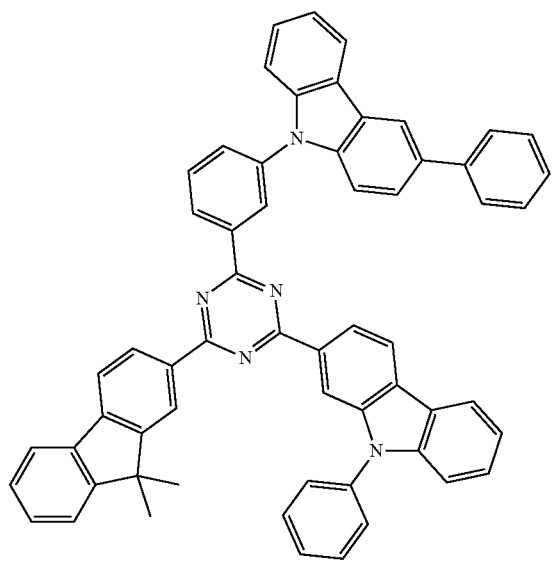

A-109

3-phenyl-9H-carbazole (3 g, 12.3 mmol), 2-(4-(3-chlorophenyl)-6-(9,9-dimethyl-9H-fluoren-2-yl)-1,3,5-triazin-2-yl)-9-phenyl-9H-carbazole (7.5 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-109 (8.1 g, yield 79%), was obtained through column chromatography.

[LCMS]: 833

FABRICATION EXAMPLE 28 FABRICATION OF COMPOUND A-113

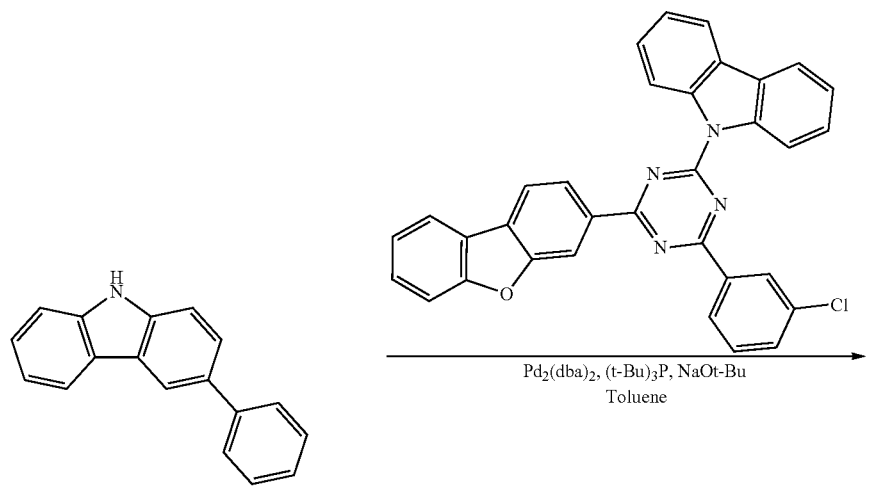

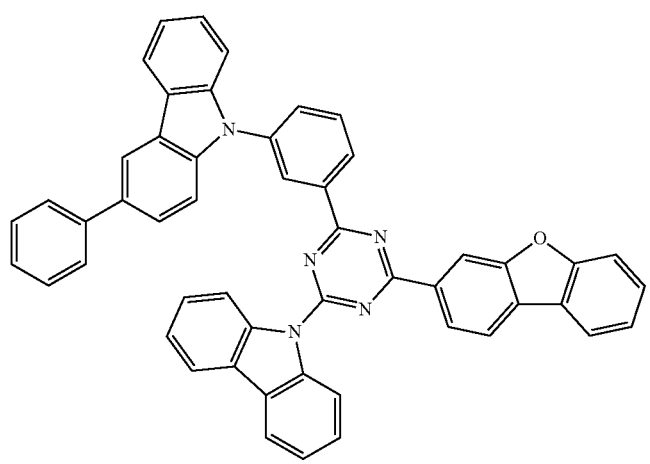

A-113

3-phenyl-9H-carbazole (3 g, 12.3 mmol), 9-(4-(3-chlorophenyl)-6-(dibenzo[b,d]furan-3-yl)-1,3,5-triazin-2-yl)-9H-carbazole (7.1 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-113 (7.1 g, yield 79%), was obtained through column chromatography.

[LCMS]: 730

FABRICATION EXAMPLE 29 FABRICATION OF COMPOUND A-121

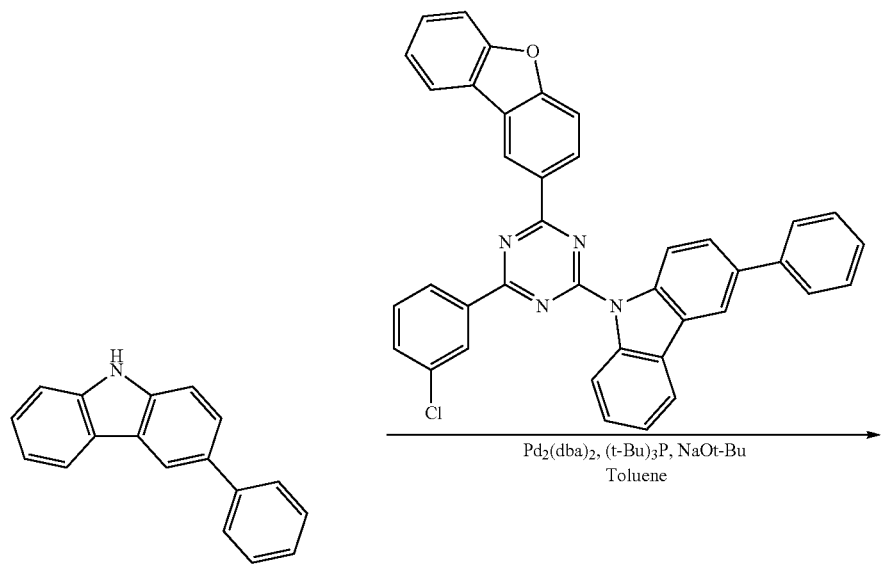

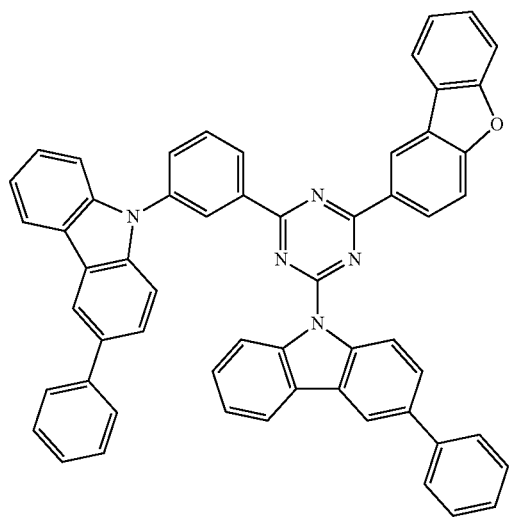

A-121

3-phenyl-9H-carbazole (3 g, 12.3 mmol), 9-(4-(3-chlorophenyl)-6-(dibenzo[b,d]furan-2-yl)-1,3,5-triazin-2-yl)-3-phenyl-9H-carbazole (8.1 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-121 (7.4 g, yield 75%), was obtained through column chromatography.

[LCMS]: 806

FABRICATION EXAMPLE 30 FABRICATION OF COMPOUND A-127

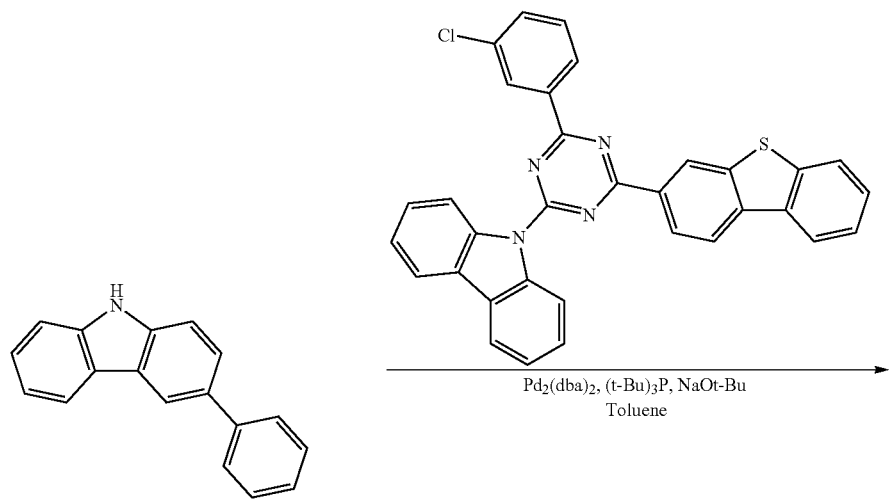

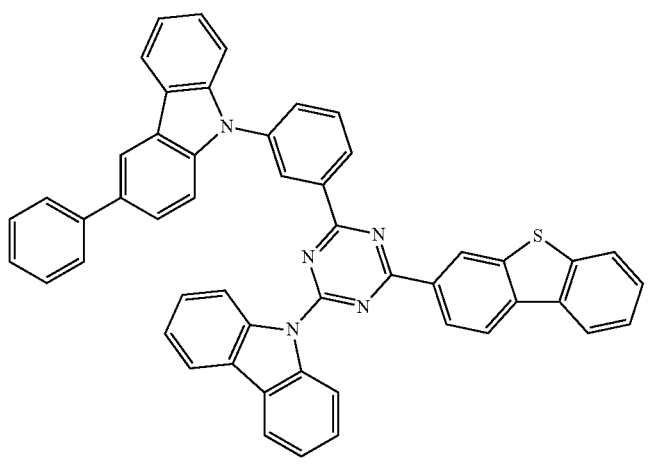

A-127

3-phenyl-9H-carbazole (3 g, 12.3 mmol), 9-(4-(3-chlorophenyl)-6-(dibenzo[b,d]thiophen-3-yl)-1,3,5-triazin-2-yl)-9H-carbazole (7.3 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-127 (6.7 g, yield 73%), was obtained through column chromatography.

[LCMS]: 746

FABRICATION EXAMPLE 31 FABRICATOIN OF COMPOUND A-131

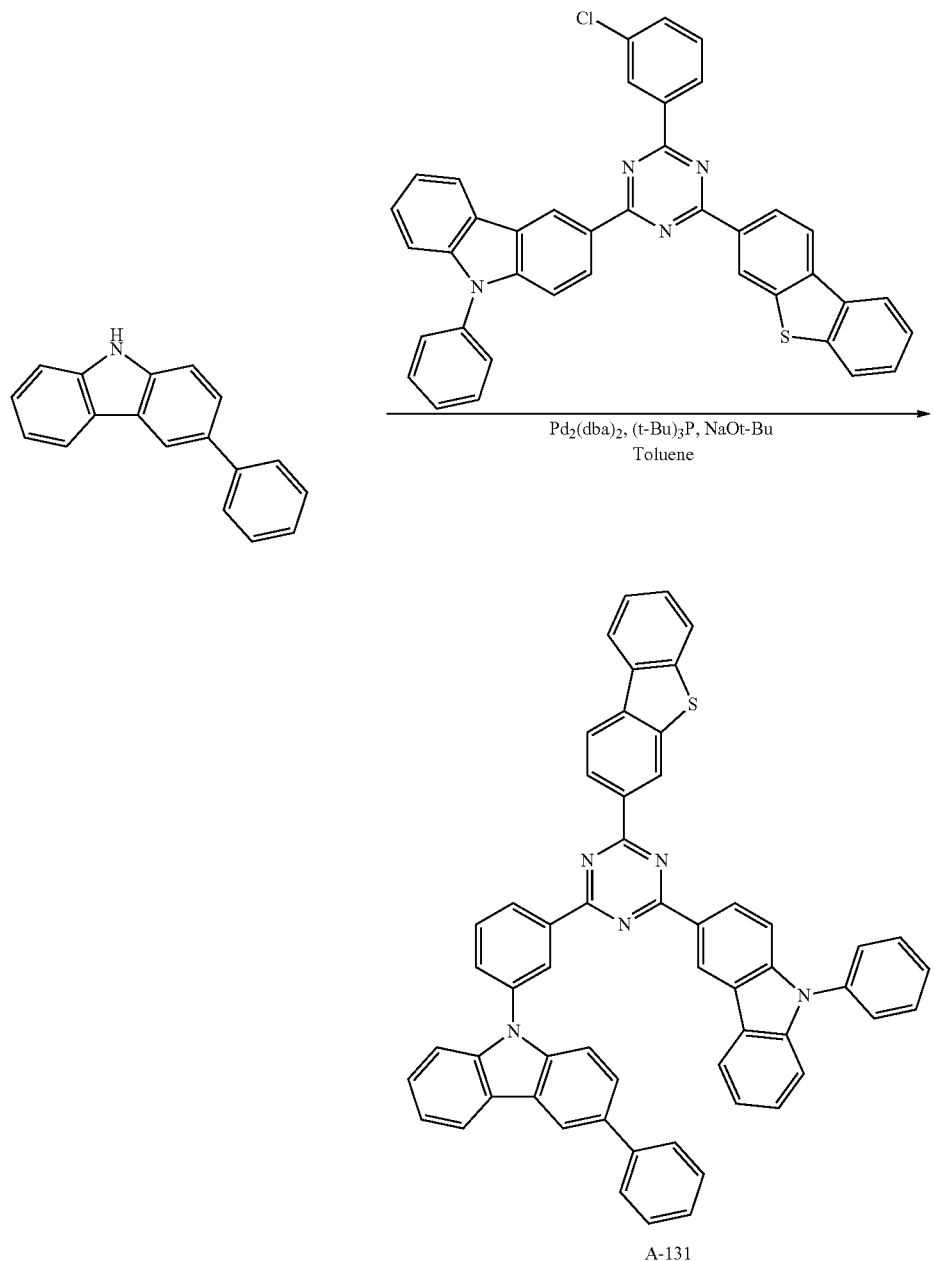

A-131

3-phenyl-9H-carbazole (3 g, 12.3 mmol), 3-(4-(3-chlorophenyl)-6-(dibenzo[b,d]thiophen-3-yl)-1,3,5-triazin-2-yl)-9-phenyl-9H-carbazole (8.3 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-131 (7.1 g, yield 70%), was obtained through column chromatography.

[LCMS]: 823

FABRICATION EXAMPLE 32 FABRICATION OF COMPOUND A-134

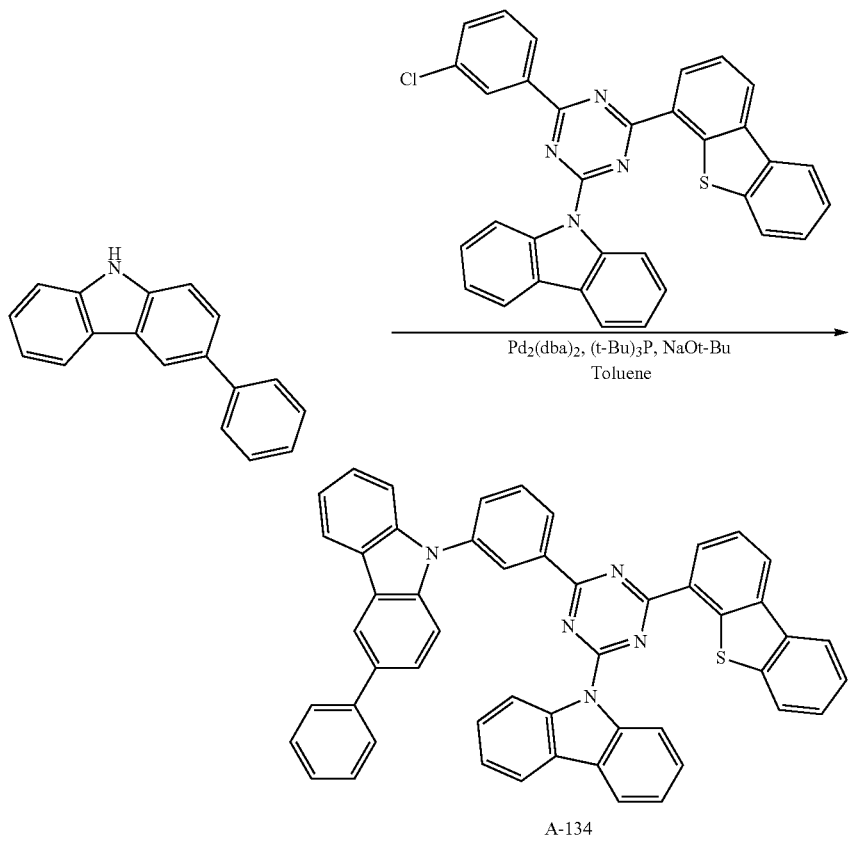

A-134

3-phenyl-9H-carbazole (3 g, 12.3 mmol), 9-(4-(3-chlorophenyl)-6-(dibenzo[b,d]thiophen-4-yl)-1,3,5-triazin-2-yl)-9H-carbazole (7.3 g, 13.5 mmol), Pd$_2$(dba)$_3$ (0.6 g, 0.6 mmol), (t-Bu)$_3$P (0.3 g, 1.3 mmol), and NaOt-Bu (2.4 g, 24.6 mmol) were added to Toluene (100 ml), and heated to reflux for 12 hours. After the reaction was completed, the organic layer was extracted by using methylene chloride, MgSO$_4$ was added thereto and the organic layer was filtered. After removing the solvent from the filtered organic layer, the target compound, Compound A-134 (7.0 g, yield 76%), was obtained through column chromatography.

[LCMS]: 746

Embodiment 1 Manufacturing of Green Organic Electroluminescent Device

The compound A-1 fabricated in the above Fabrication Example 1 was subjected to high purity sublimation purification by a commonly known method and then a green organic electroluminescent device was manufactured as follows.

First, a glass substrate thin-film-coated with indium tin oxide (ITO) to a thickness of 1500 Å was washed with distilled water ultrasonically. After washing with distilled water was completed, the glass substrate was ultrasonically cleaned with a solvent, such as isopropyl alcohol, acetone and methanol, dried, transferred to a UV OZONE cleaner (Power sonic 405, Hwasin Tech), and cleaned for 5 minutes using UV, and then the coated glass substrate was transferred to a vacuum evaporator.

On the ITO transparent electrode prepared as above, m-MTDATA (60 nm)/TCTA (80 nm)/90 wt % of Compound A-1+10 wt % of Ir(ppy)$_3$ (30 nm)/BCP (10 nm)/Alq$_3$ (30 nm)/LiF (1 nm)/Al (200 nm) were laminated in order to manufacture an organic EL device. In such a case, the structure of used m-MTDATA, TCTA, Ir(ppy)$_3$, and BCP is as follows.

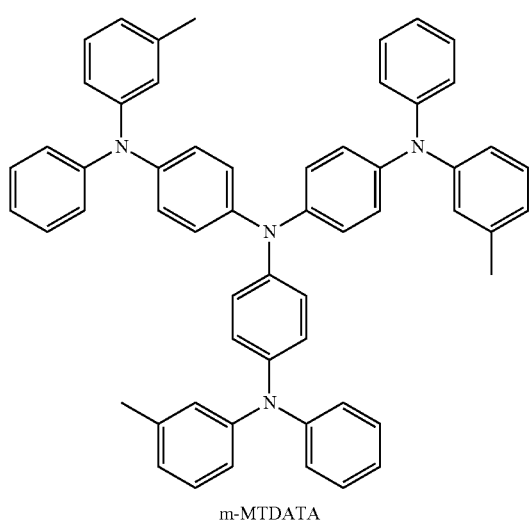

m-MTDATA

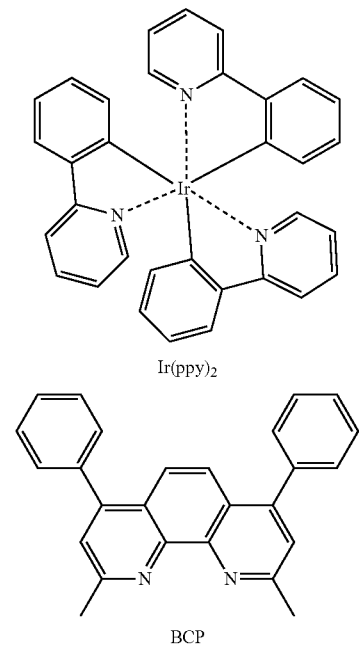

TCTA

Ir(ppy)₂

BCP

Embodiments 2 to 32 Manufacturing of Green Organic Electroluminescent Devices Green organic EL devices were manufactured in the same manner as in Embodiment 1, except that the compound shown in Table 1, instead of Compound A-1, was used as a host material when forming the emissive layer in Embodiment 1.

COMPARATIVE EXAMPLE 1 MANUFACTURING OF GREEN ORGANIC ELECTROLUMINESCENT DEVICE

A green organic EL device was manufactured in the same manner as in Embodiment 1, except that CBP, instead of Compound A-1, was used as a luminescent host material when forming the emissive layer in Embodiment 1. In such a case, the structure of used CBP is as follows.

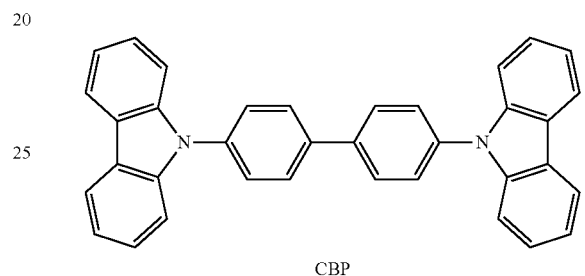

CBP

COMPARATIVE EXAMPLE 2 MANUFACTURING OF GREEN ORGANIC ELECTROLUMINESCENT DEVICE

A green organic EL device was manufactured in the same manner as in Embodiment 1, except the following Compound A, instead of Compound A-1, was used as a luminescent host material when forming the emissive layer in Embodiment 1. In such a case, the structure of used Compound A is as follows.

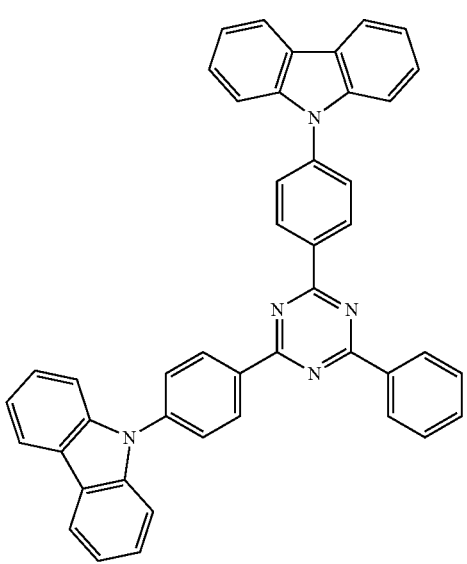

A

COMPARATIVE EXAMPLE 3
MANUFACTURING OF GREEN ORGANIC ELECTROLUMINESCENT DEVICE

A green organic EL device was manufactured in the same manner as in Embodiment 1, except the following Compound B, instead of Compound A-1, was used as a luminescent host material when forming the emissive layer in Embodiment 1. In such a case, the structure of used Compound B is as follows.

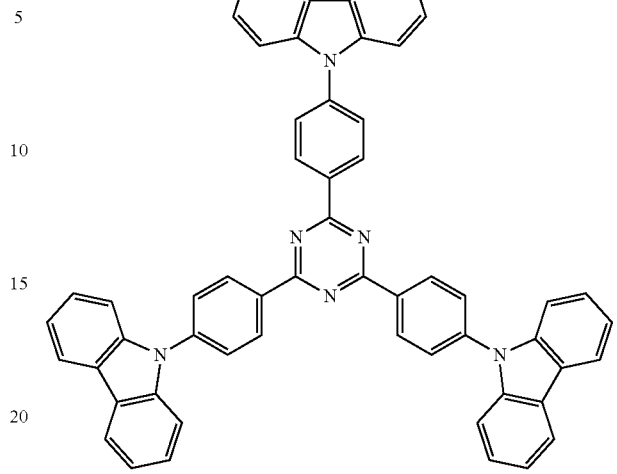

C

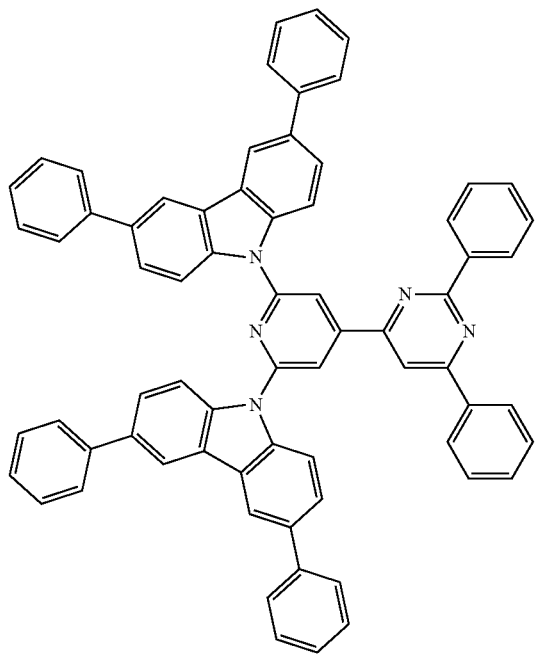

B

COMPATATIVE EXAMPLE 4
MANUFCATURING OF GREEN ORGANIC ELECTGROLUMINESCENT DEVICE

A green organic EL device was manufactured in the same manner as in Embodiment 1, except the following Compound C, instead of Compound A-1, was used as a luminescent host material when forming the emissive layer in Embodiment 1. In such a case, the structure of used Compound C is as follows.

COMPARATIVE EXAMPLE 5
MANUFACTURING OF GREEN ORGANIC ELECTGROLUMINESCENT DEVICE

A green organic EL device was manufactured in the same manner as in Embodiment 1, except the following Compound D, instead of Compound A-1, was used as a luminescent host material when forming the emissive layer in Embodiment 1. In such a case, the structure of used Compound D is as follows.

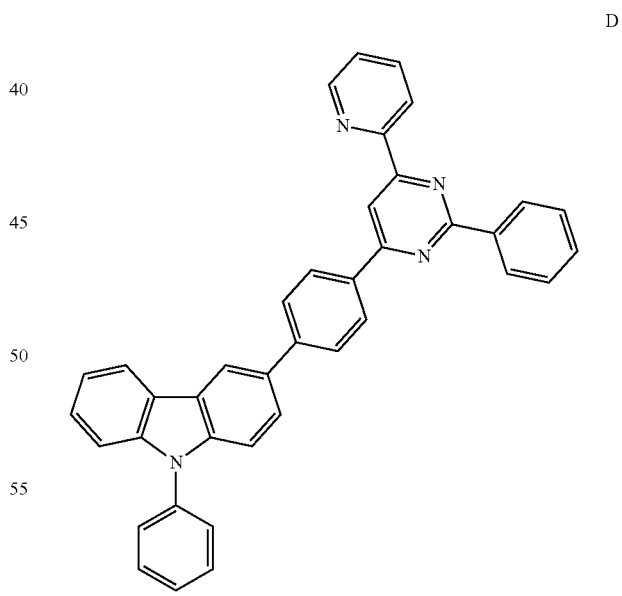

D

COMPARATIVE EXAMPLE 6
MANUFACTURING OF GREEN ORGANIC ELECTROLUMINESCENT DEVICE

A green organic EL device was manufactured in the same manner as in Embodiment 1, except the following Compound E, instead of Compound A-1, was used as a luminescent host material when forming the emissive layer in Embodiment 1. In such a case, the structure of used Compound E is as follows.

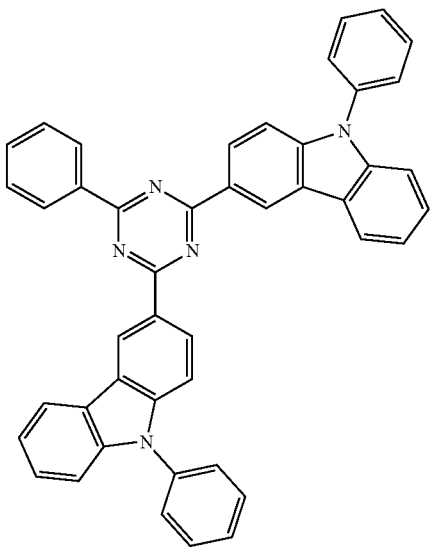

E

EVALUATION EXAMPLE 1

For each of the green organic EL devices manufactured in Embodiments 1 to 32 and Comparative Examples 1 to 6, a driving voltage, a current efficiency and an emission peak at a current density of 10 mA/cm² were measured and the results are shown in Table 1 below.

TABLE 1

| Sample | Host | Driving voltage(V) | Emission peak(nm) | Current efficiency(cd/A) |
|---|---|---|---|---|
| Embodiment 1 | A-1 | 3.8 | 458 | 54.0 |
| Embodiment 2 | A-2 | 3.8 | 458 | 59.5 |
| Embodiment 3 | A-3 | 3.7 | 458 | 56.5 |
| Embodiment 4 | A-4 | 3.8 | 458 | 58.3 |
| Embodiment 5 | A-5 | 3.7 | 459 | 59.3 |
| Embodiment 6 | A-8 | 4.1 | 458 | 57.0 |
| Embodiment 7 | A-15 | 3.9 | 458 | 59.1 |
| Embodiment 8 | A-24 | 3.9 | 458 | 57.0 |
| Embodiment 9 | A-29 | 4.0 | 459 | 59.1 |
| Embodiment 10 | A-36 | 3.6 | 458 | 58.0 |
| Embodiment 11 | A-39 | 4.1 | 458 | 60.5 |
| Embodiment 12 | A-43 | 3.8 | 459 | 57.7 |
| Embodiment 13 | A-51 | 3.7 | 458 | 58.6 |
| Embodiment 14 | A-57 | 4.1 | 458 | 55.9 |
| Embodiment 15 | A-61 | 3.8 | 458 | 58.5 |
| Embodiment 16 | A-64 | 4.1 | 458 | 57.0 |
| Embodiment 17 | A-71 | 3.8 | 458 | 59.1 |
| Embodiment 18 | A-72 | 3.9 | 458 | 58.0 |
| Embodiment 19 | A-73 | 3.6 | 458 | 60.0 |
| Embodiment 20 | A-74 | 3.8 | 459 | 58.8 |
| Embodiment 21 | A-75 | 3.8 | 457 | 54.0 |
| Embodiment 22 | A-78 | 3.7 | 458 | 57.0 |
| Embodiment 23 | A-85 | 3.8 | 459 | 59.1 |
| Embodiment 24 | A-94 | 3.8 | 458 | 58.0 |
| Embodiment 25 | A-99 | 3.7 | 457 | 54.8 |
| Embodiment 26 | A-106 | 3.7 | 457 | 60.5 |
| Embodiment 27 | A-109 | 3.8 | 458 | 57.7 |
| Embodiment 28 | A-113 | 3.8 | 459 | 58.6 |
| Embodiment 29 | A-121 | 3.7 | 458 | 55.9 |
| Embodiment 30 | A-127 | 3.8 | 457 | 58.5 |

TABLE 1-continued

| Sample | Host | Driving voltage(V) | Emission peak(nm) | Current efficiency(cd/A) |
|---|---|---|---|---|
| Embodiment 31 | A-131 | 3.8 | 458 | 59.1 |
| Embodiment 32 | A-134 | 3.7 | 458 | 60.0 |
| Comparative example 1 | CBP | 5.5 | 459 | 44.2 |
| Comparative example 2 | A | 5.0 | 457 | 50.1 |
| Comparative example 3 | B | 4.7 | 457 | 46.5 |
| Comparative example 4 | C | 4.9 | 458 | 47.1 |
| Comparative example 5 | D | 4.8 | 457 | 48.9 |
| Comparative example 6 | E | 4.7 | 458 | 46.4 |

As shown in Table 1, it was appreciated that the green organic EL devices of Embodiments 1 to 32 using the compounds A-1 to A-32 as the host material in the emissive layer according to the present disclosure exhibited excellent current efficiency and driving voltage, as compared with green organic EL devices (Comparative Examples 1 to 6) in which CBP was used as the host material in the emissive layer.

The invention claimed is:

1. A compound represented by the following Chemical Formula 1:

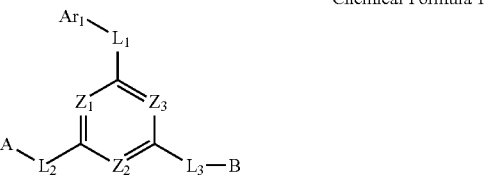

Chemical Formula 1 wherein
 $Z_1$ to $Z_3$ are the same as or different from each other, each independently being N or $C(R_1)$, wherein at least one of $Z_1$ to $Z_3$ is N,
 wherein when $C(R_1)$ are plural in number, the plurality of $R_1$, are the same or different from each other and each independently selected from the group consisting of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group and a $C_6$ to $C_{60}$ arylamine group,
 $L_1$ to $L_3$ are the same as or different from each other, each independently being a single bond, or selected from the group consisting of: a $C_6$ to $C_{18}$ arylene group and a heteroarylene group having 5 to 18 nuclear atoms,
 $Ar_1$ is selected from the group consisting of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group, and a $C_6$ to $C_{60}$ arylamine group, A is selected from the group consisting of: a substituent having an asymmetric structure of the following Chemical Formulas 2 and 3, B is selected from the group consisting of: a substituent having an asymmetric structure of the following Chemical Formula 3, and a substituent of the following Chemical Formulas 4 and 5,

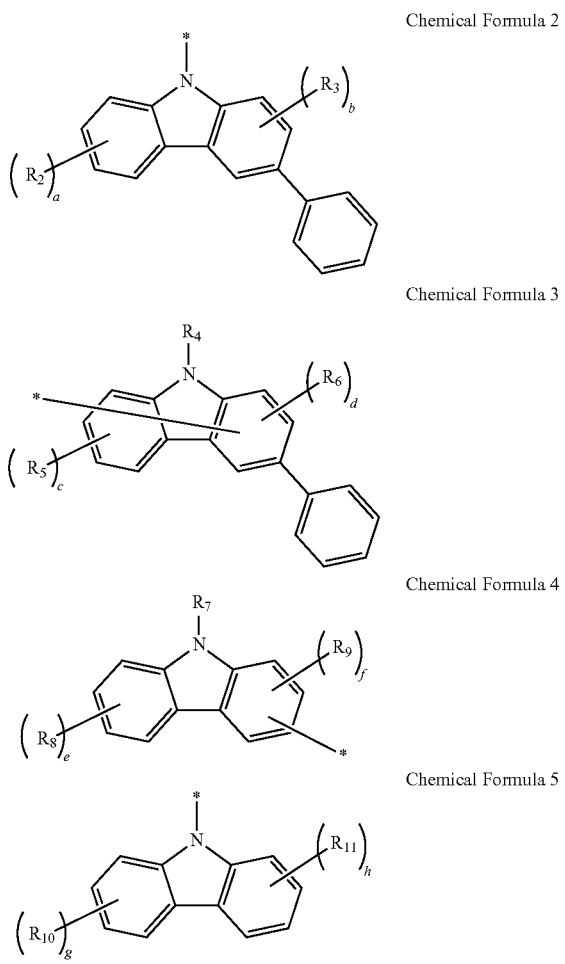

wherein

"*" are each a site connected to $L_2$ or $L_3$ of Chemical Formula 1, a, c, e, g and h are each an integer ranging from 0 to 4, while b, d and f are each an integer ranging from 0 to 3, wherein c+d is in a range of 0≤c+d≤6, wherein a plurality of $R_2$ are the same or different from each other, a plurality of $R_3$ are the same or different from each other, a plurality of $R_4$ are the same or different from each other, a plurality of $R_5$ are each the same or different from each other, a plurality of $R_6$ are the same as or different from each other, a plurality of $R_7$ are the same as or different from each other, a plurality of the $R_8$ are the same as or different from each other, a plurality of the $R_9$ are the same as or different from each other, a plurality of the $R_{10}$ are the same as or different from each other, a plurality of $R_{11}$ are each the same or different from each other, $R_2$ to $R_{11}$ are each independently selected from the group consisting of: deuterium, a halogen group, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group, or may combine with an adjacent group to form a fused ring, and the arylene group and the heteroarylene group of $L_1$ to $L_3$; and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the alkylphosphine group, the arylphosphine group, the arylphosphine oxide group and the arylamine group of $Ar_1$ and $R_1$ to $R_{11}$ are each independently substituted or unsubstituted with one or more kinds of substituents selected from the group consisting of: deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_6$ to $C_{60}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group and a $C_6$ to $C_{60}$ arylsilyl group, wherein when the substituents are plural in number, the substituents are the same as or different from each other.

2. The compound of claim 1, which is represented by any one of the following Chemical Formulas 8 to 10:

[Chemical Formula 8]

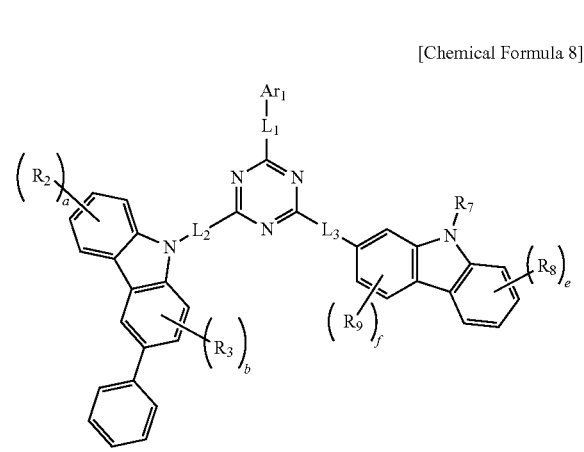

-continued

[Chemical Formula 9]

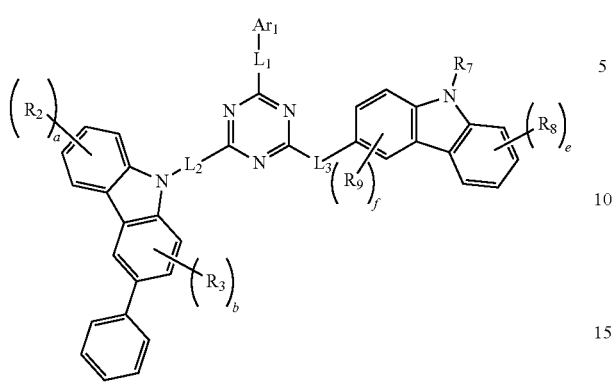

[Chemical Formula 10]

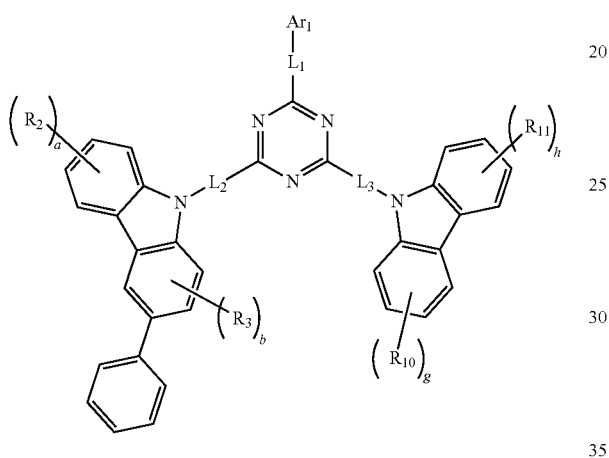

wherein

L₁ to L₃, Ar₁, R₂, R₃, R₇ to R₁₁, a, b, e, f, g and h are the same as those defined in claim 1, respectively.

3. The compound of claim 1, wherein each of $Z_1$ to $Z_3$ is N.

4. The compound of claim 1, wherein Ar₁ is selected from the group consisting of: a $C_6$ to $C_{60}$ aryl group and a heteroaryl group having 5 to 60 nuclear atoms.

5. The compound of claim 1, wherein Ar₁ is a substituent selected from the group consisting of the following substituents S1 to S8:

S1

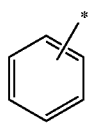

S2

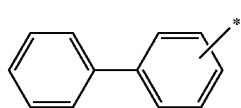

S3

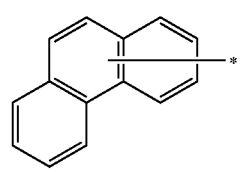

-continued

S4

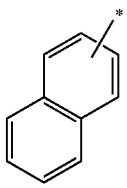

S5

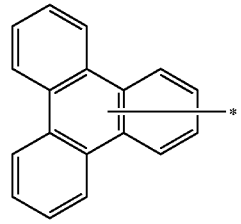

S6

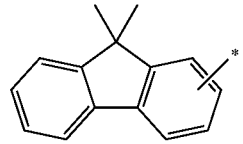

S7

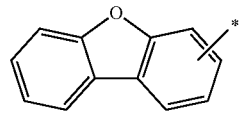

S8

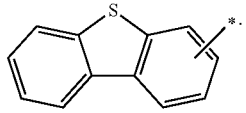

6. The compound of claim 1, wherein the compound of the Chemical Formula 1 is selected from the following Compounds:

A-1

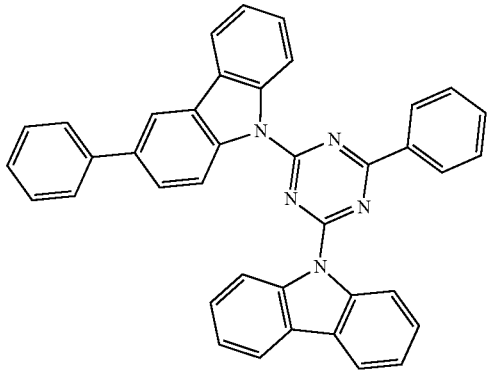

A-4
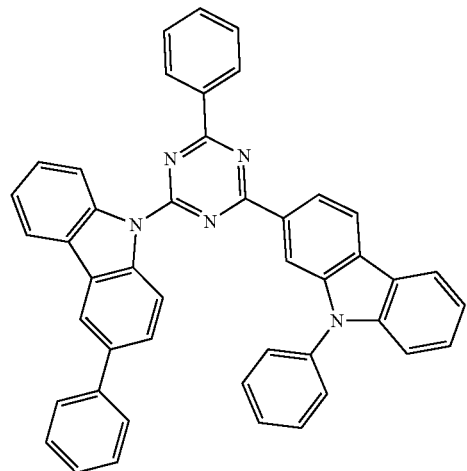
A-5
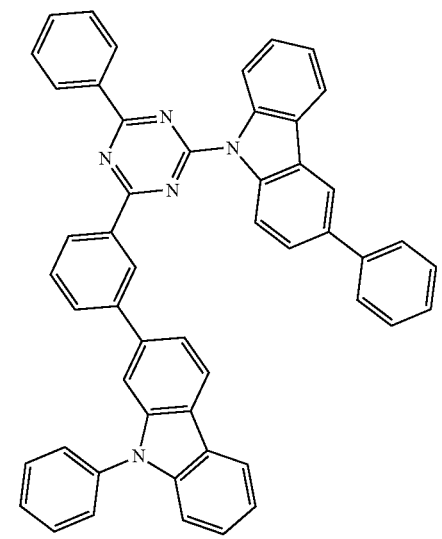
A-7
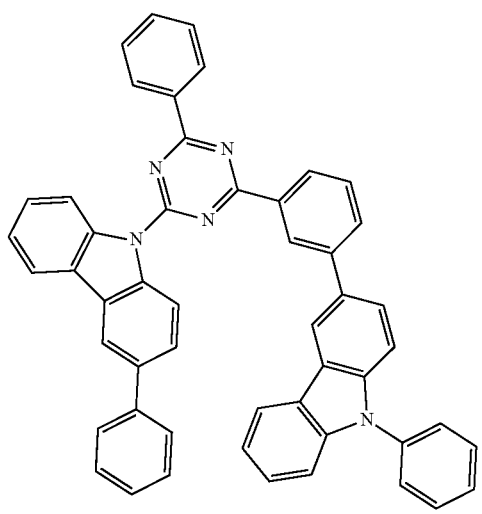
A-8
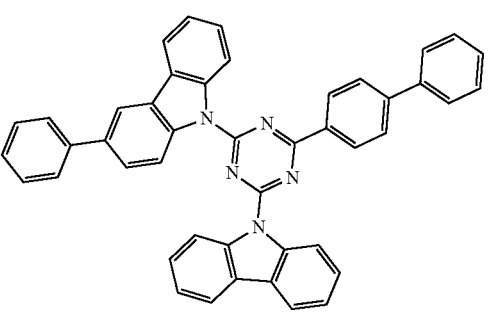
A-11
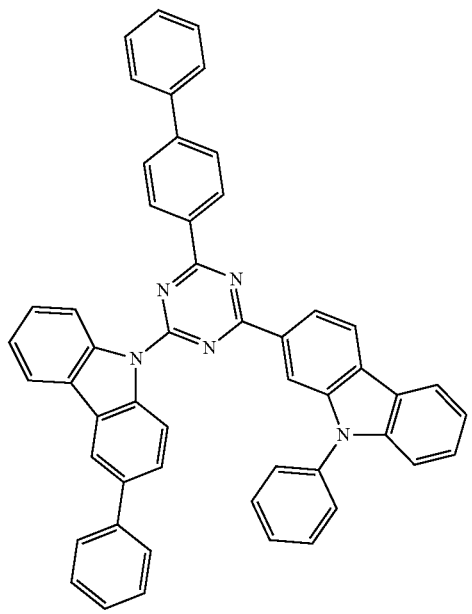

-continued
A-12
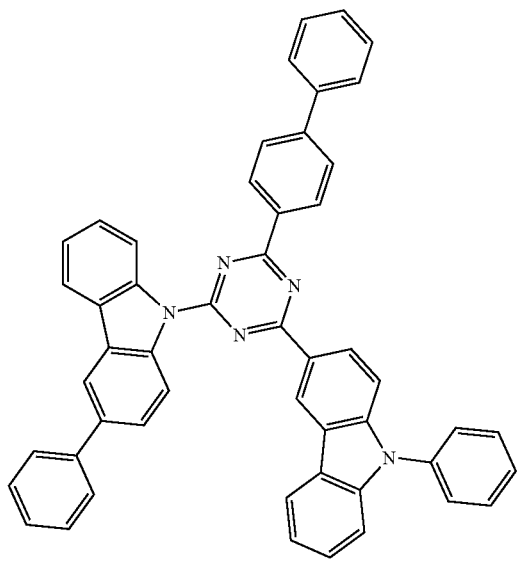
A-13
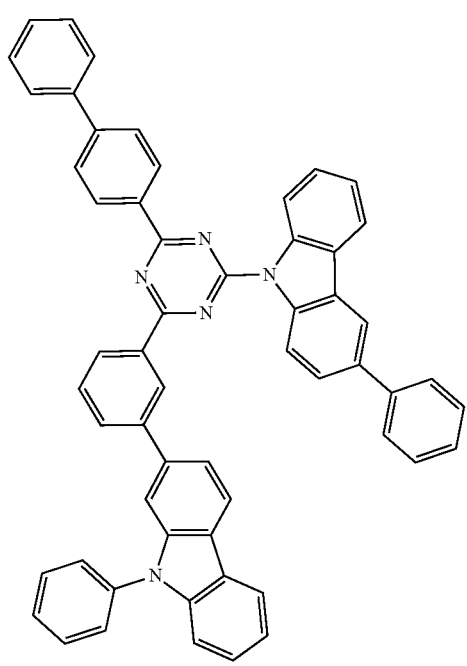
A-14
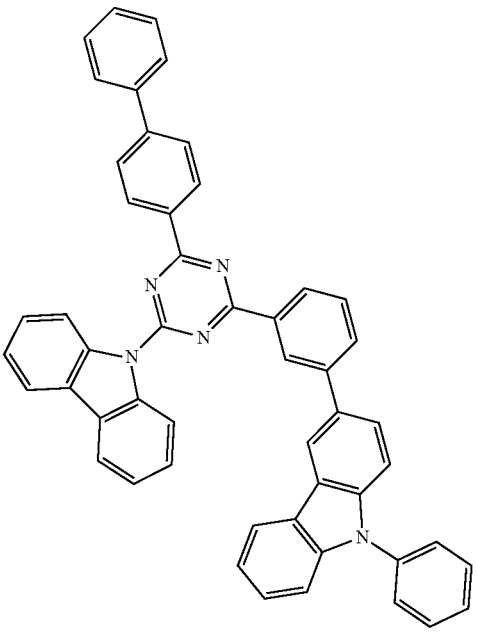
A-15
A-18
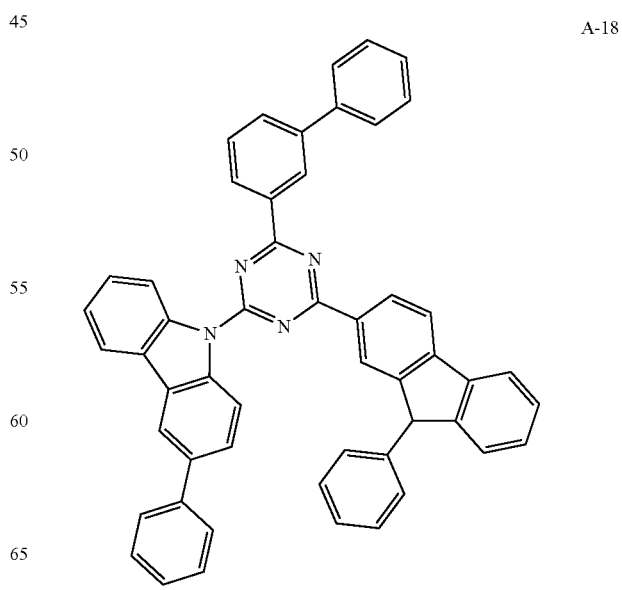

A-19
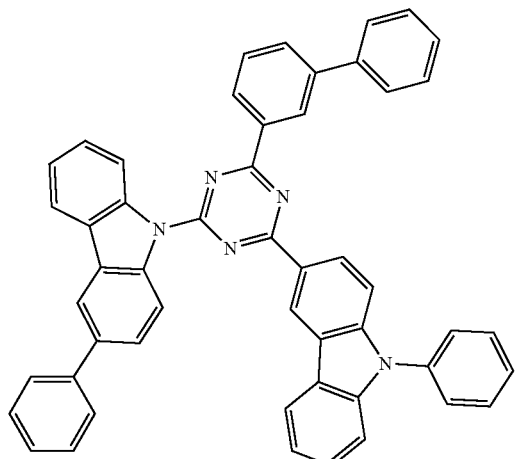
A-20
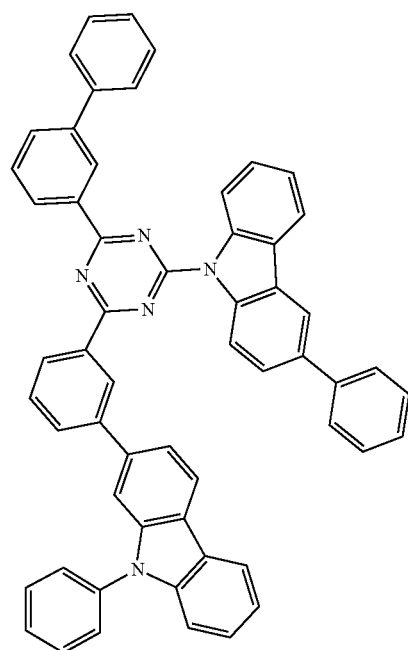
A-21
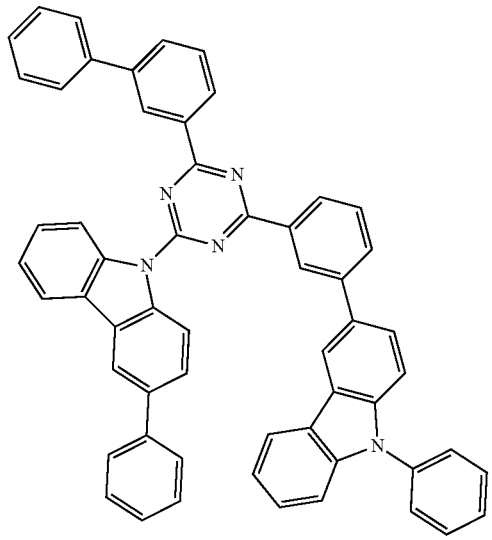
A-22
A-25
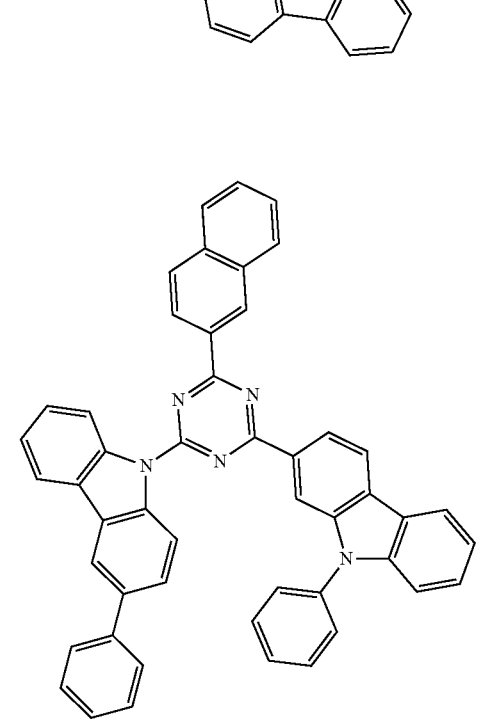

A-26
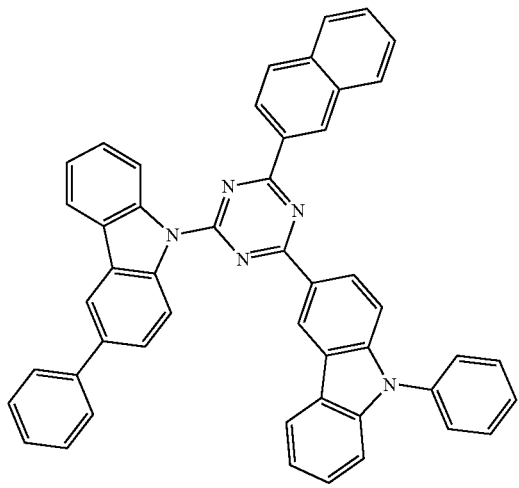
A-27
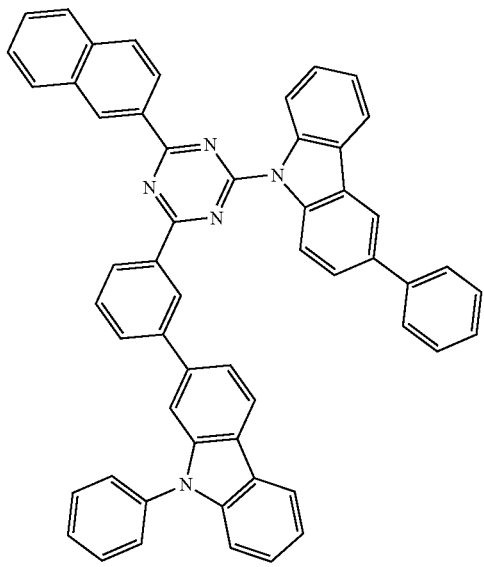
A-28
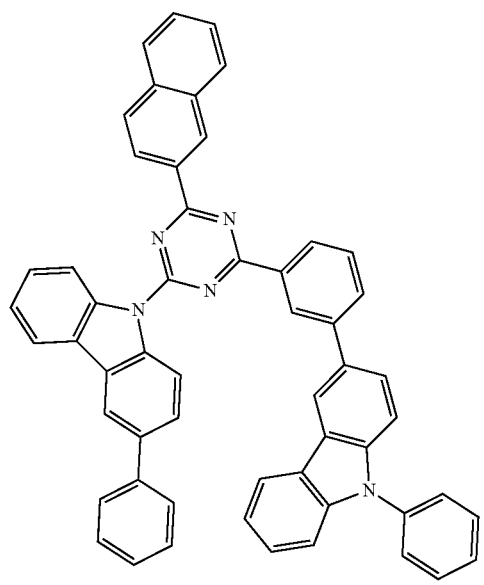
A-29
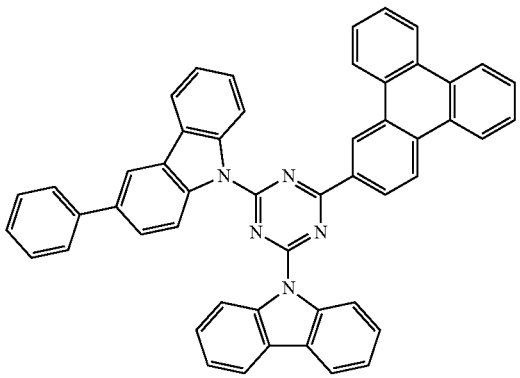
A-32
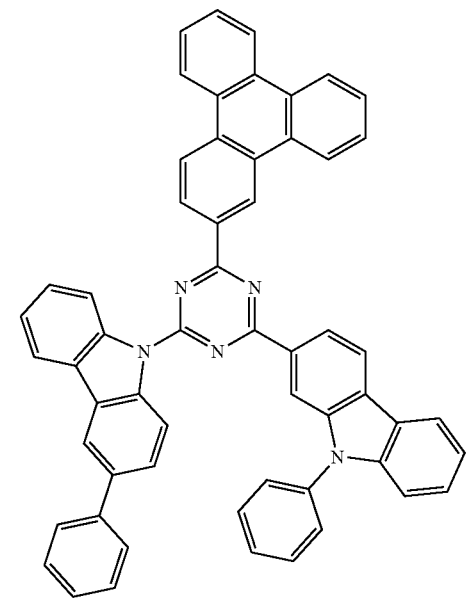
A-33
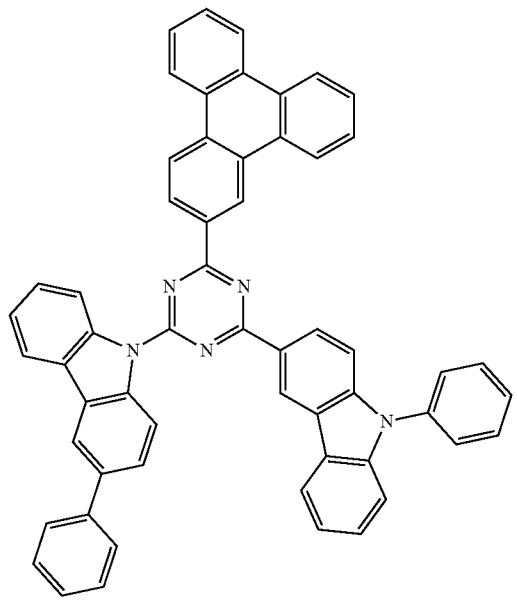

A-34
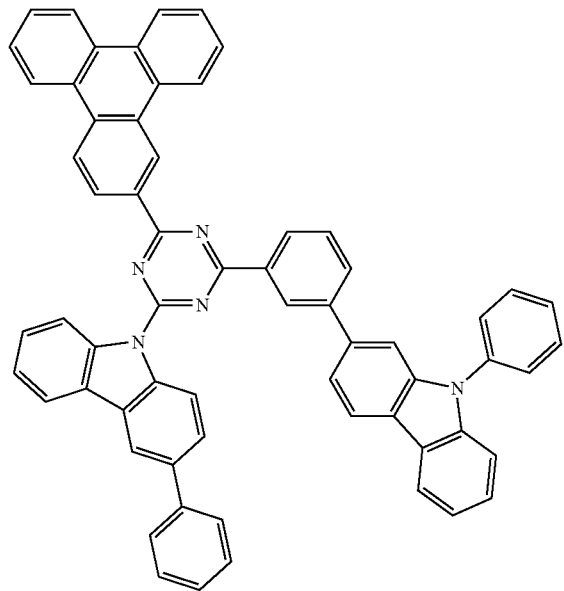
A-35
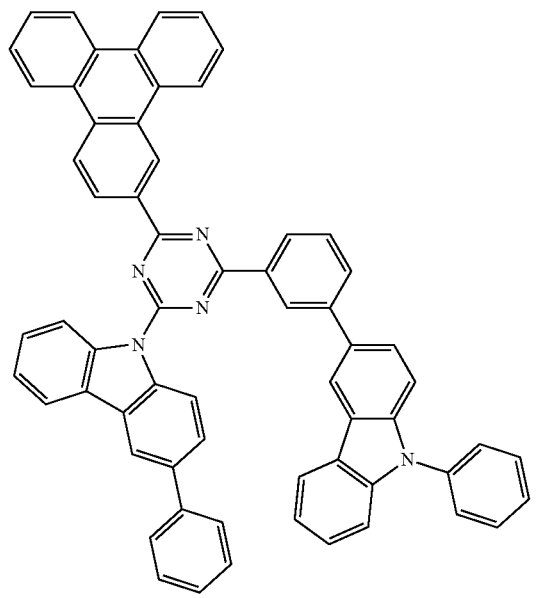
A-36
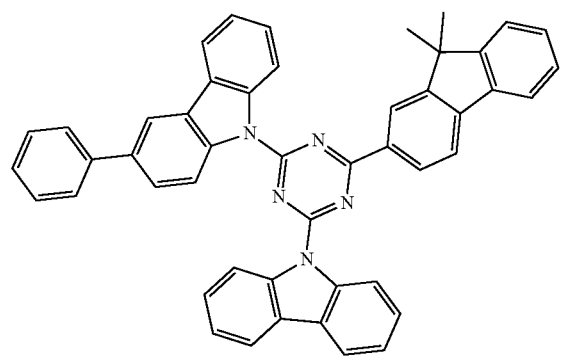
A-39
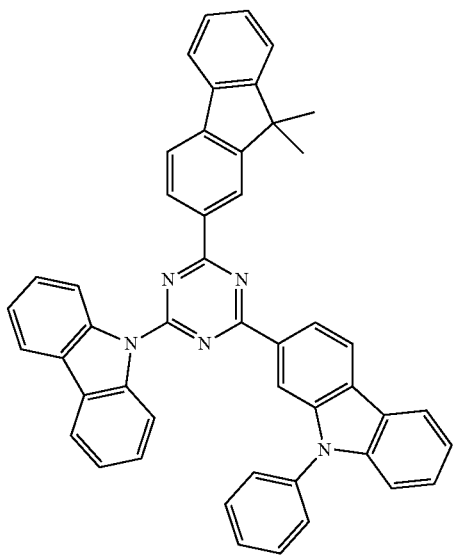
A-40
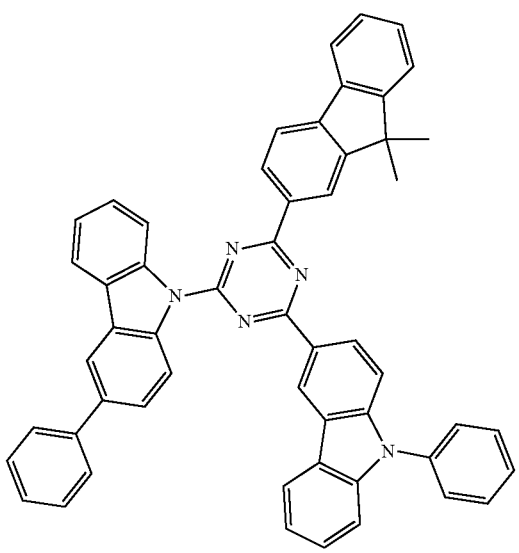

A-41
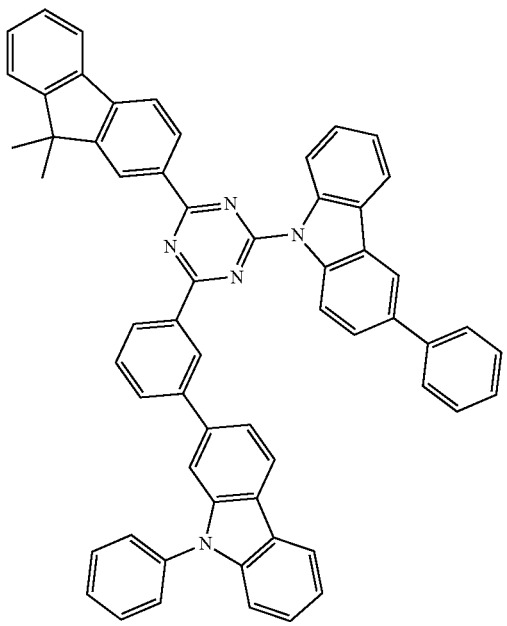
A-42
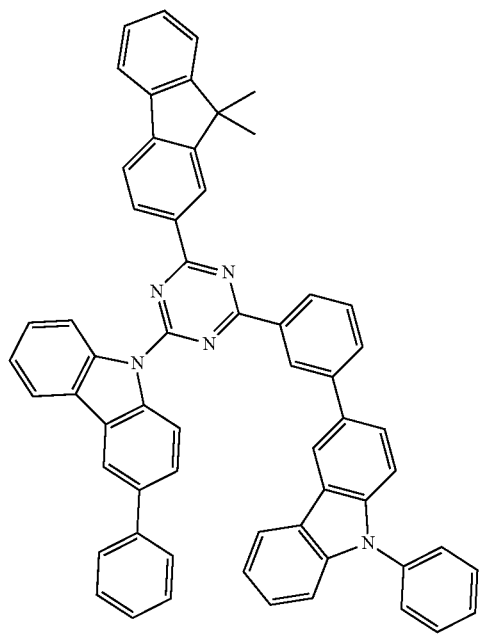
A-43
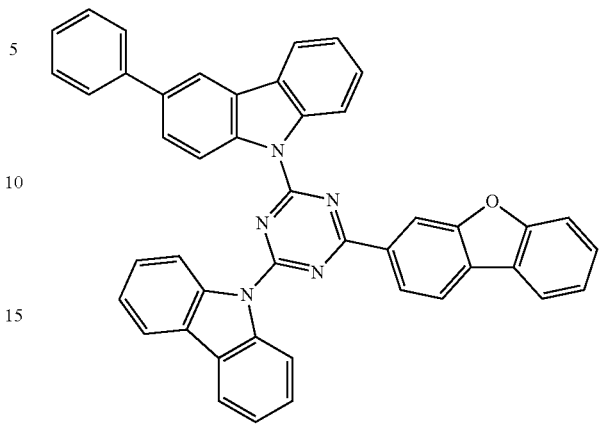
A-46
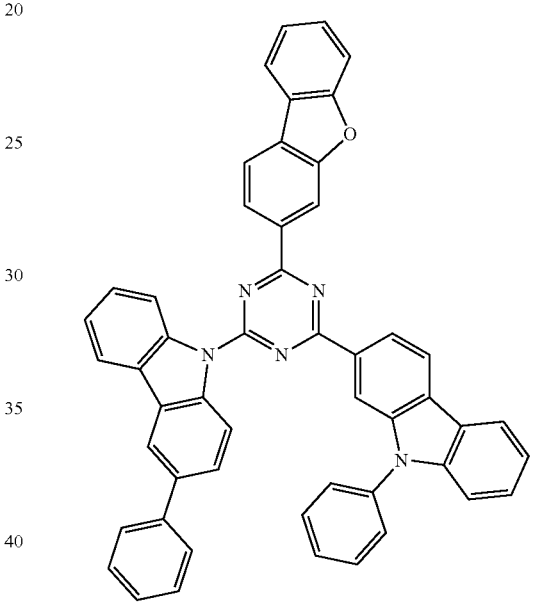
A-47
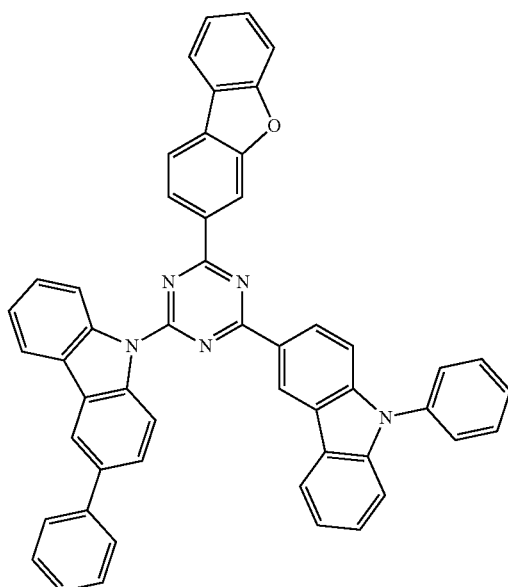

A-48
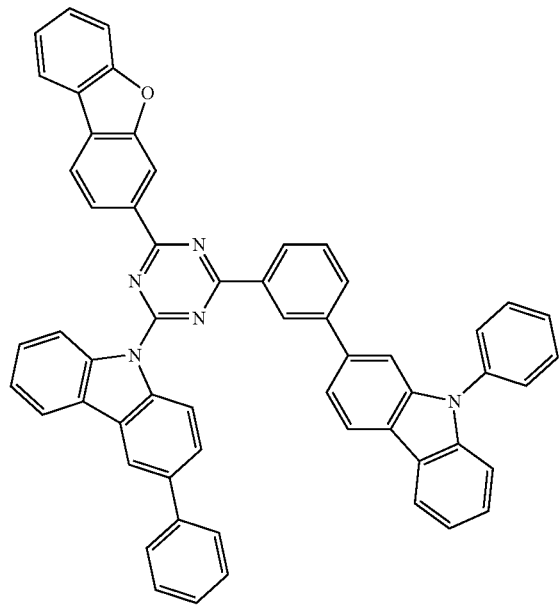
A-49
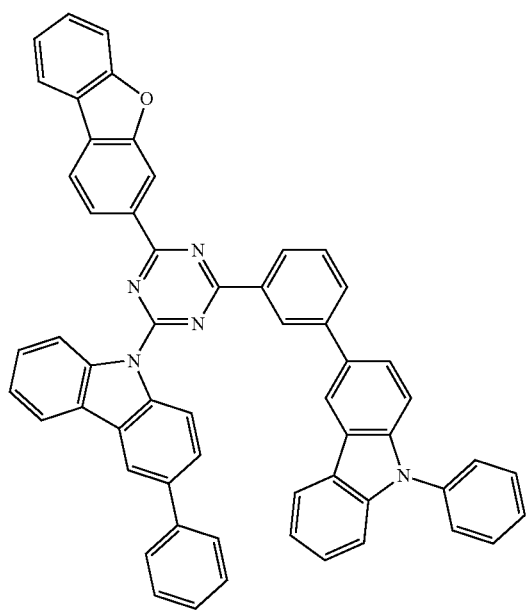
A-50
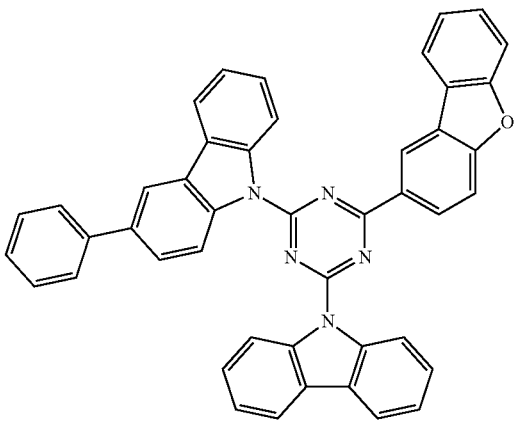
A-53
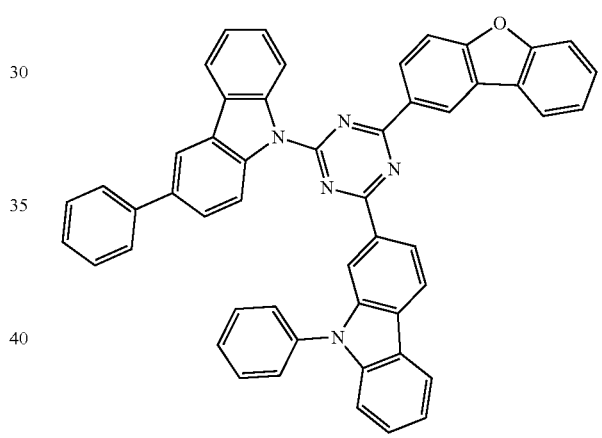
A-54
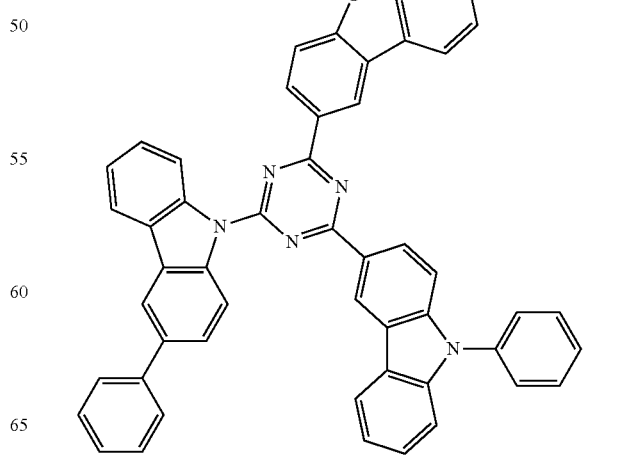

A-55
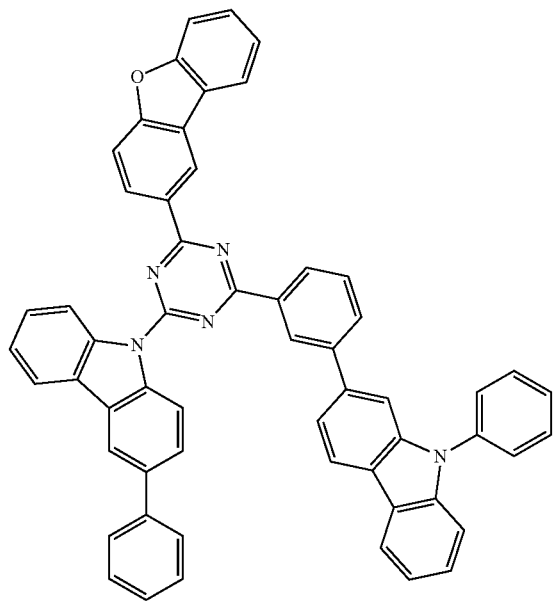
A-56
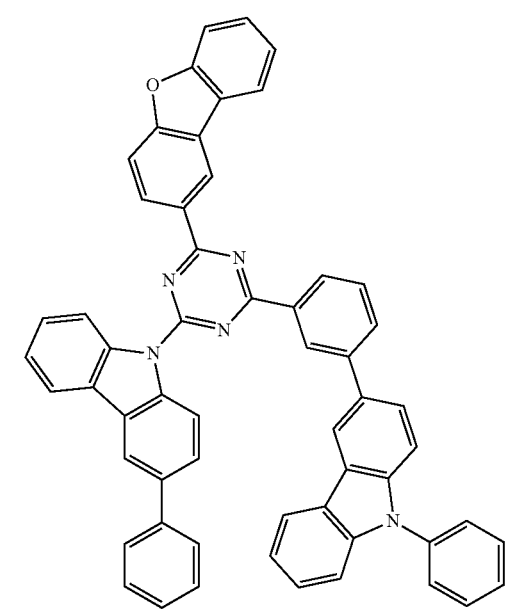
A-57
A-60
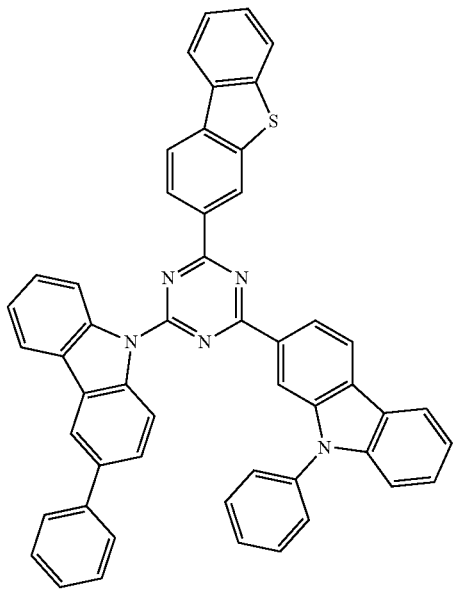
A-61
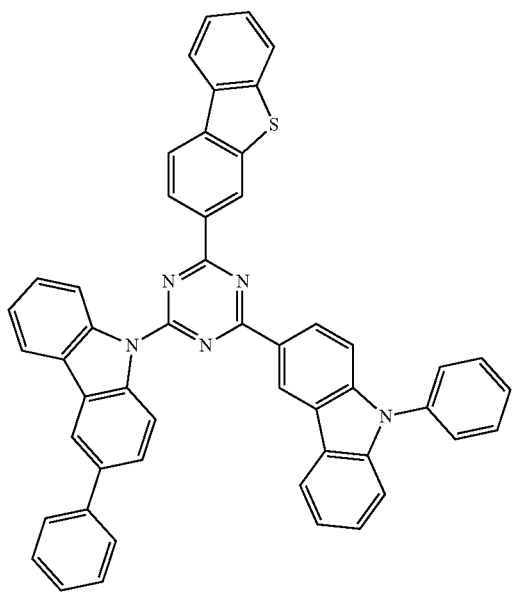

A-62
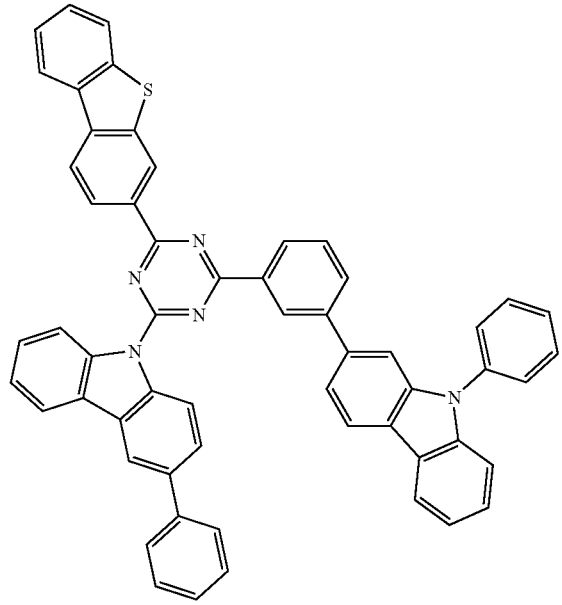
A-67
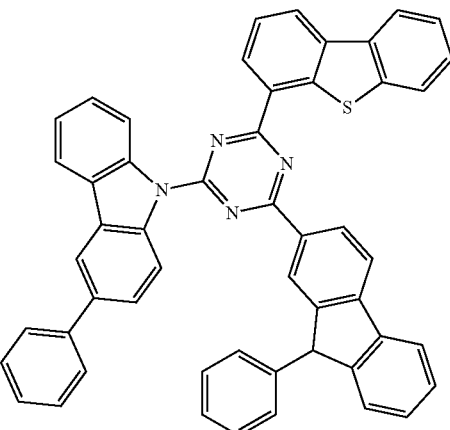
A-63
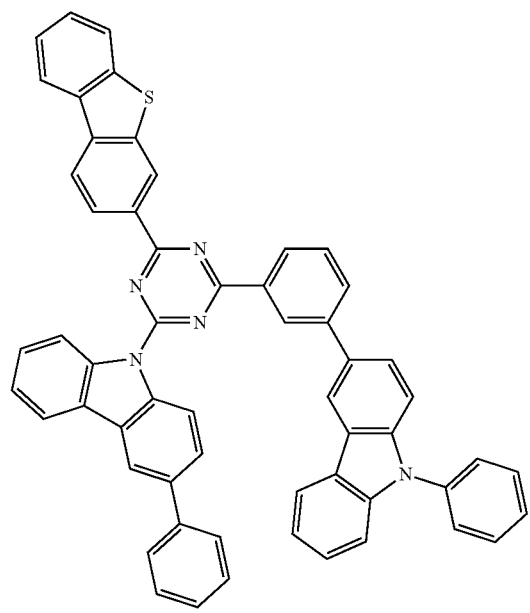
A-68
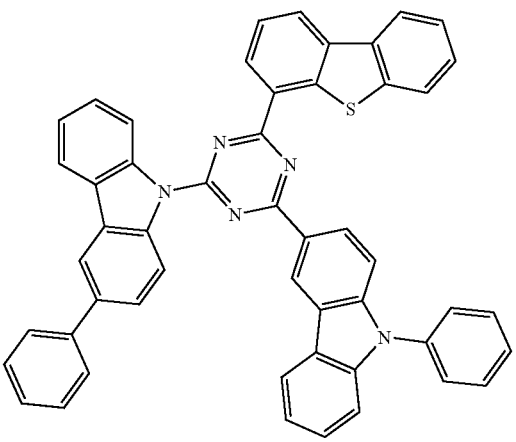
A-64
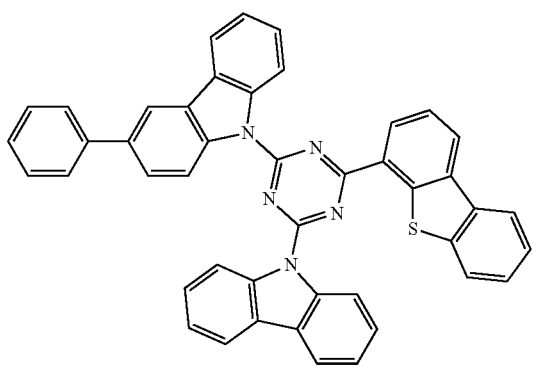
A-69
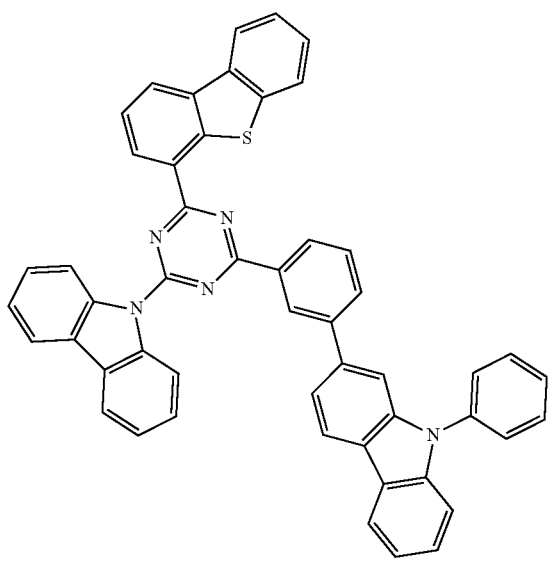

A-70
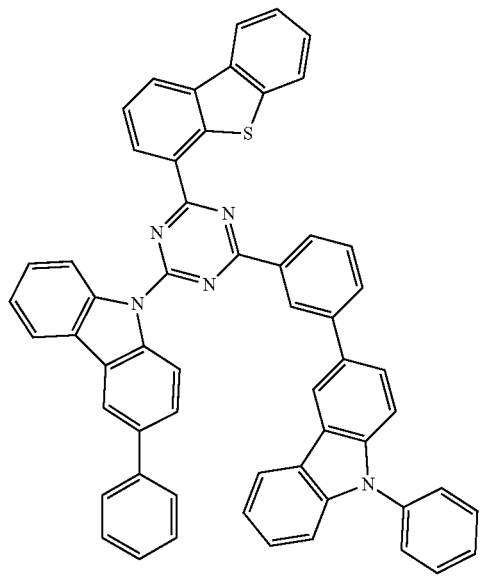
A-71
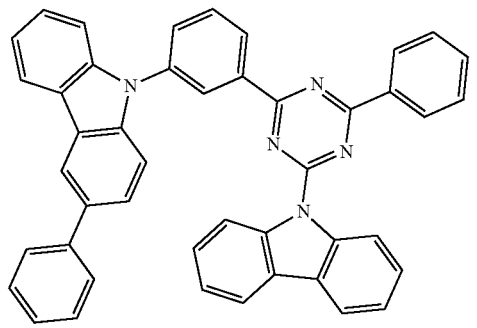
A-74
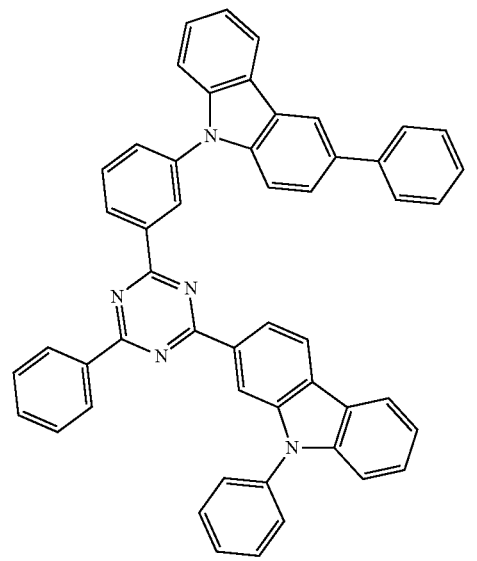
A-75
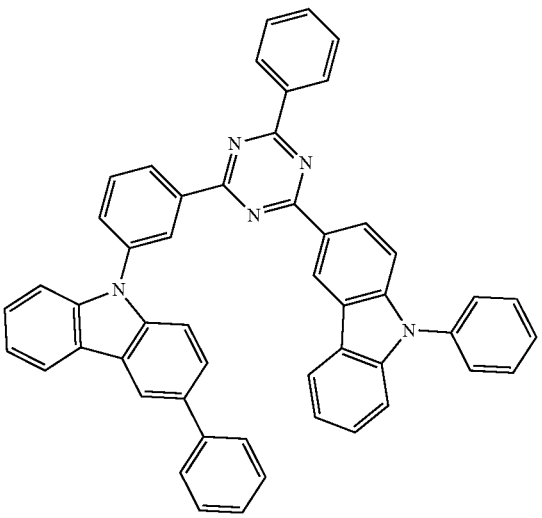
A-76
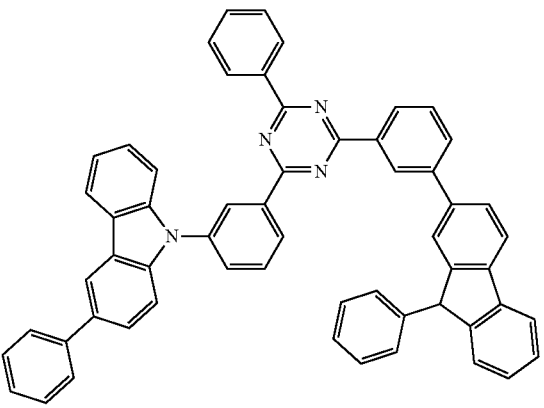
A-77
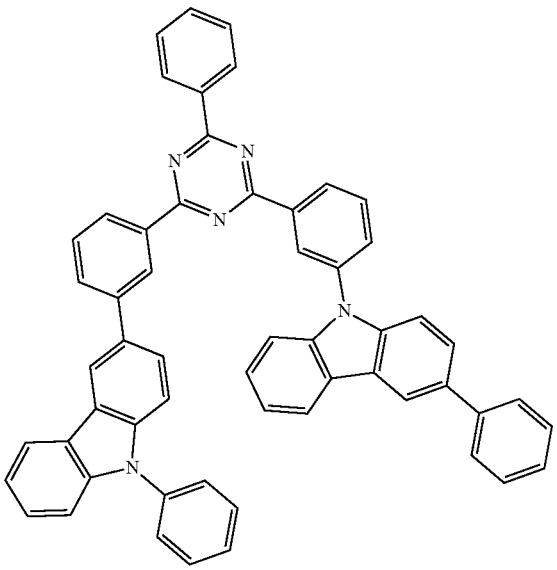

-continued
A-78
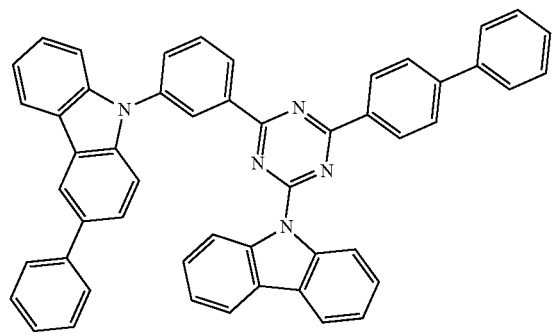
A-81
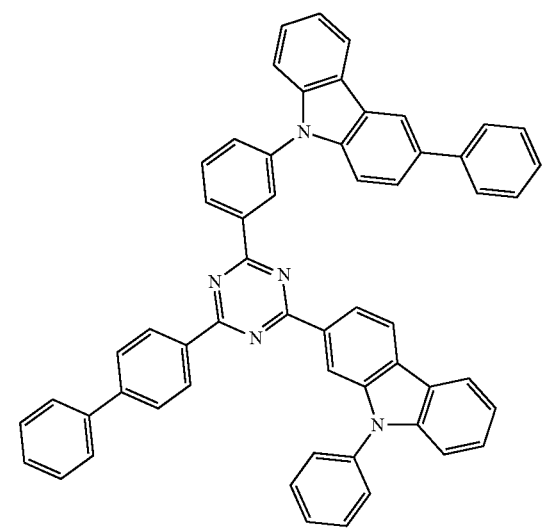
A-82
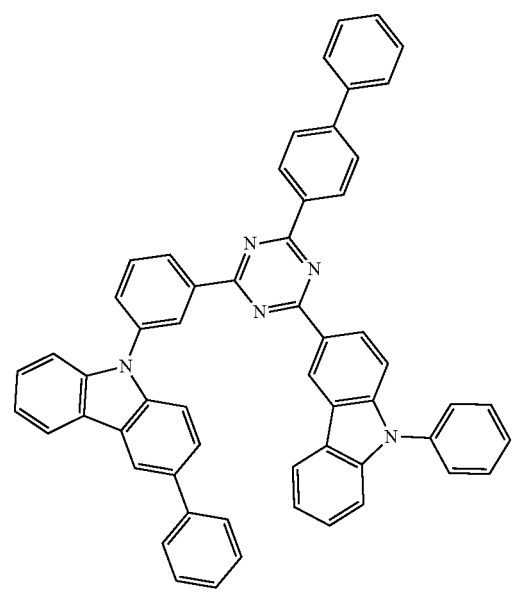
-continued
A-83
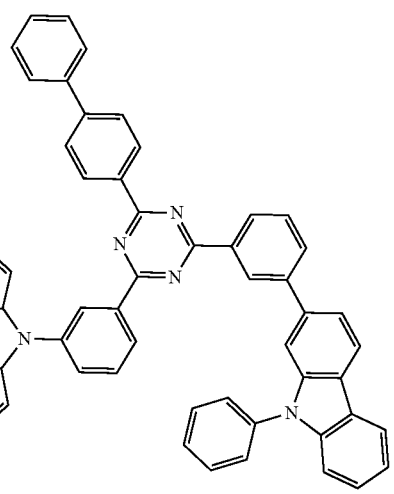
A-84
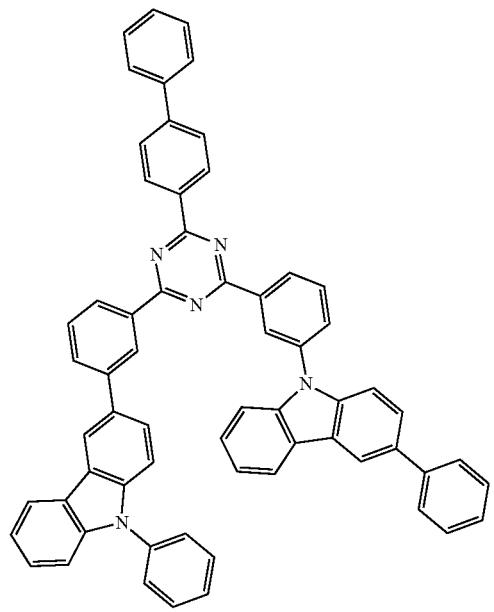
A-85
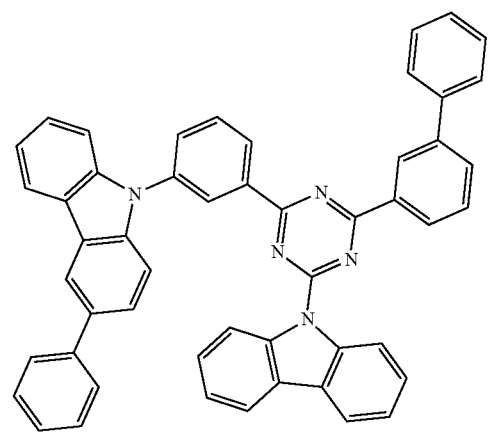

A-88
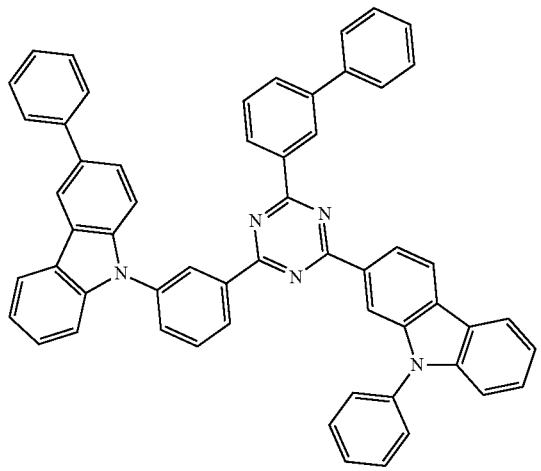
A-89
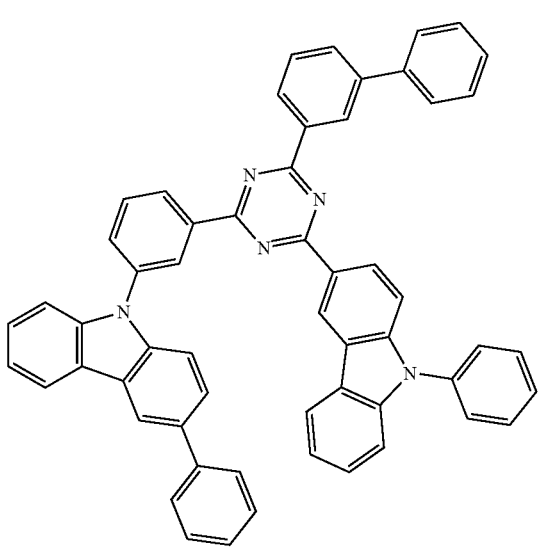
A-90
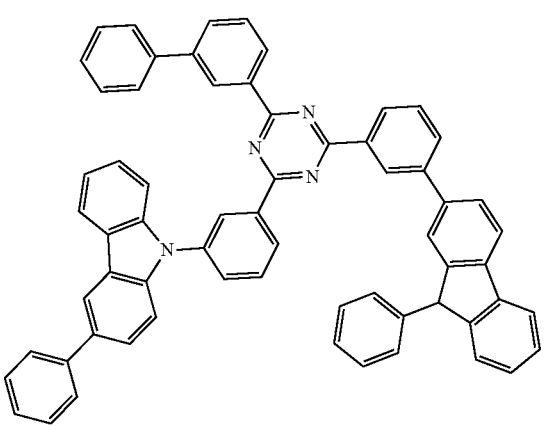
A-91
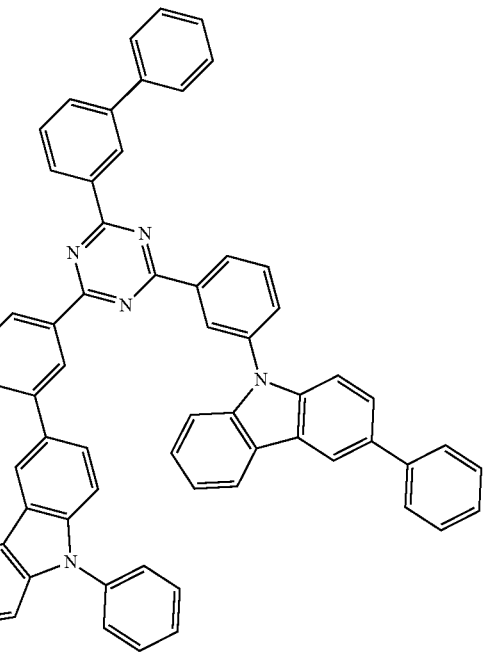
A-92
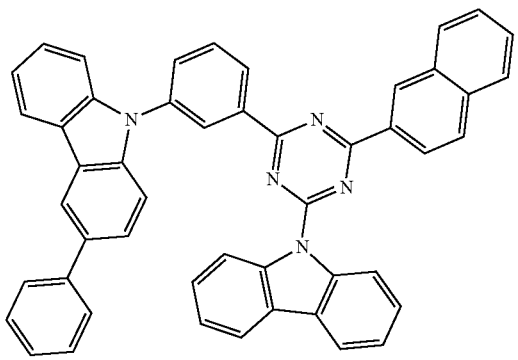
A-95
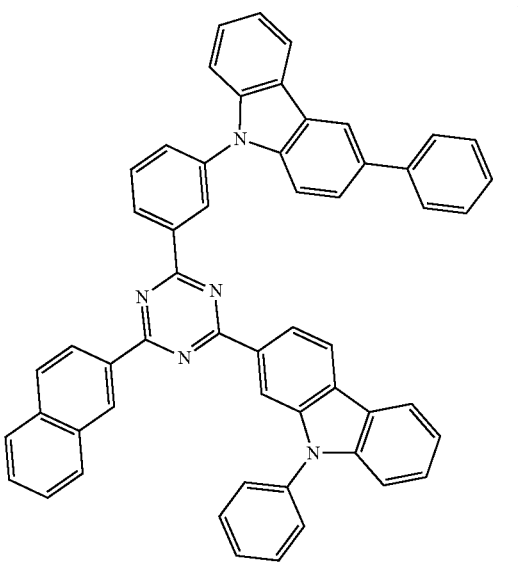

A-96
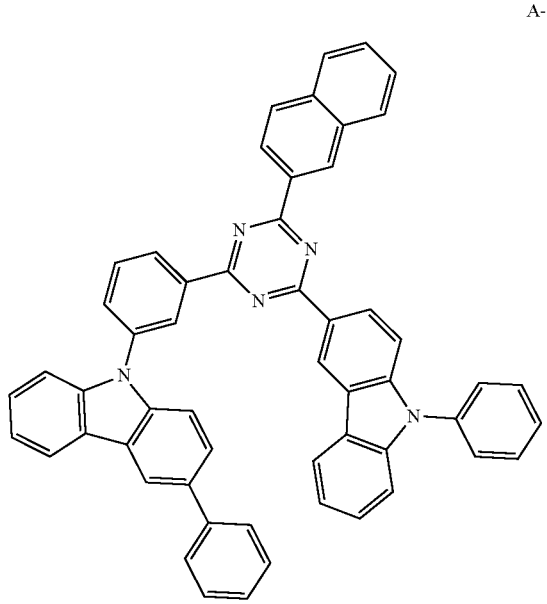
A-97
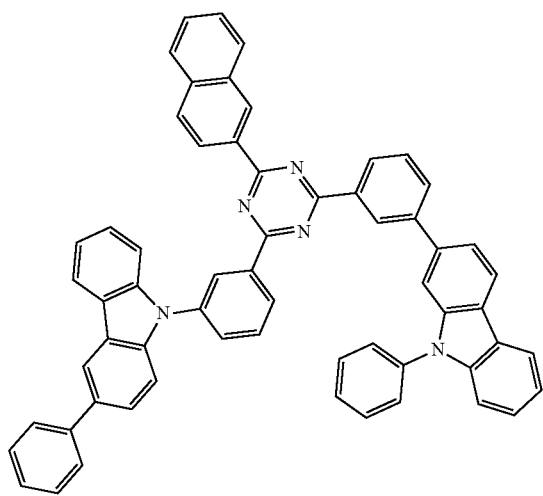
A-98
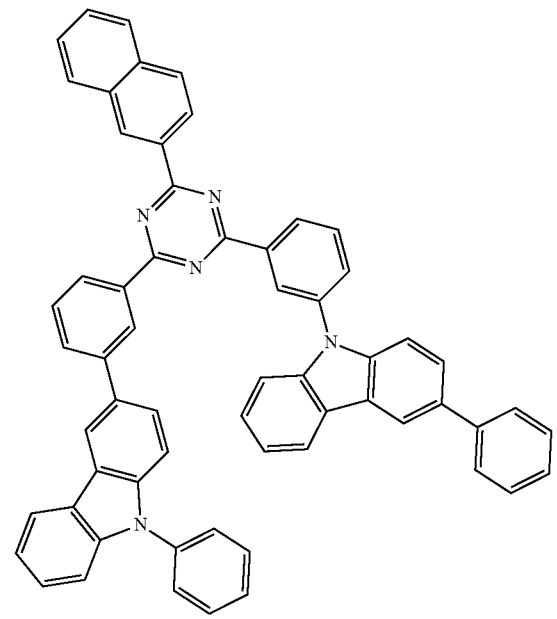
A-99
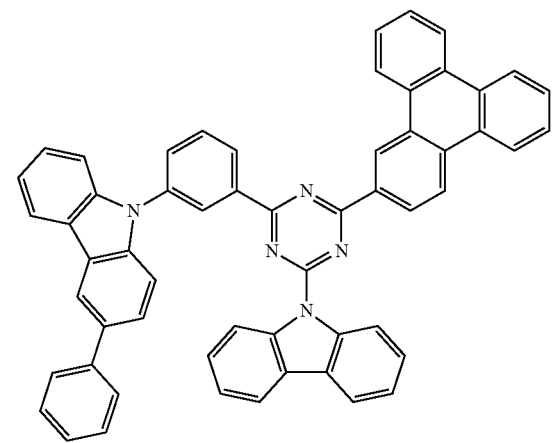

A-102
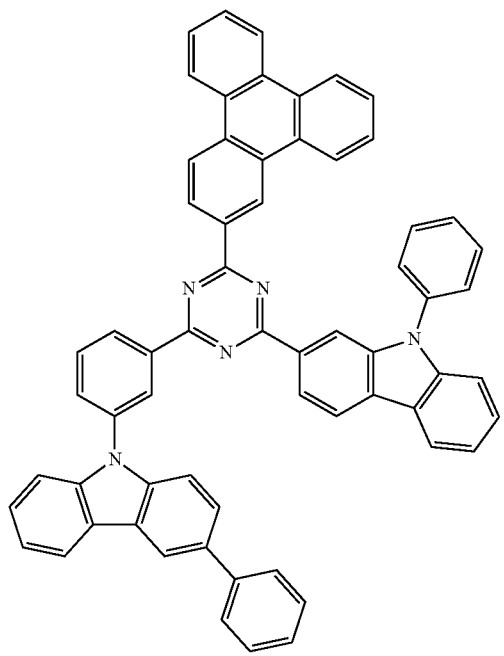
A-103
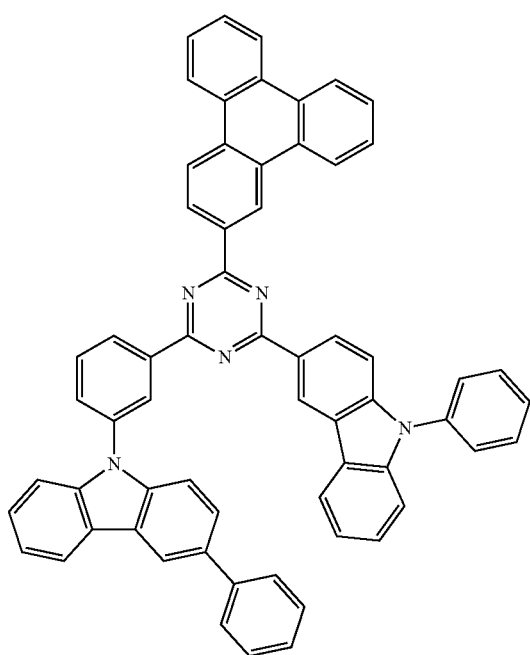
A-104
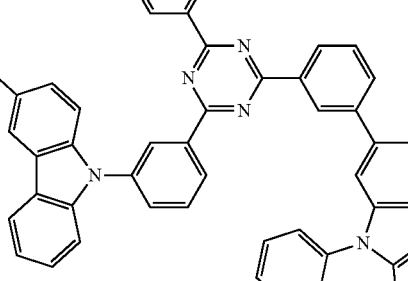
A-105
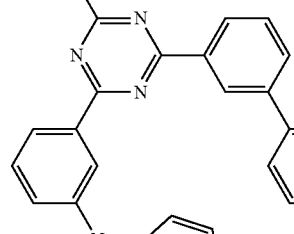
A-106
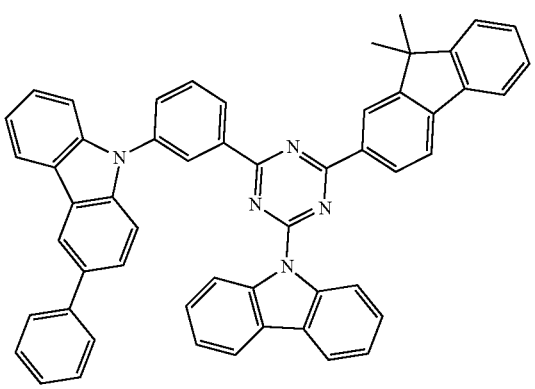

-continued
A-109
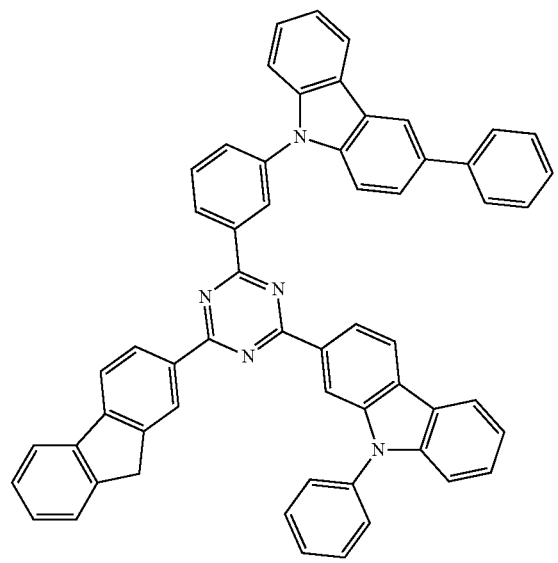
A-110
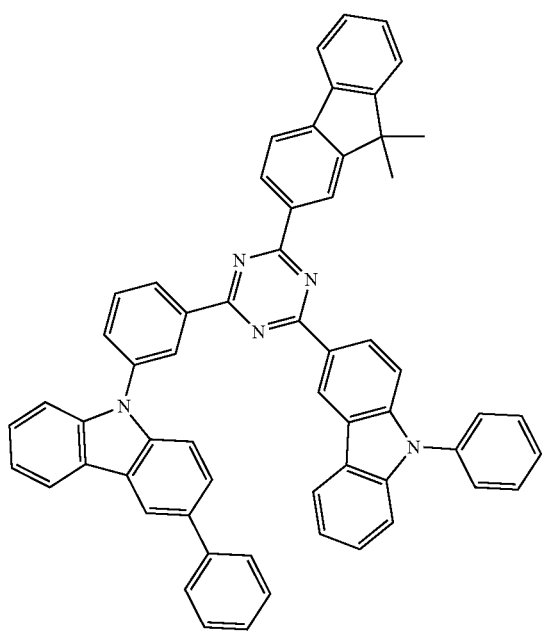
A-111
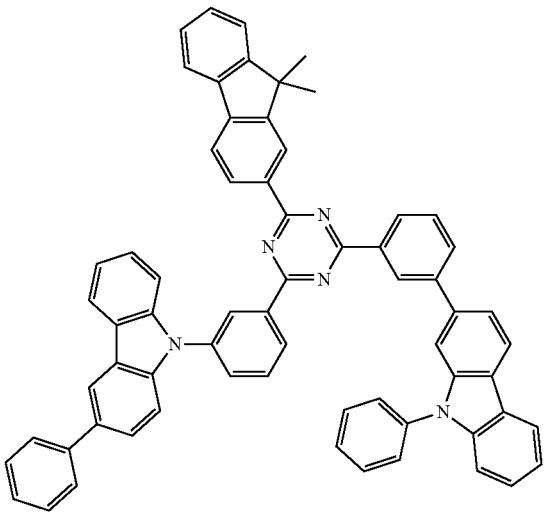
A-112
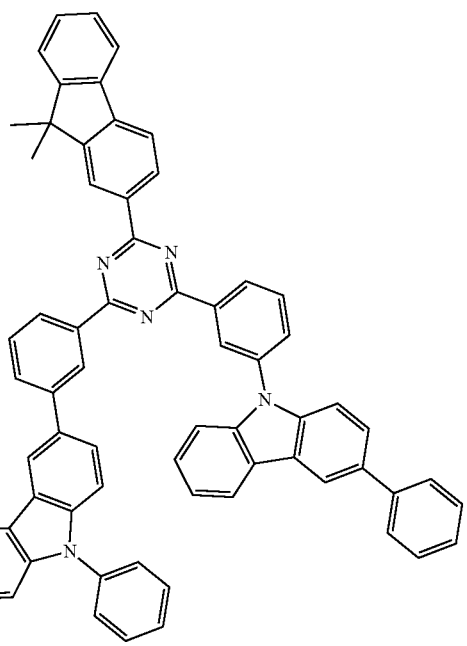
A-113
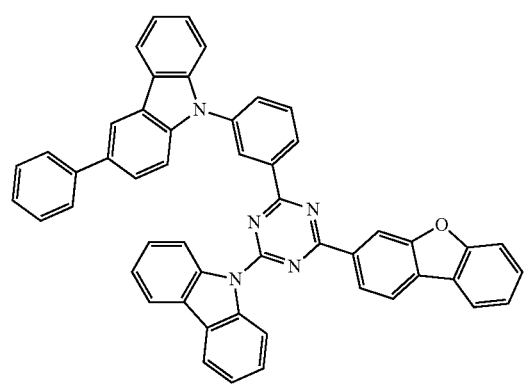

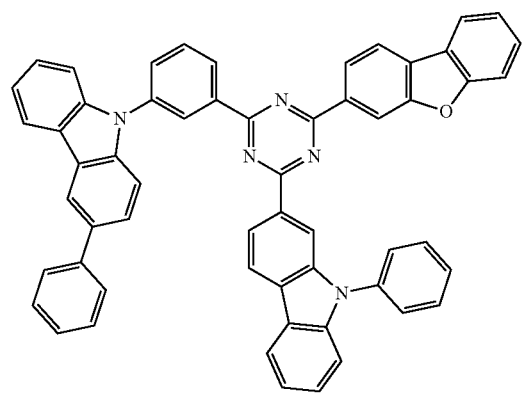
A-116
A-117
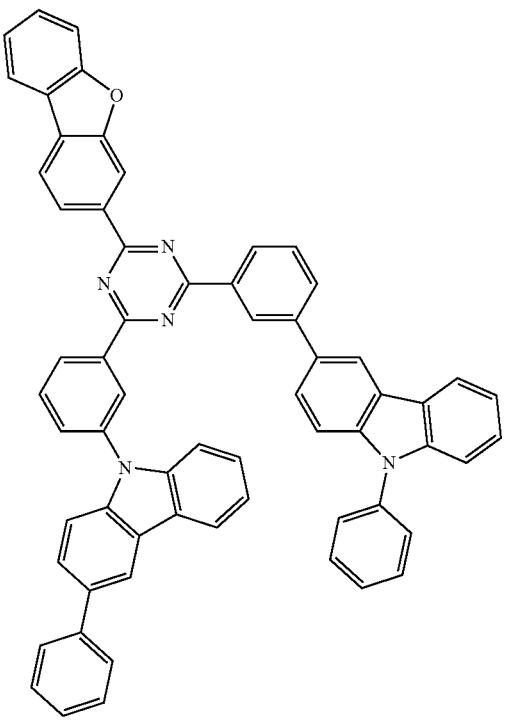
A-119
A-118
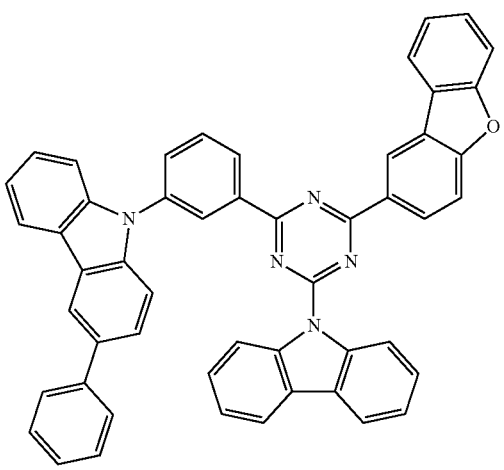
A-120

A-123
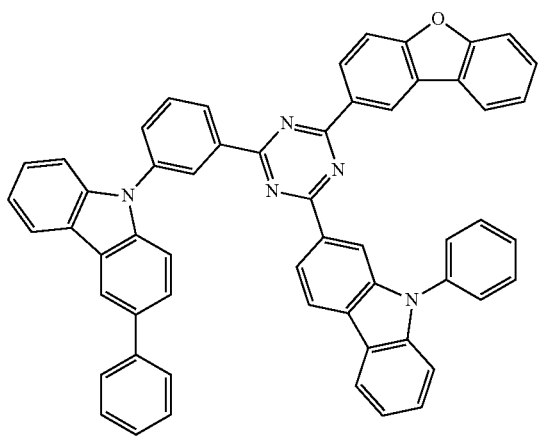
A-124
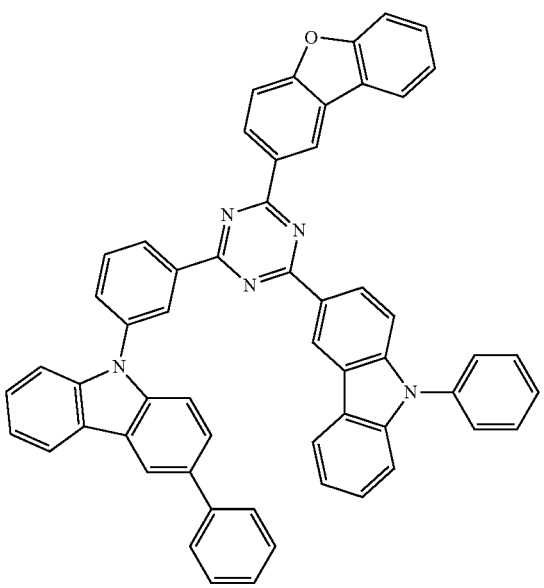
A-125
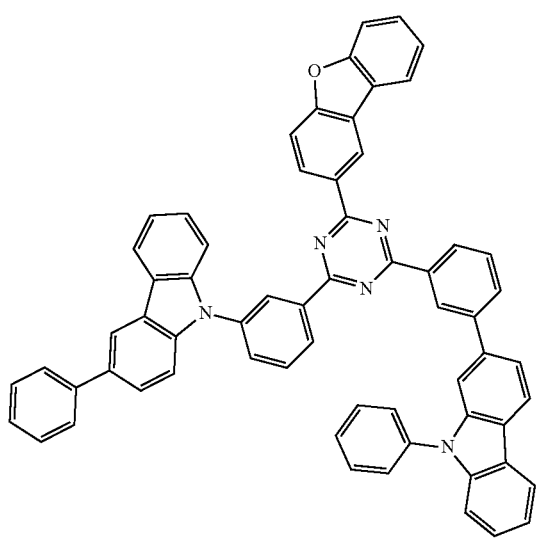
A-126
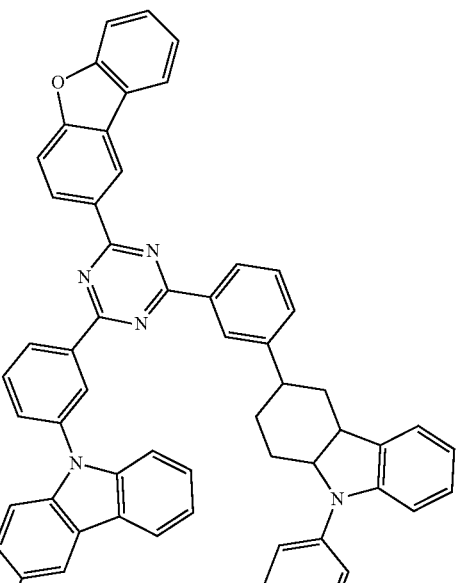
A-127
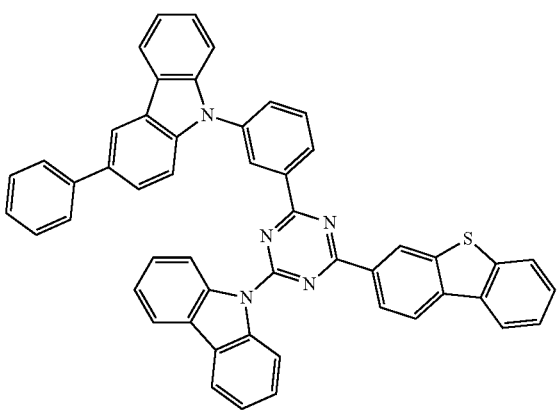
A-130
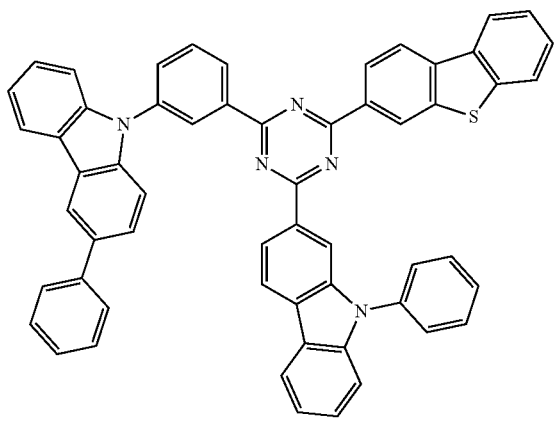

-continued
A-131
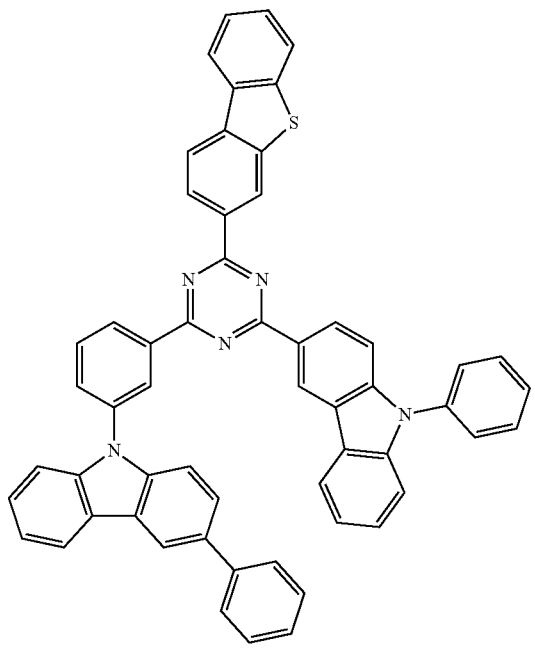
A-132
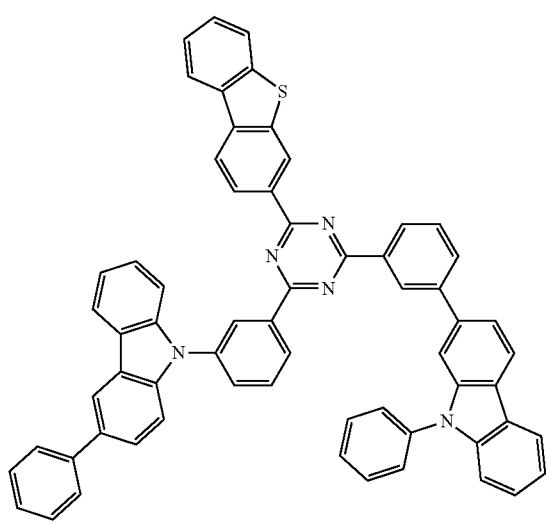
A-133
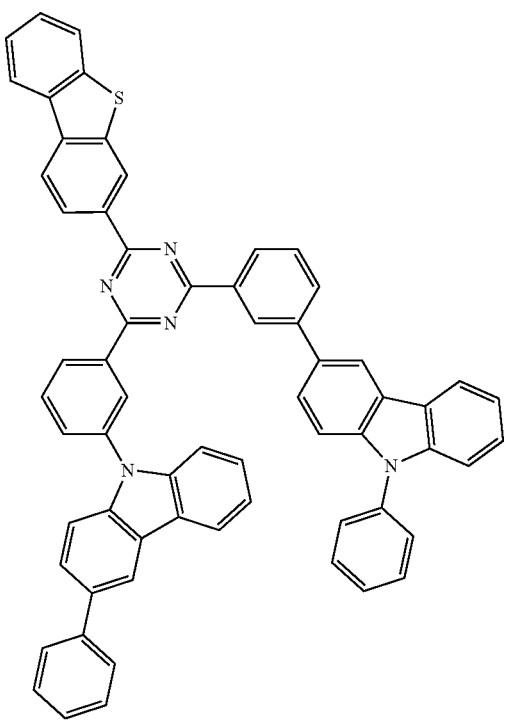
A-134
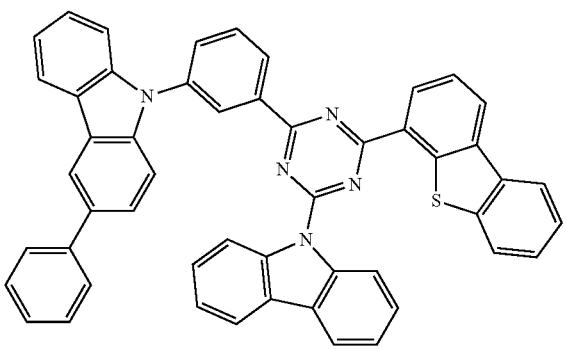

A-137

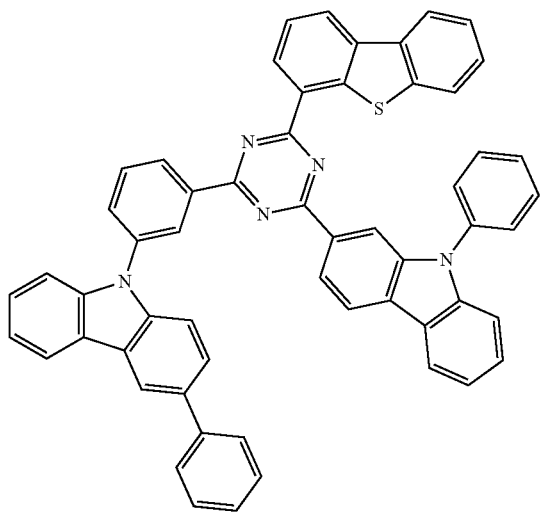

A-138

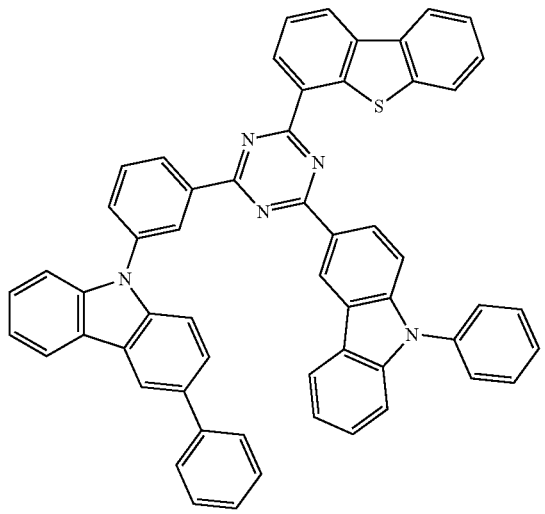

A-139

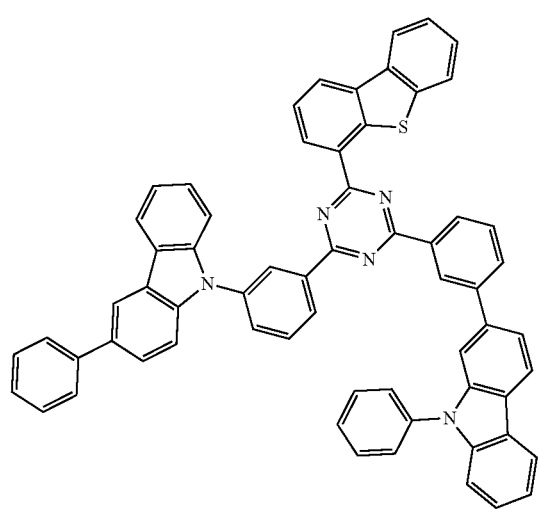

A-140

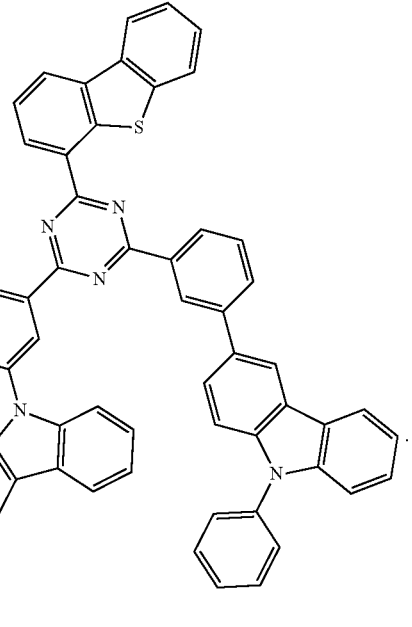

7. A compound represented by the following Chemical Formula 7:

[Chemical Formula 7]

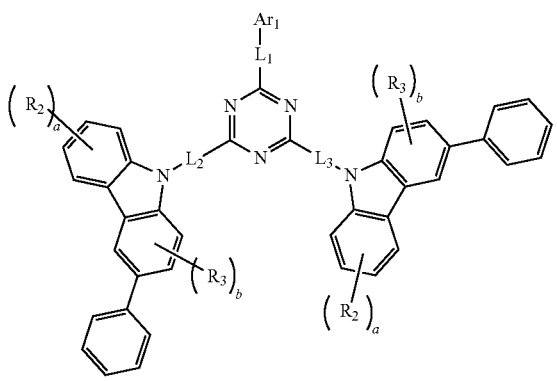

wherein
Z$_1$ to Z$_3$ are the same as or different from each other, each independently being N or C(R$_1$), wherein at least one of Z$_1$ to Z$_3$ is N,
wherein when C(R$_1$) are plural in number, the plurality of R$_1$, are the same or different from each other and each independently selected from the group consisting of: hydrogen, deuterium, halogen, a cyano group, a nitro group, a C$_1$ to C$_{40}$ alkyl group, a C$_2$ to C$_{40}$ alkenyl group, a C$_2$ to C$_{40}$ alkynyl group, a C$_3$ to C$_{40}$ cycloalkyl group, a heterocycloalkyl group having 3 to 40 nuclear atoms, a C$_6$ to C$_{60}$ aryl group, a heteroaryl group having 5 to 60 nuclear atoms, a C$_1$ to C$_{40}$ alkyloxy group, a C$_6$ to C$_{60}$ aryloxy group, a C$_3$ to C$_{40}$ alkylsilyl group, a C$_6$ to C$_{60}$ arylsilyl group, a C$_1$ to C$_{40}$ alkylboron group, a C$_6$ to C$_{60}$ arylboron group, a C$_1$ to C$_{40}$ alkylphosphine group, a C$_6$ to C$_{60}$ arylphosphine group, a C$_6$ to C$_{60}$ arylphosphine oxide group and a C$_6$ to C$_{60}$ arylamine group, $L_1$ and $L_3$ are the same as or different from each other, each independently being a single bond, or selected from the group consisting of: a $C_6$ to $C_{18}$ arylene group and a heteroarylene group having 5 to 18 nuclear atoms, $L_2$ is a single bond, or selected from the group consisting of: a heteroarylene group having 5 to 18 nuclear atoms, $Ar_1$ is selected from the group consisting of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group, and a $C_6$ to $C_{60}$ arylamine group, and a is an integer ranging from 0 to 4, while b is an integer ranging from 0 to 3, wherein a plurality of $R_2$ are the same as or different from each other, a plurality of $R_3$ are the same as or different from each other, $R_2$ and $R_3$ are each independently selected from the group consisting of: deuterium, a halogen group, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group, or may combine with an adjacent group to form a fused ring, and the arylene group and the heteroarylene group of $L_1$ and $L_3$; the heteroarylene group of $L_2$; and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the alkylphosphine group, the arylphosphine group, the arylphosphine oxide group and the arylamine group of $Ar_1$ and $R_1$ to $R_3$ are each independently substituted or unsubstituted with one or more kinds of substituents selected from the group consisting of: deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_6$ to $C_{60}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group and a $C_6$ to $C_{60}$ arylsilyl group, wherein when the substituents are plural in number, the substituents are the same as or different from each other.

8. An organic electroluminescence device, comprising an anode, a cathode and one or more organic layers disposed between the anode and the cathode, wherein at least one of the one or more organic layers comprises the compound of the Chemical Formula 1 according to claim 1:

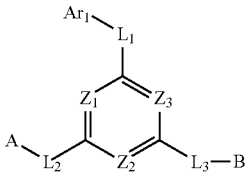

[Chemical Formula 1]

wherein, $Z_1$ to $Z_3$ are the same as or different from each other, each independently being N or $C(R_1)$, wherein at least one of $Z_1$ to $Z_3$ is N, wherein when $C(R_1)$ are plural in number, the plurality of $R_1$, are the same or different from each other and each independently selected from the group consisting of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group and a $C_6$ to $C_{60}$ arylamine group, $L_1$ to $L_3$ are the same as or different from each other, each independently being a single bond, or selected from the group consisting of: a $C_6$ to $C_{18}$ arylene group and a heteroarylene group having 5 to 18 nuclear atoms, $Ar_1$ is selected from the group consisting of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group, and a $C_6$ to $C_{60}$ arylamine group, and A is selected from the group consisting of: substituents having asymmetric structures represented by the following Chemical Formulas 2 and 3, B is selected from the group consisting of: substituents having asymmetric structures represented by the following Chemical Formula 3, and substituents represented by the following Chemical Formulas 4 and 5,

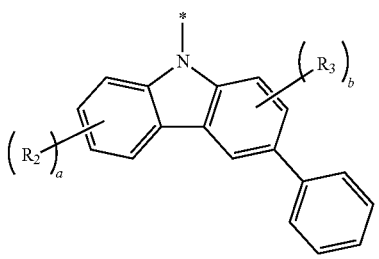
[Chemical Formula 2]

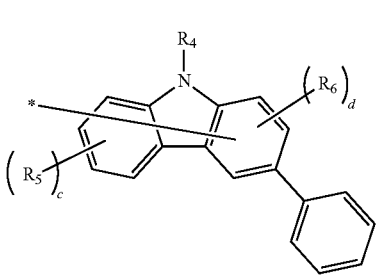
[Chemical Formula 3]

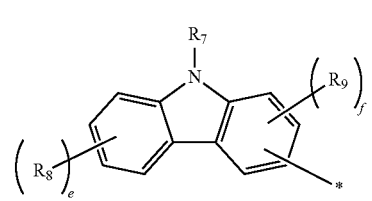
[Chemical Formula 4]

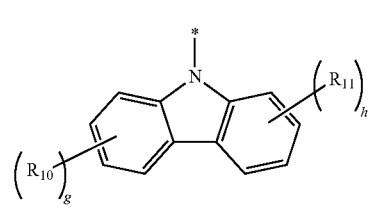
[Chemical Formula 5]

where in Chemical Formulas 2 to 5,

"*" are each a site connected to $L_2$ or $L_3$ of Chemical Formula 1, a, c, e, g and h are each an integer ranging from 0 to 4, while b, d and f are each an integer ranging from 0 to 3, wherein c+d is in a range of $0 \leq c+d \leq 6$, wherein a plurality of $R_2$ are the same or different from each other, a plurality of $R_3$ are the same or different from each other, a plurality of $R_4$ are the same or different from each other, a plurality of $R_5$ are each the same or different from each other, a plurality of $R_6$ are the same as or different from each other, a plurality of $R_7$ are the same as or different from each other, a plurality of the $R_8$ are the same as or different from each other, a plurality of the $R_9$ are the same as or different from each other, a plurality of the $R_{10}$ are the same as or different from each other, a plurality of $R_{11}$ are each the same or different from each other, $R_2$ to $R_{11}$ are each independently selected from the group consisting of: deuterium, a halogen group, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group, or may combine with an adjacent group to form a fused ring, and the arylene group and the heteroarylene group of $L_1$ to $L_3$, and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the alkylphosphine group, the arylphosphine group, the arylphosphine oxide group and the arylamine group of $Ar_1$ and $R_1$ to $R_{11}$ are each independently substituted or unsubstituted with one or more kinds of substituents selected from the group consisting of: deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_6$ to $C_{60}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group and a $C_6$ to $C_{60}$ arylsilyl group, wherein when the substituents are plural in number, the substituents are the same as or different from each other.

9. The organic electroluminescence device of claim 8, wherein the one or more organic layers comprise an emissive layer, and the emissive layer comprises the compound of the Chemical Formula 1.

10. The organic electroluminescent device of claim 8, wherein the compound of the Chemical Formula 1 is represented by any one of the following Chemical Formulas 8 to 10:

[Chemical Formula 8]

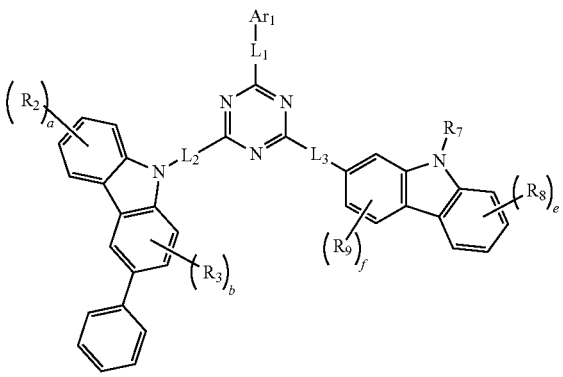

-continued

[Chemical Formula 9]

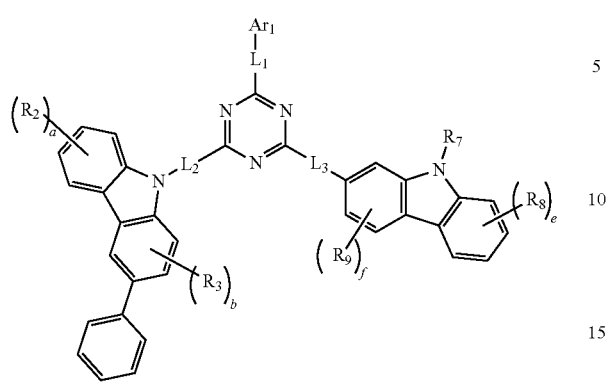

[Chemical Formula 10]

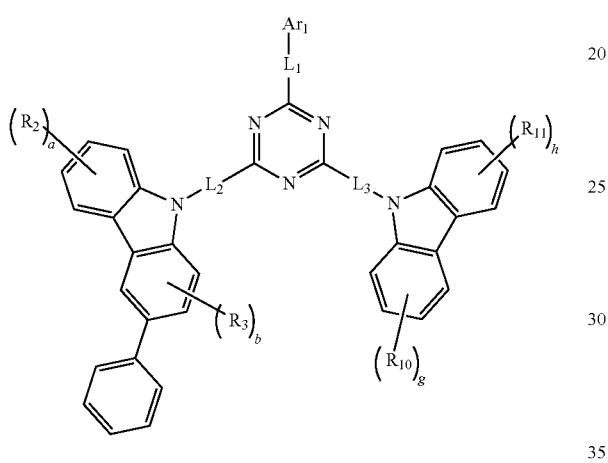

wherein
L$_1$ to L$_3$, Ar$_1$, R$_2$, R$_3$, R$_7$ to R$_{11}$, a, b, e, f, g and h are the same as those defined in claim 8, respectively.

11. The organic electroluminescent device of claim 8, wherein each of Z$_1$ to Z$_3$ is N.

12. The organic electroluminescent device of claim 8, wherein Ar$_1$ is selected from the group consisting of: a C$_6$ to C$_{60}$ aryl group and a heteroaryl group having 5 to 60 nuclear atoms.

13. The organic electroluminescent device of claim 8, wherein Ar$_1$ is a substituent selected from the group consisting of the following substituents S1 to S8:

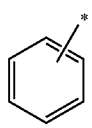
S1

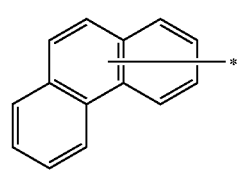
S2

S3

-continued

S4

S5

S6

S7

S8

14. The organic electroluminescent device of claim 8, wherein the compound of the Chemical Formula 1 is selected from the following Compounds:

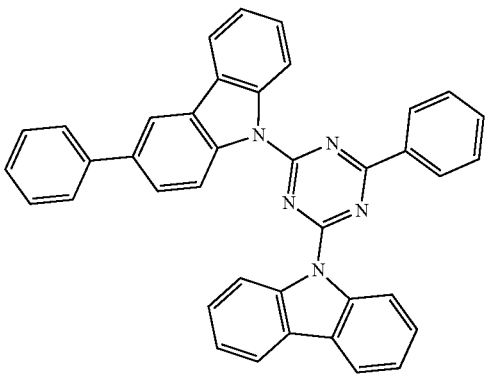
A-1

A-4
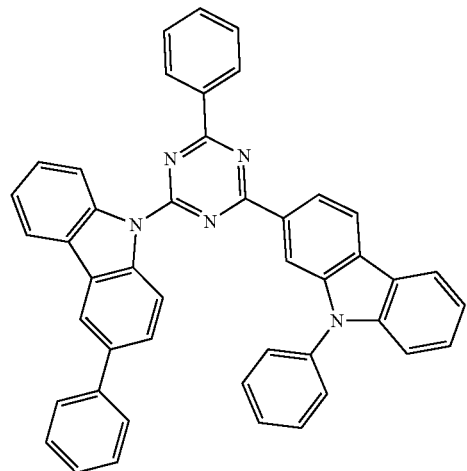
A-7
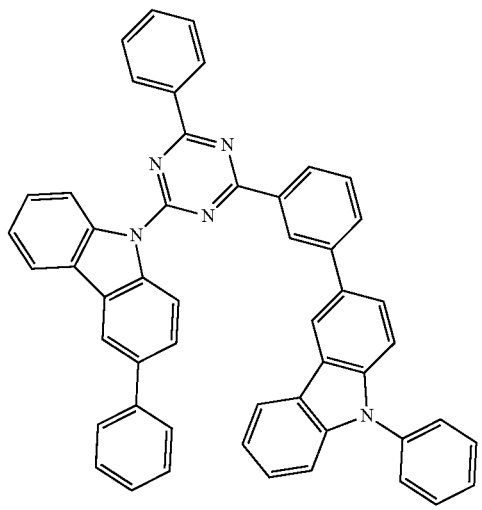
A-5
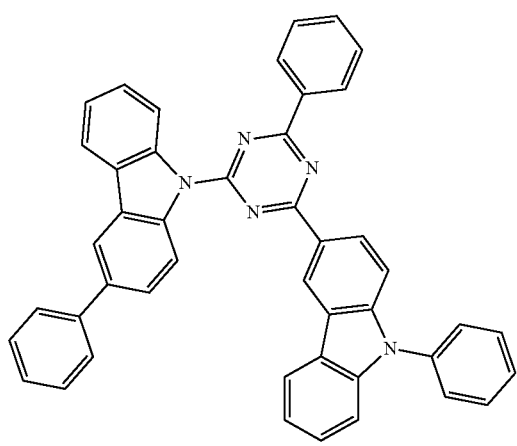
A-8
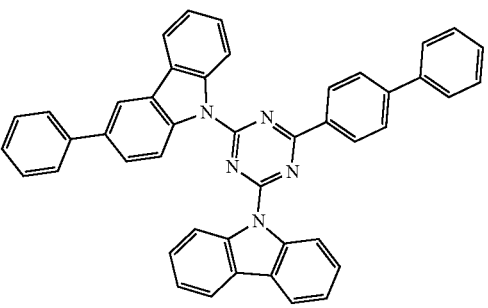
A-6
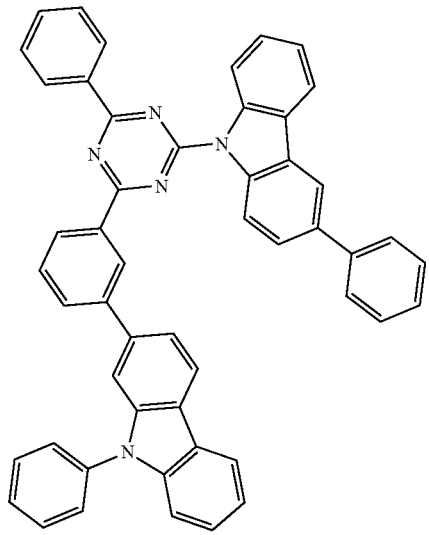
A-11
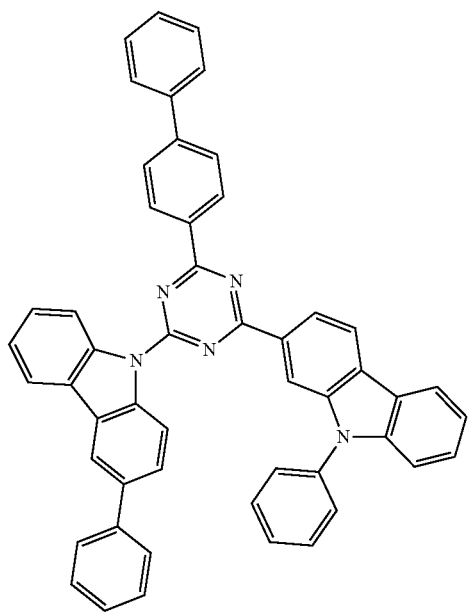

A-12
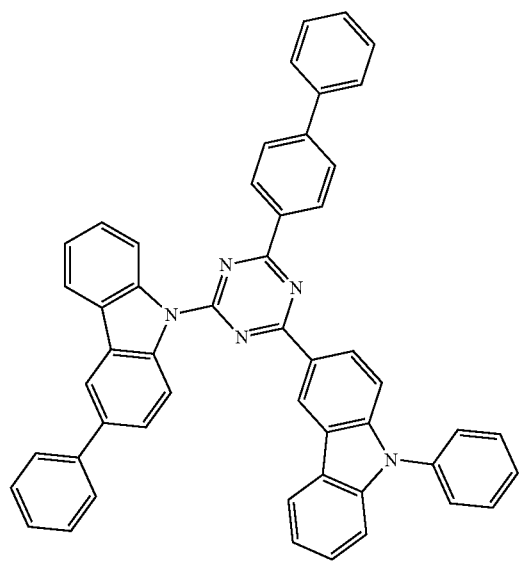
A-13
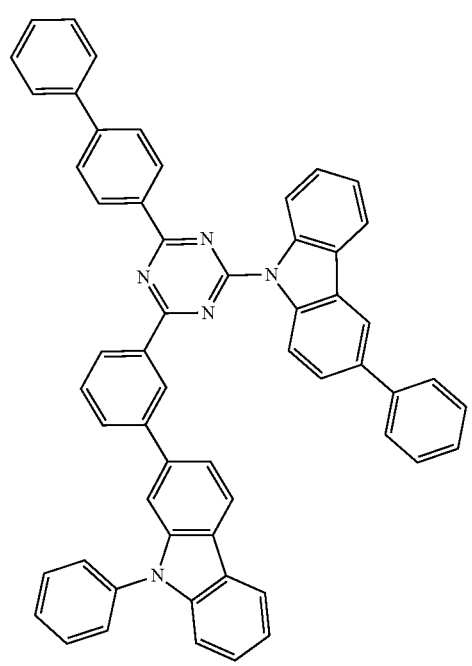
A-14
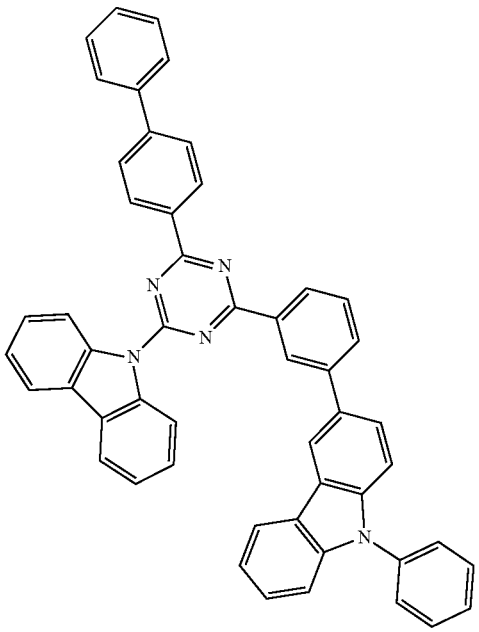
A-15
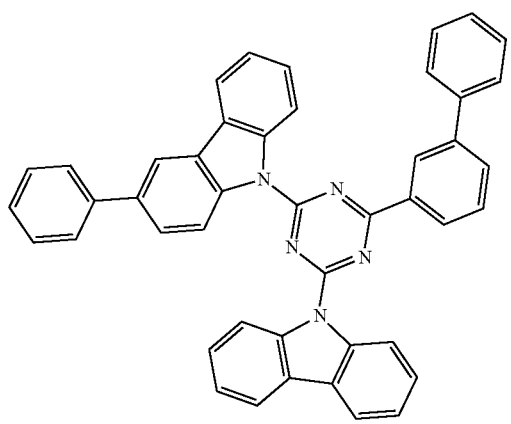
A-18
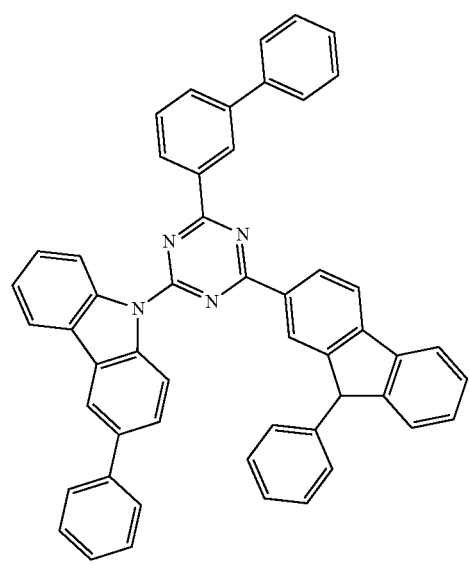

A-19
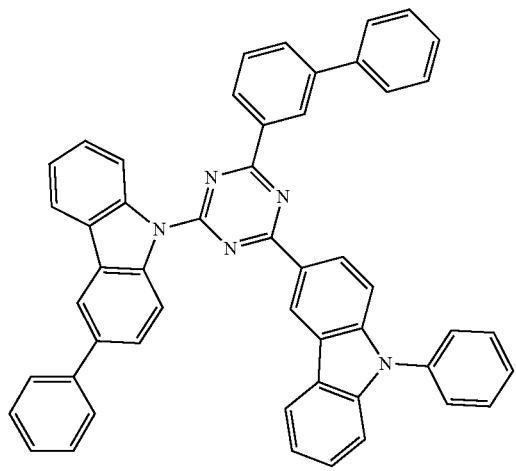
A-20
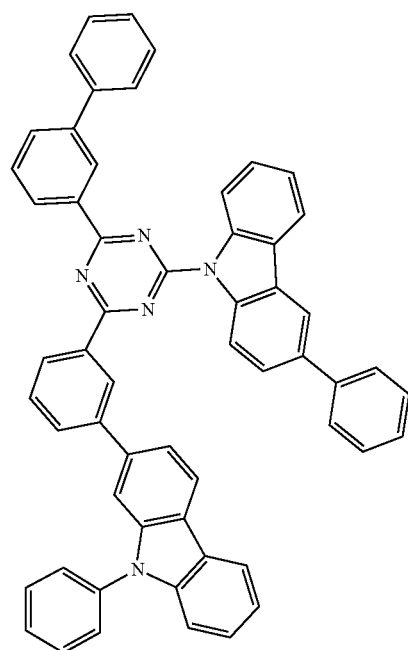
A-21
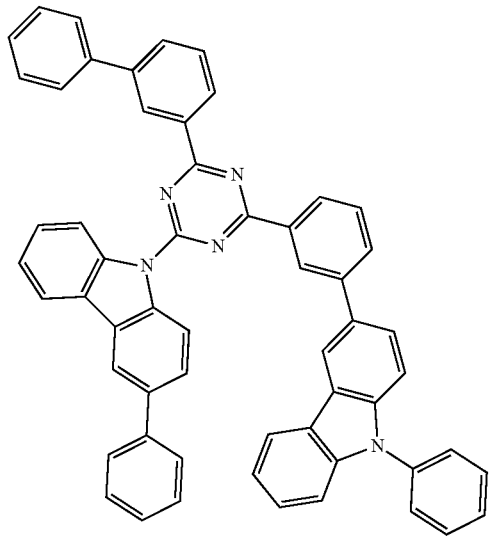
A-22
A-25
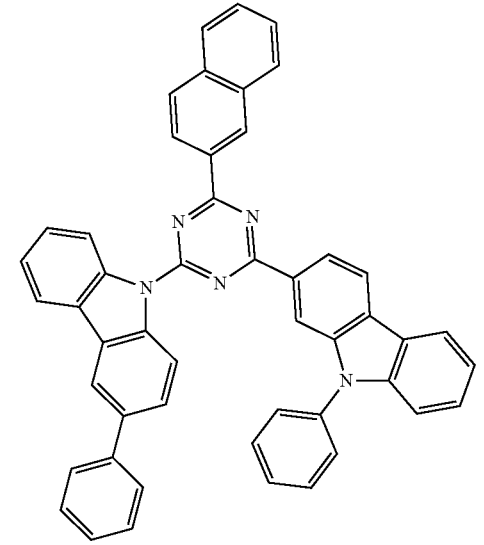

A-26
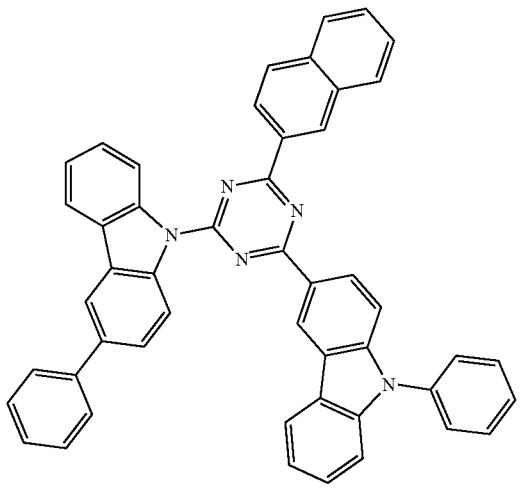
A-27
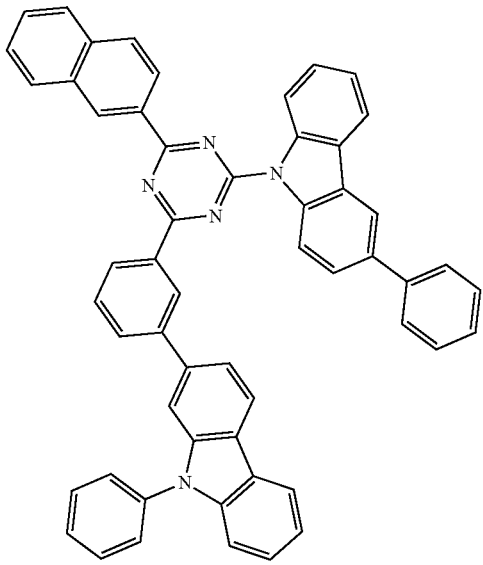
A-28
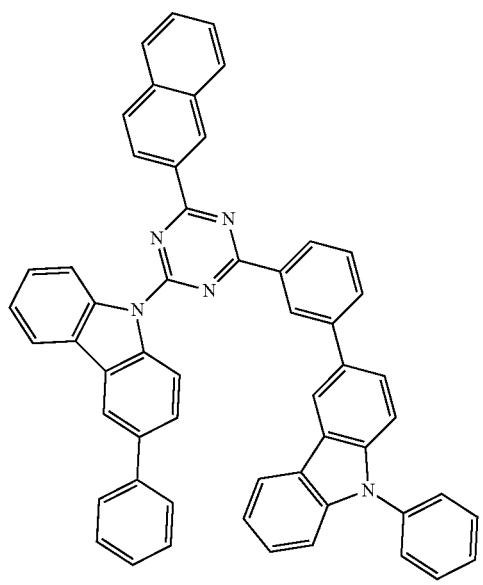
A-29
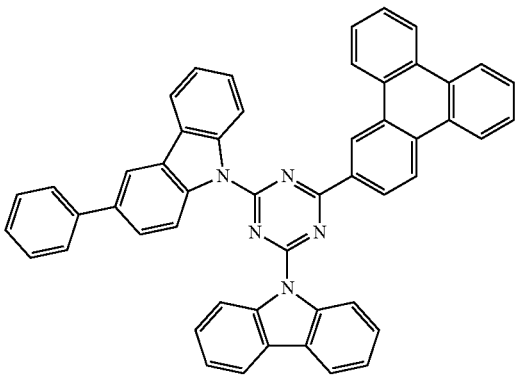
A-32
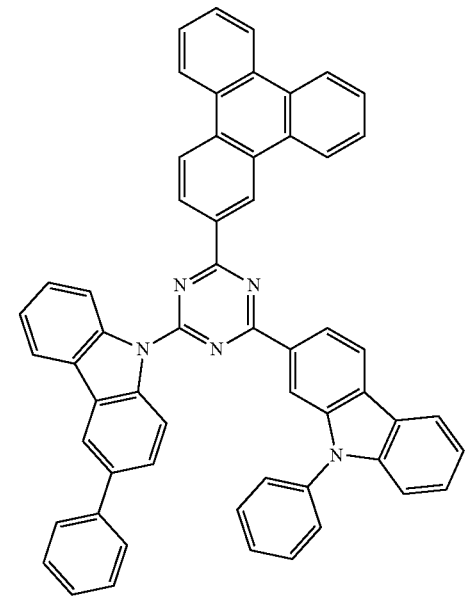
A-33
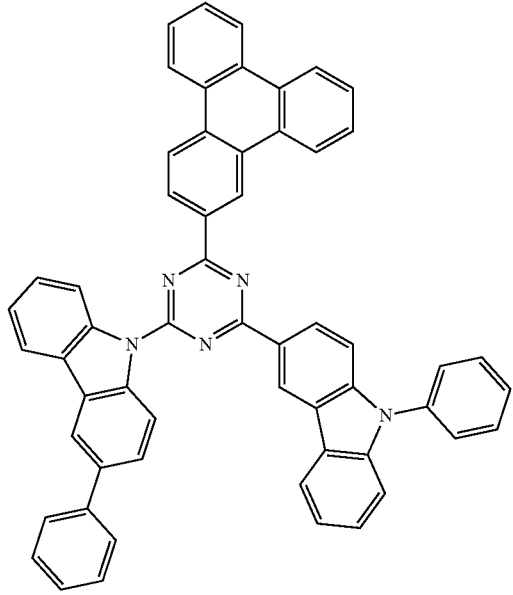

A-34
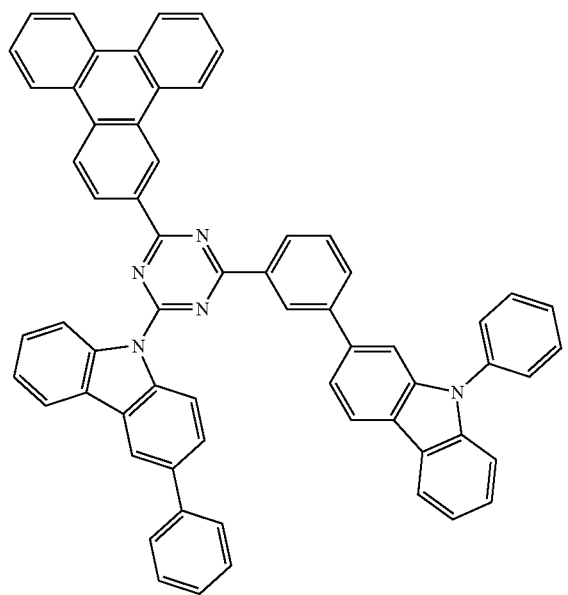
A-39
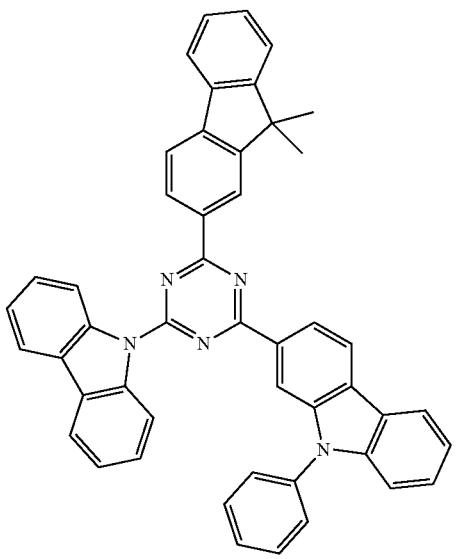
A-35
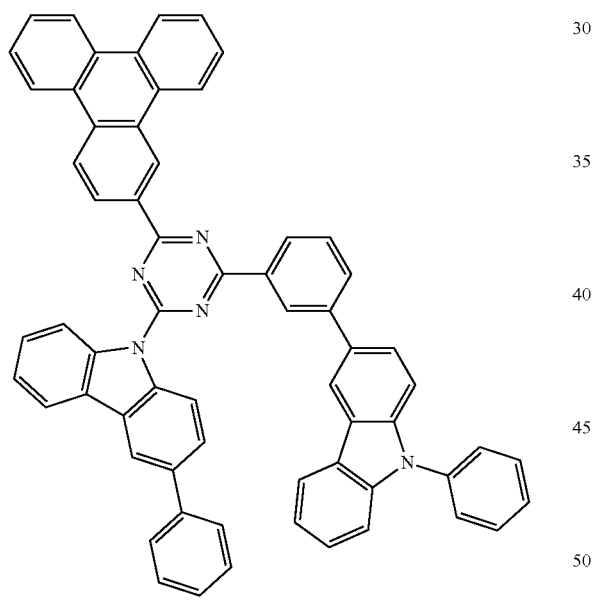
A-36
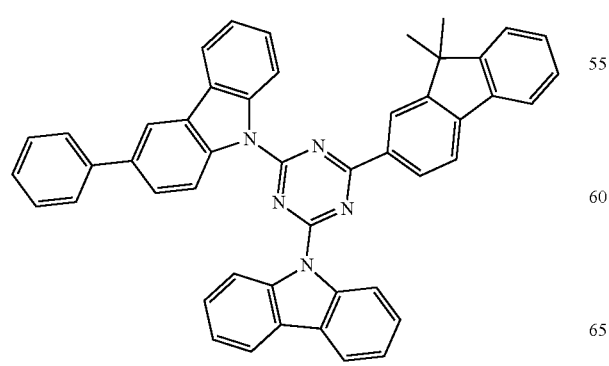
A-40
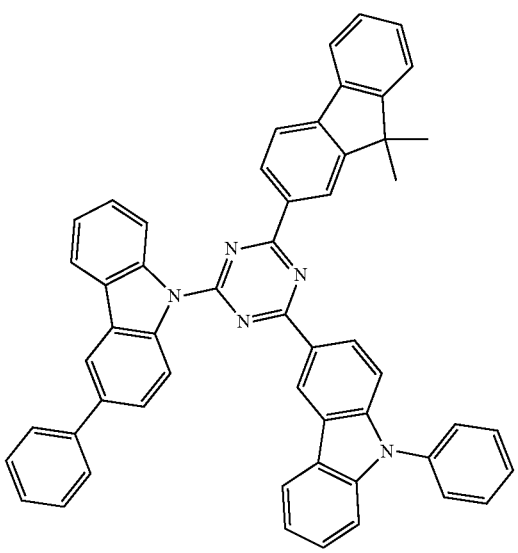

-continued
A-41
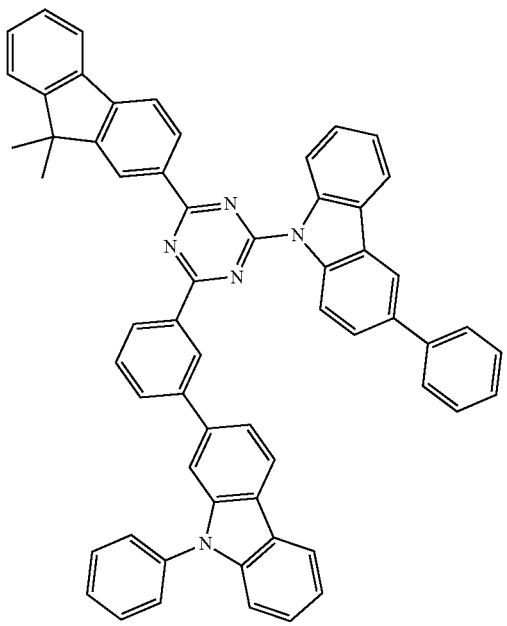
A-42
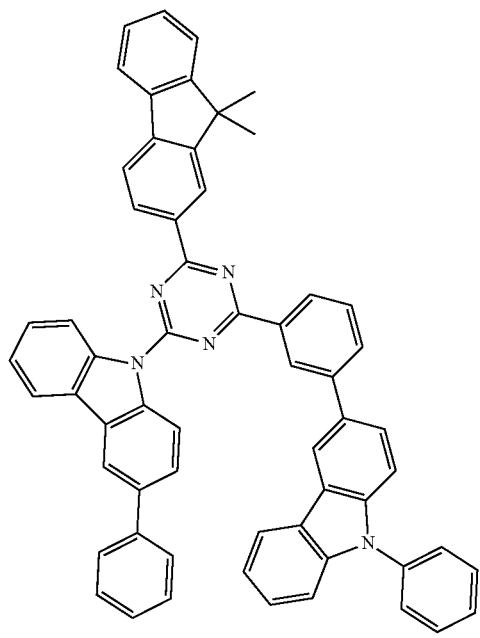
A-43
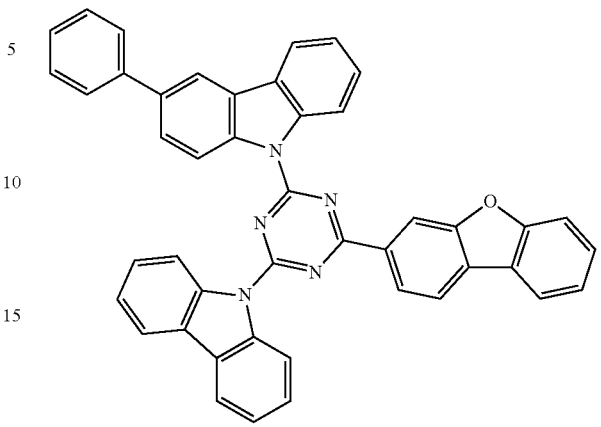
A-46
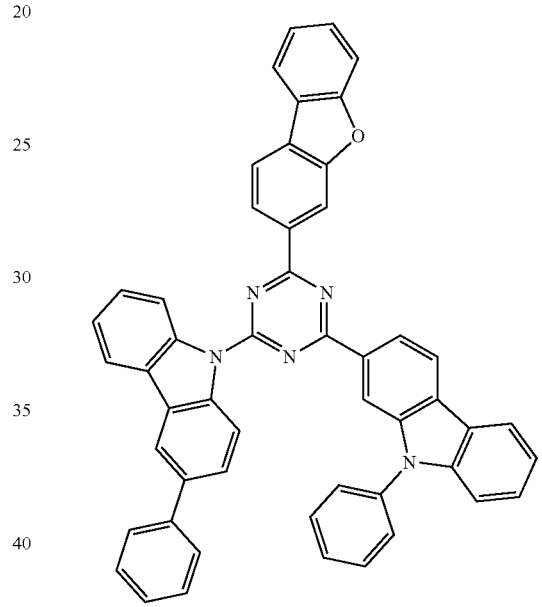
A-47
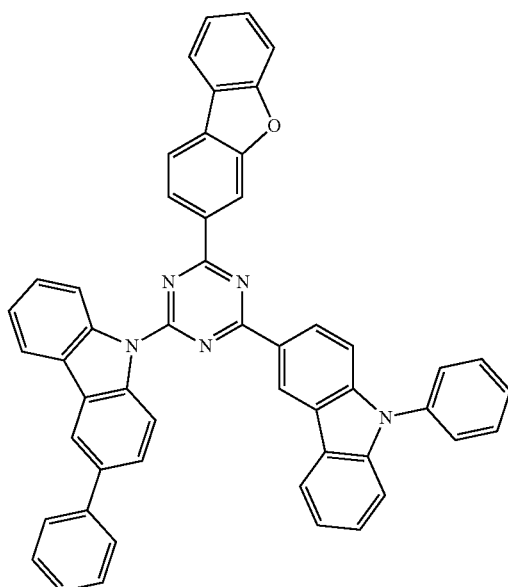

A-48
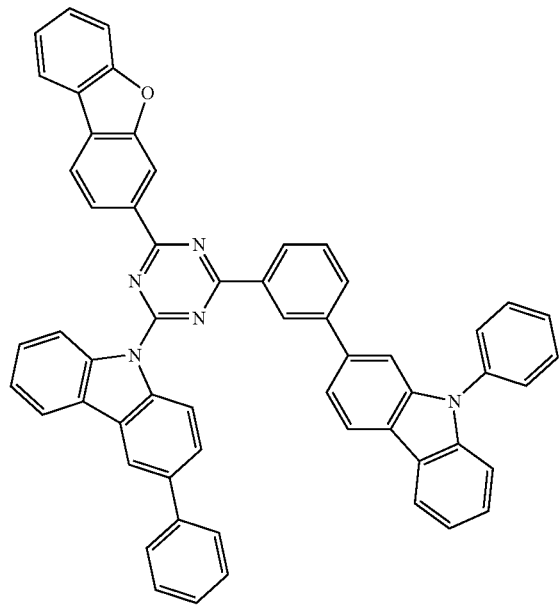
A-50
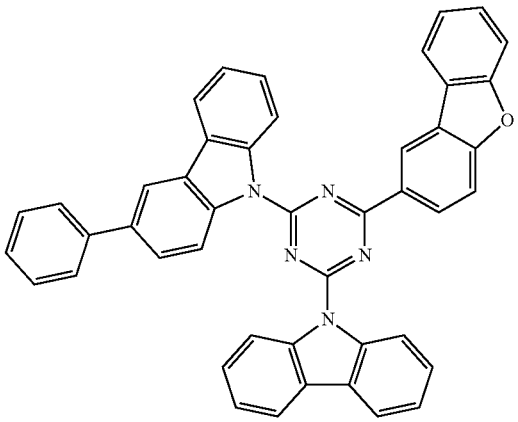
A-53
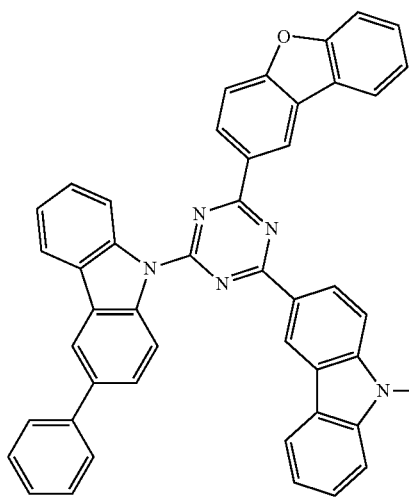
A-49
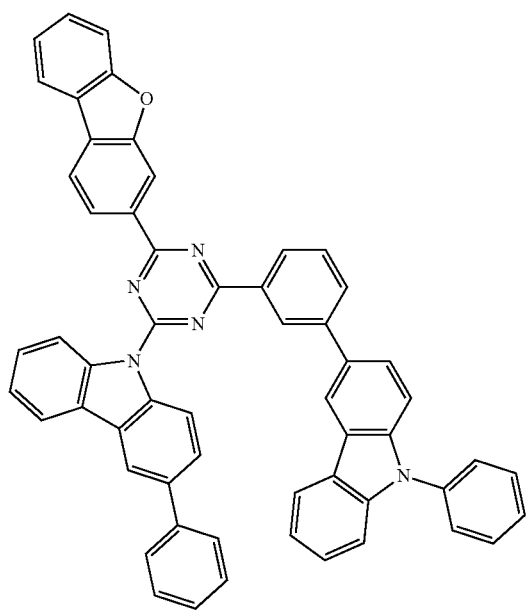
A-54

A-55
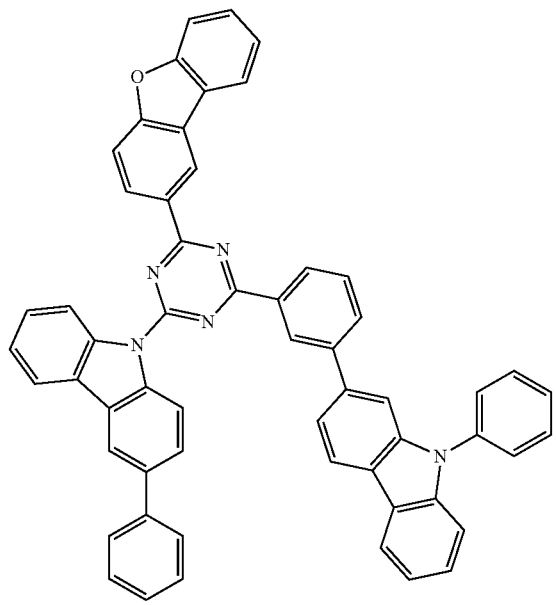
A-56
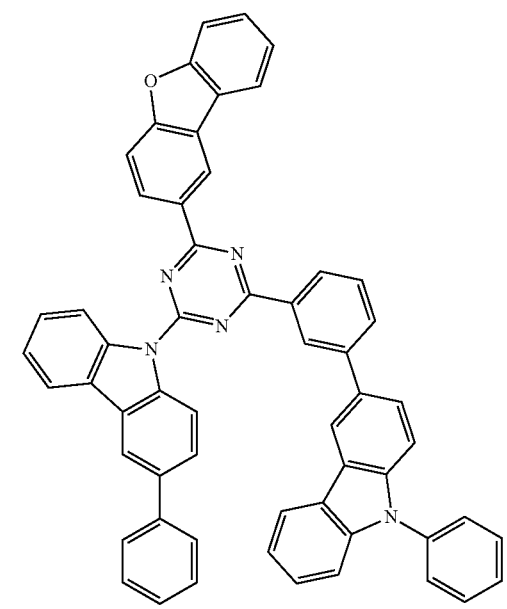
A-57
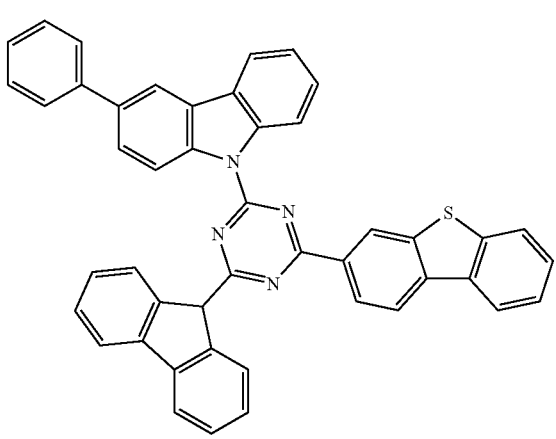
A-60
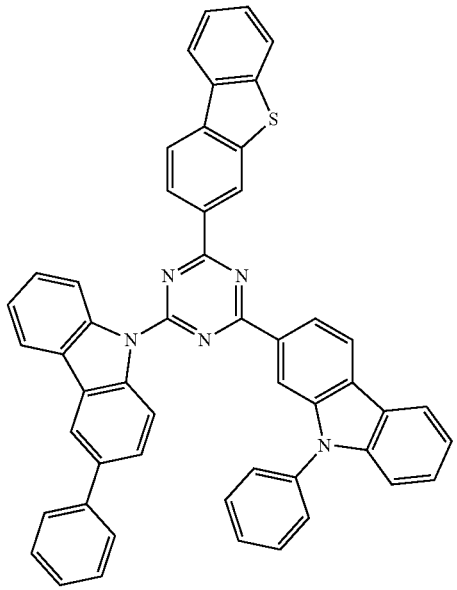
A-61
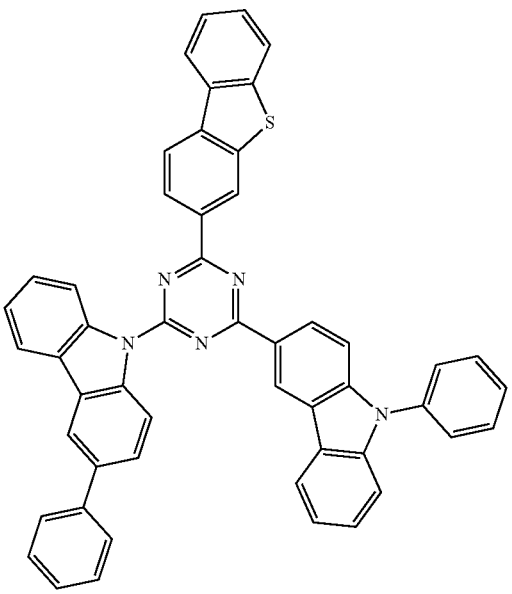

A-62
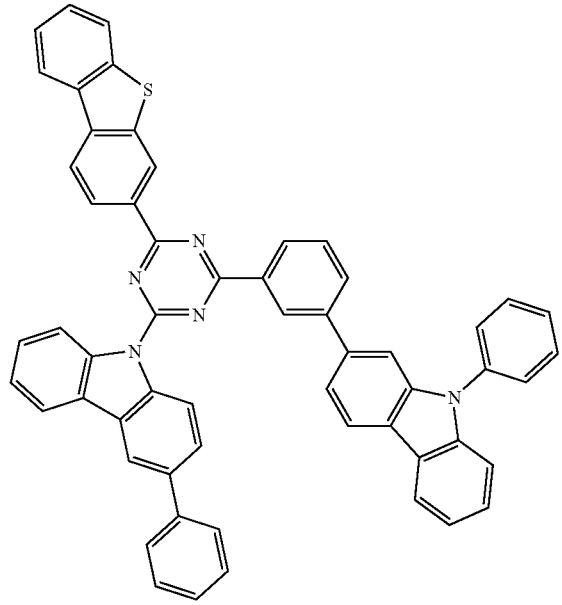
A-63
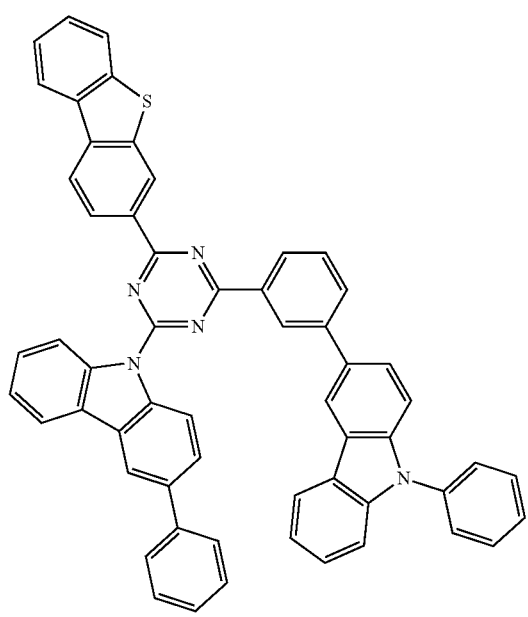
A-64
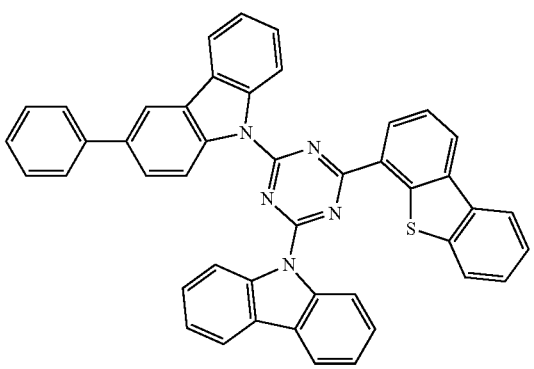
A-67
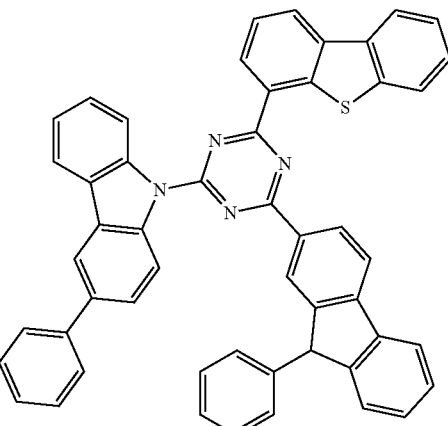
A-68
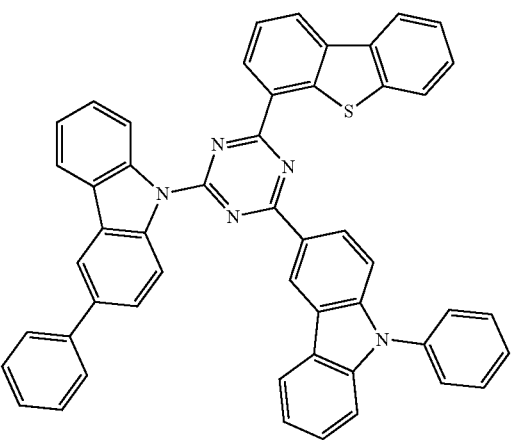
A-69
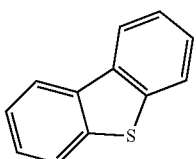
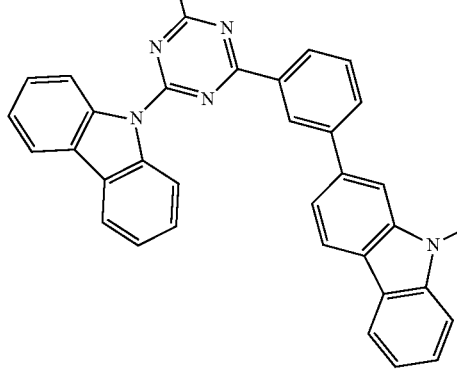

A-70
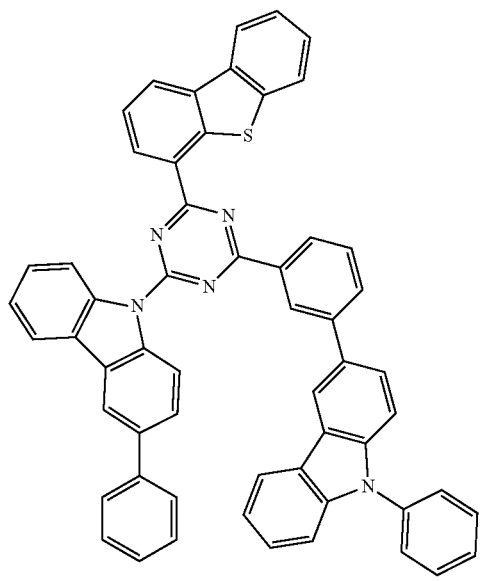
A-71
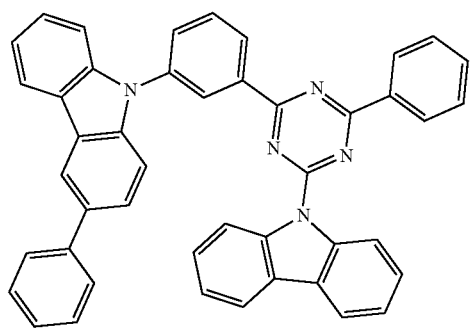
A-74
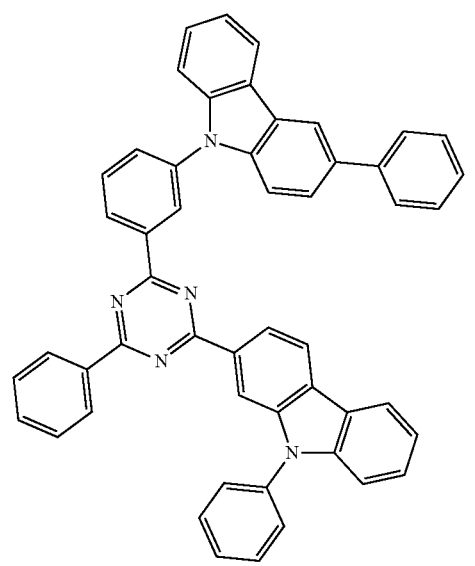
A-75
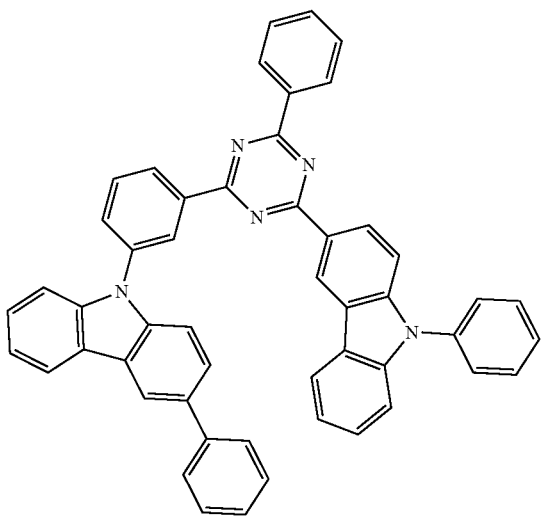
A-76
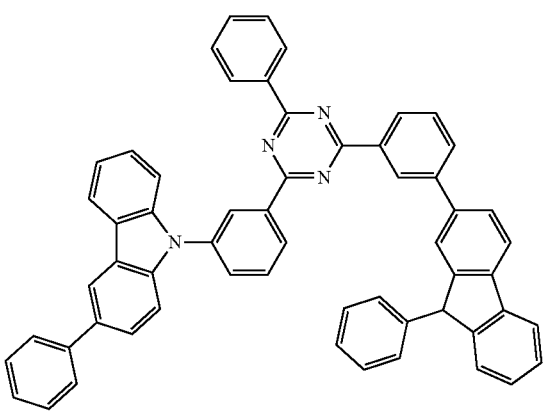
A-77
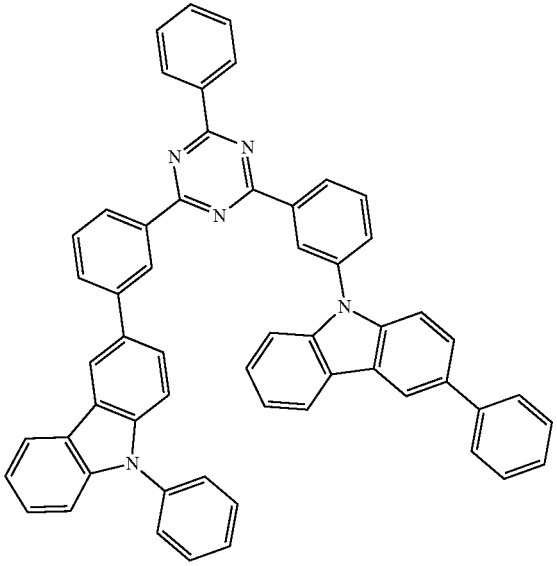

-continued
A-78
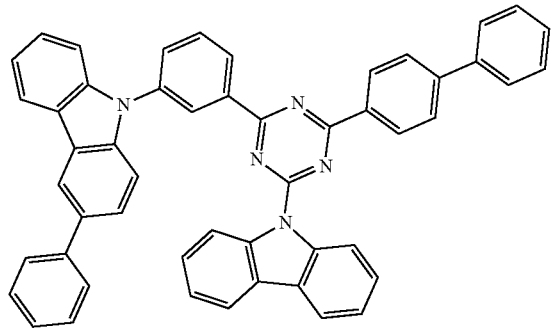
A-81
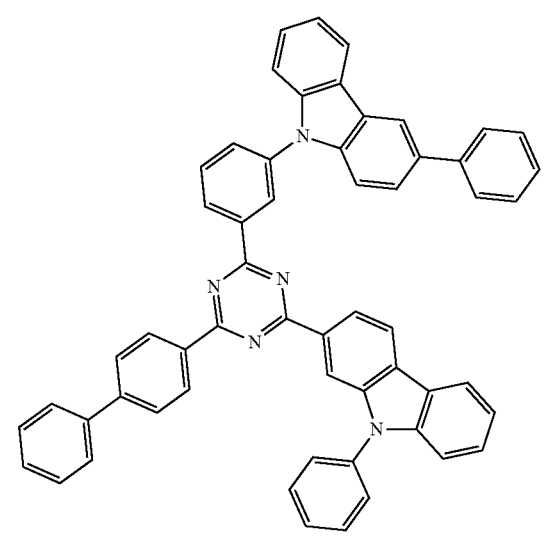
A-82
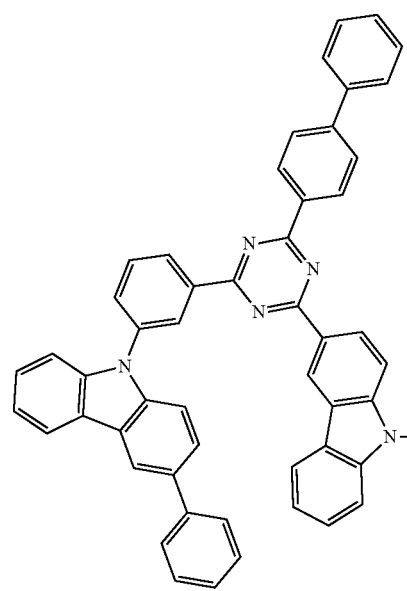
-continued
A-83
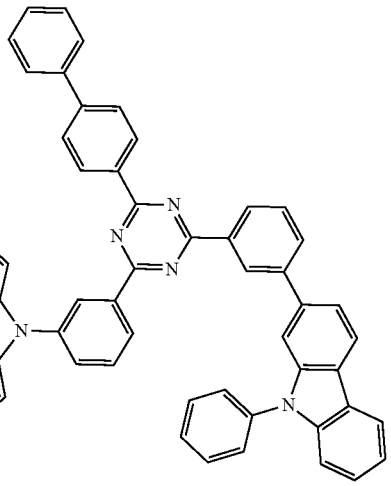
A-84
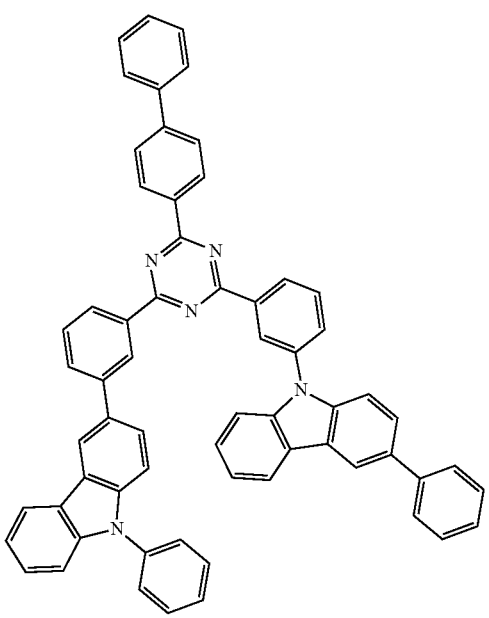
A-85
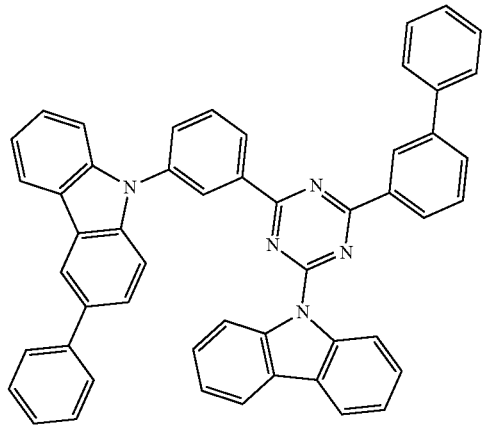

A-88
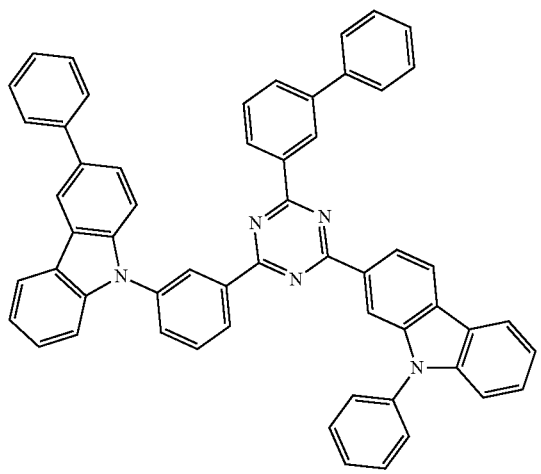
A-89
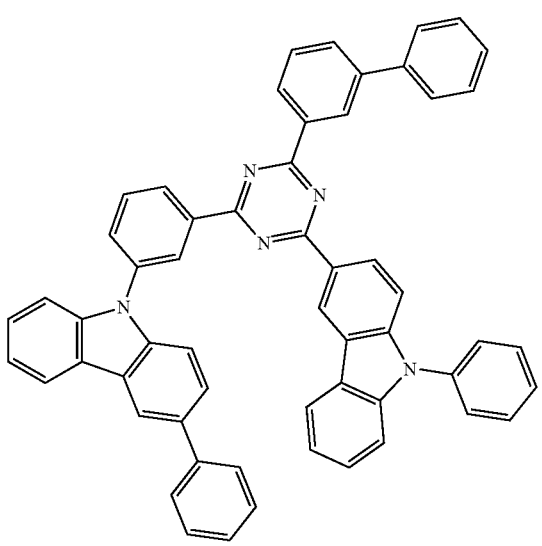
A-90
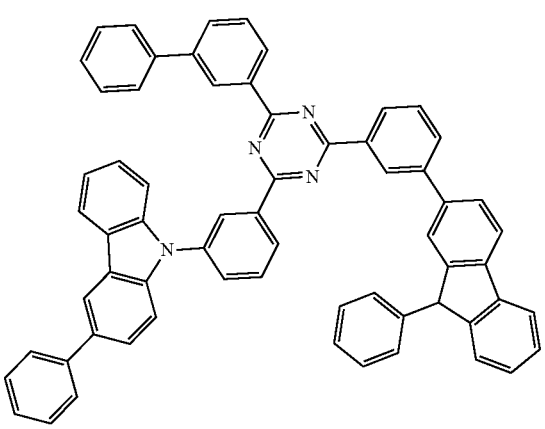
A-91
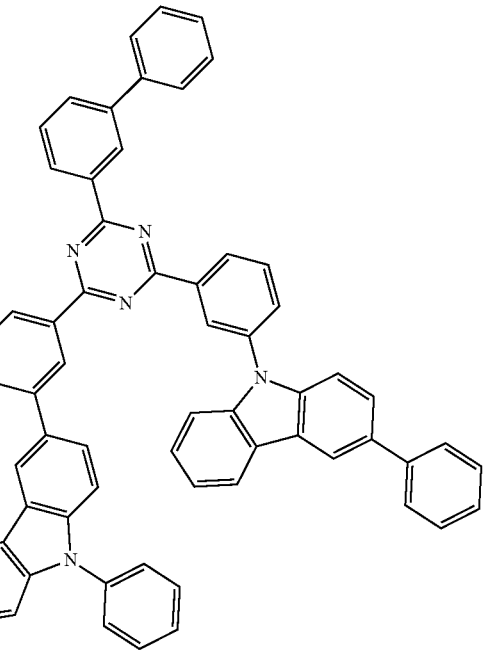
A-92
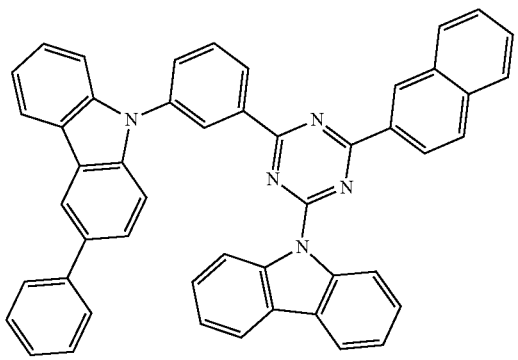
A-95
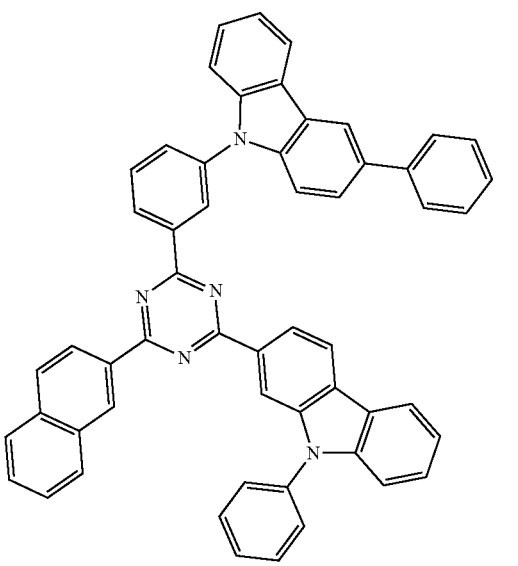

A-96
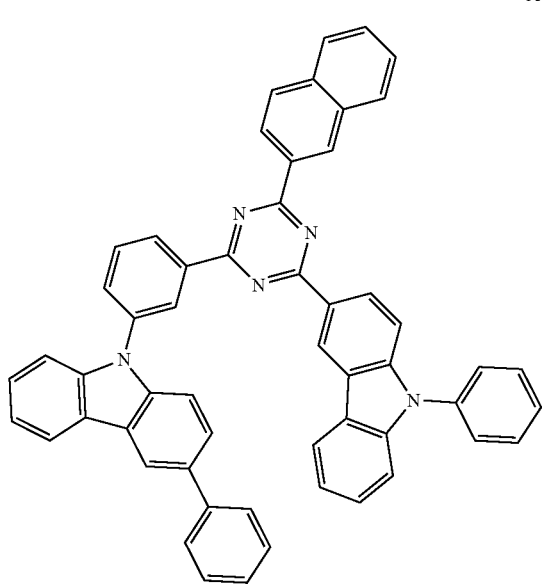
A-97
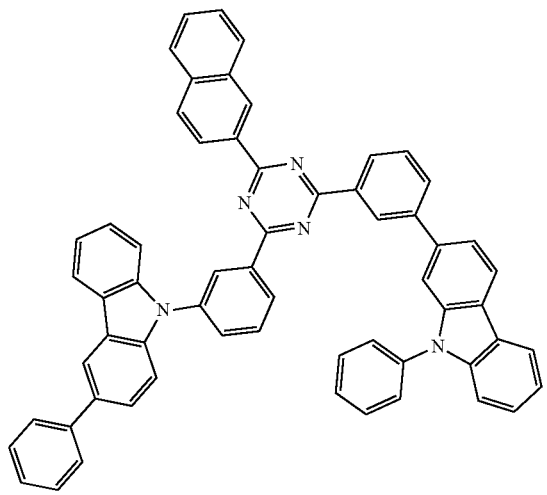
A-98
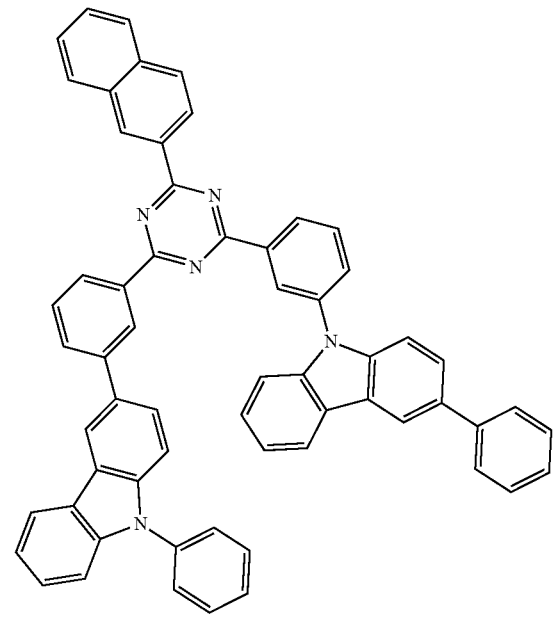
A-99
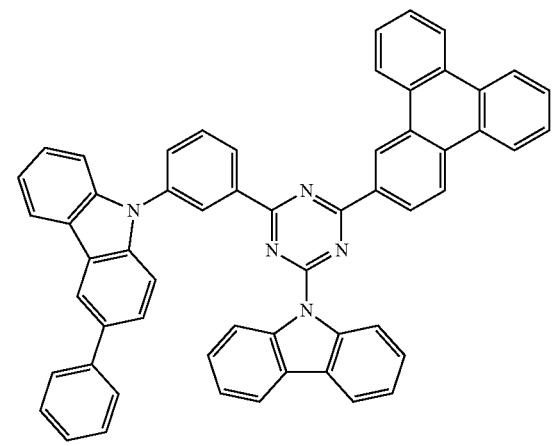

A-102
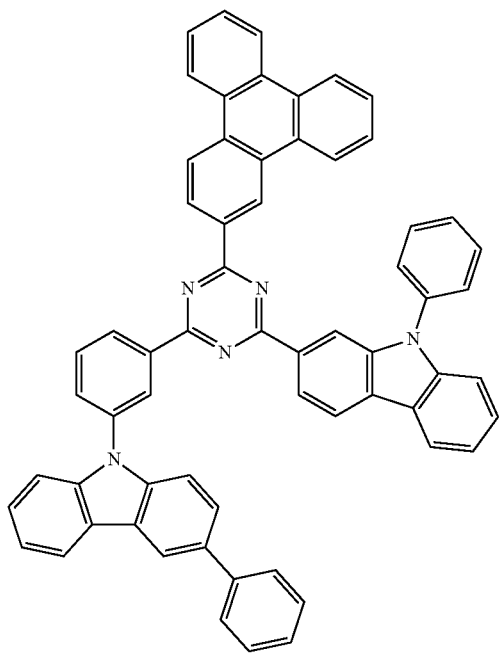
A-103
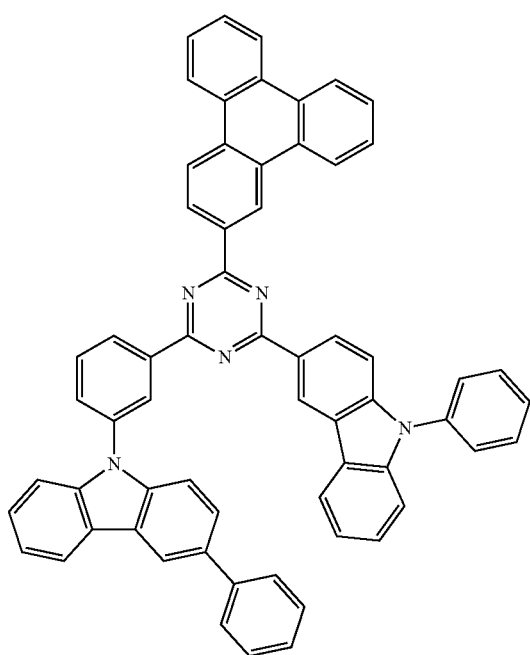
A-104
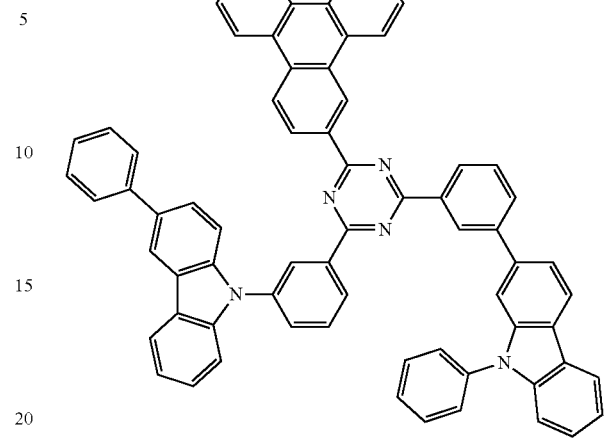
A-105
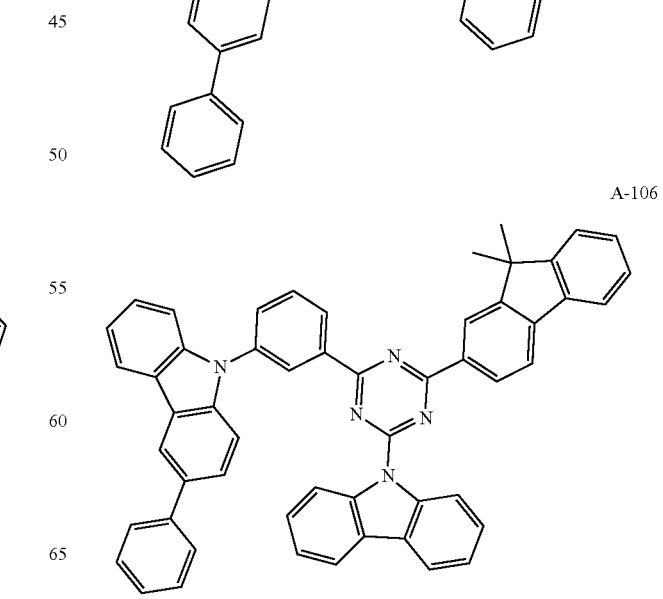
A-106

A-109
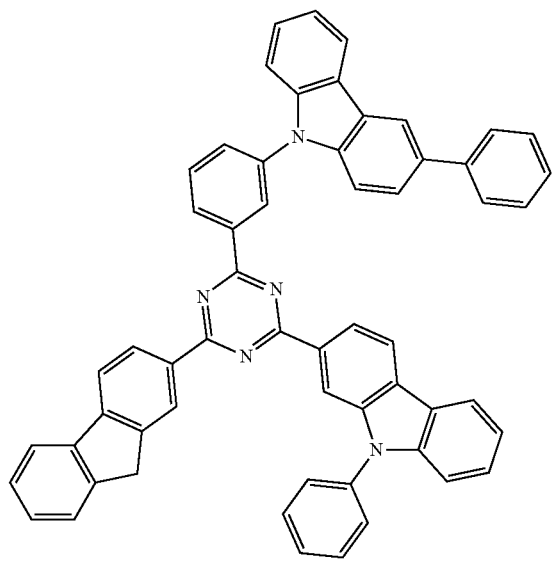
A-110
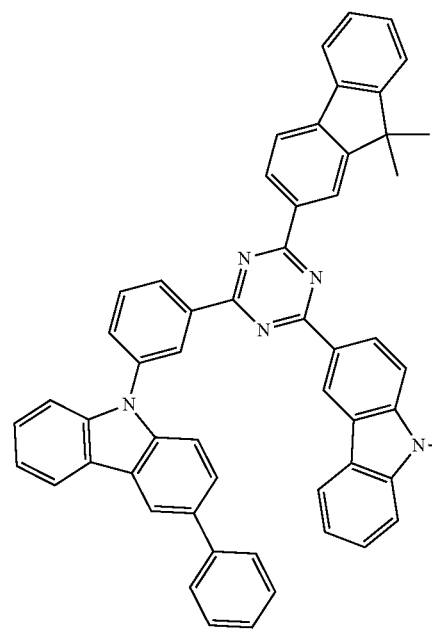
A-111
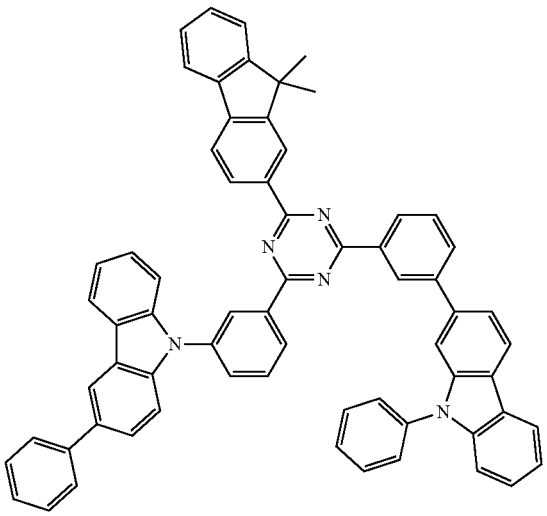
A-112
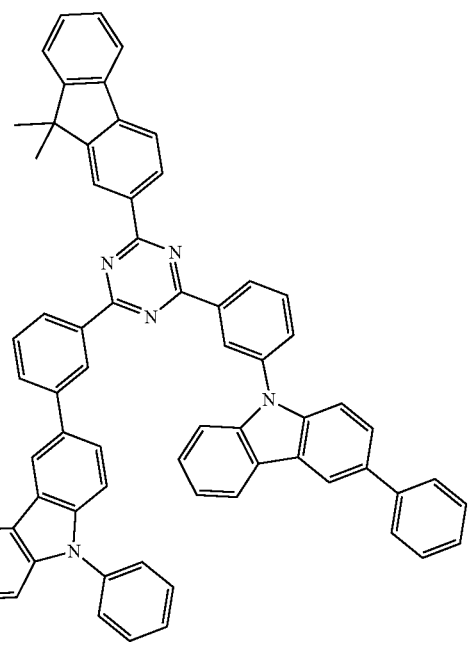
A-113
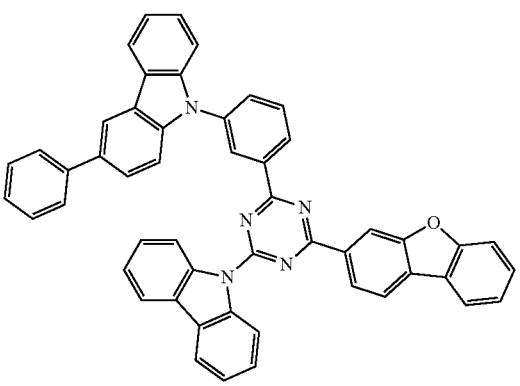

A-116
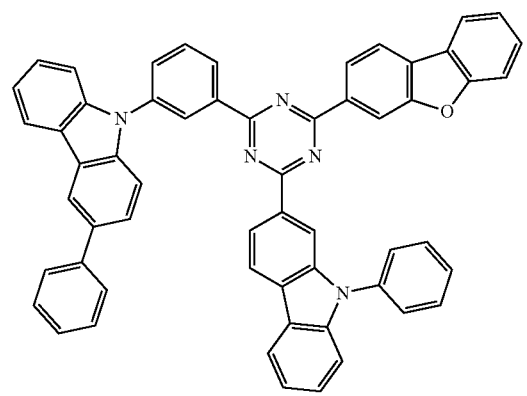
A-117
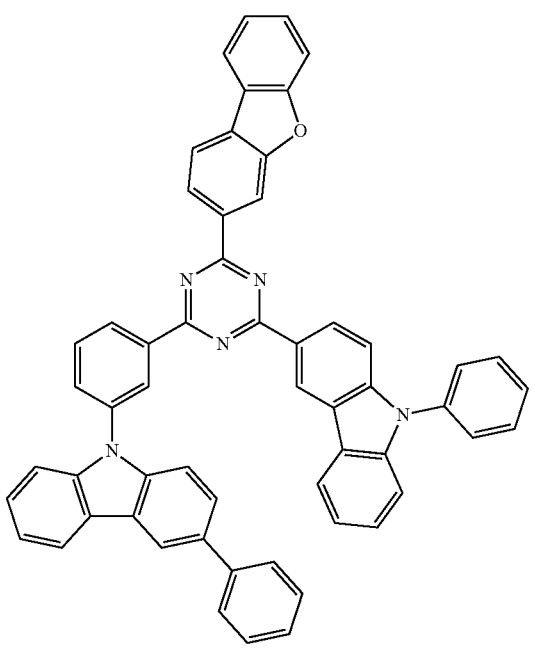
A-119
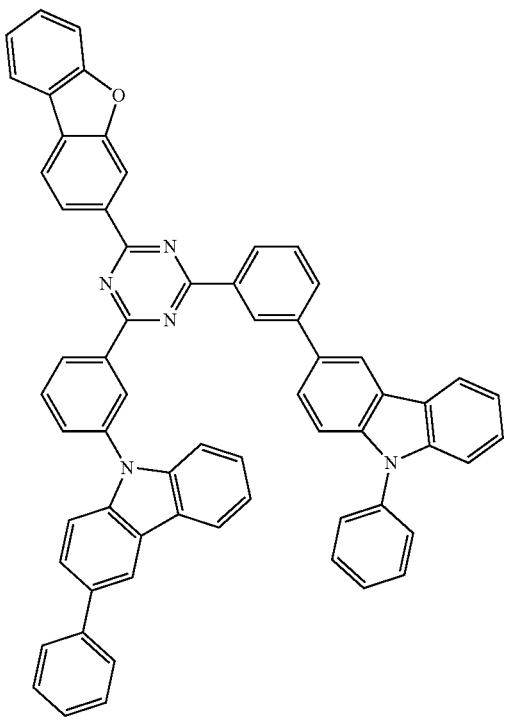
A-120
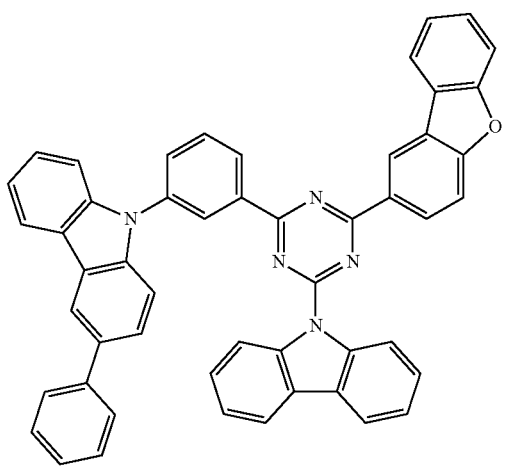

-continued
A-123
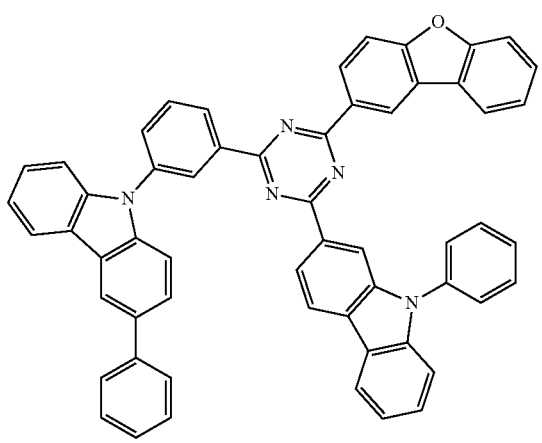
A-124
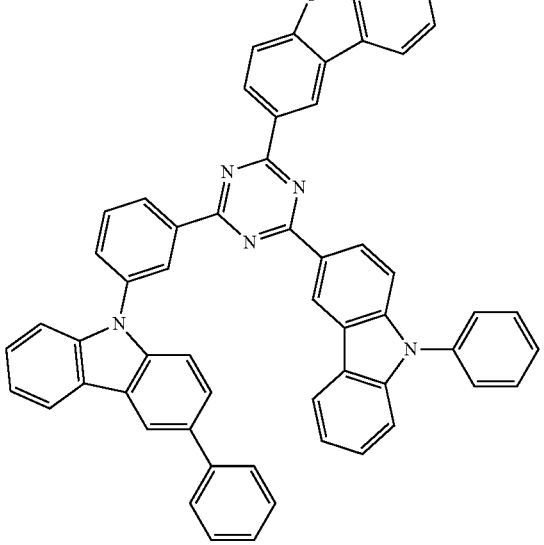
A-125
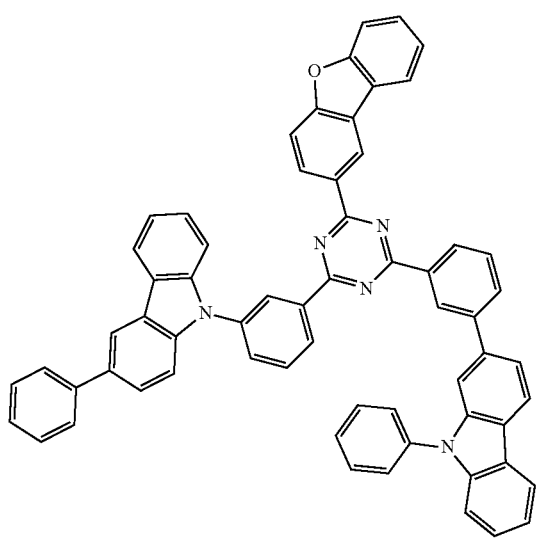
-continued
A-126
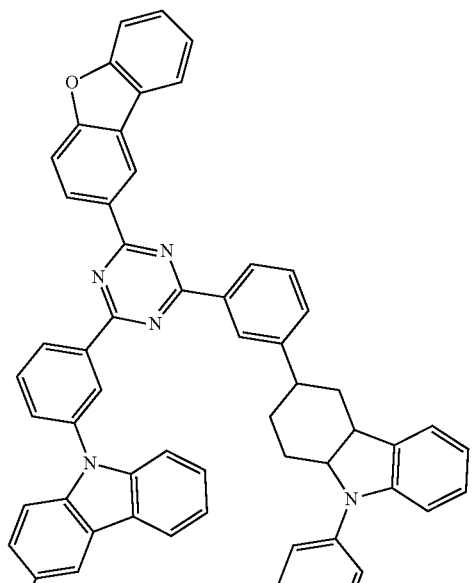
A-127
A-130
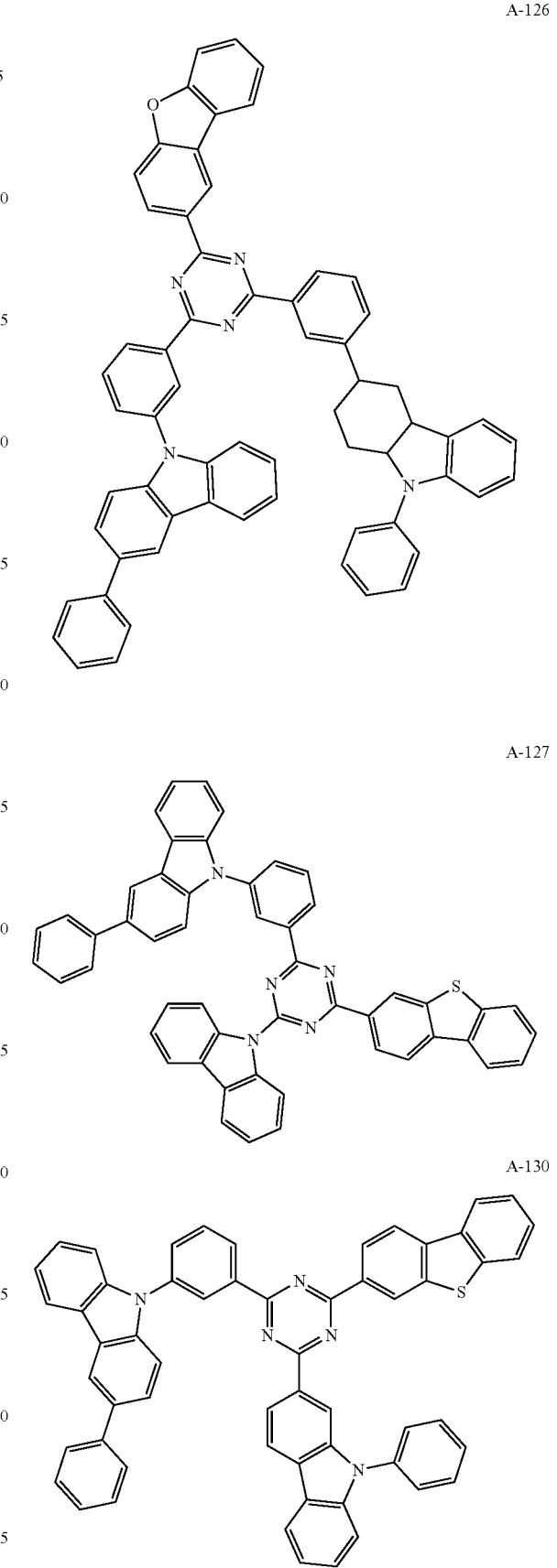

-continued
A-131
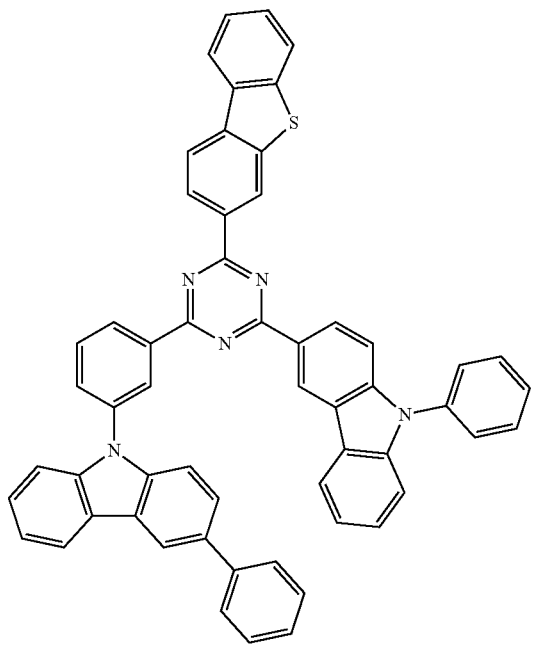
A-133
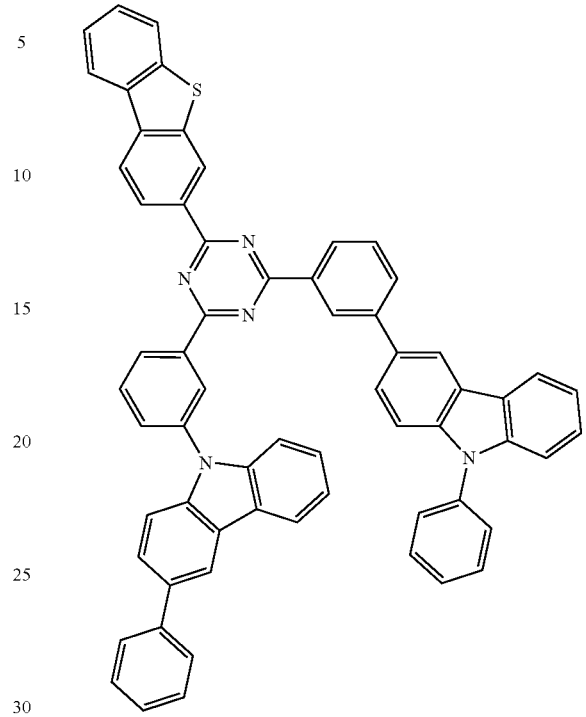
A-134
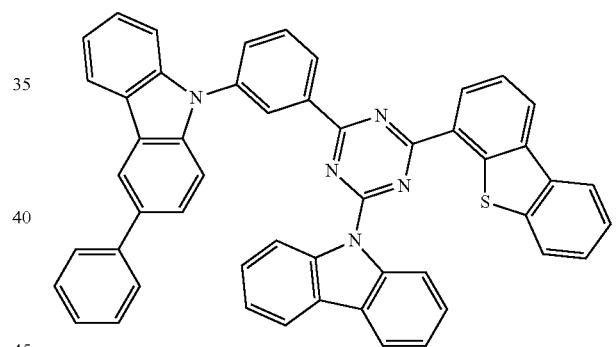
A-132
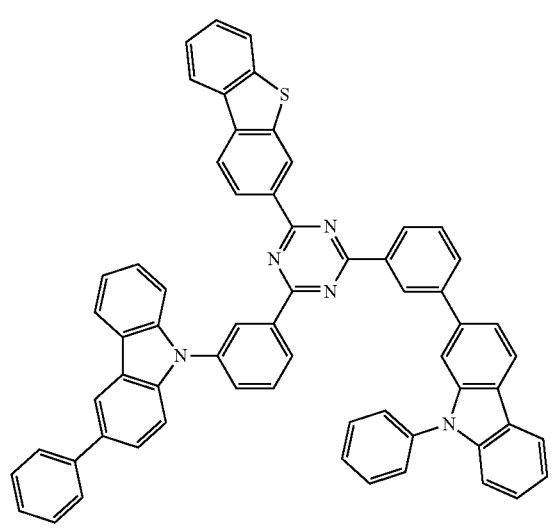
A-137
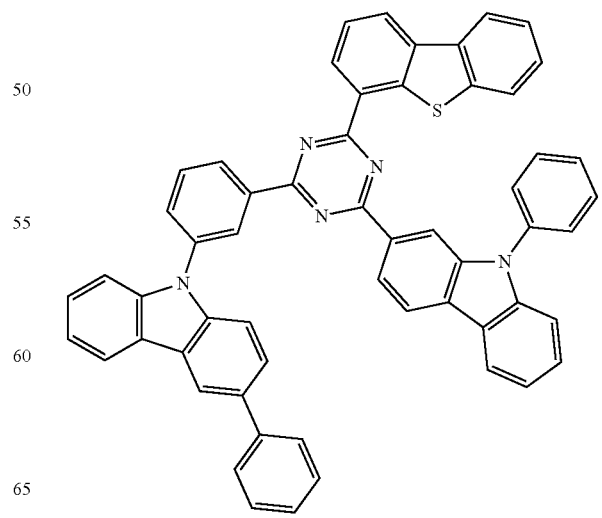

A-138

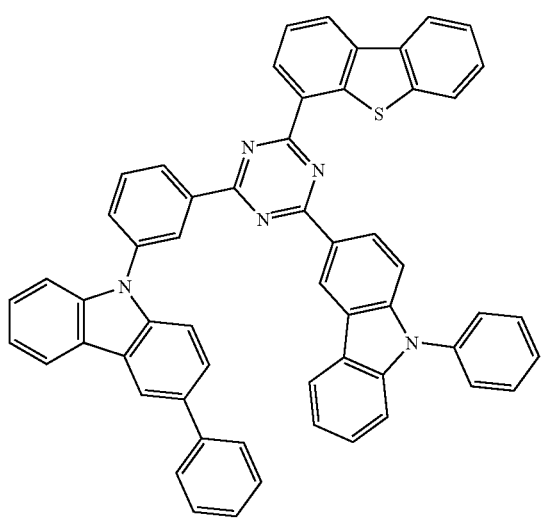

A-139

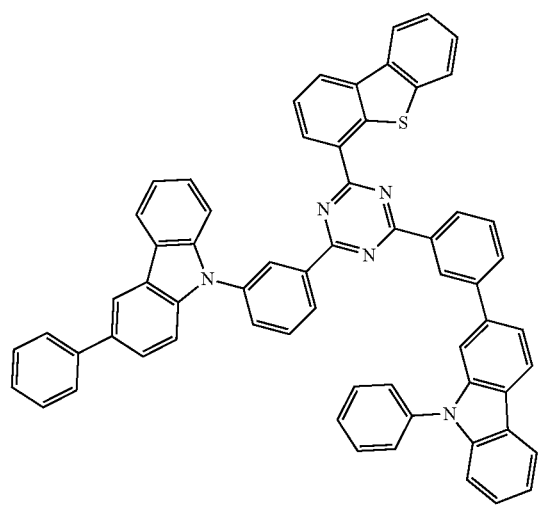

A-140

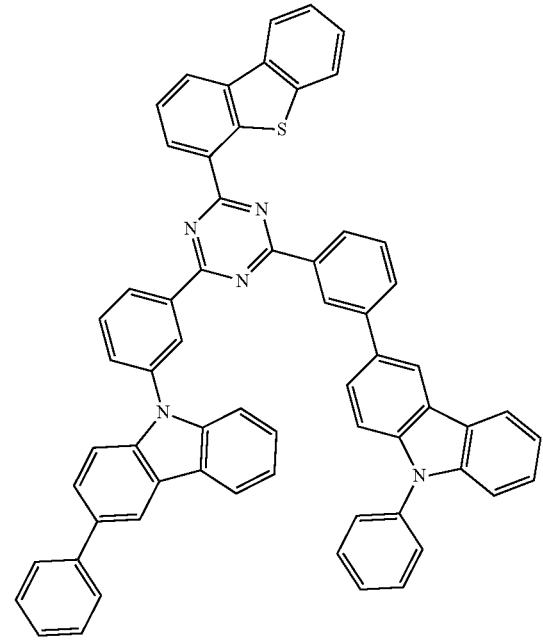

15. An organic electroluminescence device comprising an anode, a cathode, and one or more organic layers disposed between the anode and the cathode,
   wherein at least one of the one or more organic layers comprises the compound of the Chemical Formula 7 according to claim 7:

Chemical Formula 7

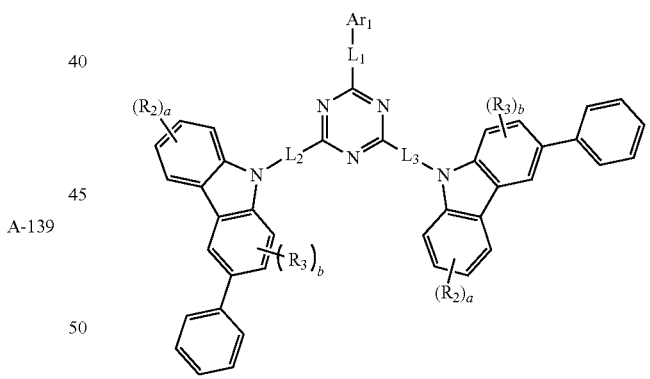

wherein
$Z_1$ to $Z_3$ are the same as or different from each other, each independently being N or $C(R_1)$, wherein at least one of $Z_1$ to $Z_3$ is N,
wherein when $C(R_1)$ are plural in number, the plurality of $R_1$, are the same or different from each other and each independently selected from the group consisting of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group and a $C_6$ to $C_{60}$ arylamine group, $L_1$ and $L_3$ are the same as or different from each other, each independently being a single bond, or selected from the group consisting of: a $C_6$ to $C_{18}$ arylene group and a heteroarylene group having 5 to 18 nuclear atoms, $L_2$ is a single bond, or selected from the group consisting of: a heteroarylene group having 5 to 18 nuclear atoms, $Ar_1$ is selected from the group consisting of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group, and a $C_6$ to $C_{60}$ arylamine group, and a is an integer ranging from 0 to 4, while b is an integer ranging from 0 to 3, wherein a plurality of $R_2$ are the same or different from each other, a plurality of $R_3$ are the same or different from each other, $R_2$ and $R_3$ are each independently selected from the group consisting of: deuterium, a halogen group, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group, or may combine with an adjacent group to form a fused ring, and the arylene group and the heteroarylene group of $L_1$ and $L_3$; the heteroarylene group of $L_2$; and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the alkylphosphine group, the arylphosphine group, the arylphosphine oxide group and the arylamine group of $Ar_1$ and $R_1$ to $R_3$ are each independently substituted or unsubstituted with one or more kinds of substituents selected from the group consisting of: deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_6$ to $C_{60}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{60}$ arylboron group, a $C_1$ to $C_{40}$ alkylphosphine group, a $C_6$ to $C_{60}$ arylphosphine group, a $C_6$ to $C_{60}$ arylphosphine oxide group and a $C_6$ to $C_{60}$ arylsilyl group, wherein when the substituents are plural in number, the substituents are the same as or different from each other.

16. The compound of claim 7, wherein the compound represented by the Chemical Formula 7 is selected from the following Compounds:

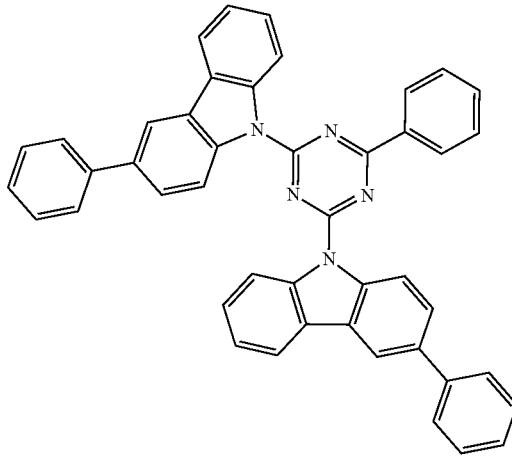

A-2

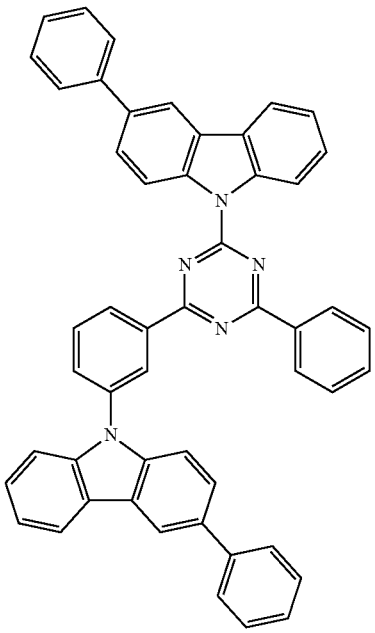

A-3

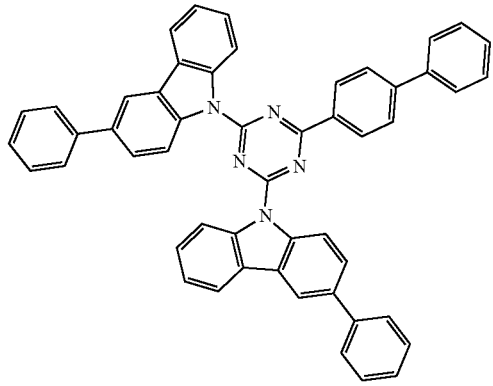

A-9

-continued
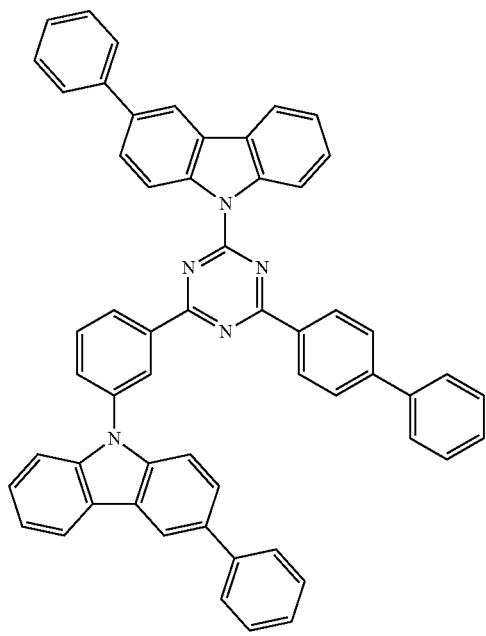
A-10
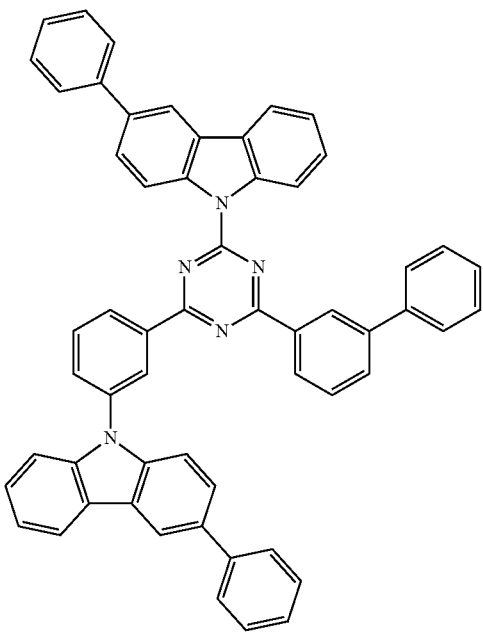
A-17
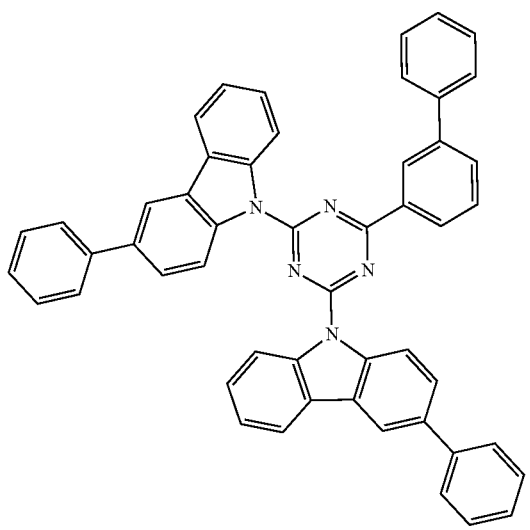
A-16
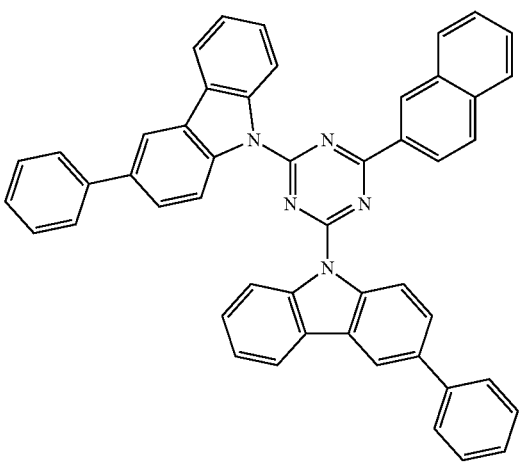
A-23

-continued
A-24
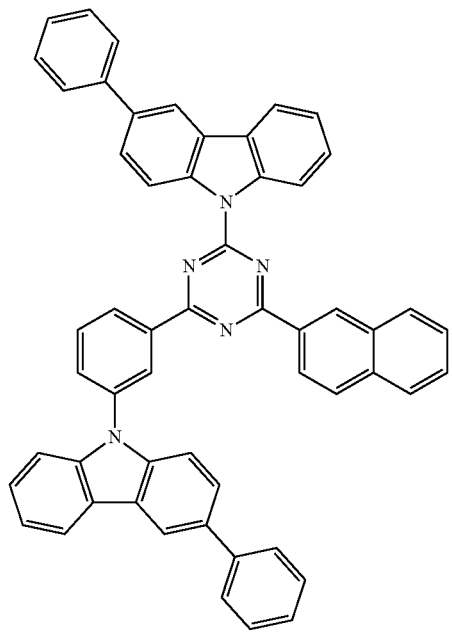
A-31
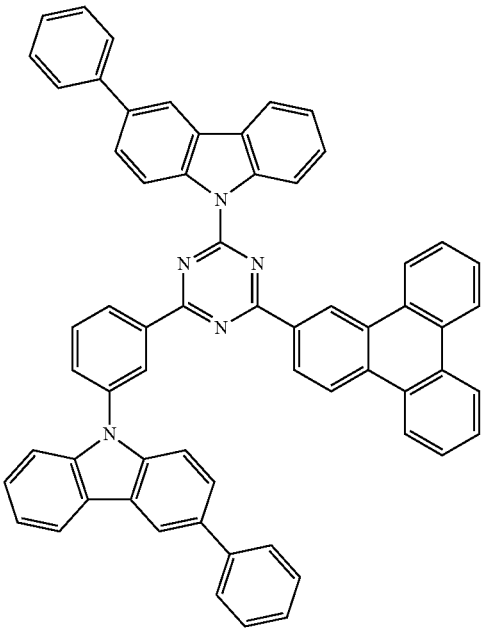
A-30
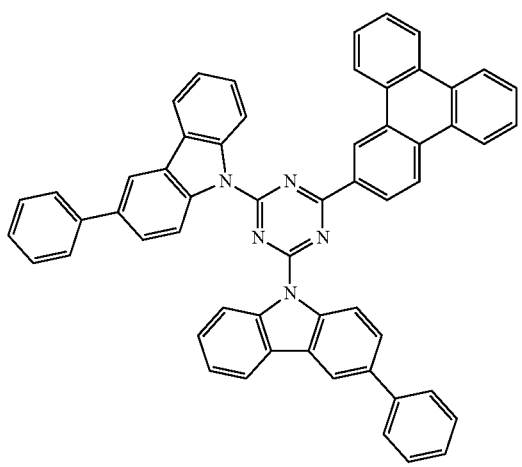
A-37
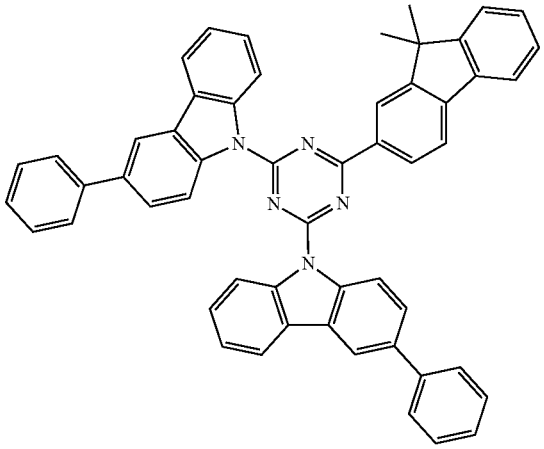

A-38
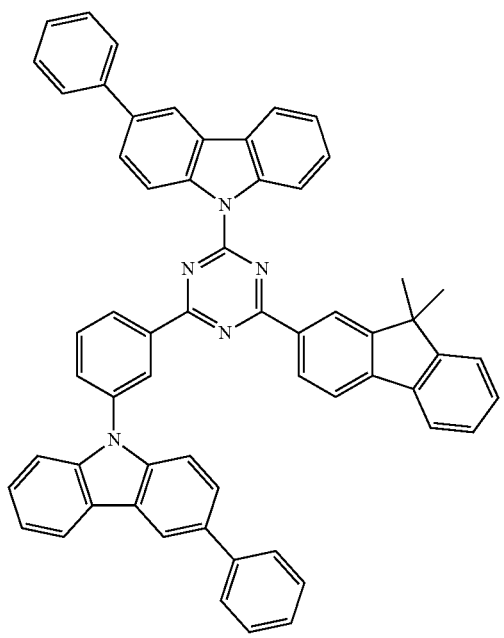
A-44
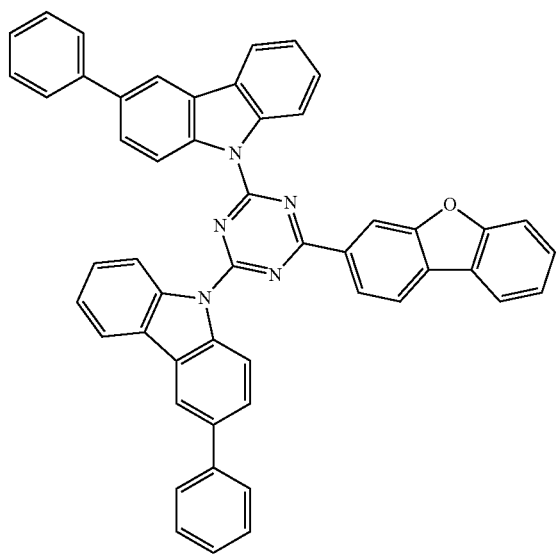
A-45
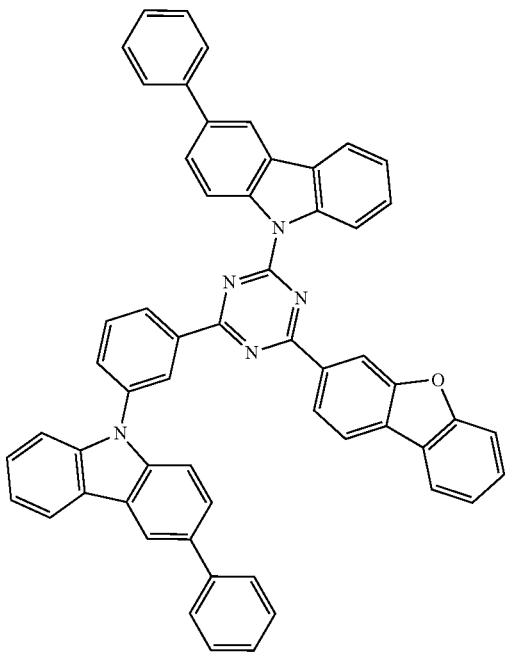
A-51
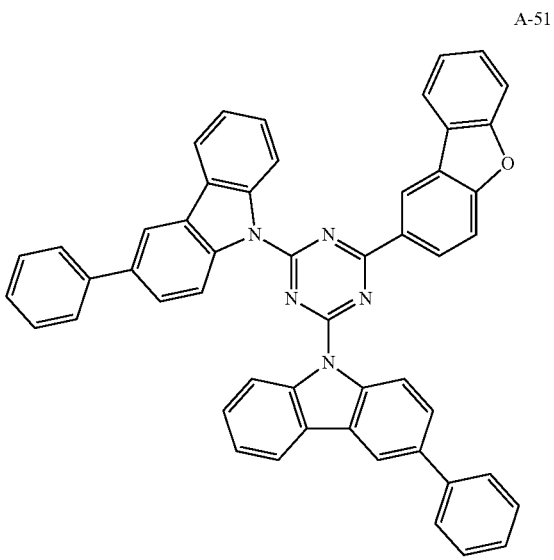 [SMILES: c1ccc(-c2ccc3c(c2)c2ccccc2n3-c2nc(-c3ccc4oc5ccccc5c4c3)nc(-n3c4ccccc4c4cc(-c5ccccc5)ccc43)n2)cc1]

A-52
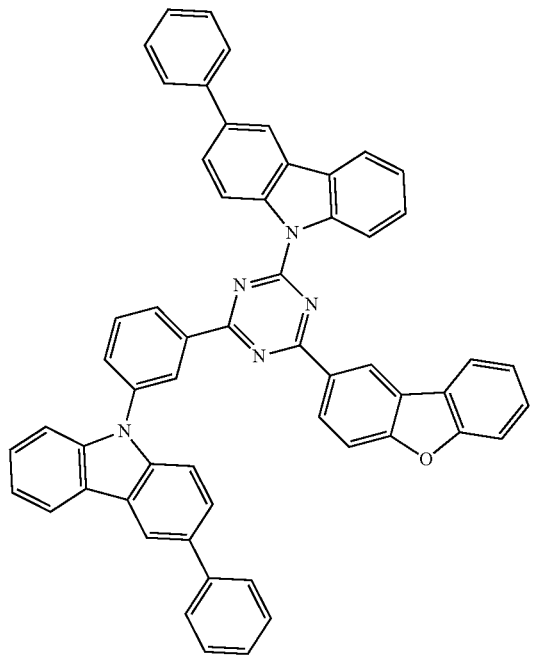
A-59
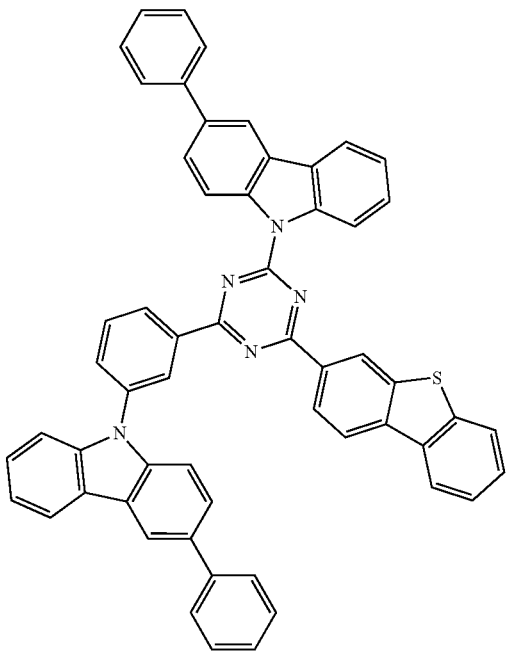
A-58
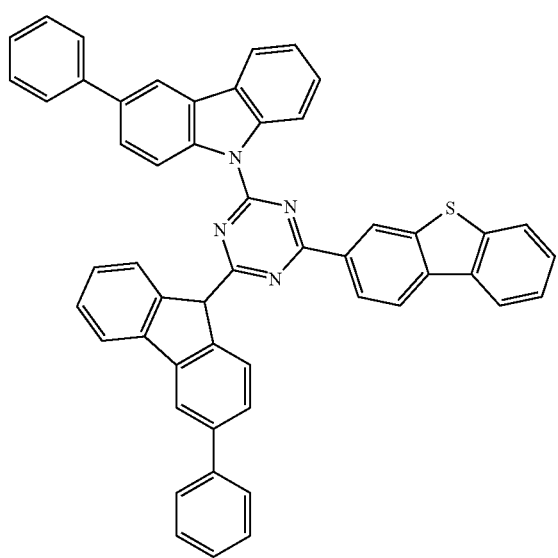
A-65
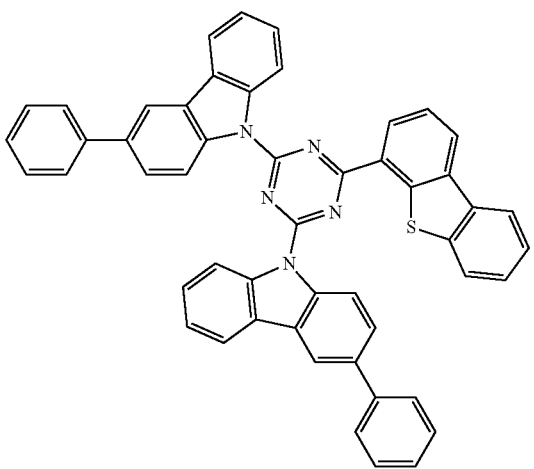

A-66
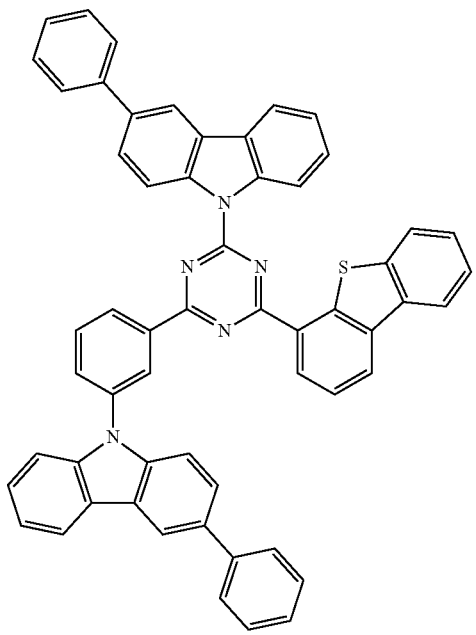
A-72
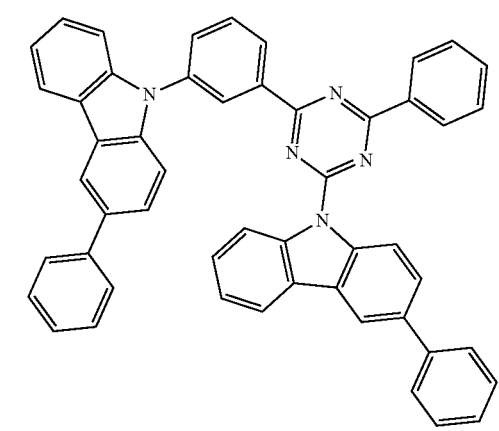
A-79
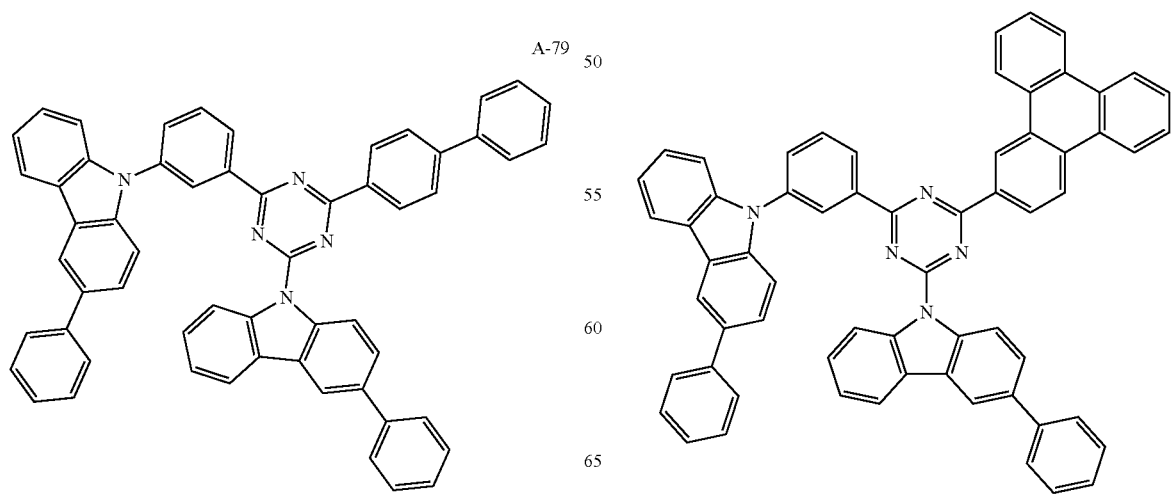
A-86
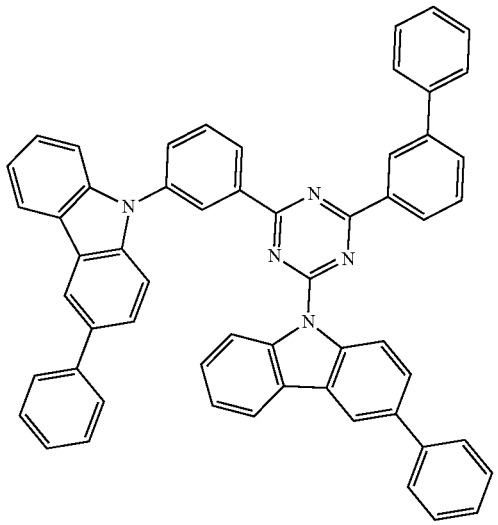
A-93
A-100

A-107
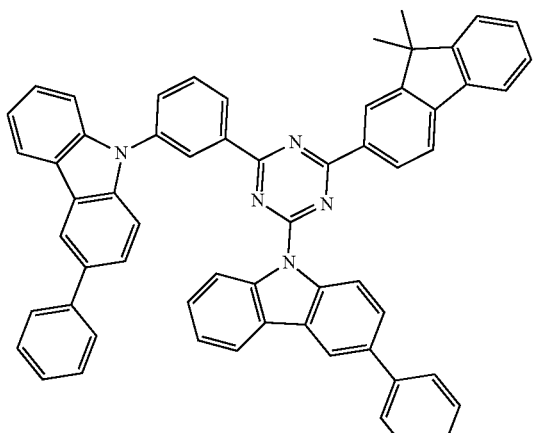
A-108
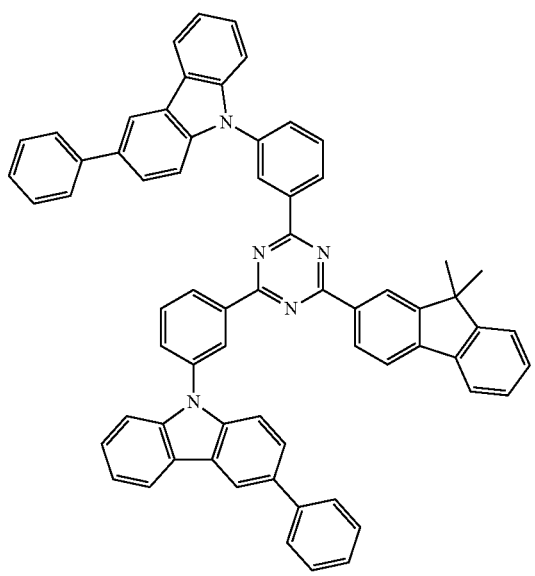
A-114
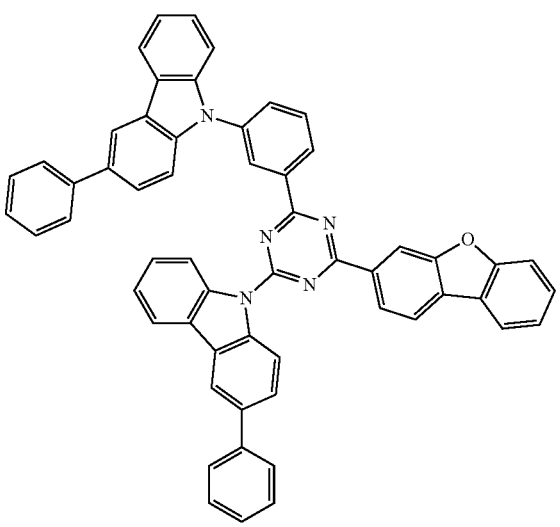
A-121
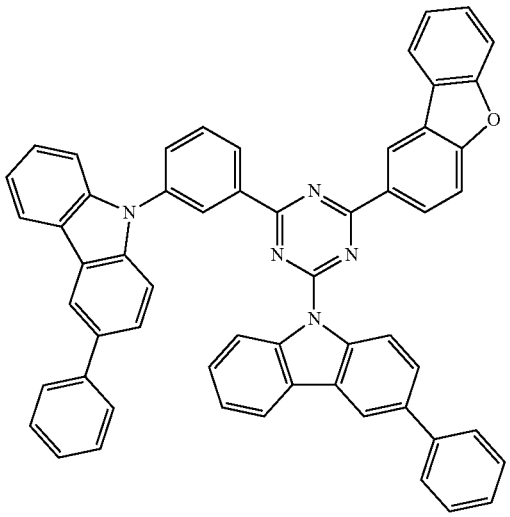
A-128
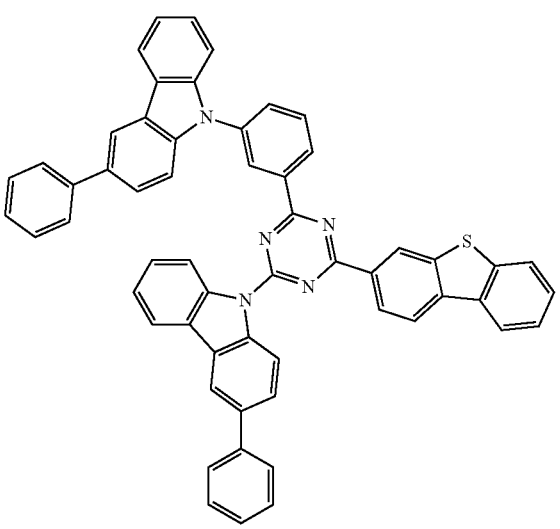
A-135
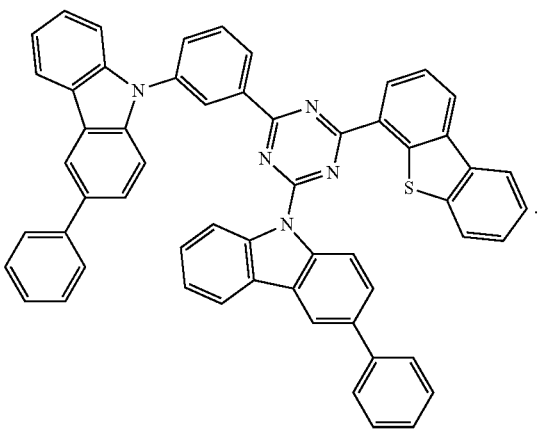
17. The organic electroluminescent device of claim 15, wherein the compound represented by the Chemical Formula 7 is selected from the following Compounds:

A-2
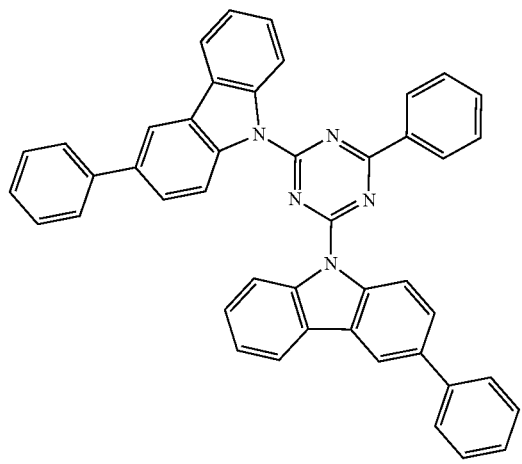
A-3
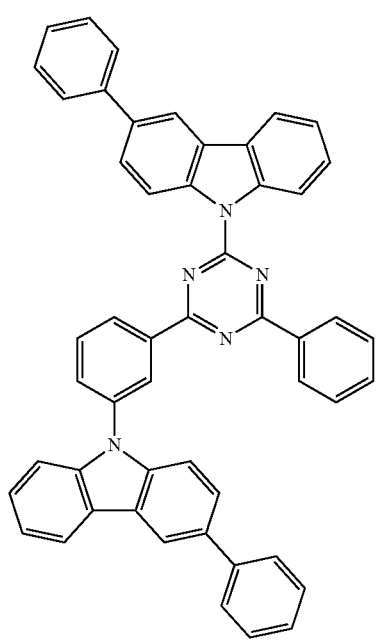
A-9
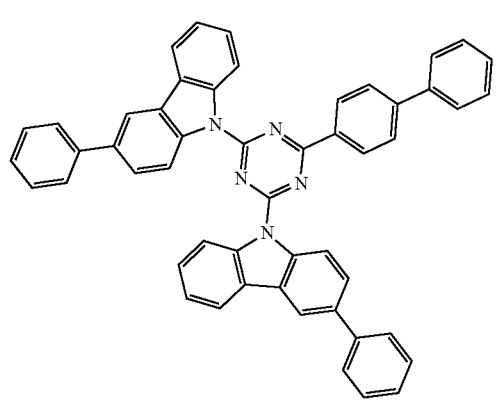
A-10
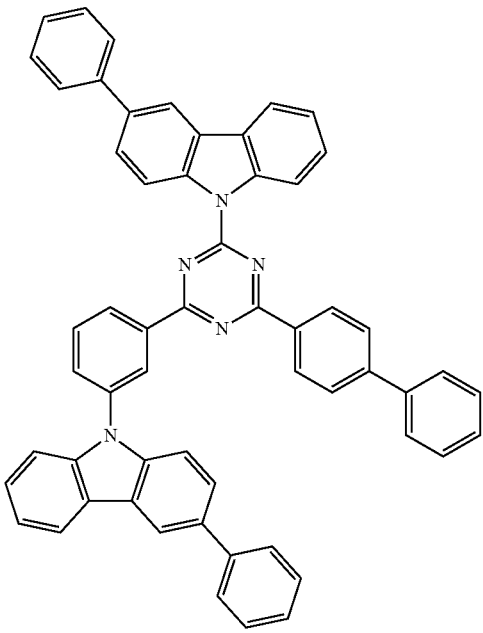
A-16
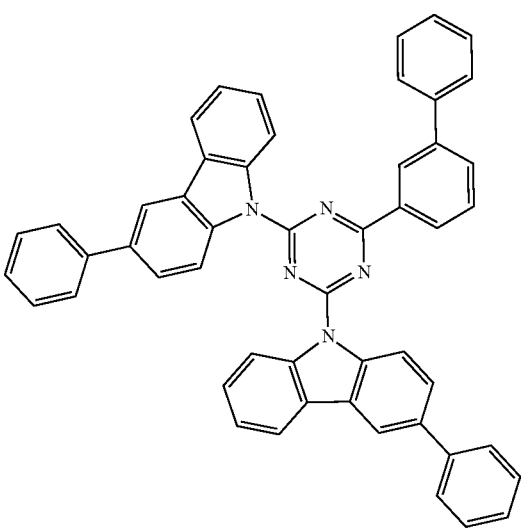

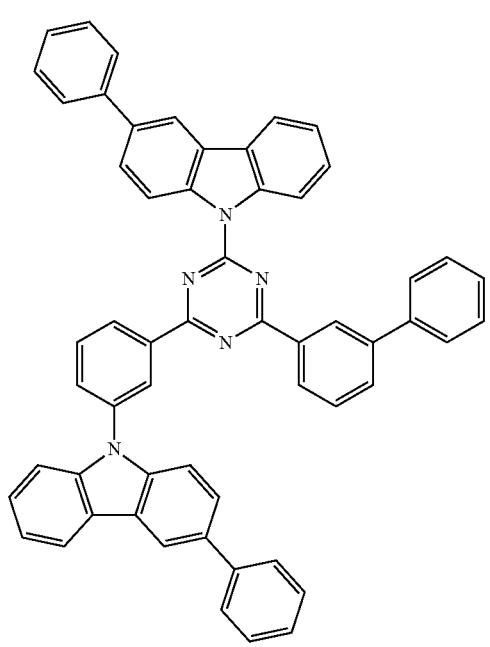
A-17
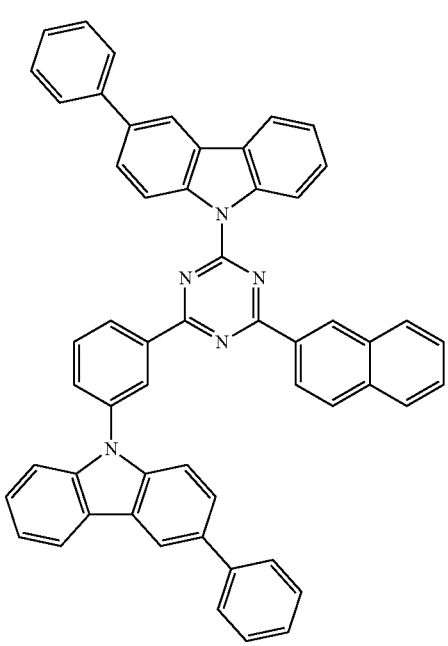
A-24
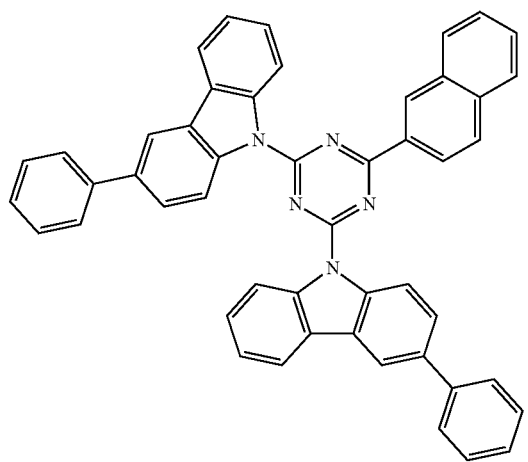
A-23
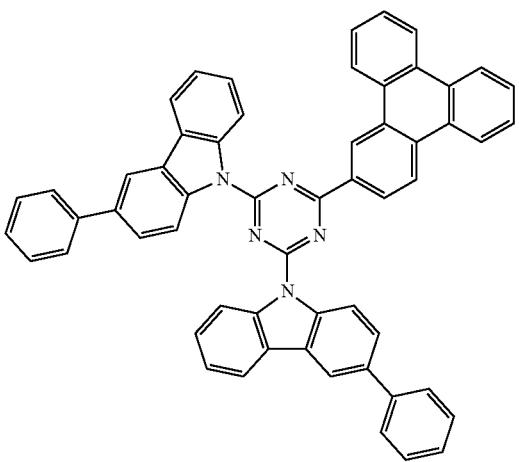
A-30

A-31
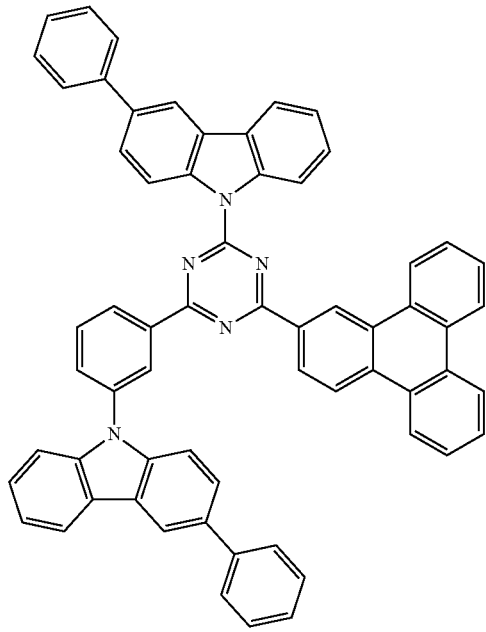
A-38
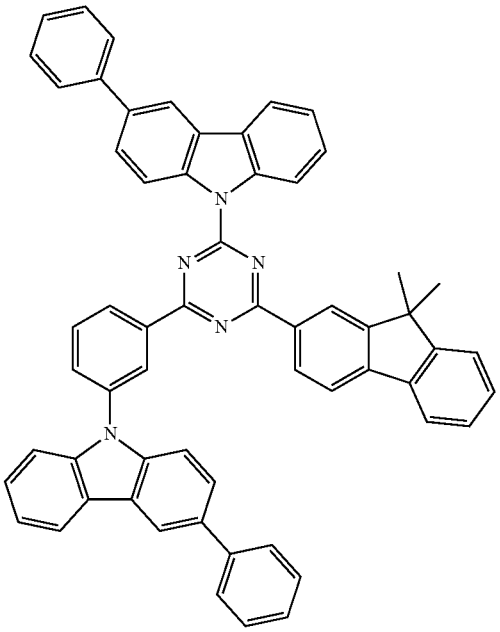
A-37
A-44
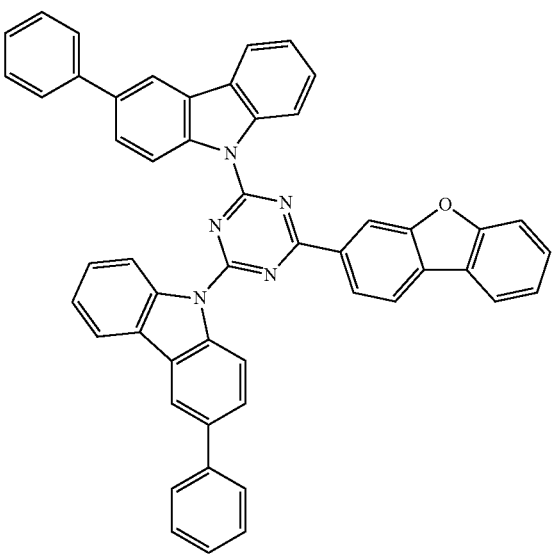

A-45
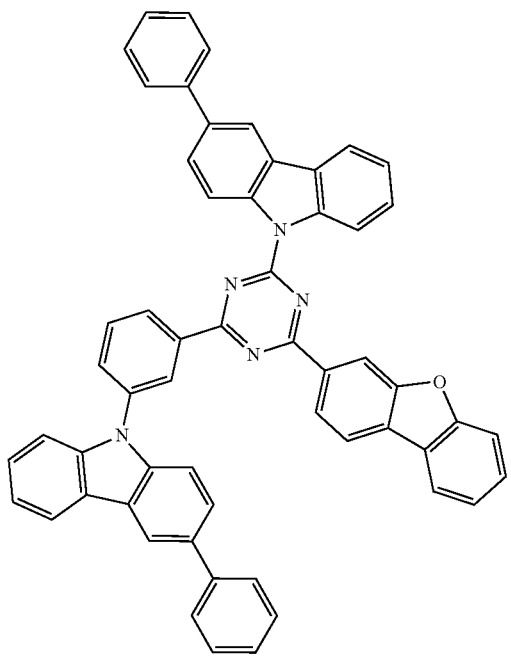
A-52
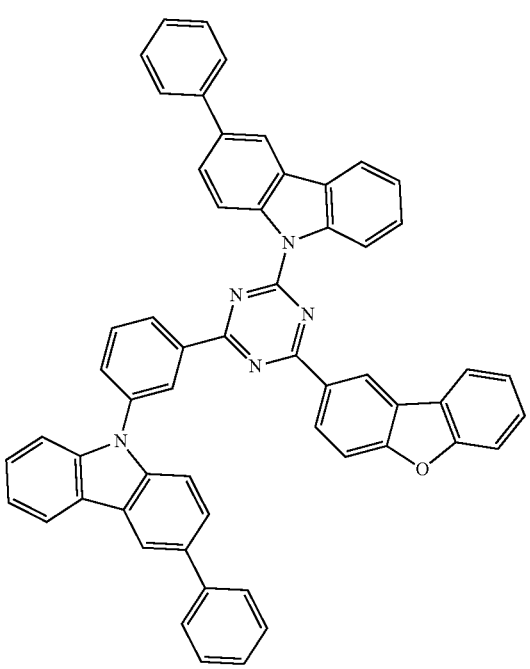
A-51
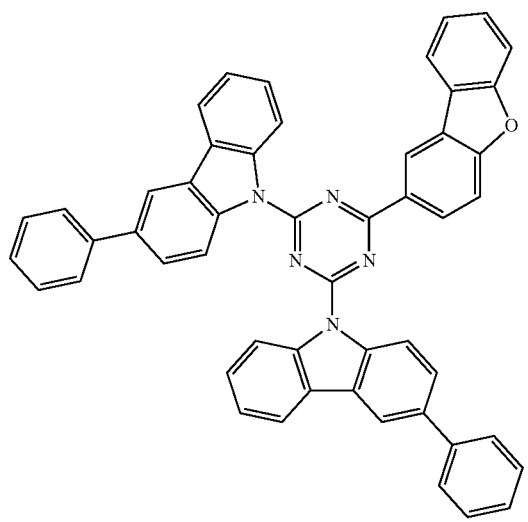
A-58
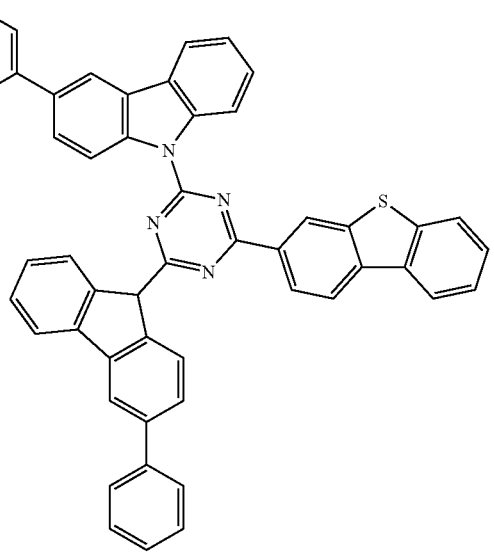

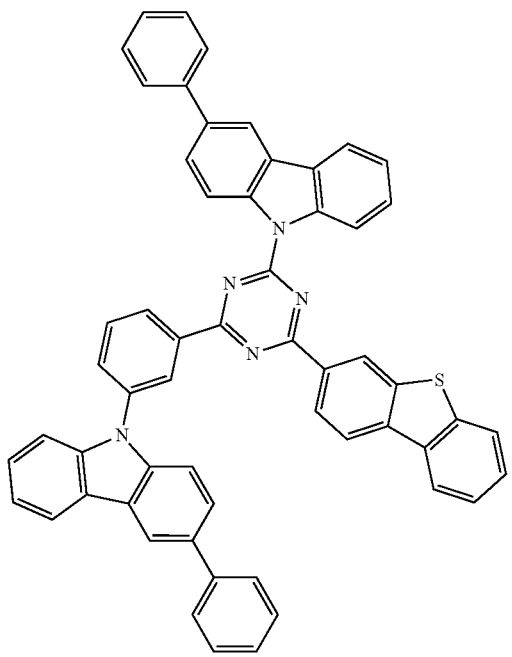
A-59
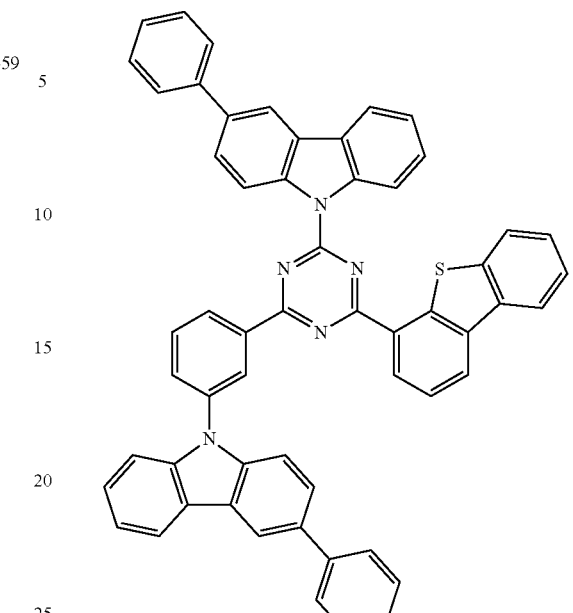
A-66
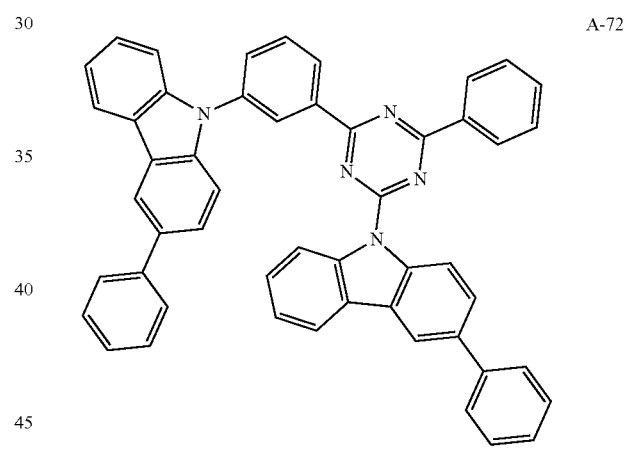
A-72
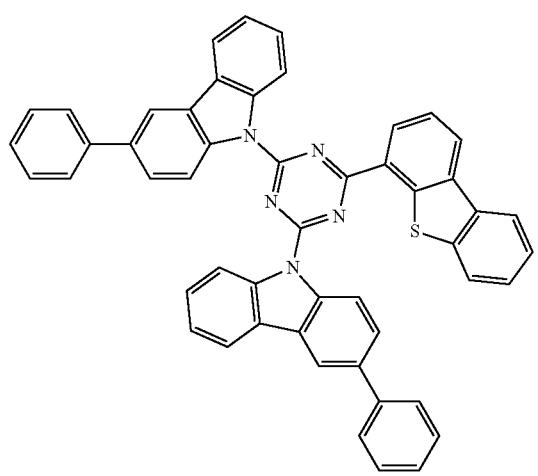
A-65
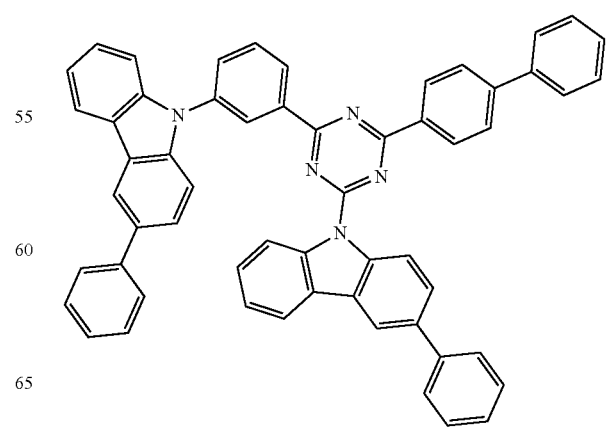
A-79

A-86
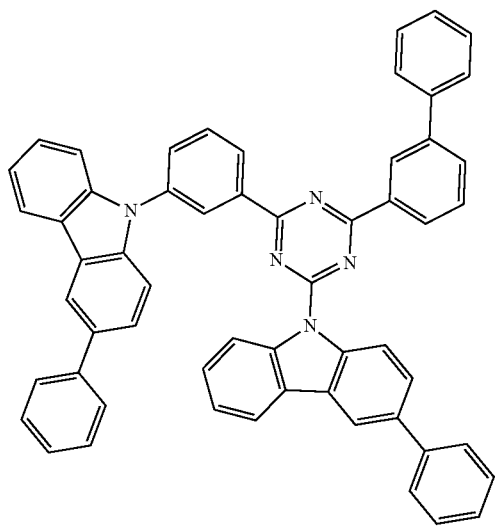
A-93
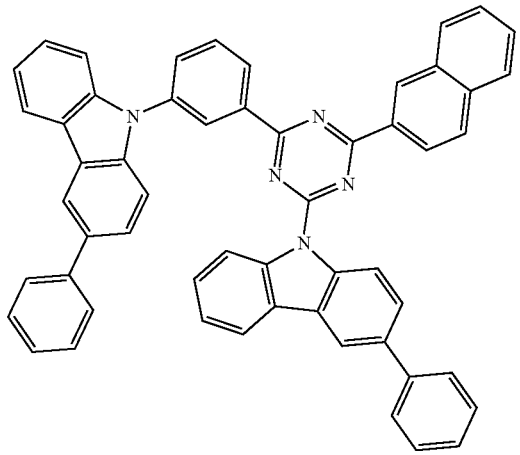
A-100
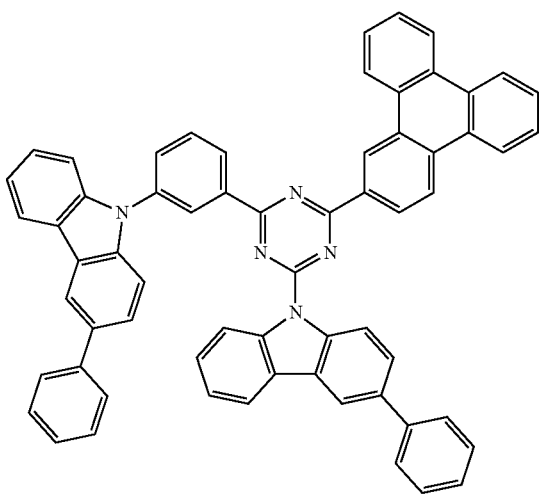
A-107
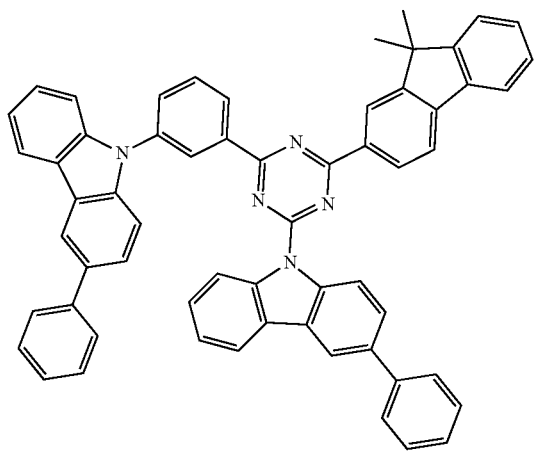
A-108
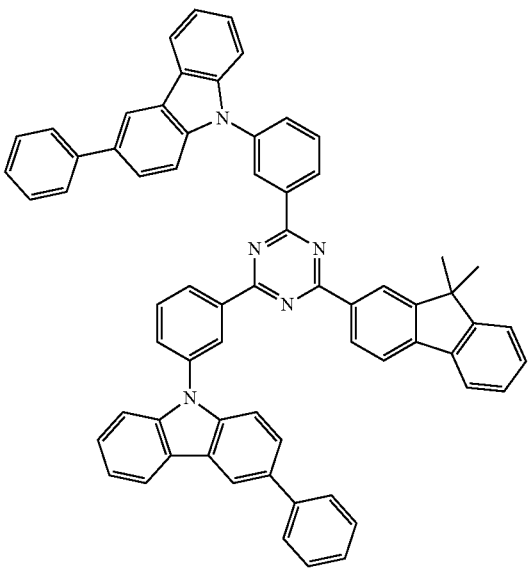
A-114
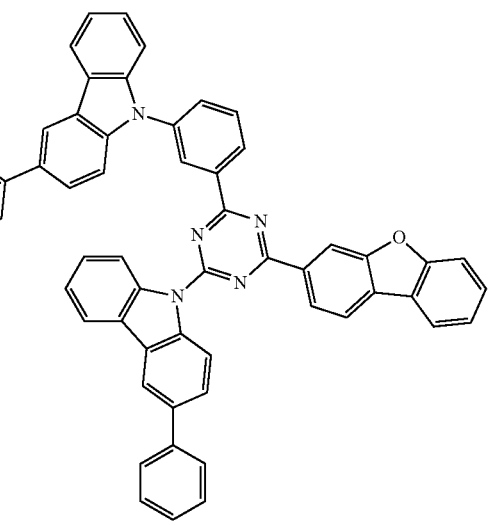

-continued
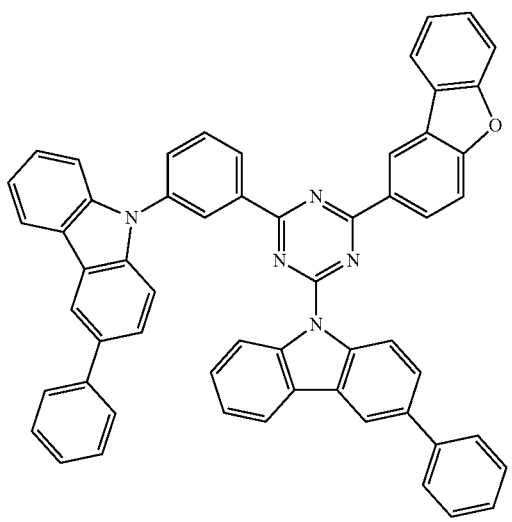
A-121
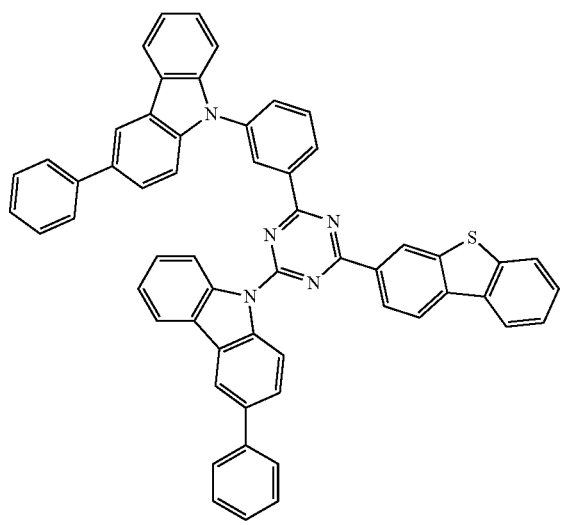
A-128
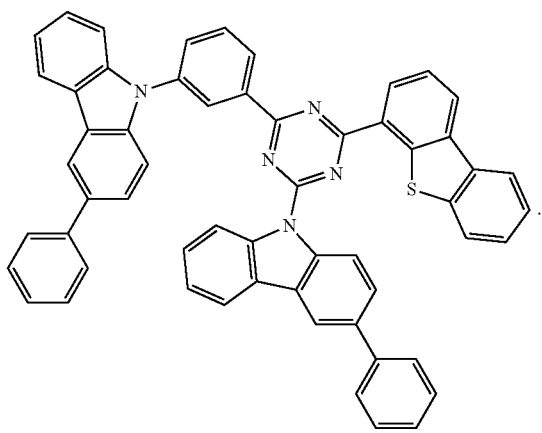
A-135
18. A compound selected from the following Compound A-73, A-80, A-87, A-94, A-101, A-108, A-115, A-122, A-129 and A-136:
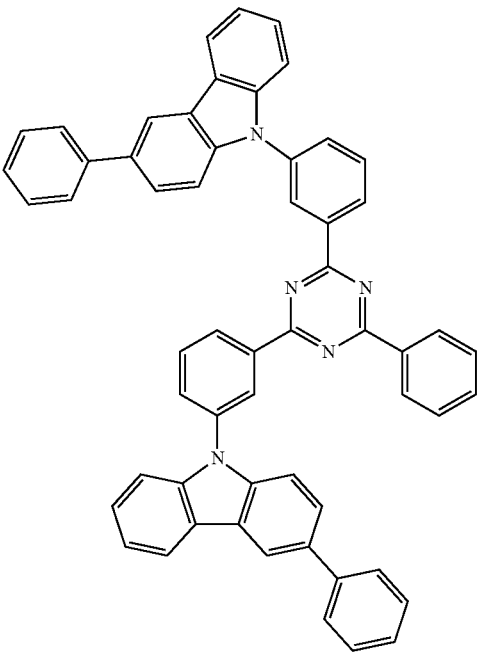
A-73
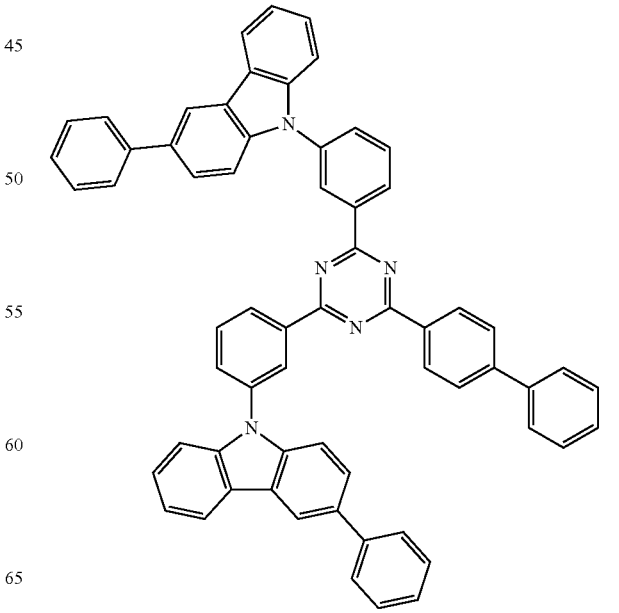
A-80

A-87
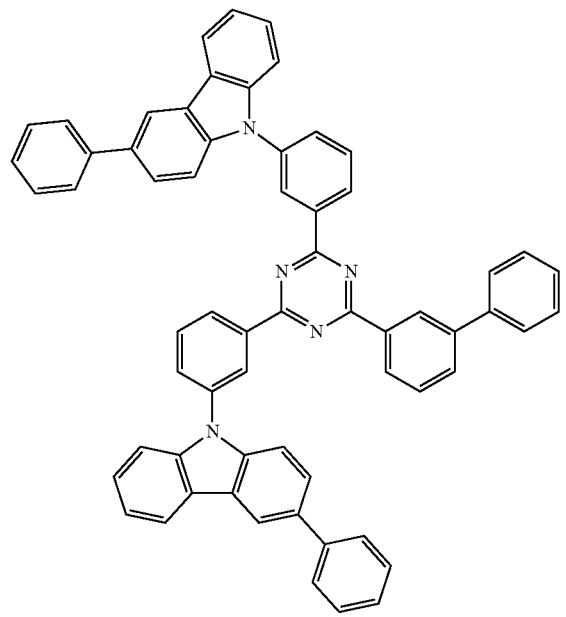
A-101
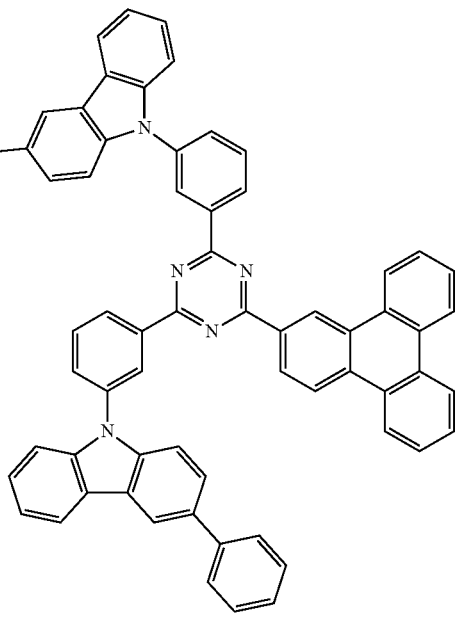
A-94
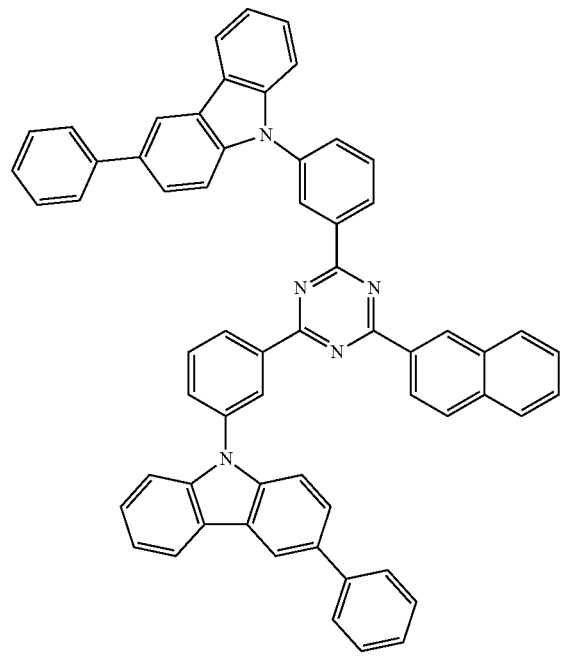
A-108
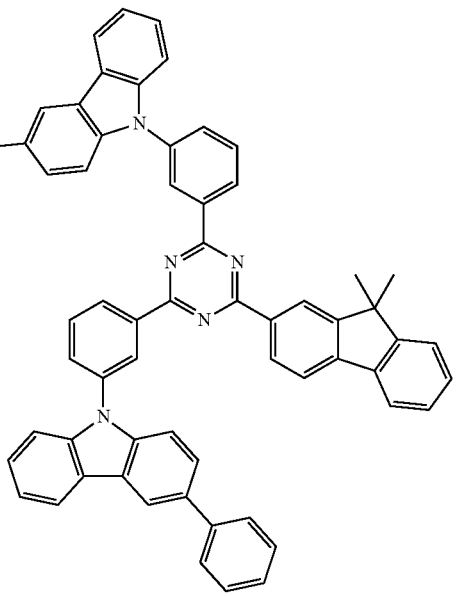

A-115
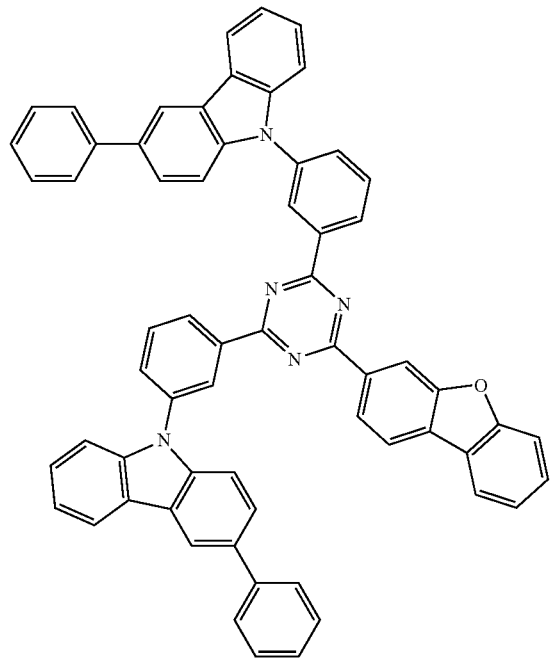
A-122
A-129
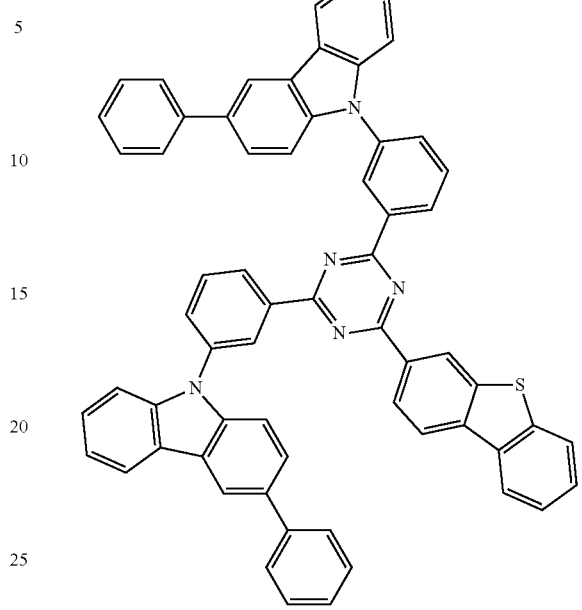
A-136
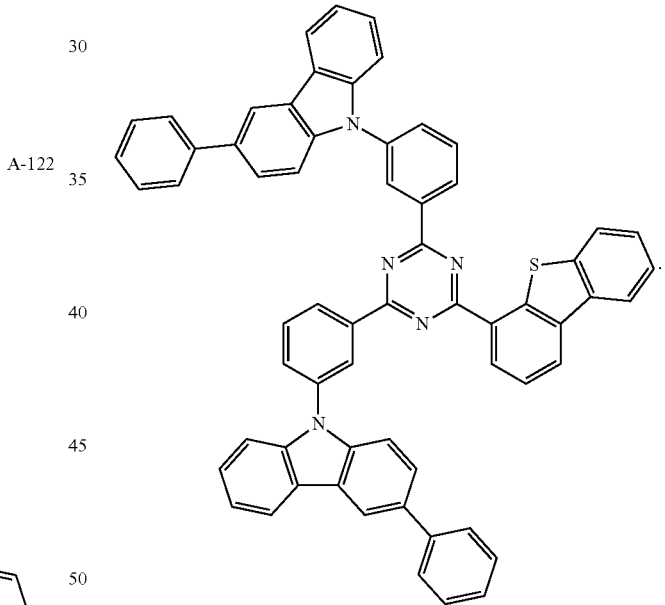
19. An organic electroluminescence device, comprising an anode, a cathode and one or more organic layers disposed between the anode and the cathode,
wherein at least one of the one or more organic layers comprises the compound selected from the Compounds A-73, A-80, A-87, A-94, A-101, A-108, A-115, A-122, A-129 and A-136 according to claim 18.
* * * * *